(12) United States Patent
Oakley et al.

(10) Patent No.: US 7,332,292 B2
(45) Date of Patent: Feb. 19, 2008

(54) CONSTITUTIVELY TRANSLOCATING CELL LINE

(75) Inventors: Robert H. Oakley, Durham, NC (US); Christine C. Hudson, Durham, NC (US)

(73) Assignee: Molecular Devices Corporation, Sunnyvale, CA (US)

( * ) Notice: Subject to any disclaimer, the term of this patent is extended or adjusted under 35 U.S.C. 154(b) by 0 days.

(21) Appl. No.: 10/788,197

(22) Filed: Feb. 26, 2004

(65) Prior Publication Data
US 2005/0032125 A1 Feb. 10, 2005

Related U.S. Application Data

(63) Continuation-in-part of application No. PCT/US03/14581, filed on May 12, 2003.

(60) Provisional application No. 60/401,698, filed on Aug. 7, 2002, provisional application No. 60/379,986, filed on May 13, 2002.

(51) Int. Cl.
*G01N 33/566* (2006.01)

(52) U.S. Cl. ............. 435/7.2; 435/7.21; 435/7.6; 436/501

(58) Field of Classification Search .......... None
See application file for complete search history.

(56) References Cited

U.S. PATENT DOCUMENTS

| | | | |
|---|---|---|---|
| 5,625,048 A | 4/1997 | Tsien et al. | |
| 5,777,079 A | 7/1998 | Tsien et al. | |
| 5,891,646 A | 4/1999 | Barak et al. | |
| 6,066,476 A | 5/2000 | Tsien et al. | |
| 6,110,693 A | 8/2000 | Barak et al. | |
| 6,528,271 B1 | 3/2003 | Bohn et al. | |
| 6,770,449 B2 | 8/2004 | Barak et al. | |
| 2003/0013137 A1 | 1/2003 | Barak et al. | |
| 2003/0049643 A1 | 3/2003 | Barak et al. | |
| 2003/0182669 A1 | 9/2003 | Rockman et al. | |

OTHER PUBLICATIONS

Chen, Zhangguo, et al., "Agonist-induced internalization of the Platelet-activating Factor Receptor Is Dependent on Arrestins but Independent of G-protein Activation", *The Journal of Biological Chemistry*, 277(9):7356-7362 (2002).

Gales, CéLine, et al., "Mutation of Asn-391 within the Conserved NPXXY Motif of the Cholecystokinin B Receptor Abolishes Gq Protein Activation without Affecting Its Association with the Receptor", *The Journal of Biological Chemistry*, 275(23):17321-17327 (2000).

Inglese, James, et al., "Isoprenylation in regulation of signal transduction by G-protein-coupled receptor kinases", *Nature*, 359:147-148 (1992).

Loudon, Robert P., et al., "Altered Activity of Palmitoylation-deficient and Isoprenylated Forms of the G Protein-coupled Receptor Kinase GRK6", *The Journal of Biological Chemistry*, 272(43):27422-27427 (1997).

*Primary Examiner*—John Ulm
(74) *Attorney, Agent, or Firm*—Edward J. Baba; David J. Brezner; Morgan Lewis & Bockius LLP

(57) ABSTRACT

The present invention relates to agonist-independent methods of screening for compounds that alter GPCR desensitization. Included in the present invention are cell lines containing GRKs, in which GPCRs are desensitized in the absence of agonist; the GRKs may be modified. The present invention relates to methods to determine if a GPCR is expressed at the plasma membrane, and if the GPCR has an affinity for arrestin. Modified GPCRs which have increased arrestin affinity are included in the present invention. These modified GPCRs are useful in methods to screen for compounds that alter desensitization, including both the agonist-independent methods and agonist-dependent methods described herein.

14 Claims, 55 Drawing Sheets

Figure 1A

Human G Protein Coupled Receptor Family
(Receptors known as of January, 1999)

| CLASS | LIGAND | NUMBER | TISSUE | PHYSIOLOGY | THERAPEUTICS |
|---|---|---|---|---|---|
| Class 1 <br> •Rhodopsin like | | | | | |
| | •Amine | | | | |
| | ·Acetylcholine (muscarinic & nicotinic) | 5 | Brain, Nerves, Heart | Neurotransmitter | Acuity, Alzheimer's |
| | ·Adrenoceptors | | | | |
| | ·Alpha Adrenoceptors | 6 | Brain, Kidney, Lung | Gluconeogenesis | Diabetes, Cardiovascular |
| | ·Beta Adrenoceptors | 3 | Kidney, Heart | Muscle Contraction | Cardiovascular, Respiratory |
| | ·Dopamine | 5 | Brain, Kidney, GI | Neurotransmitter | Cardiovascular, Parkinson's |
| | ·Histamine | 2 | Vascular, Heart, Brain | Vascular Permeability | Anti-inflammatory, Ulcers |
| | ·Serotonin (5-HT) | 16 | Most Tissues | Neurotransmitter | Depression, Insomnia, Analgesic |
| | •Peptide | | | | |
| | ·Angiotensin | 2 | Vascular, Liver, Kidney | Vasoconstriction | Cardiovascular, Endocrine |
| | ·Bradykinin | 1 | Liver, Blood | Vasodilation | Anti-inflammatory, Asthma |
| | ·C5a anaphylatoxin | 1 | Blood | Immune System | Anti-inflammatory |
| | ·Fmet-leu-phe | 3 | Blood | Chemoattractant | Anti-inflammatory |
| | ·Interleukin-8 | 1 | Blood | Chemoattractant | Anti-inflammatory |
| | ·Chemokine | 6 | Blood | Chemoattractant | Anti-inflammatory |
| | ·Orexin | 2 | Brain | Fat Metabolism | Obesity |
| | ·Nociceptin | 1 | Brain | Bronchodilator, Pain | Airway Diseases, Anesthetic |
| | ·CCK (Gastrin) | 2 | Gastrointestinal | Motility, Fat Absorption | Gastrointestinal, Obesity, Parkinson's |
| | ·Endothelin | 2 | Heart, Bronchus, Brain | Muscle Contraction | Cardiovascular, Respiratory |
| | ·Melanocortin | 5 | Kidney, Brain | Metabolic Regulation | Anti-inflammatory, Analgesics |
| | ·Neuropeptide Y | 5 | Nerves, Intestine, Blood | Neurotransmitter | Behavior, Memory, Cardiovascular |
| | ·Neurotensin | 1 | Brain, | CNS | Cardiovascular, Analgesic |

Figure 1B

| | | | | |
|---|---|---|---|---|
| Opioid | 3 | Brain, | CNS | Depression, Analgesic |
| Somatostatin | 5 | Brain, Gastrointestinal | Neurotransmitter | Oncology, Alzheimer's |
| Tachykinin (Substance P, NKA₁) | 3 | Brain Nerves | Neurohormone | Depression, Analgesic |
| Thrombin | 3 | Platelets, Blood Vessels | Coagulation | Anti-coagulant, Anti-inflammatory |
| Vasopressin-like | 4 | Arteries, Heart, Bladder | Water Balance | Anti-diuretic, Diabetic Complications |
| Galanin | 1 | Brain, Pancreas | Neurotransmitter | Analgesics, Alzheimer's |
| Hormone protein | | | | |
| Follicle stimulating hormone | 1 | Ovary, Testis | Endocrine | Infertility |
| Lutropin-choriogonadotropic | 1 | Ovary, Testis | Endocrine | Infertility |
| Thyrotropin | 1 | Thyroid | Endocrine | Thyroidism, Metabolism |
| (Rhodopsin) | | | | |
| Opsin | 5 | Eye | Photoreception | Ophthalmic Diseases |
| Olfactory | 4(~1000) | Nose | Smell | Olfactory Diseases |
| Prostanoid | | | | |
| Prostaglandin | 5 | Arterial, Gastrointestinal | Vasodilation, Pain | Cardiovascular, Analgesic |
| Lysophosphatidic Acid | 2 | Vessels, Heart, Lung | Inflammation | Cancer, Anti-Inflammatory |
| Sphingosine-1-phosphate | 2 | Most Cells | Cell proliferation | Cancer |
| Leukotriene | 1 | White Blood Cells, Bronchus | Inflammation | Asthma, Rheumatoid Arthritis |
| Prostacyclin | 1 | Arterial, Gastrointestinal | Platelet Regulation | Cardiovascular |
| Thromboxane | 1 | Arterial, Bronchus | Vasoconstriction | Cardiovascular, Respiratory |
| Nucleotide-like | | | | |
| Adenosine | 4 | Vascular, Bronchus | Multiple Effects | Cardiovascular, Respiratory |
| Purinoceptors | 4 | Vascular, Platelets | Relaxes Muscle | Cardiovascular, Respiratory |
| Cannabis | 2 | Brain | Sensory Perception | Analgesics, Memory |
| Platelet activating factor | 1 | Most Peripheral Tissues | Inflammation | Anti-inflammatory, Anti-asthmatic |

Figure 1C

| | | | |
|---|---|---|---|
| | Gonadotropin-releasing hormone like | 1 | Reproductive Organs, Pituitary | Reproduction | Prostate Cancer, Endometriosis |
| | Gonadotropin-releasing hormone | 1 | Pituitary, Brain | Thyroid Regulation | Metabolic Regulation |
| | Thyrotropin-releasing hormone | 1 | Gastrointestinal | Neuroendocrine | Oncology, Alzheimer's |
| | Growth hormone- inhibiting factor | 1 | Brain, Eye, Pituitary | Neuroendocrine | Regulation of Circadian Cycle |
| | Melatonin | 1 | | | |
| Class II | | | | | |
| Secretin like | Secretin | 1 | Gastrointestinal, Heart | Digestion | Obesity, Gastrointestinal |
| | Calcitonin | 1 | Bone, Brain | Calcium Resorption | Osteoporosis |
| | Corticotropin releasing factor/urocortin | 1 | Adrenal, Vascular, Brain | Neuroendocrine | Stress, Mood, Obesity |
| | Gastric inhibitory peptide (GIP) | 1 | Adrenals, Fat Cells | Sugar/Fat Metabolism | Diabetes, Obesity |
| | Glucagon | 1 | Liver, Fat Cells, Heart | Gluconeogenesis | Cardiovascular |
| | Glucagon-like Peptide 1 (GLP-1) | 1 | Pancreas, Stomach, Lung | Gluconeogenesis | Cardiovascular, Diabetes, Obesity |
| | Growth hormone-releasing hormone | 1 | Brain | Neuroendocrine | Growth Regulation |
| | Parathyroid hormone | 1 | Bone, Kidney | Calcium Regulation | Osteoporosis |
| | PACAP | 1 | Brain, Pancreas, Adrenals | Metabolism | Metabolic Regulation |
| | Vasoactive intestinal polypeptide (VIP) | 1 | Gastrointestinal | Motility | Gastrointestinal |
| Class III | Metabotropic Glutamate | 7 | Brain | Sensory Perception | Hearing, Vision |
| | GABA$_B$ | 1 | Brain | Neurotransmitter | Mood Disorders |
| | Extracellular Calcium Sensing | 1 | Parathyroid, Kidney, GI Tract | Calcium Regulation | Cataracts, GI Tumors |

Figure 2A

Bovine GRK2-C20 Amino Acid Sequence

MADLEAVLADVSYLMAMEKSKATPAARASKKILLPEPSIRSVMQKYLEDRGEVTFEKIFSQKLGYLLFRDFCLKHLEEAK
PLVEFYEEIKKYEKLETEEERLVCSREIFDTYIMKELLACSHPFSKSAIEHVQGHLVKKQVPPDLFQPYIEEICQNLRGD
VFQKFIESDKFTRFCQWKNVELNIHLTMNDFSVHRIIGRGGFGEVYGCRKADTGKMYAMKCLDKKRIKMKQGETLALNER
IMLSLVSTGDCPFIVCMSYAFHTPDKLSFILDLMNGGDLHYHLSQHGVFSEADMRFYAAEIILGLEHMHNRFVVYRDLKP
ANILLDEHGHVRISDLGLACDFSKKKPHASVGTHGYMAPEVLQKGVAYDSSADWFSLGCMLFKLLRGHSPFRQHKTKDKH
EIDRMTLTMAVELPDSFSPELRSLLEGLLQRDVNRRLGCLGRGAQEVKESPFFRSLDWQMVFLQKYPPPLIPPRGEVNAA
DAFDIGSFDEEDTKGIKLLDSDQELYRNFPLTISERWQQEVAETVFDTINAETDRLEARKKTKNKQLGHEEDYALGKDCI
MHGYMSKMGNPFLTQWQRRYFYLFPNRLEWRGEGEAPQSLLTMEEIQSVEETQIKERKCLLLKIRGGKQFVLQCDSDPEL
VQWKKELRDAYREAQQLVQRVPKMKNKPRSPVVELSKVPLIQRGSCVLL

SEQ ID NO: 1

Bovine GRK2-C20 Nucleotide sequence

ATGGCGGACCTGGAGGCGGTGCTGGCCGACGTGAGCTACCTGATGGCCATGGAGAAGAGCAAGGCCACGCCGGCGGCGCG
CGCCAGCAAGAAGATCCTGCTGCCCGAGCCCAGCATCCGCAGCGTCATGCAGAAGTACCTGGAGGACCGGGGCGAGGTGA
CTTTTGAGAAGATCTTCTCCCAGAAGCTGGGGTACCTGCTTTTCCGAGACTTCTGCCTGAAGCACCTGGAGGAGGCCAAG
CCCTTGGTAGAGTTCTACGAGGAGATCAAGAAATACGAGAAGCTGGAGACAGAGGAGGAGCGCCTGGTCTGCAGCCGAGA
GATCTTCGACACGTACATCATGAAGGAGCTGCTGGCCTGCTCACATCCTTTCTCGAAGAGCGCCATTGAGCACGTCCAGG
GCCATCTGGTGAAGAAGCAGGTGCCTCCGGATCTCTTCCAGCCATATATTGAAGAAATTTGCCAGAACCTCCGAGGAGAC
GTGTTCCAGAAATTCATCGAGAGCGATAAATTCACACGATTTTGCCAGTGGAAGAATGTAGAGCTCAACATCCACCTGAC
CATGAACGACTTCAGTGTGCACCGCATCATCGGGCGAGGCGGCTTCGGTGAGGTCTACGGCTGCCGGAAGGCCGACACGG
GCAAGATGTACGCCATGAAGTGTCTGGACAAGAAGCGCATCAAGATGAAGCAAGGGGAGACTCTGGCCCTGAATGAGCGC
ATCATGCTGTCGCTCGTCAGCACCGGGGACTGCCCGTTCATCGTCTGCATGTCATACGCCTTCCACACACCGGACAAGCT
CAGCTTCATCCTGGATCTCATGAACGGCGGGGACCTGCACTACCACCTGTCCCAGCACGGGGTCTTCTCCGAGGCCGACA
TGCGTTTCTACGCCGCCGAGATCATCCTGGGCCTGGAGCACATGCACAACCGCTTCGTGGTCTACCGGGACCTGAAGCCG
GCCAACATCCTGCTGGACGAGCACGGCCACGTGCGCATCTCAGACCTGGGCCTGGCCTGTGACTTCTCCAAGAAGAAGCC
TCACGCCAGTGTGGGCACCCACGGGTACATGGCTCCCGAGGTTCTACAGAAGGGTGTGGCCTACGACAGCAGCGCCGACT
GGTTCTCCCTGGGCTGCATGCTCTTCAAGCTGCTGCGAGGGCATAGCCCTTTCCGGCAGCACAAGACCAAAGACAAGCAT
GAGATCGACAGAATGACATTGACAATGGCTGTGGAGCTGCCTGACTCCTTCTCCCCTGAGCTCCGCTCCTTGCTGGAGGG
GCTGCTGCAGAGGGATGTCAACCGGAGGCTAGGCTGCCTGGGCCGAGGGGCCCAGGAGGTGAAGGAGAGCCCCTTCTTCC
GTTCCCTGGACTGGCAGATGGTCTTTTTACAAAAGTACCCTCCCCCGTTGATCCCCCCACGAGGGGAGGTGAATGCAGCC
GACGCCTTTGACATTGGCTCCTTCGATGAGGAGGACACAAAAGGAATCAAGCTACTGGACAGTGACCAGGAGCTCTACCG
CAACTTCCCCCTGACCATCTCGGAGCGGTGGCAGCAGGAGGTAGCAGAGACTGTCTTTGACACCATCAATGCTGAGACGG
ACCGGCTGGAGGCCCGCAAGAAAACCAAAAACAAGCAGTTGGGCCACGAGGAAGACTACGCCCTGGGCAAGGACTGCATC
ATGCATGGCTACATGTCCAAGATGGGCAACCCCTTCCTGACCCAGTGGCAGCGGCGGTACTTCTACCTGTTCCCTAACCG
GCTCGAGTGGCGGGGCGAGGGCGAGGCCCCGCAGAGCCTGCTGACCATGGAGGAGATCCAGTCGGTGGAGGAGACGCAGA
TCAAGGAGCGAAAGTGCCTCCTCCTCAAGATCCGAGGTGGCAAGCAGTTTGTCCTGCAGTGCGATAGTGACCCAGAGCTG
GTGCAGTGGAAGAAGGAGCTTCGAGACGCCTACCGCGAGGCCCAGCAGCTAGTGCAGCGGGTGCCCAAGATGAAGAACAA
GCCGCGCTCGCCCGTCGTGGAGCTGAGCAAGGTGCCACTGATCCAGCGCGGCAGTTGTGTGCTTCTTTAG

SEQ ID NO: 2

Figure 2B

Amino acid sequence of the GRK2 (G protein-coupled receptor kinase 2 [Homo Sapiens] ) Accession NP_001610 (Also called: Adrenergic, beta, receptor kinase 1(ADRBK1)
(Beta-adrenergic receptor kinase 1 (Bark-1))

```
MADLEAVLADVSYLMAMEKSKATPAARASKKILLPEPSIRSVMQKYLEDRGEVTFEKIFSQKLGYLLFRDFCLNHLEEAR
PLVEFYEEIKKYEKLETEEERVARSREIFDSYIMKELLACSHPFSKSATEHVQGHLGKKQVPPDLFQPYIEEICQNLRGD
VFQKFIESDKFTRFCQWKNVELNIHLTMNDFSVHRIIGRGGFGEVYGCRKADTGKMYAMKCLDKKRIKMKQGETLALNER
IMLSLVSTGDCPFIVCMSYAFHTPDKLSFILDLMNGGDLHYHLSQHGVFSEADMRFYAAEIILGLEHMHNRFVVYRDLKP
ANILLDEHGHVRISDLGLACDFSKKKPHASVGTHGYMAPEVLQKGVAYDSSADWFSLGCMLFKLLRGHSPFRQHKTKDKH
EIDRMTLTMAVELPDSFSPELRSLLEGLLQRDVNRRLGCLGRGAQEVKESPFFRSLDWQMVFLQKYPPPLIPPRGEVNAA
DAFDIGSFDEEDTKGIKLLDSDQELYRNFPLTISERWQQEVAETVPDTINAETDRLEARKKAKNKQLGHEEDYALGKDCI
MHGYMSKMGNPFLTQWQRRYFYLFPNRLEWRGEGEAPQSLLTMEEIQSVEETQIKERKCLLLKIRGGKQFILQCDSDPEL
VQWKKELRDAYREAQQLVQRVPKMKNKPRSPVVELSKVPLVQRGSANGL
```
SEQ ID NO: 3

Nucleotide sequence for the GRK2 G protein-coupled receptor kinase 2 [Homo Sapiens] Accession NM_001619 (Also called: Adrenergic, beta, receptor kinase 1(ADRBK1) (Beta-adrenergic receptor kinase 1 (Bark-1))

```
ATGGCGGACCTGGAGGCGGTGCTGGCCGACGTGAGCTACCTGATGGCCATGGAGAAGAGCAAGGCCACGCCGGCCGCGCGCGCCAGCAAGAAGA
TACTGCTGCCCGAGCCCAGCATCCGCAGTGTCATGCAGAAGTACCTGGAGGACCGGGGCGAGGTGACCTTTGAGAAGATCTTTTCCCAGAAGCT
GGGGTACCTGCTCTTCCGAGACTTCTGCCTGAACCACCTGGAGGAGGCCAGGCCCTTGGTGGAATTCTATGAGGAGATCAAGAAGTACGAGAAG
CTGGAGACGGAGGAGGAGCGTGTGGCCCGCAGCCGGGAGATCTTCGACTCATACATCATGAAGGAGCTGCTGGCCTGCTCGCATCCCTTCTCGA
AGAGTGCCACTGAGCATGTCCAAGGCCACCTGGGGAAGAAGCAGGTGCCTCCGGATCTCTTCCAGCCATACATCGAAGAGATTTGTCAAAACCT
CCGAGGGGACGTGTTCCAGAAATTCATTGAGAGCGATAAGTTCACACGGTTTTGCCAGTGGAAGAATGTGGAGCTCAACATCCACCTGACCATG
AATGACTTCAGCGTGCATCGCATCATTGGGCGCGGGGGCTTTGGCGAGGTCTATGGGTGCCGGAAGGCTGACACAGGCAAGATGTACGCCATGA
AGTGCCTGGACAAAAAGCGCATCAAGATGAAGCAGGGGGAGACCCTGGCCCTGAACGAGCGCATCATGCTCTCGCTCGTCAGCACTGGGGACTG
CCCATTCATTGTCTGCATGTCATACGCGTTCCACACGCCAGACAAGCTCAGCTTCATCCTGGACCTCATGAACGGTGGGGACCTGCACTACCAC
CTCTCCCAGCACGGGGTCTTCTCAGAGGCTGACATGCGCTTCTATGCGGCCGAGATCATCCTGGGCCTGGAGCACATGCACAACCGCTTCGTGG
TCTACCGGGACCTGAAGCCAGCCAACATCCTTCTGGACGAGCATGGCCACGTGCGGATCTCGGACCTGGGCCTGGCCTGTGACTTCTCCAAGAA
GAAGCCCCATGCCAGCGTGGGCACCCACGGGTACATGGCTCCGGAGGTCCTGCAGAAGGGCGTGGCCTACGACAGCAGTGCCGACTGGTTCTCT
CTGGGGTGCATGCTCTTCAAGTTGCTGCGGGGGCACAGCCCCTTCCGGCAGCACAAGACCAAAGACAAGCATGAGATCGACCGCATGACGCTGA
CGATGGCCGTGGAGCTGCCCGACTCCTTCTCCCCTGAACTACGCTCCCTGCTGGAGGGGTTGCTGCAGAGGGATGTCAACCGGAGATTGGGCTG
CCTGGGCCGAGGGGCTCAGGAGGTGAAAGAGAGCCCCTTTTTCCGCTCCCTGGACTGGCAGATGGTCTTCTTGCAGAAGTACCCTCCCCCGCTG
ATCCCCCCACGAGGGGAGGTGAACGCGGCCGACGCCTTCGACATTGGCTCCTTCGATGAGGAGGACACAAAAGGAATCAAGTTACTGGACAGTG
ATCAGGAGCTCTACCGCAACTTCCCCCTCACCATCTCGGAGCGGTGGCAGCAGGAGGTGGCAGAGACTGTCTTCGACACCATCAACGCTGAGAC
AGACCGGCTGGAGGCTCGCAAGAAAGCCAAGAACAAGCAGCTGGGCCATGAGGAAGACTACGCCCTGGGCAAGGACTGCATCATGCATGGCTAC
ATGTCCAAGATGGGCAACCCCTTCCTGACCCAGTGGCAGCGGCGGTACTTCTACCTGTTCCCCAACCGCCTCGAGTGGCGGGGCGAGGGCGAGG
CCCCGCAGAGCCTGCTGACCATGGAGGAGATCCAGTCGGTGGAGGAGACGCAGATCAAGGAGCGCAAGTGCCTGCTCCTCAAGATCCGCGGTGG
GAAACAGTTCATTTTGCAGTGCGATAGCGACCCTGAGCTGGTGCAGTGGAAGAAGGAGCTGCGCGACGCCTACCGCGAGGCCCAGCAGCTGGTG
CAGCGGGTGCCCAAGATGAAGAACAAGCCGCGCTCGCCCGTGGTGGAGCTGAGCAAGGTGCCGCTGGTCCAGCGCGGCAGTGCCAACGGCCTCT
GA
```
SEQ ID NO: 4

Figure 2C

GRK6 Splice Variant B (AF040751):
MELENIVANTVLLKAREGGGGNRKGKSKKWRQMLQFPHISQCEELRLSLERDYHSLCERQPIGRLLFREFCATRPELSRCVAFLDGVAEYEVTP
DDKRKACGRQLTQNFLSHTGPDLIPEVPRQLVTNCTQRLEQGPCKDLFQELTRLTHEYLSVAPFADYLDSIYFNRFLQWKWLERQPVTKNTFRQ
YRVLGKGGFGEVCACQVRATGKMYACKKLEKKRIKKRKGEAMALNEKQILEKVNSRFVVSLAYAYETKDALCLVLTLMNGGDLKFHIYHMGQAG
FPEARAVFYAAEICCGLEDLHRERIVYRDLKPENILLDDHGHIRISDLGLAVHVPEGQTIKGRVGTVGYMAPEVVKNERYTFSPDWWALGCLLY
EMIAGQSPFQQRKKKIKREEVERLVKEVPEEYSERFSPQARSLCSQLLCKDPAERLGCRGGSAREVKEHPLFKKLNFKRLGAGMLEPPPFKPDPQ
AIYCKDVLDIEQFSTVKGVELEPTDQDFYQKFATGSVPIPWQNEMVETECFQELNVFGLDGSVPPDLDWKGQPPAPPKKGLLQRLFSRQRIAVE
TAATARKSSPPASSPQPEAPTSSWR

SEQ ID NO: 5

ATGGAGCTCGAGAACATCGTAGCGAACACGGTGCTACTCAAGGCCCGGGAAGGTGGCGGTGGAAATCGCAAAGGCAAAAGCAAGAAATGGCGGC
AGATGCTCCAGTTCCCTCACATCAGCCAGTGCGAAGAGCTGCGGCTCAGCCTCGAGCGTGACTATCACAGCCTGTGCGAGCGGCAGCCCATTGG
GCGCCTGCTGTTCCGAGAGTTCTGTGCCACGAGGCCGGAGCTGAGCCGCTGCGTCGCCTTCCTGGATGGGGTGGCCGAGTATGAAGTGACCCCG
GATGACAAGCGGAAGGCATGTGGGCGGCAGCTAACGCAGAATTTTCTGAGCCACACGGGTCCTGACCTCATCCCTGAGGTCCCCCGGCAGCTGG
TGACGAACTGCACCCAGCGGCTGGAGCAGGGTCCCTGCAAAGACCTTTTCCAGGAACTCACCCGGCTGACCCACGAGTACCTGAGCGTGGCCCC
TTTTGCCGACTACCTCGACAGCATCTACTTCAACCGTTTCCTGCAGTGGAAGTGGCTGGAAAGGCAGCCAGTGACCAAAAACACCTTCAGGCAA
TACCGAGTCCTGGGCAAAGGTGGCTTTGGGGAGGTGTGCGCCTGCCAGGTGCGGGCCACAGGTAAGATGTATGCCTGCAAGAAG
CTAGAGAAAAAGCGGATCAAGAAGCGGAAAGGGGAGGCCATGGCGCTGAACGAGAAGCAGATCCTGGAGAAAGTGAACAGTAGGTTTGTAGTGA
GCTTGGCCTACGCCTATGAGACCAAGGACGCGCTGTGCCTGGTGCTGACACTGATGAACGGGGGCGACCTCAAGTTCCACATCTACCACATGGG
CCAGGCTGGCTTCCCCGAAGCGCGGGCCGTCTTCTACGCCGCCGAGATCTGCTGTGGCCTGGAGGACCTGCACCGGGAGCGCATCGTGTACAGC
GACCTGAAGCCCGAGAACATCTTGCTGGATGACCACGGCCACATCCGCATCTCTGACCTGGGACTAGCTGTGCATGTGCCCGAGGGCCAGACCA
TCAAAGGCGTGTGGGCACCGTGGGTTACATGGCTCCGGAGGTGGTGAAGAATGAACGGTACACGTTCAGCCCTGACTGGTGGGCGCTCGGCTG
CCTCCTGTACGAGATGATCGCAGGCCAGTCGCCCTTCCAGCAGAGGAAGAAGAAGATCAAGCGGGAGGAGGTGGAGCGGCTGGTGAAGGAGGTC
CCCGAGGAGTATTCCGAGCGCTTTTCCCCGCAGGCCCGCTCACTTTGCTCACAGCTCCTCTGCAAGGACCCTGCCGAACGCCTGGGGTGTCGTG
GGGGCAGTGCCCGCGAGGTGAAGGAGCACCCCCTCTTTAAGAAGCTGAACTTCAAGCGGCTGGGAGCTGGCATGCTGGAGCCGCCGTTCAAGCC
TGACCCCCAGGCCATTTACTGCAAGGATGTTCTGGACATTGAACAGTTCTCTACGGTCAAGGGCGTGGAGCTGGAGCCTACCGACCAGGACTTC
TACCAGAAGTTTGCCACAGGCAGTGTGCCCATCCCCTGGCAGAACGAGATGGTGGAGACCGAGTGCTTCCAAGAGCTGAATGTCTTTGGGCTGG
ATGGCTCAGTTCCCCCAGACCTGGACTGGAAGGGCCAGCCACCTGCACCTCCTAAAAAGGGACTGCTGCAGAGACTCTTCAGTCGCCAAAGGAT
TGCTGTGGAAACTGCAGCGACAGCGAGGAAGAGCTCCCCACCCGCCTCTAGCCCCCAGCCCGAGGCCCCCACCAGCAGTTGGCGGTAG

SEQ ID NO: 6

Figure 2D

Human GRK6 Splice Variant C (AF040752):

```
MELENIVANTVLLKAREGGGGNRKGKSKKWRQMLQFPHISQCEELRLSLERDYHSLCERQPIGRLLFREFCATRPELSRCVAFLDGVAEYEVTP
DDKRKACGRQLTQNFLSHTGPDLIPEVPRQLVTNCTQRLEQGPCKDLFQELTRLTHEYLSVAPFADYLDSIYFNRFLQWKWLERQPVTKNTFRQ
YRVLGKGGFGEVCACQVRATGKMYACKKLEKKRIKKRKGEAMALNEKQILEKVNSRPVVSLAYAYETKDALCLVLTLMNGGDLKFHIYHMGQAG
FPEARAVFYAAEICCGLEDLHRERIVYRDLKPENILLDDHGHIRISDLGLAVHVPEGQTIKGRVGTVGYMAPEVVKNERYTFSPDWWALGCLLY
EMIAGQSPFQQRKKKIKREEVERLVKEVPEEYSERFSPQARSLCSQLLCKDPAERLGCRGGSAREVKEHPLFKKLNFKRLGAGMLEPPFKPDFQ
AIYCKDVLDIEQFSTVKGVELEPTDQDFYQKFATGSVPIPWQNEMVETECFQELNVFGLDGSVPPDLDWKGQPPAPPKKGLLQRLFSRQR
```

SEQ ID NO: 7

```
ATGGAGCTCGAGAACATCGTAGCGAACACGGTGCTACTCAAGGCCCGGGAAGGTGGCGGTGGAAATCGCAAAGGCAAAAGCAAGAAATGGCGGC
AGATGCTCCAGTTCCCTCACATCAGCCAGTGCGAAGAGCTGCGGCTCAGCCTCGAGCGTGACTATCACAGCCTGTGCGAGCGGCAGCCCATTGG
GCGCCTGCTGTTCCGAGAGTTCTGTGCCACGAGGCCGGAGCTGAGCCGCTGCGTCGCCTTCCTGGATGGGGTGGCCGAGTATGAAGTGACCCCG
GATGACAAGCGGAAGGCATGTGGGCGGCAGCTAACGCAGAATTTTCTGAGCCACACGGGTCCTGACCTCATCCCTGAGGTCCCCCGGCAGCTGG
TGACGAACTGCACCCAGCGGCTGGAGCAGGGTCCCTGCAAAGACCTTTTCCAGGAACTCACCCGGCTGACCCACGAGTACCTGAGCGTGGCCCC
TTTTGCCGACTACCTCGACAGCATCTACTTCAACCGTTTCCTGCAGTGGAAGTGGCTGGAAAGGCAGCCAGTGACCAAAAACACCTTCAGGCAA
TACCGAGTCCTGGGCAAAGGTGGCTTTGGGGAGGTGTGCGCCTGCCAGGTGCGGGCCACAGGTAAGATGTATGCCTGCAAGAAGCTAGAGAAAA
AGCGGATCAAGAAGCGGAAAGGGGAGGCCATGGCGCTGAACGAGAAGCAGATCCTGGAGAAAGTGAACAGTAGGTTTGTAGTGAGCTTGGCCTA
CGCCTATGAGACCAAGGACGCGCTGTGCCTGGTGCTGACACTGATGAACGGGGGCGACCTCAAGTTCCACATCTACCACATGGGCCAGGCTGGC
TTCCCCGAAGCGCGGGCCGTCTTCTACGCCGCCGAGATCTGCTGTGGCCTGGAGGACCTGCACCGGGAGCGCATCGTGTACAGGGACCTGAAGC
CCGAGAACATCTTGCTGGATGACCACGGCCACATCCGCATCTCTGACCTGGGACTAGCTGTGCATGTGCCCGAGGGCCAGACCATCAAAGGGCG
TGTGGGCACCGTGGGTTACATGGCTCCGGAGGTGGTGAAGAATGAACGGTACACGTTCAGCCCTGACTGGTGGGCGCTCGGCTGCCTCCTGTAC
GAGATGATCGCAGGCCAGTCGCCCTTCCAGCAGAGGAAGAAGAAGATCAAGCGGGAGGAGGTGGAGCGGCTGGTGAAGGAGGTCCCCGAGGAGT
ATTCCGAGCGCTTTTCCCCGCAGGCCCGCTCACTTTGCTCACAGCTCCTCTGCAAGGACCCTGCCGAACGCCTGGGGTGTCGTGGGGCAGTGC
CCGCGAGGTGAAGGAGCACCCCCTCTTTAAGAAGCTGAACTTCAAGCGGCTGGGAGCTGGCATGCTGGAGCCGCCGTTCAAGCCTGACCCCCAG
GCCATTTACTGCAAGGATGTTCTGGACATTGAACAGTTCTCTACGGTCAAGGGCGTGGAGCTGGAGCCTACCGACCAGGACTTCTACCAGAAGT
TTGCCACAGGCAGTGTGCCCATCCCCTGGCAGAACGAGATGGTGGAGACCGAGTGCTTCCAAGAGCTGAATGTCTTTGGGCTGGATGGCTCAGT
TCCCCCAGACCTGGACTGGAAGGGCCAGCCACCTGCACCTCCTAAAAAGGGACTGCTGCAGAGACTCTTCAGTCGCCAAAGGTGA
```

SEQ ID NO: 8

Figure 2E

Human GRK6 (NM_002082):
MELENIVANTVLLKAREGGGGNRKGKSKKWRQMLQFPHISQCEELRLSLERDYHSLCERHAIGRLLFREFCATRPELSRCVAFLDGVAEYEVTP
DDKRKACGRHVTQNFLSHTGPDLIPEVPRQLVTNCTQRLEQGPCKDLFQELTRLTHEYLSVAPFADYLDSIYFNRFLQWKWLERQPVTKNTFRQ
YRVLGKGGFGEVCACQVRATGKMYACKKLEKKRIKKRKGEAMALNEKQILEKVNSRFVVSLAYAYETKDALCLVLTLMNGGDLKFHIYHMGQAG
FPEARAVFYAAEICCGLEDLHRERIVYRDLKPENILLDDHGHIRISDLGLAVHVPEGQTIKGRVGTVGYMAPEVVKNERYTFSPDWWALGCLLY
EMIAGQSPFQQRKKKIKREEVERLVKEVPEEYSERFSPQARSLCSQLLCKDPAERLGCRGGSAREVKEHPLFKKLNFKRLGAGMLEPPFKPDFQ
AIYCKDVLDIEQFSTVKGVELEPTDQDFYQKFATGSVPIPWQNEMVETECFQELNVFGLDGSVPPDLDWKGQPPAPPKKGLLQRLFSRQDCCGN
CSDSEEELPTRL

SEQ ID NO: 9

ATGGAGCTCGAGAACATCGTAGCGAACACGGTGCTACTCAAGGCCCGGGAAGGTGGCGGTGGAAATCGCAAAGGCAAAAGCAAGAAATGGCGGC
AGATGCTCCAGTTCCCTCACATCAGCCAGTGCGAAGAGCTGCGGCCTCAGCCTCGAGCGTGACTATCACAGCCTGTGCGAGCGGCACGCCATTGG
GCGCCTGCTGTTCCGAGAGTTCTGTGCCACGAGGCCGGAGCTGAGCCGCTGCGTCGCCTTCCTGGATGGGGTGGCCGAGTATGAAGTGACCCCG
GATGACAAGCGGAAGGCATGTGGGCGGCACGTAACGCAGAATTTTCTGAGCCACACGGGTCCTGACCTCATCCCTGAGGTCCCCCGGCAGCTGG
TGACGAACTGCACCCAGCGGCTGGAGCAGGGTCCCTGCAAAGACCTTTTCCAGGAACTCACCCGGCTGACCCACGAGTACCTGAGCGTGGCCCC
TTTTGCCGACTACCTCGACAGCATCTACTTCAACCGTTTCCTGCAGTGGAAGTGGCTGGAAAGGCAGCCAGTGACCAAAAACACCTTCAGGCAA
TACCGAGTCCTGGGCAAAGGTGGCTTTGGGGAGGTGTGCGCCTGCCAGGTGCGGGCCACAGGTAAGATGTATGCCTGCAAGAAGCTAGAGAAAA
AGCGGATCAAGAAGCGGAAAGGGGAGGCCATGGCGCTGAACGAGAAGCAGATCCTGGAGAAAGTGAACAGTAGGTTTGTAGTGAGCTTGGCCTA
CGCCTATGAGACCAAGGACGCGCTGTGCCTGGTGCTGACACTGATGAACGGGGGCGACCTCAAGTTCCACATCTACCACATGGGCCAGGCTGGC
TTCCCCGAAGCGCGGGCCGTCTTCTACGCCGCCGAGATCTGCTGTGGCCTGGAGGACCTGCACCGGGAGCGCATCGTGTACAGGGACCTGAAGC
CCGAGAACATCTTGCTGGATGACCACGGCCACATCCGCATCTCTGACCTGGGACTAGCTGTGCATGTGCCCGAGGGCCAGACCATCAAAGGGCG
TGTGGGCACCGTGGGTTACATGGCTCCGGAGGTGGTGAAGAATGAACGGTACACGTTCAGCCCTGACTGGTGGGCGCTCGGCTGCCTCCTGTAC
GAGATGATCGCAGGCCAGTCGCCCTTCCAGCAGAGGAAGAAGAAGATCAAGCGGGAGGAGGTGGAGCGGCTGGTGAAGGAGGTCCCCGAGGAGT
ATTCCGAGCGCTTTTCCCCGCAGGCCCGCTCACTTTGCTCACAGCTCCTCTGCAAGGACCCTGCCGAACGCCTGGGGTGTCGTGGGGGCAGTGC
CCGCGAGGTGAAGGAGCACCCCCTCTTTAAGAAGCTGAACTTCAAGCGGCTGGGAGCTGGCATGCTGGAGCCGCCGTTCAAGCCTGACCCCCAG
GCCATTTACTGCAAGGATGTTCTGGACATTGAACAGTTCTCTACGGTCAAGGGCGTGGAGCTGGAGCCTACCGACCAGGACTTCTACCAGAAGT
TTGCCACAGGCAGTGTGCCCATCCCCTGGCAGAACGAGATGGTGGAGACCTGCTTCCAAGAGCTGAATGTCTTTGGGCTGGATGGCTCAGT
TCCCCCAGACCTGGACTGGAAGGGCCAGCCACCTGCACCTCCTAAAAAGGGACTGCTGCAGAGACTCTTCAGTCGCCAAGATTGCTGTGGAAAC
TGCAGCGACAGCGAGGAAGAGCTCCCCACCCGCCTCTAGCCCCCAG

SEQ ID NO: 10

Figure 2F

Human GRK5 (XM_005969):

```
MELENIVANTVLLKAREGGGGKRKGKSKKWKEILKFPHISQCEDLRRTIDRDYCSLCDKQPIGRLLFRQFCETRPGLECYIQFLDSVAEYEVTP
DEKLGEKGKEIMTKYLTPKSPVFIAQVGQDLVSQTEEKLLQKPCKELFSACAQSVHEYLRGEPFHEYLDSMFFDRFLQWKWLERQPVTKNTFRQ
YRVLGKGGFGEVCACQVRATGKMYACKRLEKKRIKKRKGESMALNEKQILEKVNSQFVVNLAYAYETKDALCLVLTIMNGGDLKFHIYNMGNPG
FEEERALFYAAEILCGLEDLHRENTVYRDLKPENILLDDYGHIRISDLGLAVKIPEGDLIRGRVGTVGYMAPEVLNNQRYGLSPDYWGLGCLIY
EMIEGQSPFRGRKEKVKREEVDRRVLETEEVYSHKFSEEAKSICKMLLTKDAKQRLGCQEEGAAEVKRHPFFRNMNFKRLEAGMLDPPFVPDPR
AVYCKDVLDIEQFSTVKGVNLDHTDDDFYSKFSTGSVSIPWQNEMIETECFKELNVFGPNGTLPPDLNRNHPPEPPKKGLLQRLFKRQHQNNSK
SSPSSKTSFNHHINSNHVSSNSTGSS
```

SEQ ID NO: 11

```
ATGGAGCTGGAAAACATCGTGGCCAACACGGTCTTGCTGAAAGCCAGGGAAGGGGGCGGAGGAAAGCGCAAAGGGAAAAGCAAGAAGTGGAAAG
AAATCCTGAAGTTCCCTCACATTAGCCAGTGTGAAGACCTCCGAAGGACCATAGACAGAGATTACTGCAGTTTATGTGACAAGCAGCCAATCGG
GAGGCTGCTTTTCCGGCAGTTTTGTGAAACCAGGCCTGGGCTGGAGTGTTACATTCAGTTCCTGGACTCCGTGGCAGAATATGAAGTTACTCCA
GATGAAAAACTGGGAGAGAAAGGGAAGGAAATTATGACCAAGTACCTCACCCCAAAGTCCCCTGTTTTCATAGCCCAAGTTGGCCAAGACCTGG
TCTCCCAGACGGAGGAGAAGCTCCTACAGAAGCCGTGCAAAGAACTCTTTTCTGCCTGTGCACAGTCTGTCCACGAGTACCTGAGGGGAGAACC
ATTCCACGAATATCTGGACAGCATGTTTTTTGACCGCTTTCTCCAGTGGAAGTGGTTGGAAAGGCAACCGGTGACCAAAAACACTTTCAGGCAG
TATCGAGTGCTAGGAAAAGGGGGCTTCGGGGAGGTCTGTGCCTGCCAGGTTCGGGCCACGGGTAAAATGTATGCCTGCAAGCGCTTGGAGAAGA
AGAGGATCAAAAAGAGGAAAGGGAGTCCATGGCCCTCAATGAGAAGCAGATCCTCGAGAAGGTCAACAGTCAGTTTGTGGTCAACCTGGCCTA
TGCCTACGAGACCAAGGATGCACTGTGCTTGGTCCTGACCATCATGAATGGGGGTGACCTGAAGTTCCACATCTACAACATGGGCAACCCTGGC
TTCGAGGAGGAGCGGGCCTTGTTTTATGCGGCAGAGATCCTCTGCGGCTTAGAAGACCTCCACCGTGAGAACACCGTCTACCGAGATCTGAAAC
CTGAAAACATCCTGTTAGATGATTATGGCCACATTAGGATCTCAGACCTGGGCTTGGCTGTGAAGATCCCCGAGGGAGACCTGATCCGCGGCCG
GGTGGGCACTGTTGGCTACATGGCTCCAGAGGTCCTGAACAACCAGAGGTACGGCCTGAGCCCCGACTACTGGGGCCTTGGCTGCCTCATCTAT
GAGATGATCGAGGGCCAGTCGCCGTTCCGCGGCCGCAAGGAGAAGGTGAAGCGGGAGGAGGTGGACCGCCGGGTCCTGGAGACGGAGGAGGTGT
ACTCCCACAAGTTCTCCGAGGAGGCCAAGTCCATCTGCAAGATGCTGCTCACGAAAGATGCGAAGCAGAGGCTGGGCTGCCAGGAGGAGGGGC
TGCAGAGGTCAAGAGACACCCCTTCTTCAGGAACATGAACTTCAAGCGCTTAGAAGCGGGATGTTGGACCCTCCCTTCGTTCCAGACCCCCGC
GCTGTGTACTGTAAGGACGTGCTGGACATCGAGCAGTTCTCCACTGTGAAGGGCGTCAATCTGGACCACACAGACGACTTCTACTCCAAGT
TCTCCACGGGCTCTGTGTCCATCCCATGGCAAAACGAGATGATAGAAACAGAATGCTTTAAGGAGCTGAACGTGTTTGGACCTAATGGTACCCT
CCCGCCAGATCTGAACAGAAACCACCCTCCGGAACCGCCCAAGAAAGGGCTGCTCCAGAGACTCTTCAAGCGGCAGCATCAGAACAATTCCAAG
AGTTCGCCCAGCTCCAAGACCAGTTTTAACCACCACATAAACTCAAACCATGTCAGCTCGAACTCCACCGGAAGCAGCTAG
```

SEQ ID NO: 12

Figure 2G

Human GRK4 δ Splice Variant (NM_005307, L03718), also named GRK4B:

```
MELENIVAMSLLLKARQEKDYSSLCDKQPIGRRLFRQFCDTKPTLKRHIEFLDAVAEYEVADDEDRSDCGLSILDRFFNDKLAAPLPEIPPDVV
TECRLGLKEENPSKKAFEECTRVAHNYLRGEPFEEYQESSYFSQFLQWKWLERQPVTKNTFRHYRVLGKGGFGEVCACQVRATGKMYACKKLQK
KRIKKRKGEAMALNEKRILEKVQSRFVVSLAYAYETKDALCLVLTIMNGGDLKFHIYNLGNPGFDEQRAVFYAAELCCGLEDLQRERIVYRDLK
PENILLDDRGHIRISDLGLATEIPEGQRVRGRVGTVGYMAPEVVVNNEKYTFSPDWWGLGCLIYEMIQGHSPFKKYKEKVKWEEVDQRIKNDTEE
YSEKFSEDAKSICRMLLTKNPSKRLGCRGEGAAGVKQHPVFKDINFRRLEANMLEPPFCPDPHAVYCKDVLDIEQFSAVKGIYLDTADEDFYAR
FATGCVSIPWQNEDCLTMVPSEKEVEPKQC
```

SEQ ID NO: 13

```
ATGGAGCTCGAGAACATCGTGGCCAACTCGCTGCTGCTGAAAGCGCGTCAAGAAAAGGATTATAGCAGTCTTTGTGACAAGCAACCGATAGGAA
GACGTCTCTTCAGGCAGTTCTGTGATACCAAACCCACTCTAAAGAGGCACATTGAATTCTTGGATGCAGTGGCAGAATATGAAGTTGCCGATGA
TGAGGACCGAAGTGATTGTGGACTGTCAATCTTAGATAGATTCTTCAATGATAAGTTGGCAGCCCCTTTACCAGAAATACCTCCAGATGTTGTG
ACAGAATGTAGATTGGGACTGAAGGAGGAGAACCCTTCCAAAAAAGCCTTTGAGGAATGTACTAGAGTTGCCCATAACTACCTAAGAGGGGAAC
CATTTGAAGAATACCAAGAAAGCTCATATTTTTCTCAGTTTTTACAATGGAAATGGCTGGAAAGGCAACCCGTAACAAAGAACACATTTAGACA
TTACAGAGTTCTAGGGAAAAGGCGGATTTGGAGAGGTTTGCGCCTGTCAAGTGCGAGCCACAGGAAAAATGTATGCCTGCAAAAAGCTACAAAAA
AAAAGAATAAAGAAGAGGAAAGGTGAAGCTATGGCTCTAAATGAGAAAAGAATTCTGGAGAAAGTGCAAAGTAGATTCGTAGTTAGTTTAGCCT
ACGCTTATGAAACCAAAGATGCCTTGTGCTTGGTGCTCACCATTATGAATGGAGGGGATTTGAAGTTTCACATTTACAACCTGGGCAATCCCGG
CTTTGATGAGCAGAGAGCCGTTTTCTATGCTGCAGAGCTGTGTTGCGGCTTGGAAGATTTACAGAGGGAAAGAATTGTATACAGAGACTTGAAG
CCTGAGAATATTCTCCTTGATGATCGTGGACACATCCGGATTTCAGACCTCGGTTTGGCCACAGAGATCCCAGAAGGACAGAGGGTTCGAGGAA
GAGTTGGAACAGTCGGCTACATGGCACCTGAAGTTGTCAATAATGAAAAGTATACGTTTAGTCCCGATTGGTGGGGACTTGGCTGTCTGATCTA
TGAAATGATTCAGGGACATTCTCCATTCAAAAAATACAAAGAGAAAGTCAAATGGGAGGAGGTCGATCAAAGAATCAAGAATGATACCGAGGAG
TATTCTGAGAAGTTTTCAGAGGATGCCAAATCTATCTGCAGGATGTTACTCACCAAGAATCCAAGCAAGCGGCTGGGCTGCAGGGCGAGGGAG
CGGCTGGGGTGAAGCAGCACCCCGTGTTCAAGGACATCAACTTCCGGAGGCTGGAGGCAAACATGCTGGAGCCCCCTTTCTGTCCTGATCCTCA
TGCCGTTTACTGTAAGGACGTCCTGGATATCGAGCAGTTCTCGGCGGTGAAAGGGATCTACCTGGACACCGCAGATGAAGACTTCTATGCTCGG
TTTGCTACCGGGTGTGTCTCCATCCCCTGGCAGAATGAGGACTGCCTGACCATGGTCCCCAGTGAGAAGGAAGTGGAACCCAAGCAATGCTGA
```

SEQ ID NO: 14

Figure 2H

Human GRK4 β Splice Variant (U33055, X97880), also named GRK4C:

```
MELENIVANSLLLKARQEKDYSSLCDKQPIGRRLFRQFCDTKPTLKRHIEFLDAVAEYEVADDEDRSDCGLSILDRFFNDKLAAPLPEIPPDVV
TECRLGLKEENPSKKAFEECTRVAHNYLRGEPPFEEYQESSYFSQFLQWKWLERQPVTKNTFRHYRVLGKGGFGEVCACQVRATGKMYACKKLQK
KRIKKRKGEAMALNEKRILEKVQSRFVVSLAYAYETKDALCLVLTIMNGGDLKFHIYNLGNPGFDEQRAVFYAAELCCGLEDLQRERIVYRDLK
PENILLDDRGHIRISDLGLATEIPEGQRVRGRVGTVGYMAPEVVNNEKYTFSPDWWGLGCLIYEMIQGHSPFKKYKEKVKWEEVDQRIKNDTEE
YSEKFSEDAKSICRMLLTKNPSKRLGCRGEGAAGVKQHPVFKDINFRRLEANMLEPPFCPDPHAVYCKDVLDIEQFSAVKGIYLDTADEDFYAR
FATGCVSIPWQNEMIESGCFKDINKSESEEALPLDLDKNIHTPVSRPNRGFFYRLFRRGGCLTMVPSEKEVEPKQC
```
SEQ ID NO: 15

```
ATGGAGCTCGAGAACATCGTGGCCAACTCGCTGCTGCTGAAAGCGCGTCAAGAAAAGGATTATAGCAGTCTTTGTGACAAGCAACCGATAGGAA
GACGTCTCTTCAGGCAGTTCTGTGATACCAAACCCACTCTAAAGAGGCACATTGAATTCTTGGATGCAGTGGCAGAATATGAAGTTGCCCATGA
TGAGGACCGAAGTGATTGTGGACTGTCAATCTTAGATAGATTCTTCAATGATAAGTTGGCAGCCCCTTTACCAGAAATACCTCCAGATGTTGTG
ACAGAATGTAGATTGGGACTGAAGGAGGAGAACCCTTCCAAAAAAGCCTTTGAGGAATGTACTAGAGTTGCCCATAACTACCTAAGAGGGGAAC
CATTTGAAGAATACCAAGAAAGCTCATATTTTTCTCAGTTTTTACAATGGAAATGGCTGGAAAGGCAACCCGTAACAAAGAACACATTTAGACA
TTACAGAGTTCTAGGAAAAGGCGGATTTGGAGAGGTTTGCGCCTGTCAAGTGCGAGCCACAGGAAAAATGTATGCCTGCAAAAAGCTACAAAAA
AAAAGAATAAAGAAGAGGAAAGGTGAAGCTATGGCTCTAAATGAGAAAAGAATTCTGGAGAAAGTGCAAAGTAGATTCGTAGTTAGTTTAGCCT
ACGCTTATGAAACCAAAGATGCCTTGTGCTTGGTGCTCACCATTATGAATGGAGGGGATTTGAAGTTTCACATTTACAACCTGGGCAATCCCGG
CTTTGATGAGCAGAGAGCCGTTTTCTATGCTGCAGAGCTGTGTTGCGGCTTGGAAGATTTACAGAGGGAAAGAATTGTATACAGAGACTTGAAG
CCTGAGAATATTCTCCTTGATGATCGTGGACACATCCGGATTTCAGACCTCGGTTTGGCCACAGAGATCCCAGAAGGACAGAGGGTTCGAGGAA
GAGTTGGAACAGTCGGCTACATGGCACCTGAAGTTGTCAATAATGAAAAGTATACGTTTAGTCCCGATTGGTGGGGACTTGGCTGTCTGATCTA
TGAAATGATTCAGGGACATTCTCCATTCAAAAAATACAAAGAGAAAGTCAAATGGGAGGAGGTCGATCAAAGAATCAAGAATGATACCGAGGAG
TATTCTGAGAAGTTTTCAGAGGATGCCAAATCTATCTGCAGGATGTTACTCACCAAGAATCCAAGCAAGCGGCTGGGCTGCAGGGCGAGGGAG
CGGCTGGGGTGAAGCAGCACCCCGTGTTCAAGGACATCAACTTCAGGAGGCTGGAGGCAAACATGCTGGAGCCCCCTTTCTGTCCTGATCCTCA
TGCCGTTTACTGTAAGGACGTCCTGGATATCGAGCAGTTCTCGGCGGTGAAAGGGATCTACCTGGACACCGCAGATGAAGACTTCTATGCTCGG
TTTGCTACCGGGTGTGTCTCCATCCCCTGGCAGAATGAGATGATCGAATCCGGGTGTTTCAAAGACATCAACAAAAGTGAAAGTGAGGAAGCTT
TGCCATTAGATCTAGACAAGAACATACATACCCCGGTTTCCAGACCAAACAGAGGCTTCTTCTATAGACTCTTCAGAAGAGGGGGCTGCCTGAC
CATGGTCCCCAGTGAGAAGGAAGTGGAACCCAAGCAATGCTGA
```
SEQ ID NO: 16

Figure 2I

Human GRK4 α Splice Variant (U33054, X97881), also named GRK4D:

```
MELENIVANSLLLKARQGGYGKKSGRSKKWKEILTLPPVSQCSELRHSIEKDYSSLCDKQPIGRRLFRQFCDTKPTLKRHIEFLDAVAEYEVAD
DEDRSDCGLSILDRFFNDKLAAPLPEIPPDVVTECRLGLKEENPSKKAFEECTRVAHNYLRGEPFEEYQESSYFSQFLQWKWLERQPVTKNTFR
HYRVLGKGGFGEVCACQVRATGKMYACKKLQKKRIKKRKGEAMALNEKRILEKVQSRFVVSLAYAYETKDALCLVLTIMNGGDLKFHIYNLGNP
GFDEQRAVFYAAELCCGLEDLQRERIVYRDLKPENILLDDRGHIRISDLGLATEIPEGQRVRGRVGTVGYMAPEVVNNEKYTFSPDWWGLGCLI
YEMIQGHSPFKKYKEKVKWEEVDQRIKNDTEEYSEKFSEDAKSICRMLLTKNPSKRLGCRGEGAAGVKQHPVFKDINFRRLEANMLEPPFCPDP
HAVYCKDVLDIEQFSAVKGIYLDTADEDFYARFATGCVSIPWQNEMIESGCFKDINKSESEEALPLDLDKNIHTPVSRPNRGFFYRLFRRGGCL
TMVPSEKEVEPKQC
```
SEQ ID NO: 17

```
ATGGAGCTCGAGAACATCGTGGCCAACTCGCTGCTGCTGAAAGCGCGTCAAGGAGGATATGGCAAAAAAGTGGTCGTAGTAAAAAATGGAAGG
AGATACTGACACTGCCTCCTGTCAGCCAGTGCAGTGAGCTTAGACATTCCATTGAAAAGGATTATAGCAGTCTTTGTGACAAGCAACCGATAGG
AAGACGTCTCTTCAGGCAGTTCTGTGATACCAAACCCACTCTAAAGAGGCACATTGAATTCTTGGATGCAGTGGCAGAATATGAAGTTGCCGAT
GATGAGGACCGAAGTGATTGTGGACTGTCAATCTTAGATAGATTCTTCAATGATAAGTTGGCAGCCCCTTTACCAGAAATACCTCCAGATGTTG
TGACAGAATGTAGATTGGGACTGAAGGAGGAGAACCCTTCCAAAAAAGCCTTTGAGGAATGTACTAGAGTTGCCCATAACTACCTAAGAGGGGA
ACCATTTGAAGAATACCAAGAAAGCTCATATTTTTCTCAGTTTTTACAATGGAAATGGCTGGAAAGGCAACCCGTAACAAAGAACACATTTAGA
CATTACAGAGTTCTAGGAAAAGGCGGATTTGGAGAGGTTTGCGCCTGTCAAGTGCGAGCCACAGGAAAAATGTATGCCTGCAAAAAGCTACAAA
AAAAAAGAATAAAGAAGAGGAAAGGTGAAGCTATGGCTCTAAATGAGAAAAGAATTCTGGAGAAAGTGCAAAGTAGATTCGTAGTTAGTTTAGC
CTACGCTTATGAAACCAAAGATGCCTTGTGCTTGGTGCTCACCATTATGAATGGAGGGGATTTGAAGTTTCACATTTACAACCTGGGCAATCCC
GGCTTTGATGAGCAGAGAGCCGTTTTCTATGCTGCAGAGCTGTGTTGCGGCTTGGAAGATTTACAGAGGGAAAGAATTGTATACAGAGACTTGA
AGCCTGAGAATATTCTCCTTGATGATCGTGGACACATCCGGATTTCAGACCTCGGTTTGGCCACAGAGATCCCAGAAGGACAGAGGGTTCGAGG
AAGAGTTGGAACAGTCGGCTACATGGCACCTGAAGTTGTCAATAATGAAAAGTATACGTTTAGTCCCGATTGGTGGGGACTTGGCTGTCTGATC
TATGAAATGATTCAGGGACATTCTCCATTCAAAAAATACAAAGAGAAAGTCAAATGGGAGGAGGTCGATCAAAGAATCAAGAATGATACCGAGG
AGTATTCTGAGAAGTTTTCAGAGGATGCCAAATCTATCTGCAGGATGTTACTCACCAAGAATCCAAGCAAGCGGCTGGGCTGCAGGGGCGAGGG
AGCGGCTGGGGTGAAGCAGCACCCCGTGTTCAAGGACATCAACTTCAGGAGGCTGGAGGCAAACATGCTGGAGCCCCCTTTCTGTCCTGATCCT
CATGCCGTTTACTGTAAGGACGTCCTGGATATCGAGCAGTTCTCGGCGGTGAAAGGGATCTACCTGGACACCGCAGATGAAGACTTCTATGCTC
GGTTTGCTACCGGGTGTGTCTCCATCCCCTGGCAGAATGAGATGATCGAATCCGGGTGTTTCAAAGACATCAACAAAAGTGAAAGTGAGGAAGC
TTTGCCATTAGATCTAGACAAGAACATACATACCCCGTTTCCAGACCAAACAGAGGCTTCTTCTATAGACTCTTCAGAAGAGGGGCTGCCTG
ACCATGGTCCCCAGTGAGAAGGAAGTGGAACCCAAGCAATGCTGA
```
SEQ ID NO: 18

Figure 2J

Human GRK4 γ Splice Variant (U33056):

```
MELENIVANSLLLKARQGGYGKKSGRSKKWKEILTLPPVSQCSELRHSIEKDYSSLCDKQPIGRRLFRQFCDTKPTLKRHIEFLDAVAEYEVAD
DEDRSDCGLSILDRFFNDKLAAPLPEIPPDVVTECRLGLKEENPSKKAFEECTRVAHNYLRGEPFEEYQESSYFSQFLQWKWLERQPVTKNTFR
HYRVLGKGGFGEVCACQVRATGKMYACKKLQKKRIKKRKGEAMALNEKRILEKVQSRFVVSLAYAYETKDALCLVLTIMNGGDLKFHIYNLGNP
GFDEQRAVFYAAELCCGLEDLQRERIVYRDLKPENILLDDRGHIRISDLGLATEIPEGQRVRGRVGTVGYMAPEVVNNEKYTFSPDWWGLGCLI
YEMIQGHSPFKKYKEKVKWEEVDQRIKNDTEEYSEKFSEDAKSICRMLLTKNPSKRLGCRGEGAAGVKQHPVFKDINFRRLEANMLEPPFCPDP
HAVYCKDVLDIEQFSAVKGIYLDTADEDFYARFATGCVSIPWQNEGCLTMVPSEKEVEPKQC
```

SEQ ID NO: 19

```
ATGGAGCTCGAGAACATCGTGGCCAACTCGCTGCTGCTGAAAGCGCGTCAAGGAGGATATGGCAAAAAAGTGGTCGTAGTAAAAAATGGAAGG
AGATACTGACACTGCCTCCTGTCAGCCAGTGCAGTGAGCTTAGACATTCCATTGAAAAGGATTATAGCAGTCTTTGTGACAAGCAACCGATAGG
AAGACGTCTCTTCAGGCAGTTCTGTGATACCAAACCCACTCTAAAGAGGCACATTGAATTCTTGGATGCAGTGGCAGAATATGAAGTTGCCGAT
GATGAGGACCGAAGTGATTGTGGACTGTCAATCTTAGATAGATTCTTCAATGATAAGTTGGCAGCCCCTTTACCAGAAATACCTCCAGATGTTG
TGACAGAATGTAGATTGGGACTGAAGGAGGAGAACCCTTCCAAAAAAGCCTTTGAGGAATGTACTAGAGTTGCCCATAACTACCTAAGAGGGGA
ACCATTTGAAGAATACCAAGAAAGCTCATATTTTTCTCAGTTTTTACAATGGAAATGGCTGGAAAGGCAACCCGTAACAAAGAACACATTTAGA
CATTACAGAGTTCTAGGAAAAGGCGGATTTGGAGAGGTTTGCGCCTGTCAAGTGCGAGCCACAGGAAAAATGTATGCCTGCAAAAAGCTACAAA
AAAAAAGAATAAAGAAGAGGAAAGGTGAAGCTATGGCTCTAAATGAGAAAAGAATTCTGGAGAAAGTGCAAAGTAGATTCGTAGTTAGTTTAGC
CTACGCTTATGAAACCAAAGATGCCTTGTGCTTGGTGCTCACCATTATGAATGGAGGGGATTTGAAGTTTCACATTTACAACCTGGGCAATCCC
GGCTTTGATGAGCAGAGAGCCGTTTTCTATGCTGCAGAGCTGTGTTGCGGCTTGGAAGATTTACAGAGGGAAAGAATTGTATACAGAGACTTGA
AGCCTGAGAATATTCTCCTTGATGATCGTGGACACATCCGGATTTCAGACCTCGGTTTGGCCACAGAGATCCCAGAAGGACAGAGGGTTCGAGG
AAGAGTTGGAACAGTCGGCTACATGGCACCTGAAGTTGTCAATAATGAAAAGTATACGTTTAGTCCCGATTGGTGGGGACTTGGCTGTCTGATC
TATGAAATGATTCAGGGACATTCTCCATTCAAAAAATACAAAGAGAAAGTCAAATGGGAGGAGGTCGATCAAAGAATCAAGAATGATACCGAGG
AGTATTCTGAGAAGTTTTCAGAGGATGCCAAATCTATCTGCAGGATGTTACTCACCAAGAATCCAAGCAAGCGGCTGGGCTGCAGGGGCGAGGG
AGCGGCTGGGGTGAAGCAGCACCCCGTGTTCAAGGACATCAACTTCAGGAGGCTGGAGGCAAACATGCTGGAGCCCCCTTTCTGTCCTGATCCT
CATGCCGTTTACTGTAAGGACGTCCTGGATATCGAGCAGTTCTCGGCGGTGAAAGGGATCTACCTGGACACCGCAGATGAAGACTTCTATGCTC
GGTTTGCTACCGGGTGTGTCTCCATCCCCTGGCAGAATGAGGGCTGCCTGACCATGGTCCCCAGTGAGAAGGAAGTGGAACCCAAGCAATGCTG
A
```

SEQ ID NO: 20

Figure 2K

Human GRK 7 (NM_139209):

MVDMGALDNLIANTAYLQARKPSDCDSKELQRRRRSLALPGLQGCAELRQKLSLNFHSLCEQQPIGRRLFRDFLATVPTFRKAATFLEDVQNWE
LAEEGPTKDSALQGLVATCASAPAPGNPQPFLSQAVATKCQAATTEEERVAAVTLAKAEAMAFLQEQPFKDFVTSAFYDKFLQWKLFEMQPVSD
KYFTEFRVLGKGGFGEVCAVQVKNTGKMYACKKLDKKRLKKKGGEKMALLEKEILEKVSSPFIVSLAYAFESKTHLCLVMSLMNGGDLKFHIYN
VGTRGLDMSRVIFYSAQIACGMLHLHELGIVYRDMKPENVLLDDLGNCRLSDLGLAVEMKGGKPITQRAGTNGYMAPEILMEKVSYSYPVDWFA
MGCSIYEMVAGRTPFKDYKEKVSKEDLKQRTLQDEVKFQHDNFTEEAKDICRLFLAKKPEQRLGSREKSDDPRKHHFFKTINFPRLEAGLIEPP
FVPDPSVVYAKDIAEIDDFSEVRGVEFDDKDKQFFKNFATGAVPIAWQEEIIETGLFEELNDPNRPTGCEEGNSSKSGVCLLL

SEQ ID NO: 21

ATGGTGGACATGGGGGCCCTGGACAACCTGATCGCCAACACCGCCTACCTGCAGGCCCGGAAGCCCTCGGACTGCGACAGCAAAGAGCTGCAGC
GGCGGCGGCGTAGCCTGGCCCTGCCCGGGCTGCAGGGCTGCGCGGAGCTCCGCCAGAAGCTGTCCCTGAACTTCCACAGCCTGTGTGAGCAGCA
GCCCATCGGTCGCCGCCTCTTCCGTGACTTCCTAGCCACAGTGCCCACGTTCCGCAAGGCGGCAACCTTCCTAGAGGACGTGCAGAACTGGGAG
CTGGCCGAGGAGGGACCCACCAAAGACAGCGCGCTGCAGGGGCTGGTGGCCACTTGTGCGAGTGCCCCTGCCCCGGGGAACCCGCAACCCTTCC
TCAGCCAGGCCGTGGCCACCAAGTGCCAAGCAGCCACCACTGAGGAAGAGCGAGTGGCTGCAGTGACGCTGGCCAAGGCTGAGGCCATGGCTTT
CTTGCAAGAGCAGCCCTTTAAGGATTTCGTGACCAGCGCCTTCTACGACAAGTTTCTGCAGTGGAAACTCTTCGAGATGCAACCAGTGTCAGAC
AAGTACTTCACTGAGTTCAGAGTGCTGGGGAAAGGTGGTTTTGGGGAGGTATGTGCCGTCCAGGTGAAAAACACTGGGAAGATGTATGCCTGTA
AGAAACTGGACAAGAAGCGGCTGAAGAAGAAAGGTGGCGAGAAGATGGCTCTCTTGGAAAAGGAAATCTTGGAGAAGGTCAGCAGCCCTTTCAT
TGTCTCTCTGGCCTATGCCTTTGAGAGCAAGACCCATCTCTGCCTTGTCATGAGCCTGATGAATGGGGGAGACCTCAAGTTCCACATCTACAAC
GTGGGCACGCGTGGCCTGGACATGAGCCGGGTGATCTTTTACTCGGCCCAGATAGCCTGTGGGATGCTGCACCTCCATGAACTCGGCATCGTCT
ATCGGGACATGAAGCCTGAGAATGTGCTTCTGGATGACCTCGGCAACTGCAGGTTATCTGACCTGGGGCTGGCCGTGGAGATGAAGGGTGGCAA
GCCCATCACCCAGAGGGCTGGAACCAATGGTTACATGGCTCCTGAGATCCTAATGGAAAAGGTAAGTTATTCCTATCCTGTGGACTGGTTTGCC
ATGGGATGCAGCATTTATGAAATGGTTGCTGGACGAACACCATTCAAAGATTACAAGGAAAAGGTCAGTAAAGAGGATCTGAAGCAAAGAACTC
TGCAAGACGAGGTCAAATTCCAGCATGATAACTTCACAGAGGAAGCAAAAGATATTTGCAGGCTCTTCTTGGCTAAGAAACCAGAGCAACGCTT
AGGAAGCAGAGAAAAGTCTGATGATCCCAGGAAACATCATTTCTTTAAAACGATCAACTTTCCTCGCCTGGAAGCTGGCCTAATTGAACCCCCA
TTTGTGCCAGACCCTTCAGTGGTTTATGCCAAAGACATCGCTGAAATTGATGATTTCTCTGAGGTTCGGGGGGTGGAATTTGATGACAAAGATA
AGCAGTTCTTCAAAAACTTTGCGACAGGTGCTGTTCCTATAGCATGGCAGGAAGAAATTATAGAAACGGGACTGTTTGAGGAACTGAATGACCC
CAACAGACCTACGGGTTGTGAGGAGGGTAATTCATCCAAGTCTGGCGTGTGTTTGTTATTGTAA

SEQ ID NO: 22

Figure 2L

Human Rhodopsin Kinase (GRK1) (NM_002929):

```
MDFGSLETVVANSAFIAARGSFDGSSSQPSRDKKYLAKLKLPPLSKCESLRDSLSLEFESVCLEQPIGKKLFQQFLQSAEKHLPALELWKDIED
YDTADNDLQPQKAQTILAQYLDPQAKLFCSFLDEGIVAKFKEGPVEIQDGLFQPLLQATLAHLGQAPFQEYLGSLYFLRFLQWKWLEAQPMGED
WFLDFRVLGKGGFGEVSACQMKATGKLYACKKLNKKRLKKRKGYQGAMVEKKILMKVHSRFIVSLAYAFETKADLCLVMTIMNGGDIRYHIYNV
NEENPGFPEPRALFYTAQIICGLEHLHQRRIVYRDLKPENVLLDNDGNVRISDLGLAVELLDGQSKTKGYAGTPGFMAPELLQGEEYDFSVDYF
ALGVTLYEMIAARGPFRARGEKVENKELKHRIISEPVKYPDKFSQASKDFCEALLEKDPEKRLGFRDETCDKLRAHPLFKDLNWRQLEAGMLMP
PFIPDSKTVYAKDIQDVGAFSTVKGVAFDKTDTEFFQEFATGNCPIPWQEEMIETGIFGELNVWRSDGQMPDDMKGISGGSSSSSKSGMCLVS
```
SEQ ID NO: 23

```
ATGGATTTCGGGTCTTTGGAGACCGTGGTGGCCAACTCTGCCTTCATCGCCGCCCGAGGCAGCTTTGACGGCAGCAGCTCCCAACCCTCCCGGG
ACAAGAAGTACCTGGCCAAGCTCAAGCTGCCCCCGCTGTCCAAGTGTGAGTCCCTCCGCGACAGCCTCAGCCTGGAGTTTGAGAGTGTGTGCTT
GGAGCAGCCCATCGGCAAGAAGCTCTTTCAGCAGTTCCTACAATCGGCAGAGAAGCACCTGCCGGCCCTGGAGCTCTGGAAAGACATCGAGGAC
TATGACACGGCAGACAATGACCTCCAGCCACAGAAGGCCCAGACCATCCTGGCCCAGTACCTGGACCCCCAGGCCAAACTCTTCTGCAGCTTCC
TGGATGAGGGGATAGTGGCGAAGTTTAAGGAGGGGCCTGTGGAGATCCAGGACGGGCTCTTCCAGCCCCTGCTGCAGGCCACCCTGGCACACCT
GGGCCAAGCCCCCTTCCAGGAGTACCTGGGCAGCCTGTACTTCCTGAGGTTCCTGCAGTGGAAGTGGCTGGAAGCCCAGCCCATGGGGGAGGAC
TGGTTCCTGGACTTCAGGGTCCTGGGGAAAGGGGGCTTCGGGGAGGTGTCGGCCTGCCAGATGAAGGCGACCGGCAAGCTGTATGCCTGCAAGA
AGCTGAACAAGAAGCGGCTGAAGAAGAGGAAGGGCTACCAGGGTGCTATGGTGGAGAAGAAGATTCTGATGAAAGTACACAGCAGGTTCATCGT
GTCTCTGGCCTATGCGTTTGAAACCAAAGCCGACCTCTGTCTGGTGATGACCATCATGAACGGAGGTGACATCAGGTACCACATCTACAACGTG
AATGAGGAGAACCCTGGCTTCCCGGAGCCGCGCGCCCTCTTCTACACGGCGCAGATCATCTGCGGCCTGGAGCACCTGCACCAGAGGCGGATCG
TCTACCGCGACCTCAAGCCCGAGAACGTGCTGCTGGACAATGACGGCAATGTCCGGATCTCTGACCTTGGGCTGGCCGTGGAGCTGCTGGACGG
ACAGAGCAAGACCAAGGGCTACGCAGGGACCCCAGGTTTCATGGCCCCCGAGCTCCTGCAGGGCGAGGAGTACGACTTCTCCGTGGACTACTTT
GCCCTGGGGGTCACCCTGTATGAGATGATTGCGGCCAGAGGACCCTTCCGAGCCCGTGGAGAGAAGGTGGAGAACAAGGAGCTGAAGCACCGGA
TCATCTCAGAGCCCGTGAAGTACCCTGATAAGTTCAGCCAGGCAGACTTCTGCGAGGCGCTGCTGGAGAAGGACCCGGAGAAGCGCCT
GGGGTTCAGAGATGAGACCTGCGACAAGCTCCGTGCCCACCCCCTCTTCAAGGACCTTAACTGGAGGCAGCTGGAGGCTGGGATGCTGATGCCC
CCTTTCATCCCAGACTCCAAAACTGTCTACGCAAAGGATATTCAGGACGTGGGTGCCTTTTCCACCGTCAAAGGTGTGGCCTTTGACAAAACAG
ACACAGAATTCTTTCAGGAATTTGCCACTGGCAACTGCCCCATCCCCTGGCAGGAGGAGATGATCGAGACGGGCATCTTTGGCGAGCTGAACGT
GTGGCGCTCGGACGGTCAGATGCCGGACGACATGAAGGGCATCTCCGGGGGCTCCAGCTCCTCGTCCAAGTCAGGGATGTGTCTGGTTTCCTAG
```
SEQ ID NO: 24

Figure 2M

Human GRK3 (β-aderengic receptor kinase 2) (XM_037826):

```
MADLEAVLADVSYLMAMEKSKATPAARASKRIVLPEPSIRSVMQKYLAERNEITFDKIFNQKIGFLLFKDFCLNEINEAVPQVKFYEEIKEYEK
LDNEEDRLCRSRQIYDAYIMKELLSCSHPFSKQAVEHVQSHLSKKQVTSTLFQPYIEEICESLRGDIFQKFMESDKFTRFCQWKNVELNIHLTM
NEFSVHRIIGRGGFGEVYGCRKADTGKMYAMKCLDKKRIKMKQGETLALNERIMLSVSTGDCPFIVCMTYAFHTPDKLCFILDLMNGGDLHYH
LSQHGVFSEKEMRFYATEIILGLEHMHNRFVVYRDLKPANILLDEHGHARISDLGLACDFSKKKPHASVGTHGYMAPEVLQKGTAYDSSADWFS
LGCMLFKLLRGHSPFRQHKTKDKHEIDRMTLTVNVELPDTFSPELKSLLEGLLQRDVSKRLGCHGGGSQEVKEHSFFKGVDWQHVYLQKYPPPL
IPPRGEVNAADAFDIGSFDEEDTKGIKLLDCDQELYKNFPLVISERWQQEVTETVYEAVNADTDKIEARKRAKNKQLGHEEDYALGKDCIMHGY
MLKLGNPFLTQWQRRYFYLFPNRLEWRGEGESRQNLLTMEQILSVEETQIKDKKCILFRIKGGKQFVLQCESDPEFVQWKKELNETFKEAQRLL
RRAPKFLNKPRSGTVELPKPSLCHRNSNGL
```
SEQ ID NO: 25

```
ATGGCGGACCTGGAGGCTGTGCTGGCCGATGTCAGTTACCTGATGGCCATGGAGAAGAGCAAGGCGACCCCGGCCGCCCGCGCCAGCAAGAGGA
TCGTCCTGCCGGAGCCCAGTATCCGGAGTGTGATGCAGAAGTACCTTGCAGAGAGAAATGAAATAACCTTTGACAAGATTTTCAATCAGAAAAT
TGGTTTCTTGCTATTTAAAGATTTTTGTTTGAATGAAATTAATGAAGCTGTACCTCAGGTGAAGTTTTATGAAGAGATAAAGGAATATGAAAAA
CTTGATAATGAGGAAGACCGCCTTTGCAGAAGTCGACAAATTTATGATGCCTACATCATGAAGGAACTTCTTTCCTGTTCACATCCTTTCTCAA
AGCAAGCTGTAGAACACGTACAAAGTCATTTATCCAAGAAACAAGTGACATCAACTCTTTTTCAGCCATACATAGAAGAAATTTGTGAAAGCCT
TCGAGGTGACATTTTTCAAAAATTTATGAAAGTGACAAGTTCACTAGATTTTGTCAGTGGAAAAACGTTGAATTAAATATCCATTTGACCATG
AATGAGTTCAGTGTGCATAGGATTATTGGACGAGGAGGATTCGGGGAAGTTTATGGTTGCAGGAAAGCAGACACTGGAAAAATGTATGCAATGA
AATGCTTAGATAAGAAGAGGATCAAAATGAAACAAGGAGAAACATTAGCCTTAAATGAAAGAATCATGTTGTCTCTTGTCAGCACAGGAGACTG
TCCTTTCATTGTATGTATGACCTATGCCTTCCATACCCCAGATAAACTCTGCTTCATCCTGGATCTGATGAACGGGGGCGATTTGCACTACCAC
CTTTCACAACACGGTGTGTTCTCTGAGAAGGAGATGCGGTTTTATGCCACTGAAATCATTCTGGGTCTGGAACACATGCACAATCGGTTTGTTG
TCTACAGAGATTTGAAGCCAGCAAATATTCTCTTGGATGAACATGGACACGCAAGAATATCAGATCTTGGTCTTGCCTGCGATTTTCCAAAAA
GAAGCCTCATGCGAGTGTTGGCACCCATGGGTACCTGTCCCGAGGTCTGCAGAAGGGGACGGCCTATGCACAGCAGTGCCGACTGGTTCTCC
CTGGGCTGCATGCTTTTCAAACTTCTGAGAGGTCACAGCCCTTTCAGACAACATAAAACCAAAGACAAGCATGAAATTGACCGAATGACACTCA
CCGTGAATGTGGAACTTCCAGACACCTTCTCTCCTGAACTGAAGTCCCTTTTGGAGGGCTTGCTTCAGCGAGACGTTAGCAAGCGGCTGGGCTG
TCACGGAGGCGGCTCACAGGAAGTAAAAGAGCACAGCTTTTTCAAAGGTGTTGACTGGCAGCATGTCTACTTACAAAAGTACCCACCACCCTTG
ATTCCTCCCCGGGGAGAAGTCAATGCTGCTGATGCCTTTGATATTGGCTCATTTGATGAAGAGGATACCAAAGGGATTAAGCTACTTGATTGCG
ACCAAGAACTCTACAAGAACTTCCCTTTGGTCATCTCTGAACGCTGGCAGCAAGAAGTAACGGAAACAGTTTATGAAGCAGTAAATGCAGACAC
AGATAAAATCGAGGCCAGGAAGAGAGCTAAAAATAAGCAACTTGGCCACGAAGAAGATTACGCTCTGGGGAAGGACTGTATTATGCACGGGTAC
ATGCTGAAACTGGGAAACCCATTTCTGACTCAGTGGCAGCGTCGCTATTTTACCTCTTTCCAAATAGACTTGAATGGAGAGGAGAGGGAGAGT
CCCGGCAAAATTTACTGACAATGGAACAGATTCTCTCTGTGAAGAAACTCAAATTAAAGACAAAAAATGCATTTTGTTCAGAATAAAAGGAGG
GAAACAATTTGTCTTGCAATGTGAGAGTGATCCAGAGTTTGTGCAGTGGAAGAAAGAGTTGAACGAAACCTTCAAGGAGGCCCAGCGGCTATTG
CGTCGTGCCCCGAAGTTCCTCAACAAACCTCGGTCAGGTACTGTGGAGCTCCCAAAGCCATCCCTCTGTCACAGAAACAGCAACGGCCTCTAG
```
SEQ ID NO: 26

Human GRK1b Splice Variants (AF019764 and AF019765)

Figure 2N

Bovine GRK3 (β-adenergic receptor kinase 2) (M73216):

```
MADLEAVLADVSYLMAMEKSKATPAARASKKIVLPEPSIRSVMQKYLEERHEITFDKIFNQRIGFLLFKDFCLNEINEAVPQVKFYEEIKEYEK
LENEEDRLCRSRQIYDTYIMKELLSCSHPFSKQAVEHVQSHLSKKQVTSTLFQPYIEEICESLRGSIFQKFMESDKFTRFCQWKNVELNIHLTM
NDFSVHRIIGRGGFGEVYGCRKADTGKMYAMKCLDKKRIKMKQGETLALNERIMLSLVSTGDCPFIVCMTYAFHTPDKLCFILDLMNGGDLHYH
LSQHGVFSEKEMRFYATEIILGLEHMHNRFVVYRDLKPANILLDEHGHVRISDLGLACDFSKKKPHASVGTHGYMAPEVLQKGTAYDSSADWFS
LGCMLFKLLRGHSPFRQHKTKDKHEIDRMTLTMNVELPDVFSPELKSLLEGLLQRDVSKRLGCHGGSAQELKTHDFFRGIDWQHVYLQKYPPPL
IPPRGEVNAADAFDIGSFDEEDTKGIKLLDCDQELYKNFPLVISERWQQEVAETVYEAVNADTDKIEARKRAKNKQLGHEEDYALGRDCIVHGY
MLKLGNPFLTQWQRRYFYLFPNRLEWRGEGESRQSLLTMEQIVSVEETQIKDKKCILLRIKGGKQFVLQCESDPEFVQWKKELTETFMEAQRLL
RRAPKFLNKSRSAVVELSKPPLCHRNSNGL
```
SEQ ID NO: 27

```
ATGGCGGACCTGGAGGCCGTGCTGGCCGATGTCAGCTACCTGATGGCGATGGAGAAGAGCAAGGCGACCCCGGCCGCCCGCGCCAGCAAGAAGA
TCGTCCTGCCCGAGCCCAGTATCCGGAGCGTGATGCAGAAGTATCTTGAGGAGAGACACGAAATCACCTTTGACAAGATTTTTAATCAGAGAAT
TGGTTTCTTGCTATTTAAAGATTTTTGTTTGAATGAAATTAATGAAGCTGTACCTCAGGTGAAGTTTTATGAAGAGATAAAAGAATATGAAAAG
CTTGAGAATGAGGAAGATCGCCTTTGTAGAAGTCGACAGATTTATGACACTTACATCATGAAGGAGCTGCTGTCGTGTTCACATCCATTCTCAA
AGCAAGCCGTAGAACACGTACAAAGTCATCTGTCCAAGAAACAAGTGACATCAACTCTTTTTCAGCCATACATAGAAGAAATTTGTGAAAGTCT
CCGAGGCAGCATTTTTCAAAAATTCATGGAAAGTGACAAGTTTACTAGATTTTGTCAGTGGAAAAACGTGGAATTAAATATCCATTTGACCATG
AATGATTTCAGCGTGCATCGGATCATTGGACGAGGAGGATTCGGTGAAGTATACGGTTGCAGGAAAGCAGACACTGGAAAGATGTATGCAATGA
AATGCTTGGATAAGAAGAGAATCAAGATGAAACAGGGAGAAACCTTAGCCTTAAATGAAAGGATCATGTTGTCCCTGGTGAGCACAGGAGATTG
CCCTTTCATCGTCTGTATGACCTATGCCTTCCACACTCCAGATAAACTGTGCTTCATCTTGGATCTGATGAACGGGGGTGACCTGCACTATCAC
CTTTCGCAGCACGGGGTGTTTTCTGAGAAGGAGATGCGGTTTTACGCCACAGAAATCATCCTGGGGCTGGAACACATGCACAATCGGTTTGTTG
TTTACAGAGACTTGAAGCCCGCCAATATCCTCCTGGATGAGCACGGACATGTGAGGATATCAGACCTTGGTCTTGCCTGCGATTTTTCCAAAAA
GAAGCCGCACGCGAGCGTGGGCACCCACGGGTACATGGCGCCCGAAGTTCTGCAGAAGGGGACCGCCTACGACAGCAGTGCCGACTGGTTCTCC
CTGGGCTGTATGCTTTTCAAACTTCTGAGAGGTCACAGCCCTTTCAGACAACATAAAACCAAAGATAAGCATGAGATAGACCGAATGACTCTCA
CCATGAACGTGGAACTTCCAGACGTCTTCTCCCCTGAGCTCAAGTCCCTTCTGGAAGGCCTGCTTCAGCGAGATGTCAGTAAGCGCCTCGGCTG
CCATGGAGGCAGCGCACAGGAGCTAAAAACGCACGACTTCTTCAGAGGCATCGACTGGCAGCACGTCTACCTGCAGAAGTACCCTCCACCCTTG
ATCCCTCCCCGAGGGGAAGTCAATGCAGCCGACGCCTTTGACATCGGCTCATTTGATGAAGAGGATACCAAAGGCATCAAGCTTCTTGATTGCG
ACCAAGAACTCTACAAGAACTTCCCTCTGGTGATCTCTGAGCGCTGGCAGCAGGAAGTGGCGGAAACAGTTTATGAAGCAGTAAATGCAGACAC
GGATAAAATCGAGGCCAGGAAGAGAGCTAAAAATAAGCAGCTTGGCCACGAAGAAGATTACGCCCTGGGAAGAGACTGCATCGTGCACGGGTAC
ATGCTGAAGCTGGGGAACCCTTTCCTGACCCAGTGGCAGCGCCGCTATTTTTACCTCTTTCCGAACAGACTTGAGTGGAGGGAGAAGGCGAGT
CGCGACAAAGTTTACTGACAATGGAACAGATTGTGTCCGTGGAAGAAACTCAGATTAAAGACAAAAAGTGCATTTTGTTGAGAATAAAAGGAGG
GAAGCAGTTCGTTTTGCAGTGTGAGAGTGACCCAGAGTTTGTGCAGTGGAAGAAAGAGCTGACGGAGACATTCATGGAGGCCCAGCGGCTGCTA
CGGCGAGCCCCCAAGTTCCTCAACAAATCCCGCTCAGCCGTCGTGGAACTCTCAAAGCCTCCCCTCTGCCATAGGAACAGCAACGGCCTCTGA
```
SEQ ID NO: 28

Figure 20

Human GRK2 (G protein-coupled receptor kinase 2) (NM_001619)
Adrenergic, beta, receptor kinase 1(ADRBK1)
(Beta-adrenergic receptor kinase 1 (Bark-1):

```
MADLEAVLADVSYLMAMEKSKATPAARASKKILLPEPSIRSVMQKYLEDRGEVTFEKIFSQKLGYLLFRDFCLNHLEEARPLVEFYEEIKKYEK
LETEEERVARSREIFDSYIMKELLACSHPFSKSATEHVQGHLGKKQVPPDLFQPYIEEICQNLRGDVFQKFIESDKFTRFCQWKNVELNIHLTM
NDFSVHRIIGRGGFGEVYGCRKADTGKMYAMKCLDKKRIKMKQGETLALNERIMLSLVSTGDCPFIVCMSYAFHTPDKLSFILDLMNGGDLHYH
LSQHGVFSEADMRFYAAEIILGLEHMHNRFVVYRDLKPANILLDEHGHVRISDLGLACDFSKKKPHASVGTHGYMAPEVLQKGVAYDSSADWFS
LGCMLFKLLRGHSPFRQHKTKDKHEIDRMTLTMAVELPDSFSPELRSLLEGLLQRDVNRRLGCLGRGAQEVKESPFFRSLDWQMVFLQKYPPPL
IPPRGEVNAADAFDIGSFDEEDTKGIKLLDSDQELYRNFPLTISERWQQEVAETVFDTINAETDRLEARKKAKNKQLGHEEDYALGKDCIMHGY
MSKMGNPFLTQWQRRYFYLFPNRLEWRGEGEAPQSLLTMEEIQSVEETQIKERKCLLLKIRGGKQFILQCDSDPELVQWKKELRDAYREAQQLV
QRVPKMKNKPRSPVVELSKVPLVQRGSANGL
```
SEQ ID NO: 29

```
ATGGCGGACCTGGAGGCGGTGCTGGCCGACGTGAGCTACCTGATGGCCATGGAGAAGAGCAAGGCCACGCCGGCCGCGCGCGCCAGCAAGAAGA
TACTGCTGCCCGAGCCCAGCATCCGCAGTGTCATGCAGAAGTACCTGGAGGACCGGGGCGAGGTGACCTTTGAGAAGATCTTTTCCCAGAAGCT
GGGGTACCTGCTCTTCCGAGACTTCTGCCTGAACCACCTGGAGGAGGCCAGGCCCTTGGTGGAATTCTATGAGGAGATCAAGAAGTACGAGAAG
CTGGAGACGGAGGAGGAGCGTGTGGCCCGCAGCCGGGAGATCTTCGACTCATACATCATGAAGGAGCTGCTGGCCTGCTCGCATCCCTTCTCGA
AGAGTGCCACTGAGCATGTCCAAGGCCACCTGGGGAAGAAGCAGGTGCCTCCGGATCTCTTCCAGCCATACATCGAAGAGATTTGTCAAAACCT
CCGAGGGGACGTGTTCCAGAAATTCATTGAGAGCGATAAGTTCACACGGTTTTGCCAGTGGAAGAATGTGGAGCTCAACATCCACCTGACCATG
AATGACTTCAGCGTGCATCGCATCATTGGGCGCGGGGGCTTTGGCGAGGTCTATGGGTGCCGGAAGGCTGACACAGGCAAGATGTACGCCATGA
AGTGCCTGGACAAAAAGCGCATCAAGATGAAGCAGGGGGAGACCCTGGCCCTGAACGAGCGCATCATGCTCTCGCTCGTCAGCACTGGGGACTG
CCCATTCATTGTCTGCATGTCATACGCGTTCCACACGCCAGACAAGCTCAGCTTCATCCTGGACCTCATGAACGGTGGGGACCTGCACTACCAC
CTCTCCCAGCACGGGGTCTTCTCAGAGGCTGACATGCGCTTCTATGCGGCCGAGATCATCCTGGGCCTGGAGCACATGCACAACCGCTTCGTGG
TCTACCGGGACCTGAAGCCAGCCAACATCCTTCTGGACGAGCATGGCCACGTGCGGATCTCGGACCTGGGCCTGGCCTGTGACTTCTCCAAGAA
GAAGCCCCATGCCAGCGTGGGCACCCACGGGTACATGGCTCCGGAGGTCCTGCAGAAGGGCGTGGCCTACGACAGCAGTGCCGACTGGTTCTCT
CTGGGGTGCATGCTCTTCAAGTTGCTGCGGGGGCACAGCCCCTTCCGGCAGCACAAGACCAAAGACAAGCATGAGATCGACCGCATGACGCTGA
CGATGGCCGTGGAGCTGCCCGACTCCTTCTCCCCTGAACTACGCTCCCTGCTGGAGGGGTTGCTGCAGAGGGATGTCAACGGAGATTGGGCTG
CCTGGGCGAGGGGCTCAGGAGGTGAAAGAGAGCCCCTTTTTCCGCTCCCTGGACTGGCAGATGGTCTTCTTGCAGAAGTACCCTCCCCCGCTG
ATCCCCCCACGAGGGGAGGTGAACGCGGCCGACGCCTTCGACATTGGCTCCTTCGATGAGGAGGACACAAAAGGAATCAAGTTACTGGACAGTG
ATCAGGAGCTCTACCGCAACTTCCCCCTCACCATCTCGGAGCGGTGGCAGCAGGAGGTGGCAGAGACTGTCTTCGACACCATCAACGCTGAGAC
AGACCGGCTGGAGGCTCGCAAGAAAGCCAAGAACAAGCAGCTGGGCCATGAGGAAGACTACGCCCTGGGCAAGGACTGCATCATGCATGGCTAC
ATGTCCAAGATGGGCAACCCCTTCCTGACCCAGTGGCAGCGGCGGTACTTCTACCTGTTCCCCAACCGCCTCGAGTGGCGGGGCGAGGGCGAGG
CCCCGCAGAGCCTGCTGACCATGGAGGAGATCCAGTCGGTGGAGGAGACGCAGATCAAGGAGCGCAAGTGCCTGCTCCTCAAGATCCGCGGTGG
GAAACAGTTCATTTTGCAGTGCGATAGCGACCCTGAGCTGGTGCAGTGGAAGAAGGAGCTGCGCGACGCCTACCGCGAGGCCCAGCAGCTGGTG
CAGCGGGTGCCCAAGATGAAGAACAAGCCGCGCTCGCCCGTGGTGGAGCTGAGCAAGGTGCCGCTGGTCCAGCGCGGCAGTGCCAACGGCCTCT
GA
```
SEQ ID NO: 30

Figure 2P

Human GRK2 (C20)(G protein-coupled receptor kinase 2) (NM_001619)
Adrenergic, beta, receptor kinase 1(ADRBK1)
(Beta-adrenergic receptor kinase 1 (Bark-1):

```
MADLEAVLADVSYLMAMEKSKATPAARASKKILLPEPSIRSVMQKYLEDRGEVTFEKIFSQKLGYLLFRDFCLNHLEEARPLVEFYEEIKKYEK
LETEEERVARSREIFDSYIMKELLACSHPFSKSATEHVQGHLGKKQVPPDLFQPYIEEICQNLRGDVFQKFIESDKFTRFCQWKNVELNIHLTM
NDFSVHRIIGRGGFGEVYGCRKADTGKMYAMKCLDKKRIKMKQGETLALNERIMLSLVSTGDCPFIVCMSYAFHTPDKLSFILDLMNGGDLHYH
LSQHGVFSEADMRFYAAEIILGLEHMHNRFVVYRDLKPANILLDEHGHVRISDLGLACDFSKKKPHASVGTHGYMAPEVLQKGVAYDSSADWFS
LGCMLFKLLRGHSFFRQHKTKDKHEIDRMTLTMAVELPDSFSPELRSLLEGLLQRDVNRRLGCLGRGAQEVKESPFFRSLDWQMVFLQKYPPPL
IPPRGEVNAADAFDIGSFDEEDTKGIKLLDSDQELYRNFPLTISERWQQEVAETVFDTINAETDRLEARKKAKNKQLGHEEDYALGKDCIMHGY
MSKMGNPFLTQWQRRYFYLFPNRLEWRGEGEAPQSLLTMEEIQSVEETQIKERKCLLLKIRGGKQFILQCDSDPELVQWKKELRDAYREAQQLV
QRVPKMKNKPRSPVVELSKVPLVQRGSCVLL
```
SEQ ID NO: 31

```
ATGGCGGACCTGGAGGCGGTGCTGGCCGACGTGAGCTACCTGATGGCCATGGAGAAGAGCAAGGCCACGCCGGCCGCGCGCGCCAGCAAGAAGA
TACTGCTGCCCGAGCCCAGCATCCGCAGTGTCATGCAGAAGTACCTGGAGGACCGGGGCGAGGTGACCTTTGAGAAGATCTTTTCCCAGAAGCT
GGGGTACCTGCTCTTCCGAGACTTCTGCCTGAACCACCTGGAGGAGGCCAGGCCCTTGGTGGAATTCTATGAGGAGATCAAGAAGTACGAGAAG
CTGGAGACGGAGGAGGAGCGTGTGGCCCGCAGCCGGGAGATCTTCGACTCATACATCATGAAGGAGCTGCTGGCCTGCTCGCATCCCTTCTCGA
AGAGTGCCACTGAGCATGTCCAAGGCCACCTGGGGAAGAAGCAGGTGCCTCCGGATCTCTTCCAGCCATACATCGAAGAGATTTGTCAAAACCT
CCGAGGGGACGTGTTCCAGAAATTCATTGAGAGCGATAAGTTCACACGGTTTTGCCAGTGGAAGAATGTGGAGCTCAACATCCACCTGACCATG
AATGACTTCAGCGTGCATCGCATCATTGGGCGCGGGGGCTTTGGCGAGGTCTATGGGTGCCGGAAGGCTGACACAGGCAAGATGTACGCCATGA
AGTGCCTGGACAAAAAGCGCATCAAGATGAAGCAGGGGGAGACCCTGGCCCTGAACGAGCGCATCATGCTCTCGCTCGTCAGCACTGGGGACTG
CCCATTCATTGTCTGCATGTCATACGCGTTCCACACGCCAGACAAGCTCAGCTTCATCCTGGACCTCATGAACGGTGGGGACCTGCACTACCAC
CTCTCCCAGCACGGGGTCTTCTCAGAGGCTGACATGCGCTTCTATGCGGCCGAGATCATCCTGGGCCTGGAGCACATGCACAACCGCTTCGTGG
TCTACCGGGACCTGAAGCCAGCCAACATCCTTCTGGACGAGCATGGCCACGTGCGGATCTCTGACCTGGGCCTGGCCTGTGACTTCTCCAAGAA
GAAGCCCCATGCCAGCGTGGGCACCCACGGGTACATGGCTCCGGAGGTCCTGCAGAAGGGCGTGGCCTACGACAGCAGTGCCGACTGGTTCTCT
CTGGGGTGCATGCTCTTCAAGTTGCTGCGGGGGCACAGCCCCTTCCGGCAGCACAAGACCAAAGACAAGCATGAGATCGACCGCATGACGCTGA
CGATGGCCGTGGAGCTGCCCGACTCCTTCTCCCCTGAACTACGCTCCCTGCTGGAGGGGTTGCTGCAGAGGGATGTCAACCGGAGATTGGGCTG
CCTGGGCCGAGGGGCTCAGGAGGTGAAAGAGAGCCCCTTTTTCCGCTCCCTGGACTGGCAGATGGTCTTCTTGCAGAAGTACCCTCCCCCGCTG
ATCCCCCCACGAGGGGAGGTGAACGCGGCCGACGCCTTCGACATTGGCTCCTTCGATGAGGAGGACACAAAAGGAATCAAGTTACTGGACAGTG
ATCAGGAGCTCTACCGCAACTTCCCCCTCACCATCTCGGAGCGGTGGCAGCAGGAGGTGGCAGAGACTGTCTTCGACACCATCAACGCTGAGAC
AGACCGGCTGGAGGCTCGCAAGAAAGCCAAGAACAAGCAGCTGGGCCATGAGGAAGACTACGCCCTGGGCAAGGACTGCATCATGCATGGCTAC
ATGTCCAAGATGGGCAACCCCTTCCTGACCCAGTGGCAGCGGCGGTACTTCTACCTGTTCCCCAACCGCCTCGAGTGGCGGGGCGAGGGCGAGG
CCCCGCAGAGCCTGCTGACCATGGAGGAGATCCAGTCGGTGGAGGAGACGCAGATCAAGGAGCGCAAGTGCCTGCTCCTCAAGATCCGCGGTGG
GAAACAGTTCATTTTGCAGTGCGATAGCGACCCTGAGCTGGTGCAGTGGAAGAAGGAGCTGCGCGACGCCTACCGCGAGGCCCAGCAGCTGGTG
CAGCGGGTGCCCAAGATGAAGAACAAGCCGCGCTCGCCCGTGGTGGAGCTGAGCAAGGTGCCGCTGGTCCAGCGCGGCAGTTGTGTGCTTCTTT
AG
```
SEQ ID NO: 32

Figure 2Q

Bovine GRK2 (G protein-coupled receptor kinase 2) (M34019.1)
Bovine beta-adrenergic receptor kinase (beta-ARK):

MADLEAVLADVSYLMAMEKSKATPAARASKKILLPEPSIRSVMQKYLEDRGEVTFEKIFSQKLGYLLFRDFCLKHLEEAKPLVEFYEEIKKYEK
LETEEERLVCSREIFDTYIMKELLACSHPFSKSAIEHVQGHLVKKQVPPDLFQPYIEEICQNLRGDVFQKFIESDKFTRFCQWKNVELNIHLTM
NDFSVHRIIGRGGFGEVYGCRKADTGKMYAMKCLDKKRIKMKQGETLALNERIMLSLVSTGDCPFIVCMSYAFHTPDKLSFILDLMNGGDLHYH
LSQHGVFSEADMRFYAAEIILGLEHMHNRFVVYRDLKPANILLDEHGHVRISDLGLACDFSKKKPHASVGTHGYMAPEVLQKGVAYDSSADWFS
LGCMLFKLLRGHSPFRQHKTKDKHEIDRMTLTMAVELPDSFSPELRSLLEGLLQRDVNRRLGCLGRGAQEVKESPFFRSLDWQMVFLQKYPPPL
IPPRGEVNAADAFDIGSFDEEDTKGIKLLDSDQELYRNFPLTISERWQQEVAETVFDTINAETDRLEARKKTKNKQLGHEEDYALGKDCIMHGY
MSKMGNPFLTQWQRRYFYLFPNRLEWRGEGEAPQSLLTMEEIQSVEETQIKERKCLLLKIRGGKQFVLQCDSDPELVQWKKELRDAYREAQQLV
QRVPKMKNKPRSPVVELSKVPLIQRGSANGL
SEQ ID NO: 33

ATGGCGGACCTGGAGGCGGTGCTGGCCGACGTGAGCTACCTGATGGCCATGGAGAAGAGCAAGGCCACGCCGGCGGCGCGCGCCAGCAAGAAGA
TCCTGCTGCCCGAGCCCAGCATCCGCAGCGTCATGCAGAAGTACCTGGAGGACCGGGGCGAGGTGACTTTTGAGAAGATCTTCTCCCAGAAGCT
GGGGTACCTGCTTTTCCGAGACTTCTGCCTGAAGCACCTGGAGGAGGCCAAGCCCTTGGTAGAGTTCTACGAGGAGATCAAGAAATACGAGAAG
CTGGAGACAGAGGAGGAGCGCCTGGTCTGCAGCCGAGAGATCTTCGACACGTACATCATGAAGGAGCTGCTGGCCTGCTCACATCCTTTCTCGA
AGAGCGCCATTGAGCACGTCCAGGGCCATCTGGTGAAGAAGCAGGTGCCTCCGGATCTCTTCCAGCCATATATTGAAGAAATTTGCCAGAACCT
CCGAGGAGACGTGTTCCAGAAATTCATCGAGAGCGATAAATTCACACGATTTTGCCAGTGGAAGAATGTAGAGCTCAACATCCACCTGACCATG
AACGACTTCAGTGTGCACCGCATCATCGGGCGAGGCGGCTTCGGTGAGGTCTACGGCTGCCGGAAGGCCGACACGGGCAAGATGTACGCCATGA
AGTGTCTGGACAAGAAGCGCATCAAGATGAAGCAAGGGGAGACTCTGGCCCTGAATGAGCGCATCATGCTGTCGCTCGTCAGCACCGGGGACTG
CCCGTTCATCGTCTGCATGTCATACGCCTTCCACACACCGGACAAGCTCAGCTTCATCCTGGATCTCATGAACGGCGGGGACCTGCACTACCAC
CTGTCCCAGCACGGGGTCTTCTCCGAGGCCGACATGCGTTTCTACGCCGCCGAGATCATCCTGGGCCTGGAGCACATGCACAACCGCTTCGTGG
TCTACCGGGACCTGAAGCCGGCCAACATCCTGCTGGACGAGCACGGCCACGTGCGCATCTCAGACCTGGGCCTGGCCTGTGACTTCTCCAAGAA
GAAGCCTCACGCCCAGTGTGGGCACCCACGGGTACATGGCTCCCGAGGTTCTACAGAAGGGTGTGGCCTACGACAGCAGCGCCGACTGGTTCTCC
CTGGGCTGCATGCTCTTCAAGCTGCTGCGAGGGCATAGCCCTTTCCGGCAGCACAAGACCAAAGACAAGCATGAGATCGACAGAATGACATTGA
CAATGGCTGTGGAGCTGCCTGACTCCTTCTCCCCTGAGCTCCGCTCCTTGCTGGAGGGGCTGCTGCAGAGGGATGTCAACCGGAGGCTAGGCTG
CCTGGGCCGAGGGGCCCAGGAGGTGAAGGAGAGCCCCTTCTTCCGTTCCCTGGACTGGCAGATGGTCTTTTTACAAAAGTACCCTCCCCCGTTG
ATCCCCCCACGAGGGGAGGTGAATGCAGCCGACGCCTTTGACATTGGCTCCTTCGATGAGGAGGACACAAAAGGAATCAAGCTACTGGACAGTG
ACCAGGAGCTCTACCGCAACTTCCCCCTGACCATCTCGGAGCGGTGGCAGCAGGAGGTAGCAGAGACTGTCTTTGACACCATCAATGCTGAGAC
GGACCGGCTGGAGGCCCGCAAGAAAACCAAAAACAAGCAGTTGGGCCACGAGGAAGACTACGCCCTGGGCAAGGACTGCATCATGCATGGCTAC
ATGTCCAAGATGGGCAACCCCTTCCTGACCCAGTGGCAGCGGCGGTACTTCTACCTGTTCCCTAACCGGCTCGAGTGGCGGGGCGAGGGCGAGG
CCCCGCAGAGCCTGCTGACCATGGAGGAGATCCAGTCGGTGGAGGAGACGCAGATCAAGGAGCGCAAAAGTGCCTCCTCCTCAAGATCCGAGGTGG
CAAGCAGTTTGTCCTGCAGTGCGATAGTGACCCAGAGCTGGTGCAGTGGAAGAAGGAGCTTCGAGACGCCTACCGCGAGGCCCAGCAGCTAGTG
CAGCGGGTGCCCAAGATGAAGAACAAGCCGCGCTCGCCCGTCGTGGAGCTGAGCAAGGTGCCACTGATCCAGCGCGGCAGTGCCAACGGCCTCT
GA
SEQ ID NO: 34

Figure 3A

Amino Acid sequence of wild-type hGPR3 ACCESSION NP_005272

```
MMWGAGSPLAWLSAGSGNVNVSSVGPAEGPTGPAAPLPSPKAWDVVLCISGTLVSCENALVVAIIVGTPAFRAPMFLLVG
SLAVADLLAGLGLVLHFAAVFCIGSAEMSLVLVGVLAMAFTASIGSLLAITVDRYLSLYNALTYYSETTVTRTYVMLALV
WGGALGLGLLPVLAWNCLDGLTTCGVVYPLSKNHLVVLAIAFFMVFGIMLQLYAQICRIVCRHAQQIALQRHLLPASHYV
ATRKGIATLAVVLGAFAACWLPFTVYCLLGDAHSPPLYTYLTLLPATYNSMINPIIYAFRNQDVQKVLWAVCCCCSSSKI
PFRSRSPSDV
```

SEQ ID No:35

Nucleotide sequence of wild-type hGPR3 ACCESSION NM_005281

```
ATGATGTGGGGTGCAGGCAGCCCTCTGGCCTGGCTCTCAGCTGGCTCAGGCAACGTGAATGTAAGCAGCGTGGGCCCAGC
AGAGGGGCCCACAGGTCCAGCCGCACCACTGCCCTCGCCTAAGGCCTGGGATGTGGTGCTCTGCATCTCAGGCACCCTGG
TGTCCTGCGAGAATGCGCTAGTGGTGGCCATCATCGTGGGCACTCCTGCCTTCCGTGCCCCCATGTTCCTGCTGGTGGGC
AGCCTGGCCGTGGCAGACCTGCTGGCAGGCCTGGGCCTGGTCCTGCACTTTGCTGCTGTCTTCTGCATCGGCTCAGCGGA
GATGAGCCTGGTGCTGGTTGGCGTGCTGGCAATGGCCTTTACCGCCAGCATCGGCAGTCTACTGGCCATCACTGTCGACC
GCTACCTTTCTCTGTACAATGCCCTCACCTACTATTCAGAGACAACAGTGACACGGACCTATGTGATGCTGGCCTTAGTG
TGGGGAGGTGCCCTGGGCCTGGGGCTGCTGCCTGTGCTGGCCTGGAACTGCCTGGATGGCCTGACCACATGTGGCGTGGT
TTATCCACTCTCCAAGAACCATCTGGTAGTTCTGGCCATTGCCTTCTTCATGGTGTTTGGCATCATGCTGCAGCTCTACG
CCCAAATCTGCCGCATCGTCTGCCGCCATGCCCAGCAGATTGCCCTTCAGCGGCACCTGCTGCCTGCCTCCCACTATGTG
GCCACCCGCAAGGGCATTGCCACACTGGCCGTGGTGCTTGGAGCCTTTGCCGCCTGCTGGTTGCCCTTCACTGTCTACTG
CCTGCTGGGTGATGCCCACTCTCCACCTCTCTACACCTATCTTACCTTGCTCCCTGCCACCTACAACTCCATGATCAACC
CTATCATCTACGCCTTCCGCAACCAGGATGTGCAGAAAGTGCTGTGGGCTGTCTGCTGCTGCTGTTCCTCTTCCAAGATC
CCCTTCCGATCCCGCTCCCCCAGTGATGTCTAG
```

SEQ ID No:36

Figure 3B
Amino Acid sequence of HA tagged hGPR3

MYPYDVPDYAAAAAMMWGAGSPLAWLSAGSGNVNVSSVGPAEGPTGPAAPLPSPKAWDVVLCISGTLVSCENALVVAIIVG
TPAFRAPMFLLVGSLAVADLLAGLGLVLHPAAVFCIGSAEMSLVLVGVLAMAFTASIGSLLAITVDRYLSLYNALTYYSET
TVTRTYVMLALVWGGALGLGLLPVLAWNCLDGLTTCGVVYPLSKNHLVVLAIAFFMVFGIMLQLYAQICRIVCRHAQQIAL
QRHLLPASHYVATRKGIATLAVVLGAFAACWLPFTVYCLLGDAHSPPLYTYLTLLPATYNSMINPIIYAFRNQDVQKVLWA
VCCCCSSSKIPFRSRSPSDV

SEQ ID No:37

Nucleotide sequence of HA tagged hGPR3

ATGTACCCATACGACGTACCTGATTACGCAGCAGCAGCAGCAATGATGTGGGGTGCAGGCAGCCCTCTGGCCTGGCTCTCAG
CTGGCTCAGGCAACGTGAATGTAAGCAGCGTGGGCCCAGCAGAGGGGCCCACAGGTCCAGCCGCACCACTGCCCTCGCCTAA
GGCCTGGGATGTGGTGCTCTGCATCTCAGGCACCCTGGTGTCCTGCGAGAATGCGCTAGTGGTGGCCATCATCGTGGGCACT
CCTGCCTTCCGTGCCCCCATGTTCCTGCTGGTGGGCAGCCTGGCCGTGGCAGACCTGCTGGCAGGCCTGGGCCTGGTCCTGC
ACTTTGCTGCTGTCTTCTGCATCGGCTCAGCGGAGATGAGCCTGGTGCTGGTTGCGTGCTGGCAATGGCCTTTACCGCCAG
CATCGGCAGTCTACTGGCCATCACTGTCGACCGCTACCTTTCTCTGTACAATGCCCTCACCTACTATTCAGAGACAACAGTG
ACACGGACCTATGTGATGCTGGCCTTAGTGTGGGGAGGTGCCCTGGGCCTGGGGCTGCTGCCTGTGCTGGCCTGGAACTGCC
TGGATGGCCTGACCACATGTGGCGTGGTTTATCCACTCTCCAAGAACCATCTGGTAGTTCTGGCCATTGCCTTCTTCATGGT
GTTTGGCATCATGCTGCAGCTCTACGCCCAAATCTGCCGCATCGTCTGCCGCCATGCCCAGCAGATTGCCCTTCAGCGGCAC
CTGCTGCCTGCCTCCCACTATGTGGCCACCCGCAAGGGCATTGCCACACTGGCCGTGGTGCTTGGAGCCTTTGCCGCCTGCT
GGTTGCCCTTCACTGTCTACTGCCTGCTGGGTGATGCCCACTCTCCACCTCTCTACACCTATCTTACCTTGCTCCCTGCCAC
CTACAACTCCATGATCAACCCTATCATCTACGCCTTCCGCAACCAGGATGTGCAGAAAGTGCTGTGGGCTGTCTGCTGCTGC
TGTTCCTCTTCCAAGATCCCCTTCCGATCCCGCTCCCCAGTGATGTCTAG

SEQ ID No:38

Figure 3C

Amino Acid sequence of the hGPR3- Enhanced Receptor

```
MMWGAGSPLAWLSAGSGNVNVSSVGPAEGPTGPAAPLPSPKAWDVVLCISGTLVSCENALVVAIIVGTPAFRAPMFLLVG
SLAVADLLAGLGLVLHFAAVFCIGSAEMSLVLVGVLAMAFTASIGSLLAITVDRYLSLYNALTYYSETTVTRTYVMLALV
WGGALCLGLLPVLAWNCLDGLTTCSVVYPLSKNHLVVLAIAFFMVFGIMLQLYAQICRIVCRHAQQIALQRHLLPASHYV
ATRKGIATLAVVLGAFAACWLPFTVYCLLGDAHSPPLYTYLTLLPATYNSMINPIIYAFRNQDVQKVLWAVCCCCAAARG
RTPPSLGPQDESCTTASSSLAKDTSS
```

SEQ ID No:39

Nucleotide sequence of the hGPR3- Enhanced Receptor

```
ATGATGTGGGGTGCAGGCAGCCCTCTGGCCTGGCTCTCAGCTGGCTCAGGCAACGTGAATGTAAGCAGCGTGGGCCCAGC
AGAGGGGCCCACAGGTCCAGCCGCACCACTGCCCTCGCCTAAGGCCTGGGATGTGGTGCTCTGCATCTCAGGCACCCTGG
TGTCCTGCGAGAATGCGCTAGTGGTGGCCATCATCGTGGGCACTCCTGCCTTCCGTGCCCCCATGTTCCTGCTGGTGGGC
AGCCTGGCCGTGGCAGACCTGCTGGCAGGCCTGGGCCTGGTCCTGCACTTTGCTGCTGTCTTCTGCATCGGCTCAGCGGA
GATGAGCCTGGTGCTGGTTGGCGTGCTGGCAATGGCCTTTACYGCCAGCATCGGCAGTCTACTGGCCATCACTGTCGACC
GCTACCTTTCTCTGTACAATGCCCTCACCTACTATTCAGAGACAACAGTGACACGGACCTATGTGATGCTGGCCTTAGTG
TGGGGAGGTGCCCTGGGCCTGGGGCTGCTGCCTGTGCTGGCCTGGAACTGCCTGGATGGCCTGACCACATGTGGCGTGGT
TTATCCACTCTCCAAGAACCATCTGGTAGTTCTGGCCATTGCCTTCTTCATGGTGTTTGGCATCATGCTGCAGCTCTACG
CCCAAATCTGCCGCATCGTCTGCCGCCATGCCCAGCAGATTGCCCTTCAGCGGCACCTGCTGCCTGCCTCCCACTATGTG
GCCACCCGCAAGGGCATTGCCACACTGGCCGTGGTGCTTGGAGCCTTTGCCGCCTGCTGGTTGCCCTTCACTGTCTACTG
CCTGCTGGGTGATGCCCACTCTCCACCTCTCTACACCTATCTTACCTTGCTCCCTGCCACCTACAACTCCATGATCAACC
CTATCATCTACGCCTTCCGCAACCAGGATGTGCAGAAAGTGCTGTGGGCTGTCTGCTGCTGCTGTGCGGCCGCACGGGGA
CGCACCCCACCCAGCCTGGGTCCCCAAGATGAGTCCTGCACCACCGCCAGcTCCTCCCTGGCCAAGGACACTTCATCGTG
A
```

SEQ ID No:40

Figure 3D

Amino Acid sequence of the HA tagged hGPR3- Enhanced Receptor

MYPYDVPDYAAAAAMMWGAGSPLAWLSAGSGNVNVSSVGPAEGPTGPAAPLPSPKAWDVVLCISGTLVSCENALVVAIIV
GTPAFRAPMFLLVGSLAVADLLAGLGLVLHFAAVFCIGSAEMSLVLVGVLAMAFTASIGSLLAITVDRYLSLYNALTYYS
ETTVTRTYVMLALVWGGALGLGLLPVLAWNCLDGLTTCGVVYPLSKNHLVVLAIAFFMVFGIMLQLYAQICRIVCRHAQQ
IALQRHLLPASHYVATRKGIATLAVVLGAFAACWLPFTVYCLLGDAHSPPLYTYLTLLPATYNSMINPIIYAFRNQDVQK
VLWAVCCCCAAARGRTPPSLGPQDESCTTASSSLAKDTSS
SEQ ID No:41

Nucleotide sequence of the HA tagged hGPR3- Enhanced Receptor

ATGTACCCATACGACGTACCTGATTACGCAGCAGCAGCAGCAATGATGTGGGGTGCAGGCAGCCCTCTGGCCTGGCTCTC
AGCTGGCTCAGGCAACGTGAATGTAAGCAGCGTGGGCCCAGCAGAGGGGCCCACAGGTCCAGCCGCACCACTGCCCTCGC
CTAAGGCCTGGGATGTGGTGCTCTGCATCTCAGGCACCCTGGTGTCCTGCGAGAATGCGCTAGTGGTGGCCATCATCGTG
GGCACTCCTGCCTTCCGTGCCCCCATGTTCCTGCTGGTGGGCAGCCTGGCCGTGGCAGACCTGCTGGCAGGCCTGGGCCT
GGTCCTGCACTTTGCTGCTGTCTTCTGCATCGGCTCAGCGGAGATGAGCCTGGTGCTGGTTGGCGTGCTGGCAATGGCCT
TTACTGCCAGCATCGGCAGTCTACTGGCCATCACTGTCGACCGCTACCTTTCTCTGTACAATGCCCTCACCTACTATTCA
GAGACAACAGTGACACGGACCTATGTGATGCTGGCCTTAGTGTGGGGAGGTGCCCTGGGCCTGGGGCTGCTGCCTGTGCT
GGCCTGGAACTGCCTGGATGGCCTGACCACATGTGGCGTGGTTTATCCACTCTCCAAGAACCATCTGGTAGTTCTGGCCA
TTGCCTTCTTCATGGTGTTTGGCATCATGCTGCAGCTCTACGCCCAAATCTGCCGCATCGTCTGCCGCCATGCCCAGCAG
ATTGCCCTTCAGCGGCACCTGCTGCCTGCCTCCCACTATGTGGCCACCCGCAAGGGCATTGCCACACTGGCCGTGGTGCT
TGGAGCCTTTGCCGCCTGCTGGTTGCCCTTCACTGTCTACTGCCTGCTGGGTGATGCCCACTCTCCACCTCTCTACACCT
ATCTTACCTTGCTCCCTGCCACCTACAACTCCATGATCAACCCTATCATCTACGCCTTCCGCAACCAGGATGTGCAGAAA
GTGCTGTGGGCTGTCTGCTGCTGCTGTGCGGCCGCACGGGGACGCACCCCACCCAGCCTGGGTCCCCAAGATGAGTCCTG
CACCACCGCCAGCTCCTCCCTGGCCAAGGACACTTCATCGTGA
SEQ ID No:42

Figure 3E
Amino Acid sequence of the wild-type hGPR6 ACCESSION NP_005275

MNASAASLNDSQVVVVAAEGAAAAATAAGGPDTGEWGPPAAAALGAGGGANGSLELSSQLSAGPPGLLLPAVNPWDVLLC
VSGTVIAGENALVVALIASTPALRTPMFVLVGSLATADLLAGCGLILHFVFQYLVPSETVSLLTVGFLVASFAASVSSLL
AITVDRYLSLYNALTYYSRRTLLGVHLLLAATWTVSLGLGLLPVLGWNCLAERAACSVVRPLARSHVALLSAAFFMVFGI
MLHLYVRICQVVWRHAHQIALQQHCLAPPHLAATRKGVGTLAVVLGTFGASWLPFAIYCVVGSHEDPAVYTYATLLPATY
NSMINPIIYAFRNQEIQRALWLLLCGCFQSKVPFRSRSPSEV

SEQ ID No:43

Nucleotide sequence of the wild-type hGPR6 ACCESSION NM_005284

ATGAACGCGAGCGCCGCCTCGCTCAACGACTCCCAGGTGGTGGTAGTGGCGGCCGAAGGAGCGGCGGCGGCGGCCACAGC
AGCAGGGGGGCCGGACACGGGCGAATGGGGACCCCCTGCTGCGGCGGCTCTAGGAGCCGGCGGCGGAGCTAATGGGTCTC
TGGAGCTGTCCTCGCAGCTGTCGGCTGGGCCACCGGGACTCCTGCTGCCAGCGGTGAATCCGTGGGACGTGCTCCTGTGC
GTGTCGGGGACAGTGATCGCTGGAGAAAACGCGCTGGTGGTGGCGCTCATCGCGTCCACTCCGGCGCTGCGCACGCCCAT
GTTCGTGCTGGTAGGCAGCCTGGCCACCGCTGACCTGTTGGCGGGCTGTGGCCTCATCTTGCACTTTGTGTTCCAGTACT
TGGTGCCCTCGGAGACTGTGAGTCTGCTCACGGTGGGCTTCCTCGTGGCCTCCTTCGCCGCCTCTGTCAGCAGCCTGCTG
GCCATTACGGTGGACCGCTACCTGTCCCTGTATAACGCGCTCACCTATTACTCGCGCCGGACCCTGTTGGGCGTGCACCT
CCTGCTTGCCGCCACTTGGACCGTGTCCCTAGGCCTGGGCTGCTGCCCGTGCTGGGCTGGAACTGCCTGGCAGAGCGCG
CCGCCTGCAGCGTGGTGCGCCCGCTGGCGCGCAGCCACGTGGCTCTGCTCTCCGCCGCCTTCTTCATGGTCTTCGGCATC
ATGCTGCACCTGTACGTGCGCATCTGCCAGGTGGTCTGGCGCCACGCGCACCAGATCGCGCTGCAGCAGCACTGCCTGGC
GCCACCCCATCTCGCTGCCACCAGAAAGGGTGTGGGTACACTGGCTGTGGTGCTGGGCACTTTCGGCGCCAGCTGGCTGC
CCTTCGCCATCTATTGCGTGGTGGGCAGCCATGAGGACCCGGCGGTCTACACTTACGCCACCCTGCTGCCCGCCACCTAC
AACTCCATGATCAATCCCATCATCTATGCCTTCCGCAACCAGGAGATCCAGCGCGCCCTGTGGCTCCTGCTCTGTGGCTG
TTTCCAGTCCAAAGTGCCCTTTCGTTCCAGGTCTCCCAGCGAGGTCTGA

SEQ ID No:44

Figure 3F

Amino Acid sequence of the HA tagged wild-type hGPR6

MYPYDVPDYAAAAAMNASAASLNDSQVVVVAAEGAAAAATAAGGPDTGEWGPPAAAALGAGGGANGSLELSSQLSAGPPGL
LLPAVNPWDVLLCVSGTVIAGENALVVALIASTPALRTPMFVLVGSLATADLLAGCGLILHFVFQYLVPSETVSLLTVGFL
VASFAASVSSLLAITVDRYLSLYNALTYYSRRTLLGVHLLLAATWTVSLGLGLLPVLGWNCLAERAACSVVRPLARSHVAL
LSAAFFMVFGIMLHLYVRICQVVWRHAHQIALQQHCLAPPHLAATRKGVGTLAVVLGTFGASWLPFAIYCVVGSHEDPAVY
TYATLLPATYNSMINPIIYAFRNQEIQRALWLLLCGCFQSKVPFRSRSPSEV

SEQ ID No:45

Nucleotide sequence of the HA tagged wild-type hGPR6

ATGTACCCATACGACGTACCTGATTACGCAGCAGCAGCAGCAATGAACGCGAGCGCCGCCTCGCTCAACGACTCCCAGGTGGT
GGTAGTGGCGGCCGAAGGAGCGGCGGCGGCCACAGCAGCAGGGGGGCCGGACACGGGCGAATGGGGACCCCCTGCTGCGG
CGGCTCTAGGAGCCGGCGGCGGAGCTAATGGGTCTCTGGAGCTGTCCTCGCAGCTGTCGGCTGGGCCACCGGGACTCCTGCTG
CCAGCGGTGAATCCGTGGGACGTGCTCCTGTGCGTGTCGGGGACAGTGATCGCTGGAGAAAACGCGCTGGTGGTGGCGCTCAT
CGCGTCCACTCCGGCGCTGCGCACGCCCATGTTCGTGCTGGTAGGCAGCCTGGCCACCGCTGACCTGTTGGCGGGCTGTGGCC
TCATCTTGCACTTTGTGTTCCAGTACTTGGTGCCCTCGGAGACTGTGAGTCTGCTCACGGTGGGCTTCCTCGTGGCCTCCTTC
GCCGCCTCTGTCAGCAGCCTGCTGGCCATTACGGTGGACCGCTACCTGTCCCTGTATAACGCGCTCACCTATTACTCGCGCCG
GACCCTGTTGGGCGTGCACCTCCTGCTTGCCGCCACTTGGACCGTGTCCCTAGGCCTGGGGCTGCTGCCCGTGCTGGGCTGGA
ACTGCCTGGCAGAGCGCGCCGCCTGCAGCGTGGTGCGCCCGCTGGCGCGCAGCCACGTGGCTCTGCTCTCCGCCGCCTTCTTC
ATGGTCTTCGGCATCATGCTGCACCTGTACGTGCGCATCTGCCAGGTGGTCTGGCGCCACGCGCACCAGATCGCGCTGCAGCA
GCACTGCCTGGCGCCACCCCATCTCGCTGCCACCAGAAAGGGTGTGGGTACACTGGCTGTGGTGCTGGGCACTTTCGGCGCCA
GCTGGCTGCCCTTCGCCATCTATTGCGTGGTGGGCAGCCATGAGGACCCGGCGGTCTACACTTACGCCACCCTGCTGCCCGCC
ACCTACAACTCCATGATCAATCCCATCATCTATGCCTTCCGCAACCAGGAGATCCAGCGCGCCCTGTGGCTCCTGCTCTGTGG
CTGTTTCCAGTCCAAAGTGCCCTTTCGTTCCAGGTCTCCCAGCGAGGTCTGA

SEQ ID No:46

Figure 3G

Amino Acid sequence of the hGPR6- Enhanced Receptor

MNASAASLNDSQVVVVAAEGAAAAATAAGGPDTGEWGPPAAAALGAGGGANGSLELSSQLSAGPPGLLLPAVNPWDVLLC
VSGTVIAGENALVVALIASTPALRTPMFVLVGSLATADLLAGCGLILHFVFQYLVPSETVSLLTVGFLVASFAASVSSLL
AITVDRYLSLYNALTYYSRRTLLGVHLLLAATWTVSLGLGLLPVLGWNCLAERAACSVVRPLARSHVALLSAAFFMVFGI
MLHLYVRICQVVWRHAHQIALQQHCLAPPHLAATRKGVGTLAVVLGTFGASWLPFAIYCVVGSHEDPAVYTYATLLPATY
NSMINPIIYAFRNQEIQRALWLLLCGCAAARGRTPPSLGPQDESCTTASSSLAKDTSS

SEQ ID No:47

Nucleotide sequence of the hGPR6- Enhanced Receptor

ATGAACGCGAGCGCCGCCTCGCTCAACGACTCCCAGGTGGTGGTAGTGGCGGCCGAAGGAGCGGCGGCGGCGGCCACAGC
AGCAGGGGGGCCGGACACGGGCGAATGGGGACCCCCTGCTGCGGCGGCTCTAGGAGCCGGCGGCGGAGCTAATGGGTCTC
TGGAGCTGTCCTCGCAGCTGTCGGCTGGGCCACCGGGACTCCTGCTGCCAGCGGTGAATCCGTGGGACGTGCTCCTGTGC
GTGTCGGGGACAGTGATCGCTGGAGAAAACGCGCTGGTGGTGGCGCTCATCGCGTCCACTCCGGCGCTGCGCACGCCCAT
GTTCGTGCTGGTAGGCAGCCTGGCCACCGCTGACCTGTTGGCGGGCTGTGGCCTCATCTTGCACTTTGTGTTCCAGTACT
TGGTGCCCTCGGAGACTGTGAGTCTGCTCACGGTGGGCTTCCTCGTGGCCTCCTTCGCCGCCTCTGTCAGCAGCCTGCTG
GCCATTACGGTGGACCGCTACCTGTCCCTGTATAACGCGCTCACCTATTACTCGCGCCGGACCCTGTTGGGCGTGCACCT
CCTGCTTGCCGCCACTTGGACCGTGTCCCTAGGCCTGGGGCTGCTGCCCGTGCTGGGCTGGAACTGCCTGGCAGAGCGCG
CCGCCTGCAGCGTGGTGCGCCCGCTGGCGCGCAGCCACGTGGCTCTGCTCTCCGCCGCCTTCTTCATGGTCTTCGGCATC
ATGCTGCACCTGTACGTGCGCATCTGCCAGGTGGTCTGGCGCCACGCGCACCAGATCGCGCTGCAGCAGCACTGCCTGGC
GCCACCCCATCTCGCTGCCACCAGAAAGGGTGTGGGTACACTGGCTGTGGTGCTGGGCACTTTCGGCGCCAGCTGGCTGC
CCTTCGCCATCTATTGCGTGGTGGGCAGCCATGAGGACCCGGCGGTCTACACTTACGCCACCCTGCTGCCCGCCACCTAC
AACTCCATGATCAATCCCATCATCTATGCCTTCCGCAACCAGGAGATCCAGCGCGCCCTGTGGCTCCTGCTCTGTGGCTG
TGCGGCCGCACGGGGACGCACCCCACCCAGCCTGGGTCCCCAAGATGAGTCCTGCACCACCGCCAGCTCCTCCCTGGCCA
AGGACACTTCATCGTGA

SEQ ID No:48

Figure 3H

Amino Acid sequence of the HA tagged hGPR6- Enhanced Receptor

MYPYDVPDYAAAAAMNASAASLNDSQVVVVAAEGAAAAATAAGGPDTGEWGPPAAAALGAGGGANGSLELSSQLSAGPPG
LLLPAVNPWDVLLCVSGTVIAGENALVVALIASTPALRTPMFVLVGSLATADLLAGCGLILHFVFQYLVPSETVSLLTVG
FLVASFAASVSSLLAITVDRYLSLYNALTYYSRRTLLGVHLLLAATWTVSLGLGLLPVLGWNCLAERAACSVVRPLARSH
VALLSAAFFMVFGIMLHLYVRICQVVWRHAHQIALQQHCLAPPHLAATRKGVGTLAVVLGTFGASWLPFAIYCVVGSHED
PAVYTYATLLPATYNSMINPIIYAFRNQEIQRALWLLLCGCAAARGRTPPSLGPQDESCTTASSSLAKDTSS

SEQ ID No:49

Nucleotide sequence of the HA tagged hGPR6- Enhanced Receptor

ATGTACCCATACGACGTACCTGATTACGCAGCAGCAGCAATGAACGCGAGCGCCGCCTCGCTCAACGACTCCCAGGT
GGTGGTAGTGGCGGCCGAAGGAGCGGCGGCGGCCACAGCAGCAGGGGGCCGGACACGGGCGAATGGGGACCCCCTG
CTGCGGCGGCTCTAGGAGCCGGCGGCGGAGCTAATGGGTCTCTGGAGCTGTCCTCGCAGCTGTCGGCTGGGCCACCGGGA
CTCCTGCTGCCAGCGGTGAATCCGTGGGACGTGCTCCTGTGCGTGTCGGGGACAGTGATCGCTGGAGAAAACGCGCTGGT
GGTGGCGCTCATCGCGTCCACTCCGGCGCTGCGCACGCCCATGTTCGTGCTGGTAGGCAGCCTGGCCACCGCTGACCTGT
TGGCGGGCTGTGGCCTCATCTTGCACTTTGTGTTCCAGTACTTGGTGCCCTCGGAGACTGTGAGTCTGCTCACGGTGGGC
TTCCTCGTGGCCTCCTTCGCCGCCTCTGTCAGCAGCCTGCTGGCCATTACGGTGGACCGCTACCTGTCCCTGTATAACGC
GCTCACCTATTACTCGCGCCGGACCCTGTTGGGCGTGCACCTCCTGCTTGCCGCCACTTGGACCGTGTCCCTAGGCCTGG
GGCTGCTGCCCGTGCTGGGCTGGAACTGCCTGGCAGAGCGCGCCGCCTGCAGCGTGGTGCGCCCGCTGGCGCGCAGCCAC
GTGGCTCTGCTCTCCGCCGCCTTCTTCATGGTCTTCGGCATCATGCTGCACCTGTACGTGCGCATCTGCCAGGTGGTCTG
GCGCCACGCGCACCAGATCGCGCTGCAGCAGCACTGCCTGGCGCCACCCCATCTCGCTGCCACCAGAAAGGGTGTGGGTA
CACTGGCTGTGGTGCTGGGCACTTTCGGCGCCAGCTGGCTGCCCTTCGCCATCTATTGCGTGGTGGGCAGCCATGAGGAC
CCGGCGGTCTACACTTACGCCACCCTGCTGCCCGCCACCTACAACTCCATGATCAATCCCATCATCTATGCCTTCCGCAA
CCAGGAGATCCAGCGCGCCCTGTGGCTCCTGCTCTGTGGCTGTGCGGCCGCACGGGGACGCACCCCACCCAGCCTGGGTC
CCCAAGATGAGTCCTGCACCACCGCCAGCTCCTCCCTGGCCAAGGACACTTCATCGTGA

SEQ ID No:50

Figure 3I

Amino Acid sequence of the wild-type hGPR12 ACCESSION NP_005279

```
MNEDLKVNLSGLPRDYLDAAAAENISAAVSSRVPAVEPEPELVVNPWDIVLCTSGTLISCENAIVVLIIFHNPSLRAPMF
LLIGSLALADLLAGIGLITNFVFAYLLQSEATKLVTIGLIVASFSASVCSLLAITVDRYLSLYYALTYHSERTVTFTYVM
LVMLWGTSICLGLLPVMGWNCLRDESTCSVVRPLTKNNAAILSVSFLFMFALMLQLYIQICKIVMRHAHQIALQHHFLAT
SHYVTTRKGVSTLAIILGTFAACWMPFTLYSLIADYTYPSIYTYATLLPATYNSIINPVIYAFRNQEIQKALCLICCGCI
PSSLAQRARSPSDV
```
SEQ ID No:51

Nucleotide sequence of the wild-type hGPR12 ACCESSION NM_005288

```
ATGAATGAAGACCTGAAGGTCAATTTAAGCGGGCTGCCTCGGGATTATTTAGATGCCGCTGCTGCGGAGAACATCTCGGC
TGCTGTCTCCTCCCGGGTTCCTGCCGTAGAGCCAGAGCCTGAGCTCGTAGTCAACCCCTGGGACATTGTCTTGTGTACCT
CGGGAACCCTCATCTCCTGTGAAAATGCCATTGTGGTCCTTATCATCTTCCACAACCCCAGCCTGCGAGCACCCATGTTC
CTGCTAATAGGCAGCCTGGCTCTTGCAGACCTGCTGGCCGGCATTGGACTCATCACCAATTTTGTTTTTGCCTACCTGCT
TCAGTCAGAAGCCACCAAGCTGGTCACGATCGGCCTCATTGTCGCCTCTTTCTCTGCCTCTGTCTGCAGCTTGCTGGCTA
TCACTGTTGACCGCTACCTCTCACTGTACTACGCTCTGACGTACCATTCGGAGAGGACGGTCACGTTTACCTATGTCATG
CTCGTCATGCTCTGGGGACCTCCATCTGCCTGGGGCTGCTGCCCGTCATGGGCTGGAACTGCCTCCGAGACGAGTCCAC
CTGCAGCGTGGTCAGACCGCTCACCAAGAACAACGCGGCCATCCTCTCGGTGTCCTTCCTCTTCATGTTTGCGCTCATGC
TTCAGCTCTACATCCAGATCTGTAAGATTGTGATGAGGCACGCCCATCAGATAGCCCTGCAGCACCACTTCCTGGCCACG
TCGCACTATGTGACCACCCGGAAAGGGGTCTCCACCCTGGCTATCATCCTGGGGACGTTTGCTGCTTGCTGGATGCCTTT
CACCCTCTATTCCTTGATAGCGGATTACACCTACCCCTCCATCTATACCTACGCCACCCTCCTGCCCGCCACCTACAATT
CCATCATCAACCCTGTCATATATGCTTTCAGAAACCAAGAGATCCAGAAAGCGCTCTGTCTCATTTGCTGCGGCTGCATC
CCGTCCAGTCTCGCCCAGAGAGCGCGCTCGCCCAGTGATGTGTAG
```
SEQ ID No:52

Figure 3J

Amino Acid sequence of the HA tagged wild-type hGPR12

MYPYDVPDYAAAAAMNEDLKVNLSGLPRDYLDAAAAENISAAVSSRVPAVEPEPELVVNPWDIVLCTSGTLISCENAIVVLI
IFHNPSLRAPMFLLIGSLALADLLAGIGLITNFVFAYLLQSEATKLVTIGLIVASFSASVCSLLAITVDRYLSLYYALTYHS
ERTVTFTYVMLVMLWGTSICLGLLPVMGWNCLRDESTCSVVRPLTKNNAAILSVSFLFMFALMLQLYIQICKIVMRHAHQIA
LQHHFLATSHYVTTRKGVSTLAIILGTFAACWMPFTLYSLIADYTYPSIYTYATLLPATYNSIINPVIYAFRNQEIQKALCL
ICCGCIPSSLAQRARSPSDV

SEQ ID No:53

Nucleotide sequence of the HA tagged wild-type hGPR12

ATGTACCCATACGACGTACCTGATTACGCAGCAGCAGCAGCAATGAATGAAGACCTGAAGGTCAATTTAAGCGGGCTGCCT
CGGGATTATTTAGATGCCGCTGCTGCGGAGAACATCTCGGCTGCTGTCTCCTCCCGGGTTCCTGCCGTAGAGCCAGAGCCT
GAGCTCGTAGTCAACCCCTGGGACATTGTCTTGTGTACCTCGGGAACCCTCATCTCCTGTGAAAATGCCATTGTGGTCCTT
ATCATCTTCCACAACCCCAGCCTGCGAGCACCCATGTTCCTGCTAATAGGCAGCCTGGCTCTTGCAGACCTGCTGGCCGGC
ATTGGACTCATCACCAATTTTGTTTTTGCCTACCTGCTTCAGTCAGAAGCCACCAAGCTGGTCACGATCGGCCTCATTGTC
GCCTCTTTCTCTGCCTCTGTCTGCAGCTTGCTGGCTATCACTGTTGACCGCTACCTCTCACTGTACTACGCTCTGACGTAC
CATTCGGAGAGGACGGTCACGTTTACCTATGTCATGCTCGTCATGCTCTGGGGGACCTCCATCTGCCTGGGGCTGCTGCCC
GTCATGGGCTGGAACTGCCTCCGAGACGAGTCCACCTGCAGCGTGGTCAGACCGCTCACCAAGAACAACGCGGCCATCCTC
TCGGTGTCCTTCCTCTTCATGTTTGCGCTCATGCTTCAGCTCTACATCCAGATCTGTAAGATTGTGATGAGGCACGCCCAT
CAGATAGCCCTGCAGCACCACTTCCTGGCCACGTCGCACTATGTGACCACCCGGAAAGGGGTCTCCACCCTGGCTATCATC
CTGGGGACGTTTGCTGCTTGCTGGATGCCTTTCACCCTCTATTCCTTGATAGCGGATTACACCTACCCCTCCATCTATACC
TACGCCACCCTCCTGCCCGCCACCTACAATTCCATCATCAACCCTGTCATATATGCTTTCAGAAACCAAGAGATCCAGAAA
GCGCTCTGTCTCATTTGCTGCGGCTGCATCCCGTCCAGTCTCGCCCAGAGAGCGCGCTCGCCCAGTGATGTGTAG

SEQ ID No:54

Figure 3K

Amino Acid sequence of the hGPR12- Enhanced Receptor

MNEDLKVNLSGLPRDYLDAAAAENISAAVSSRVPAVEPEPELVVNPWDIVLCTSGTLISCENAIVVLIIFHNPSLRAPMF
LLIGSLALADLLAGIGLITNFVFAYLLQSEATKLVTIGLIVASFSASVCSLLAITVDRYLSLYYALTYHSERTVTFTYVM
LVMLWGTSICLGLLPVMGWNCLRDESTCSVVRPLTKNNAAILSVSFLFMFALMLQLYIQICKIVMRHAHQIALQHHFLAT
SHYVTTRKGVSTLAIILGTFAACWMPFTLYSLIADYTYPSIYTYATLLPATYNSIINPVIYAFRNQEIQKALCLICCGCA
AARGRTPPSLGPQDESCTTASSSLAKDTSS

SEQ ID No:55

Nucleotide sequence of the hGPR12- Enhanced Receptor

ATGAATGAAGACCTGAAGGTCAATTTAAGCGGGCTGCCTCGGGATTATTTAGATGCCGCTGCTGCGGAGAACATCTCGGC
TGCTGTCTCCTCCCGGGTTCCTGCCGTAGAGCCAGAGCCTGAGCTCGTAGTCAACCCCTGGGACATTGTCTTGTGTACCT
CGGGAACCCTCATCTCCTGTGAAAATGCCATTGTGGTCCTTATCATCTTCCACAACCCCAGCCTGCGAGCACCCATGTTC
CTGCTAATAGGCAGCCTGGCTCTTGCAGACCTGCTGGCCGGCATTGGACTCATCACCAATTTTGTTTTTGCCTACCTGCT
TCAGTCAGAAGCCACCAAGCTGGTCACGATCGGCCTCATTGTCGCCTCTTTCTCTGCCTCTGTCTGCAGCTTGCTGGCTA
TCACTGTTGACCGCTACCTCTCACTGTACTACGCTCTGACGTACCATTCGGAGAGGACGGTCACGTTTACCTATGTCATG
CTCGTCATGCTCTGGGGGACCTCCATCTGCCTGGGGCTGCTGCCCGTCATGGGCTGGAACTGCCTCCGAGACGAGTCCAC
CTGCAGCGTGGTCAGACCGCTCACCAAGAACAACGCGGCCATCCTCTCGGTGTCCTTCCTCTTCATGTTTGCGCTCATGC
TTCAGCTCTACATCCAGATCTGTAAGATTGTGATGAGGCACGCCCATCAGATAGCCCTGCAGCACCACTTCCTGGCCACG
TCGCACTATGTGACCACCCGGAAAGGGGTCTCCACCCTGGCTATCATCCTGGGGACGTTTGCTGCTTGCTGGATGCCTTT
CACCCTCTATTCCTTGATAGCGGATTACACCTACCCCTCCATCTATACCTACGCCACCCTCCTGCCCGCCACCTACAATT
CCATCATCAACCCTGTCATATATGCTTTCAGAAACCAAGAGATCCAGAAAGCGCTCTGTCTCATTTGCTGCGGCTGCGCG
GCCGCACGGGGACGCACCCCACCCAGCCTGGGTCCCCAAGATGAGTCCTGCACCACCGCCAGCTCCTCCCTGGCCAAGGA
CACTTCATCGTGA

SEQ ID No:56

Figure 3L
Amino Acid sequence of the HA tagged hGPR12- Enhanced Receptor

MYPYDVPDYAAAAAMNEDLKVNLSGLPRDYLDAAAAENISAAVSSRVPAVEPEPELVVNPWDIVLCTSGTLISCENAIVV
LIIFHNPSLRAPMFLLIGSLALADLLAGIGLITNFVFAYLLQSEATKLVTIGLIVASFSASVCSLLAITVDRYLSLYYAL
TYHSERTVTFTYVMLVMLWGTSICLGLLPVMGWNCLRDESTCSVVRPLTKNNAAILSVSFLFMFALMLQLYIQICKIVMR
HAHQIALQHHFLATSHYVTTRKGVSTLAIILGTFAACWMPFTLYSLIADYTYPSIYTYATLLPATYNSIINPVIYAFRNQ
EIQKALCLICCGCAAARGRTPPSLGPQDESCTTASSSLAKDTSS
SEQ ID No:57

Nucleotide sequence of the HA tagged hGPR12-Enhanced Receptor

ATGTACCCATACGACGTACCTGATTACGCAGCAGCAGCAGCAATGAATGAAGACCTGAAGGTCAATTTAAGCGGGCTGCC
TCGGGATTATTTAGATGCCGCTGCTGCGGAGAACATCTCGGCTGCTGTCTCCTCCGGGTTCCTGCCGTAGAGCCAGAGC
CTGAGCTCGTAGtCAACCCCTGGGACATTgTCTTGTGTACCTCGGGAACCCTCATCTCCTGTGAAAATGCCATTGTGGTC
CTTATCATCTTCCACAACCCCAGCCTGCGAGCACCCATGTTCCTGCTAATAGGCAGCCTGGCTCTTGCAGACCTGCTGGC
CGGCATTGGACTCATCACCAATTTTGTTTTTGCCTACCTGCTTCAGTCAGAAGCCACCAAGCTGGTCACGATCGGCCTCA
TTGTCGCCTCTTTCTCTGCCTCTGTCTGCAGCTTGCTGGCTATCACTGTTGACCGCTACCTCTCACTGTACTACGCTCTG
ACGTACCATTCGGAGAGGACGGTCACGTTTACCTATGTCATGCTCGTCATGCTCTGGGGGACCTCCATCTGCCTGGGGCT
GCTGCCCGTCATGGGCTGGAACTGCCTCCGAGACGAGTCCACCTGCAGCGTGGTCAGACCGCTCACCAAGAACAACGCGG
CCATCCTCTCGGTGTCCTTCCTCTTCATGTTTGCGCTCATGCTTCAGCTCTACATCCAGATCTGTAAGATTGTGATGAGG
CACGCCCATCAGATAGCCCTGCAGCACCACTTCCTGGCCACGTCGCACTATGTGACCACCCGGAAAGGGGTCTCCACCCT
GGCTATCATCCTGGGGACGTTTGCTGCTTGCTGGATGCCTTTCACCCTCTATTCCTTGATAGCGGATTACACCTACCCCT
CCATCTATACCtACGCCACCCTCCTGCCCGCCACCTACAATTCCATCATCAACCCTGTCATATATGCTTTCAGAAACCAA
GAGATCCAGAAAGCGCTCTGTCTCATTTGCTGCGGCTGCGCGGCCGCACGGGGACGCACCCCACCCAGCCTGGGTCCCCA
AGATGAGTCCTGCACCACCGCCAGCTCCTCCCTGGCCAAGGACACTTCATCGTGA
SEQ ID No:58

Figure 3M

Amino Acid sequence of the wild-type hSREB3 ACCESSION NP_061842

MANTTGEPEEVSGALSPPSASAYVKLVLLGLIMCVSLAGNAILSLLVLKERALHKAPYYFLLDLCLADGIRSAVCFPFVL
ASVRHGSSWTFSALSCKIVAFMAVLFCFHAAFMLFCISVTRYMAIAHHRFYAKRMTLWTCAAVICMAWTLSVAMAFPPVF
DVGTYKFIREEDQCIFEHRYFKANDTLGFMLMLAVLMAATHAVYGKLLLFEYRHRKMKPVQMVPAISQNWTFHGPGATGQ
AAANWIAGFGRGPMPPTLLGIRQNGHAASRRLLGMDEVKGEKQLGRMFYAITLLFLLLWSPYIVACYWRVFVKACAVPHR
YLATAVWMSFAQAAVNPIVCFLLNKDLKKCLRTHAPCWGTGGAPAPREPYCVM

SEQ ID No:59

Nucleotide sequence of the wild-type hSREB3 ACCESSION NM_018969

ATGGCCAACACTACCGGAGAGCCTGAGGAGGTGAGCGGCGCTCTGTCCCCACCGTCCGCATCAGCTTATGTGAAGCTGGT
ACTGCTGGGACTGATTATGTGCGTGAGCCTGGCGGGTAACGCCATCTTGTCCCTGCTGGTGCTCAAGGAGCGTGCCCTGC
ACAAGGCTCCTTACTACTTCCTGCTGGACCTGTGCCTGGCCGATGGCATACGCTCTGCCGTCTGCTTCCCCTTTGTGCTG
GCTTCTGTGCGCCACGGCTCTTCATGGACCTTCAGTGCACTCAGCTGCAAGATTGTGGCCTTTATGGCCGTGCTCTTTTG
CTTCCATGCGGCCTTCATGCTGTTCTGCATCAGCGTCACCCGCTACATGGCCATCGCCCACCACCGCTTCTACGCCAAGC
GCATGACACTCTGGACATGCGCGGCTGTCATCTGCATGGCCTGGACCCTGTCTGTGGCCATGGCCTTCCCACCTGTCTTT
GACGTGGGCACCTACAAGTTTATTCGGGAGGAGGACCAGTGCATCTTTGAGCATCGCTACTTCAAGGCCAATGACACGCT
GGGCTTCATGCTTATGTTGGCTGTGCTCATGGCAGCTACCCATGCTGTCTACGGCAAGCTGCTCCTCTTCGAGTATCGTC
ACCGCAAGATGAAGCCAGTGCAGATGGTGCCAGCCATCAGCCAGAACTGGACATTCCATGGTCCCGGGGCCACCGGCCAG
GCTGCTGCCAACTGGATCGCCGGCTTTGGCCGTGGGCCCATGCCACCAACCCTGCTGGGTATCCGGCAGAATGGGCATGC
AGCCAGCCGGCGGCTACTGGGCATGGACGAGGTCAAGGGTGAAAAGCAGCTGGGCCGCATGTTCTACGCGATCACACTGC
TCTTTCTGCTCCTCTGGTCACCCTACATCGTGGCCTGCTACTGGCGAGTGTTTGTGAAAGCCTGTGCTGTGCCCCACCGC
TACCTGGCCACTGCTGTTTGGATGAGCTTCGCCCAGGCTGCCGTCAACCCAATTGTCTGCTTCCTGCTCAACAAGGACCT
CAAGAAGTGCCTGAGGACTCACGCCCCTGCTGGGGCACAGGAGGTGCCCCGGCTCCCAGAGAACCCTACTGTGTCATGT
GA

SEQ ID No:60

Figure 3N

Amino Acid sequence of the HA tagged wild-type hSREB3

MYPYDVPDYAAAAAMANTTGEPEEVSGALSPPSASAYVKLVLLGLIMCVSLAGNAILSLLVLKERALHKAPYYFLLDLCLADGIRS
AVCFPFVLASVRHGSSWTFSALSCKIVAFMAVLFCFHAAFMLFCISVTRYMAIAHHRFYAKRMTLWTCAAVICMAWTLSVAMAFPP
VFDVGTYKFIREEDQCIFEHRYFKANDTLGFMLMLAVLMAATHAVYGKLLLFEYRHRKMKPVQMVPAISQNWTFHGPGATGQAAAN
WIAGFGRGPMPPTLLGIRQNGHAASRRLLGMDEVKGEKQLGRMFYAITLLFLLLWSPYIVACYWRVFVKACAVPHRYLATAVWMSF
AQAAVNPIVCFLLNKDLKKCLRTHAPCWGTGGAPAPREPYCVM

SEQ ID No:61

Nucleotide sequence of the HA tagged wild-type hSREB3

ATGTACCCATACGACGTACCTGATTACGCAGCAGCAGCAGCAATGGCCAACACTACCGGAGAGCCTGAGGAGGTGAGCGG
CGCTCTGTCCCCACCGTCCGCATCAGCTTATGTGAAGCTGGTACTGCTGGGACTGATTATGTGCGTGAGCCTGGCGGGTA
ACGCCATCTTGTCCCTGCTGGTGCTCAAGGAGCGTGCCCTGCACAAGGCTCCTTACTACTTCCTGCTGGACCTGTGCCTG
GCCGATGGCATACGCTCTGCCGTCTGCTTCCCCTTTGTGCTGGCTTCTGTGCGCCACGGCTCTTCATGGACCTTCAGTGC
ACTCAGCTGCAAGATTGTGGCCTTTATGGCCGTGCTCTTTTGCTTCCATGCGGCCTTCATGCTGTTCTGCATCAGCGTCA
CCCGCTACATGGCCATCGCCCACCACCGCTTCTACGCCAAGCGCATGACACTCTGGACATGCGCGGCTGTCATCTGCATG
GCCTGGACCCTGTCTGTGGCCATGGCCTTCCCACCTGTCTTTGACGTGGGCACCTACAAGTTTATTCGGGAGGAGGACCA
GTGCATCTTTGAGCATCGCTACTTCAAGGCCAATGACACGCTGGGCTTCATGCTTATGTTGGCTGTGCTCATGGCAGCTA
CCCATGCTGTCTACGGCAAGCTGCTCCTCTTCGAGTATCGTCACCGCAAGATGAAGCCAGTGCAGATGGTGCCAGCCATC
AGCCAGAACTGGACATTCCATGGTCCCGGGGCCACGGCCCAGGCTGCTGCCAACTGGATCGCCGGCTTTGGCCGTGGGCC
CATGCCACCAACCCTGCTGGGTATCCGGCAGAATGGGCATGCAGCCAGCCGGCGGCTACTGGGCATGGACGAGGTCAAGG
GTGAAAAGCAGCTGGCCGCATGTTCTACGCGATCACACTGCTCTTTCTGCTCCTCTGGTCACCCTACATCGTGGCCTGC
TACTGGCGAGTGTTTGTGAAAGCCTGTGCTGTGCCCCACCGCTACCTGGCCACTGCTGTTTGGATGAGCTTCGCCCAGGC
TGCCGTCAACCCAATTGTCTGCTTCCTGCTCAACAAGGACCTCAAGAAGTGCCTGAGGACTCACGCCCCCTGCTGGGGCA
CAGGAGGTGCCCCGGCTCCCAGAGAACCCTACTGTGTCATGTGA

SEQ ID No:62

Figure 30

Amino Acid sequence of the hSREB3- Enhanced Receptor

```
MANTTGEPEEVSGALSPPSASAYVKLVLLGLIMCVSLAGNAILSLLVLKERALHKAPYYFLLDLCLADGIRSAVCFPFVL
ASVRHGSSWTFSALSCKIVAFMAVLFCFHAAFMLFCISVTRYMAIAHHRFYAKRMTLWTCAAVICMAWTLSVAMAFPPVF
DVGTYKFIREEDQCIFEHRYFKANDTLGFMLMLAVLMAATHAVYGKLLLFEYRHRKMKPVQMVPAISQNWTFHGPGATGQ
AAANWIAGFGRGPMPPTLLGIRQNGHAASRRLLGMDEVKGEKQLGRMFYAITLLFLLLWSPYIVACYWRVFVKACAVPHR
YLATAVWMSFAQAAVNPIVCFLLNKDLKKCLRTHAPCAAARGRTPPSLGPQDESCTTASSSLAKDTSS
```
SEQ ID No:63

Nucleotide sequence of the hSREB3- Enhanced Receptor

```
ATGGCCAACACTACCGGAGAGCCTGAGGAGGTGAGCGGCGCTCTGTCCCCACCGTCCGCATCAGCTTATGTGAAGCTGGT
ACTGCTGGGACTGATTATGTGCGTGAGCCTGGCGGGTAACGCCATCTTGTCCCTGCTGGTGCTCAAGGAGCGTGCCCTGC
ACAAGGCTCCTTACTACTTCCTGCTGGACCTGTGCCTGGCCGATGGCATACGCTCTGCCGTCTGCTTCCCCTTTGTGCTG
GCTTCTGTGCGCCACGGCTCTTCATGGACCTTCAGTGCACTCAGCTGCAAGATTGTGGCCTTTATGGCCGTGCTCTTTTG
CTTCCATGCGGCCTTCATGCTGTTCTGCATCAGCGTCACCCGCTACATGGCCATCGCCCACCACCGCTTCTACGCCAAGC
GCATGACACTCTGGACATGCGCGGCTGTCATCTGCATGGCCTGGACCCTGTCTGTGGCCATGGCCTTCCCACCTGTCTTT
GACGTGGGCACCTACAAGTTTATTCGGGAGGAGGACCAGTGCATCTTTGAGCATCGCTACTTCAAGGCCAATGACACGCT
GGGCTTCATGCTTATGTTGGCTGTGCTCATGGCAGCTACCCATGCTGTCTACGGCAAGCTGCTCCTCTTCGAGTATCGTC
ACCGCAAGATGAAGCCAGTGCAGATGGTGCCAGCCATCAGCCAGAACTGGACATTCCATGGTCCCGGGGCCACCGGCCAG
GCTGCTGCCAACTGGATCGCCGGCTTTGGCCGTGGGCCCATGCCACCAACCCTGCTGGGTATCCGGCAGAATGGGCATGC
AGCCAGCCGGCGGCTACTGGGCATGGACGAGGTCAAGGGTGAAAAGCAGCTGGGCCGCATGTTCTACGCGATCACACTGC
TCTTTCTGCTCCTCTGGTCACCCTACATCGTGGCCTGCTACTGGCGAGTGTTTGTGAAAGCCTGTGCTGTGCCCCACCGC
TACCTGGCCACTGCTGTTTGGATGAGCTTCGCCCAGGCTGCCGTCAACCCAATTGTCTGCTTCCTGCTCAACAAGGACCT
CAAGAAGTGCCTGAGGACTCACGCCCCCTGCGCGGCCGCACGGGGACGCACCCCACCCAGCCTGGGTCCCCAAGATGAGT
CCTGCACCACCGCCAGCTCCTCCCTGGCCAAGGACACTTCATCGTGA
```
SEQ ID No:64

Figure 3P

Amino Acid sequence of the HA tagged hSREB3- Enhanced Receptor

```
MYPYDVPDYAAAAAMANTTGEPEEVSGALSPPSASAYVKLVLLGLIMCVSLAGNAILSLLVLKERALHKAPYYFLLDLCLA
DGIRSAVCFPFVLASVRHGSSWTFSALSCKIVAFMAVLFCFHAAFMLFCISVTRYMAIAHHRFYAKRMTLWTCAAVICMAW
TLSVAMAFPPVFDVGTYKFIREEDQCIFEHRYFKANDTLGFMLMLAVLMAATHAVYGKLLLFEYRHRKMKPVQMVPAISQN
WTFHGPGATGQAAANWIAGFGRGPMPPTLLGIRQNGHAASRRLLGMDEVKGEKQLGRMFYAITLLFLLLWSPYIVACYWRV
FVKACAVPHRYLATAVWMSFAQAAVNPIVCFLLNKDLKKCLRTHAPCAAARGRTPPSLGPQDESCTTASSSLAKDTSS
```
SEQ ID No:65

Nucleotide sequence of the HA tagged hSREB3- Enhanced Receptor

```
ATGTACCCATACGACGTACCTGATTACGCAGCAGCAGCAGCAATGGCCAACACTACCGGAGAGCCTGAGGAGGTGAGCGGCG
CTCTGTCCCCACCGTCCGCATCAGCTTATGTGAAGCTGGTACTGCTGGGACTGATTATGTGCGTGAGCCTGGCGGGTAACGC
CATCTTGTCCCTGCTGGTGCTCAAGGAGCGTGCCCTGCACAAGGCTCCTTACTACTTCCTGCTGGACCTGTGCCTGGCCGAT
GGCATACGCTCTGCCGTCTGCTTCCCCTTTGTGCTGGCTTCTGTGCGCCACGGCTCTTCATGGACCTTCAGTGCACTCAGCT
GCAAGATTGTGGCCTTTATGGCCGTGCTCTTTTGCTTCCATGCGGCCTTCATGCTGTTCTGCATCAGCGTCACCCGCTACAT
GGCCATCGCCCACCACCGCTTCTACGCCAAGCGCATGACACTCTGGACATGCGCGGCTGTCATCTGCATGGCCTGGACCCTG
TCTGTGGCCATGGCCTTCCCCACCTGTCTTTGACGTGGGCACCTACAAGTTTATTCGGGAGGAGGACCAGTGCATCTTTGAGC
ATCGCTACTTCAAGGCCAATGACACGCTGGGCTTCATGCTTATGTTGGCTGTGCTCATGGCAGCTACCCATGCTGTCTACGG
CAAGCTGCTCCTCTTCGAGTATCGTCACCGCAAGATGAAGCCAGTGCAGATGGTGCCAGCCATCAGCCAGAACTGGACATTC
CATGGTCCCGGGGCCACCGGCCAGGCTGCTGCCAACTGGATCGCCGGCTTTGGCCGTGGGCCCATGCCACCAACCCTGCTGG
GTATCCGGCAGAATGGGCATGCAGCCAGCCGGCGGCTACTGGGCATGGACGAGGTCAAGGGTGAAAAGCAGCTGGGCCGCAT
GTTCTACGCGATCACACTGCTCTTTCTGCTCCTCTGGTCACCCTACATCGTGGCCTGCTACTGGCGAGTGTTTGTGAAAGCC
TGTGCTGTGCCCCACCGCTACCTGGCCACTGCTGTTTGGATGAGCTTCGCCCAGGCTGCCGTCAACCCAATTGTCTGCTTCC
TGCTCAACAAGGACCTCAAGAAGTGCCTGAGGACTCACGCCCCCTGCGCGGCCGCACGGGGACGCACCCCACCCAGCCTGGG
TCCCCAAGATGAGTCCTGCACCACCGCCAGCTCCTCCCTGGCCAAGGACACTTCATCGTGA
```
SEQ ID No:66

Figure 3Q

Amino Acid sequence of the wild-type hSREB2 ACCESSION NP_061843

```
MANYSHAADNILQNLSPLTAFLKLTSLGFIIGVSVVGNLLISILLVKDKTLHRAPYYFLLDLCCSDILRSAICFPFVFNS
VKNGSTWTYGTLTCKVIAFLGVLSCFHTAFMLFCISVTRYLAIAHHRFYTKRLTFWTCLAVICMVWTLSVAMAFPPVLDV
GTYSFIREEDQCTFQHRSFRANDSLGFMLLLALILLATQLVYLKLIFFVHDRRKMKPVQFVAAVSQNWTFHGPGASGQAA
ANWLAGFGRGPTPPTLLGIRQNANTTGRRRLLVLDEFKMEKRISRMFYIMTFLFLTLWGPYLVACYWRVFARGPVVPGGF
LTAAVWMSFAQAGINPFVCIFSNRELRRCFSTTLLYCRKSRLPREPYCVI
```

SEQ ID No:67

Nucleotide sequence of the wild-type hSREB2 ACCESSION NM_018970

```
ATGGCGAACTATAGCCATGCAGCTGACAACATTTTGCAAAATCTCTCGCCTCTAACAGCCTTTCTGAAACTGACTTCCTT
GGGTTTCATAATAGGAGTCAGCGTGGTGGGCAACCTCCTGATCTCCATTTTGCTAGTGAAAGATAAGACCTTGCATAGAG
CACCTTACTACTTCCTGTTGGATCTTTGCTGTTCAGATATCCTCAGATCTGCAATTTGTTTCCCATTTGTGTTCAACTCT
GTCAAAAATGGCTCTACCTGGACTTATGGGACTCTGACTTGCAAAGTGATTGCCTTTCTGGGGGTTTTGTCCTGTTTCCA
CACTGCTTTCATGCTCTTCTGCATCAGTGTCACCAGATACTTAGCTATCGCCCATCACCGCTTCTATACAAAGAGGCTGA
CCTTTTGGACGTGTCTGGCTGTGATCTGTATGGTGTGGACTCTGTCTGTGGCCATGGCATTTCCCCCGGTTTTAGACGTG
GGCACTTACTCATTCATTAGGGAGGAAGATCAATGCACCTTCCAACACCGCTCCTTCAGGGCTAATGATTCCTTAGGATT
TATGCTGCTTCTTGCTCTCATCCTCCTAGCCACACAGCTTGTCTACCTCAAGCTGATATTTTTCGTCCACGATCGAAGAA
AAATGAAGCCAGTCCAGTTTGTAGCAGCAGTCAGCCAGAACTGGACTTTTCATGGTCCTGGAGCCAGTGGCCAGGCAGCT
GCCAATTGGCTAGCAGGATTTGGAAGGGGTCCCACACCACCCACCTTGCTGGGCATCAGGCAAAATGCAAACACCACAGG
CAGAAGAAGGCTATTGGTCTTAGACGAGTTCAAAATGGAGAAAAGAATCAGCAGAATGTTCTATATAATGACTTTTCTGT
TTCTAACCTTGTGGGGCCCCTACCTGGTGGCCTGTTATGGAGAGTTTTTGCAAGAGGGCCTGTAGTACCAGGGGGATTT
CTAACAGCTGCTGTCTGGATGAGTTTTGCCCAAGCAGGAATCAATCCTTTTGTCTGCATTTTCTCAAACAGGGAGCTGAG
GCGCTGTTTCAGCACAACCCTTCTTTACTGCAGAAAATCCAGGTTACCAAGGGAACCTTACTGTGTTATATGA
```

SEQ ID No:68

Figure 3R

Amino Acid sequence of the HA tagged wild-type hSREB2

MYPYDVPDYAAAAAMANYSHAADNILQNLSPLTAFLKLTSLGFIIGVSVVGNLLISILLVKDKTLHRAPYYFLLDLCCSDI
LRSAICFPFVFNSVKNGSTWTYGTLTCKVIAFLGVLSCFHTAFMLFCISVTRYLAIAHHRFYTKRLTFWTCLAVICMVWTL
SVAMAFPPVLDVGTYSFIREEDQCTFQHRSFRANDSLGFMLLLALILLATQLVYLKLIFFVHDRRKMKPVQFVAAVSQNWT
FHGPGASGQAAANWLAGFGRGPTPPTLLGIRQNANTTGRRRLLVLDEFKMEKRISRMFYIMTFLFLTLWGPYLVACYWRVF
ARGPVVPGGFLTAAVWMSFAQAGINPFVCIFSNRELRRCFSTTLLYCRKSRLPREPYCVI

SEQ ID No:69

Nucleotide sequence of the HA tagged wild-type hSREB2

ATGTACCCATACGACGTACCTGATTACGCAGCAGCAGCAGCAATGGCGAACTATAGCCATGCAGCTGACAACATTTTGCAA
AATCTCTCGCCTCTAACAGCCTTTCTGAAACTGACTTCCTTGGGTTTCATAATAGGAGTCAGCGTGGTGGGCAACCTCCTG
ATCTCCATTTTGCTAGTGAAAGATAAGACCTTGCATAGAGCACCTTACTACTTCCTGTTGGATCTTTGCTGTTCAGATATC
CTCAGATCTGCAATTTGTTTCCCATTTGTGTTCAACTCTGTCAAAAATGGCTCTACCTGGACTTATGGGACTCTGACTTGC
AAAGTGATTGCCTTTCTGGGGGTTTTGTCCTGTTTCCACACTGCTTTCATGCTCTTCTGCATCAGTGTCACCAGATACTTA
GCTATCGCCCATCACCGCTTCTATACAAAGAGGCTGACCTTTTGGACGTGTCTGGCTGTGATCTGTATGGTGTGGACTCTG
TCTGTGGCCATGGCATTTCCCCCGGTTTTAGACGTGGGCACTTACTCATTCATTAGGGAGGAAGATCAATGCACCTTCCAA
CACCGCTCCTTCAGGGCTAATGATTCCTTAGGATTTATGCTGCTTCTTGCTCTCATCCTCCTAGCCACACAGCTTGTCTAC
CTCAAGCTGATATTTTCGTCCACGATCGAAGAAAAATGAAGCCAGTCCAGTTTGTAGCAGCAGTCAGCCAGAACTGGACT
TTTCATGGTCCTGGAGCCAGTGGCCAGGCAGCTGCCAATTGGCTAGCAGGATTGGAAGGGGTCCCACACCACCCACCTTG
CTGGGCATCAGGCAAAATGCAAACACCACAGGCAGAAGAAGGCTATTGGTCTTAGACGAGTTCAAAATGGAGAAAAGAATC
AGCAGAATGTTCTATATAATGACTTTTCTGTTTCTAACCTTGTGGGCCCCTACCTGGTGGCCTGTTATTGGAGAGTTTTT
GCAAGAGGGCCTGTAGTACCGGGGGATTTCTAACAGCTGCTGTCTGGATGAGTTTTGCCCAAGCAGGAATCAATCCTTTT
GTCTGCATTTTCTCAAACAGGGAGCTGAGGCGCTGTTTCAGCACAACCCTTCTTTACTGCAGAAAATCCAGGTTACCAAGG
GAACCTTACTGTGTTATATGA

SEQ ID No:70

Figure 3S
Amino Acid sequence of the hSREB2- Enhanced Receptor

MANYSHAADNILQNLSPLTAFLKLTSLGFIIGVSVVGNLLISILLVKDKTLHRAPYYFLLDLCCSDILRSAICFPFVFNS
VKNGSTWTYGTLTCKVIAFLGVLSCFHTAFMLFCISVTRYLAIAHHRFYTKRLTFWTCLAVICMVWTLSVAMAFPPVLDV
GTYSFIREEDQCTFQHRSFRANDSLGFMLLLALILLATQLVYLKLIFFVHDRRKMKPVQFVAAVSQNWTFHGPGASGQAA
ANWLAGFGRGPTPPTLLGIRQNANTTGRRRLLVLDEFKMEKRISRMFYIMTFLFLTLWGPYLVACYWRVFARGPVVPGGF
LTAAVWMSFAQAGINPFVCIFSNRELRRCFSTTLLYCAAARGRTPPSLGPQDESCTTASSSLAKDTSS

SEQ ID No:71

Nucleotide sequence of the hSREB2- Enhanced Receptor

ATGGCGAACTATAGCCATGCAGCTGACAACATTTTGCAAAATCTCTCGCCTCTAACAGCCTTTCTGAAACTGACTTCCTT
GGGTTTCATAATAGGAGTCAGCGTGGTGGGCAACCTCCTGATCTCCATTTTGCTAGTGAAAGATAAGACCTTGCATAGAG
CACCTTACTACTTCCTGTTGGATCTTTGCTGTTCAGATATCCTCAGATCTGCAATTTGTTTCCCATTTGTGTTCAACTCT
GTCAAAAATGGCTCTACCTGGACTTATGGGACTCTGACTTGCAAAGTGATTGCCTTTCTGGGGGTTTTGTCCTGTTTCCA
CACTGCTTTCATGCTCTTCTGCATCAGTGTCACCAGATACTTAGCTATCGCCCATCACCGCTTCTATACAAAGAGGCTGA
CCTTTTGGACGTGTCTGGCTGTGATCTGTATGGTGTGGACTCTGTCTGTGGCCATGGCATTTCCCCCGGTTTTAGACGTG
GGCACTTACTCATTCATTAGGGAGGAAGATCAATGCACCTTCCAACACCGCTCCTTCAGGGCTAATGATTCCTTAGGATT
TATGCTGCTTCTtGCTCTCATCCTCCTAGCCACCACAGCTTGTCTACCTCAAGCTGATATTTTTCGTCCACGATCGAAGAA
AAATGAAGCCAGTCCAGTTTGTAGCAGCAGTCAGCCAGAACTGGACTTTTCATGGTCCTGGAGCCAGTGGCCAGGCAGCT
GCCAATTGGCTAGCAGGATTTGGAAGGGGTCCCACACCACCCACCTTGCTGGGCATCAGGCAAAATGCAAACACCACAGG
CAGAAGAAGGCTATTGGTCTTAGACGAGTTCAAAATGGAGAAAAGAATCAGCAGAATGTTCTATATAATGACTTTTCTGT
TTCTAACCTTGTGGGGCCCCTACCTGGTGGCCTGTTATTGGAGAGTTTTTGCAAGAGGGCCTGTAGTACCAGGGGGATTT
CTAACAGCTGCTGTCTGGATGAGTTTTGCCCAAGCAGGAATCAATCCTTTTGTCTGCATTTTCTCAAACAGGGAGCTGAG
GCGCTGTTTCAGCACAACCCTTCTTTACTGCGCGGCCGCACGGGACGCACCCCACCCAGCCTGGGTCCCCAAGATGAGT
CCTGCACCACCGCCAGCTCCTCCCTGGCCAAGGACACTTCATCGTGA

SEQ ID No:72

Figure 3T

Amino Acid sequence of the HA tagged hSREB2- Enhanced Receptor

```
MYPYDVPDYAAAAAMANYSHAADNILQNLSPLTAFLKLTSLGFIIGVSVVGNLLISILLVKDKTLHRAPYYFLLDLCCSD
ILRSAICFPFVFNSVKNGSTWTYGTLTCKVIAFLGVLSCFHTAFMLFCISVTRYLAIAHHRFYTKRLTFWTCLAVICMVW
TLSVAMAFPPVLDVGTYSFIREEDQCTFQHRSFRANDSLGFMLLLALILLATQLVYLKLIFFVHDRRKMKPVQFVAAVSQ
NWTFHGPGASGQAAANWLAGFGRGPTPPTLLGIRQNANTTGRRRLLVLDEFKMEKRISRMFYIMTFLFLTLWGPYLVACY
WRVFARGPVVPGGFLTAAVWMSFAQAGINPFVCIFSNRELRRCFSTTLLYCAAARGRTPPSLGPQDESCTTASSSLAKDT
SS
```

SEQ ID No:73

Nucleotide sequence of the HA tagged hSREB2- Enhanced Receptor

```
ATGTACCCATACGACGTACCTGATTACGCAGCAGCAGCAGCAATGGCGAACTATAGCCATGCAGCTGACAACATTTTGCA
AAATCTCTCGCCTCTAACAGCCTTTCTGAAACTGACTTCCTTGGGTTTCATAATAGGAGTCAGCGTGGTGGGCAACCTCC
TGATCTCCATTTTGCTAGTGAAAGATAAGACCTTGCATAGAGCACCTTACTACTTCCTGTTGGATCTTTGCTGTTCAGAT
ATCCTCAGATCTGCAATTTGTTTCCCATTTGTGTTCAACTCTGTCAAAAATGGCTCTACCTGGACTTATGGGACTCTGAC
TTGCAAAGTGATTGCCTTTCTGGGGGTTTTGTCCTGTTTCCACACTGCTTTCATGCTCTTCTGCATCAGTGTCACCAGAT
ACTTAGCTATCGCCCATCACCGCTTCTATACAAAGAGGCTGACCTTTTGGACGTGTCTGGCTGTGATCTGTATGGTGTGG
ACTCTGTCTGTGGCCATGGCATTTCCCCCGGTTTTAGACGTGGGCACTTACTCATTCATTAGGGAGGAAGATCAATGCAC
CTTCCAACACCGCTCCTTCAGGGCTAATGATTCCTTAGGATTTATGCTGCTTCTtGCTCTCATCCTCCTAGCCACACAGC
TTGTCTACCTCAAGCTGATATTTTTCGTCCACGATCGAAGAAAAATGAAGCCAGTCCAGTTTGTAGCAGCAGTCAGCCAG
AACTGGACTTTTCATGGTCCTGGAGCCAGTGGCCAGGCAGCTGCCAATTGGCTAGCAGGATTTGGAAGGGGTCCCACACC
ACCCACCTTGCTGGGCATCAGGCAAAATGCAAACACCACAGGCAGAAGAAGGCTATTGGTCTTAGACGAGTTCAAAATGG
AGAAAAGAATCAGCAGAATGTTCTATATAATGACTTTTCTGTTTCTAACCTTGTGGGGCCCCTACCTGGTGGCCTGTTAT
TGGAGAGTTTTTGCAAGAGGGCCTGTAGTACCAGGGGGATTTCTAACAGCTGCTGTCTGGATGAGTTTTGCCCAAGCAGG
AATCAATCCTTTTGTCTGCATTTTCTCAAACAGGGAGCTGAGGCGCTGTTTCAGCACAACCCTTCTTTACTGCGCGGCCG
CACGGGGACGCACCCCACCCAGCCTGGGTCCCCAAGATGAGTCCTGCACCACCGCCAGCTCCTCCCTGGCCAAGGACACT
TCATCGTGA
```

SEQ ID No:74

Figure 3U

Amino Acid sequence of the wild-type hGPR8 ACCESSION NP_005277.1

```
MQAAGHPEPLDSRGSFSLPTMGANVSQDNGTGHNATFSEPLPFLYVLLPAVYSGICAVGLTGNTAVILVILRAPKMKTVT
NVFILNLAVADGLFTLVLPVNIAEHLLQYWPFGELLCKLVLAVDHYNIFSSIYFLAVMSVDRYLVVLATVRSRHMPWRTY
RGAKVASLCVWLGVTVLVLPFFSFAGVYSNELQVPSCGLSFPWPERVWFKASRVYTLVLGFVLPVCTICVLYTDLLRRLR
AVRLRSGAKALGKARRKVTVLVLVVLAVCLLCWTPFHLASVVALTTDLPQTPLVISMSYVITSLXYANSCLNPFLYAFLD
DNFRKNFRSILRC
```

SEQ ID No:75

Nucleotide sequence of the wild-type hGPR8 ACCESSION NM_ 005286

```
ATGCAGGCCGCTGGGCACCCAGAGCCCCTTGACAGCAGGGGCTCCTTCTCCCTCCCCACGATGGGTGCCAACGTCTCTCA
GGACAATGGCACTGGCCACAATGCCACCTTCTCCGAGCCACTGCCGTTCCTCTATGTGCTCCTGCCCGCCGTGTACTCCG
GGATCTGTGCTGTGGGGCTGACTGGCAACACGGCCGTCATCCTTGTAATCCTAAGGGCGCCCAAGATGAAGACGGTGACC
AACGTGTTCATCCTGAACCTGGCCGTCGCCGACGGGCTCTTCACGCTGGTACTGCCCGTCAACATCGCGGAGCACCTGCT
GCAGTACTGGCCCTTCGGGGAGCTGCTCTGCAAGCTGGTGCTGGCCGTCGACCACTACAACATCTTCTCCAGCATCTACT
TCCTAGCCGTGATGAGCGTGGACCGATACCTGGTGGTGCTGGCCACCGTGAGGTCCCGCCACATGCCCTGGCGCACCTAC
CGGGGGGCGAAGGTCGCCAGCCTGTGTGTCTGGCTGGGCGTCACGGTCCTGGTTCTGCCCTTCTTCTCTTTCGCTGGCGT
CTACAGCAACGAGCTGCAGGTCCCAAGCTGTGGGCTGAGCTTCCCGTGGCCCGAGCGGGTCTGGTTCAAGGCCAGCCGTG
TCTACACTTTGGTCCTGGGCTTCGTGCTGCCCGTGTGCACCATCTGTGTGCTCTACACAGACCTCCTGCGCAGGCTGCGG
GCCGTGCGGCTCCGCTCTGGAGCCAAGGCTCTAGGCAAGGCCAGGCGGAAGGTGACCGTCCTGGTCCTCGTCGTGCTGGC
CGTGTGCCTCCTCTGCTGGACGCCCTTCCACCTGGCCTCTGTCGTGGCCCTGACCACGGACCTGCCCCAGACCCCACTGG
TCATCAGTATGTCCTACGTCATCACCAGCCTCASSTACGCCAACTCGTGCCTGAACCCCTTCCTCTACGCCTTTCTAGAT
GACAACTTCCGGAAGAACTTCCGCAGCATATTGCGGTGCTGA
```

SEQ ID No:76

Figure 3V

Amino Acid sequence of the HA tagged wild-type hGPR8

MYPYDVPDYAAAAAMQAAGHPEPLDSRGSFSLPTMGANVSQDNGTGHNATFSEPLPFLYVLLPAVYSGICAVGLTGNTAVI
LVILRAPKMKTVTNVFILNLAVADGLFTLVLPVNIAEHLLQYWPFGELLCKLVLAVDHYNIFSSIYFLAVMSVDRYLVVLA
TVRSRHMPWRTYRGAKVASLCVWLGVTVLVLPFFSFAGVYSNELQVPSCGLSFPWPERVWFKASRVYTLVLGFVLPVCTIC
VLYTDLLRRLRAVRLRSGAKALGKARRKVTVLVLVVLAVCLLCWTPFHLASVVALTTDLPQTPLVISMSYVITSLXYANSC
LNPFLYAFLDDNFRKNFRSILRC

SEQ ID No:77

Nucleotide sequence of the HA tagged wild-type hGPR8

ATGTACCCATACGACGTACCTGATTACGCAGCAGCAGCAGCAATGCAGGCCGCTGGGCACCCAGAGCCCCTTGACAGCAGG
GGCTCCTTCTCCCTCCCCACGATGGGTGCCAACGTCTCTCAGGACAATGGCACTGGCCACAATGCCACCTTCTCCGAGCCA
CTGCCCGTTCCTCTATGTGCTCCTGCCCGCCGTGTACTCCGGGATCTGTGCTGTGGGGCTGACTGGCAACACGGCCGTCATC
CTTGTAATCCTAAGGGCGCCCAAGATGAAGACGGTGACCAACGTGTTCATCCTGAACCTGGCCGTCGCCGACGGGCTCTTC
ACGCTGGTACTGCCCGTCAACATCGCGGAGCACCTGCTGCAGTACTGGCCCTTCGGGGAGCTGCTCTGCAAGCTGGTGCTG
GCCGTCGACCACTACAACATCTTCTCCAGCATCTACTTCCTAGCCGTGATGAGCGTGGACCGATACCTGGTGGTGCTGGCC
ACCGTGAGGTCCCGCCACATGCCCTGGCGCACCTACCGGGGGGCGAAGGTCGCCAGCCTGTGTGTCTGGCTGGGCGTCACG
GTCCTGGTTCTGCCCTTCTTCTCTTTCGCTGGCGTCTACAGCAACGAGCTGCAGGTCCCAAGCTGTGGGCTGAGCTTCCCG
TGGCCCGAGCGGGTCTGGTTCAAGGCCAGCCGTGTCTACACTTTGGTCCTGGGCTTCGTGCTGCCCGTGTGCACCATCTGT
GTGCTCTACACAGACCTCCTGCGCAGGCTGCGGGCCGTGCGGCTCCGCTCTGGAGCCAAGGCTCTAGGCAAGGCCAGGCGG
AAGGTGACCGTCCTGGTCCTCGTCGTGCTGGCCGTGTGCCTCCTCTGCTGGACGCCCTTCCACCTGGCCTCTGTCGTGGCC
CTGACCACGGACCTGCCCCAGACCCCACTGGTCATCAGTATGTCCTACGTCATCACCAGCCTCASSTACGCCAACTCGTGC
CTGAACCCCTTCCTCTACGCCTTTCTAGATGACAACTTCCGGAAGAACTTCCGCAGCATATTGCGGTGCTGA

SEQ ID No:78

Figure 3W

Amino Acid sequence of the hGPR8- Enhanced Receptor

MQAAGHPEPLDSRGSFSLPTMGANVSQDNGTGHNATFSEPLPFLYVLLPAVYSGICAVGLTGNTAVILVILRAPKMKTVT
NVFILNLAVADGLFTLVLPVNIAEHLLQYWPFGELLCKLVLAVDHYNIFSSIYFLAVMSVDRYLVVLATVRSRHMPWRTY
RGAKVASLCVWLGVTVLVLPFFSFAGVYSNELQVPSCGLSFPWPERVWFKASRVYTLVLGFVLPVCTICVLYTDLLRRLR
AVRLRSGAKALGKARRKVTVLVLVVLAVCLLCWTPFHLASVVALTTDLPQTPLVISMSYVITSLSYANSCLNPFLYAFLD
DNFRKNFRSILRCAAARGRTPPSLGPQDESCTTASSSLAKDTSS
SEQ ID No:79

Nucleotide sequence of the hGPR8- Enhanced Receptor

ATGCAGGCCGCTGGGCACCCAGAGCCCCTTGACAGCAGGGGCTCCTTCTCCCTCCCCACGATGGGTGCCAACGTCTCTCA
GGACAATGGCACTGGCCACAATGCCACCTTCTCCGAGCCACTGCCGTTCCTCTATGTGCTCCTGCCCGCCGTGTACTCCG
GGATCTGTGCTGTGGGGCTGACTGGCAACACGGCCGTCATCCTTGTAATCCTAAGGGCGCCCAAGATGAAGACGGTGACC
AACGTGTTCATCCTGAACCTGGCCGTCGCCGACGGGCTCTTCACGCTGGTACTGCCCGTCAACATCGCGGAGCACCTGCT
GCAGTACTGGCCCTTCGGGGAGCTGCTCTGCAAGCTGGTGCTGGCCGTCGACCACTACAACATCTTCTCCAGCATCTACT
TCCTAGCCGTGATGAGCGTGGACCGATACCTGGTGGTGCTGGCCACCGTGAGGTCCCGCCACATGCCCTGGCGCACCTAC
CGGGGGGCGAAGGTCGCCAGCCTGTGTGTCTGGCTGGGCGTCACGGTCCTGGTTCTGCCCTTCTTCTCTTTCGCTGGCGT
CTACAGCAACGAGCTGCAGGTCCCAAGCTGTGGGCTGAGCTTCCCGTGGCCCGAGCGGGTCTGGTTCAAGGCCAGCCGTG
TCTACACTTTGGTCCTGGGCTTCGTGCTGCCCGTGTGCACCATCTGTGTGCTCTACACAGACCTCCTGCGCAGGCTGCGG
GCCGTGCGGCTCCGCTCTGGAGCCAAGGCTCTAGGCAAGGCCAGGCGGAAGGTGACCGTCCTGGTCCTCGTCGTGCTGGC
CGTGTGCCTCCTCTGCTGGACGCCCTTCCACCTGGCCTCTGTCGTGGCCCTGACCACGGACCTGCCCCAGACCCCACTGG
TCATCAGTATGTCCTACGTCATCACCAGCCTCAGCTACGCCAACTCGTGCCTGAACCCCTTCCTCTACGCCTTTCTAGAT
GACAACTTCCGGAAGAACTTCCGCAGCATATTGCGGTGCGCGGCCGCACGGGGACGCACCCCACCCAGCCTGGGTCCCCA
AGATGAGTCCTGCACCACCGCCAGCTCCTCCCTGGCCAAGGACACTTCATCGTGA
SEQ ID No:80

Figure 3X
Amino Acid sequence of the HA tagged hGPR8- Enhanced Receptor

MYPYDVPDYAAAAAMQAAGHPEPLDSRGSFSLPTMGANVSQDNGTGHNATFSEPLPFLYVLLPAVYSGICAVGLTGNTAVI
LVILRAPKMKTVTNVFILNLAVADGLFTLVLPVNIAEHLLQYWPFGELLCKLVLAVDHYNIFSSIYFLAVMSVDRYLVVLA
TVRSRHMPWRTYRGAKVASLCVWLGVTVLVLPFFSFAGVYSNELQVPSCGLSFPWPERVWFKASRVYTLVLGFVLPVCTIC
VLYTDLLRRLRAVRLRSGAKALGKARRKVTVLVLVVLAVCLLCWTPFHLASVVALTTDLPQTPLVISMSYVITSLSYANSC
LNPFLYAFLDDNFRKNFRSILRCAAARGRTPPSLGPQDESCTTASSSLAKDTSS

SEQ ID No:81

Nucleotide sequence of the HA tagged hGPR8- Enhanced Receptor

ATGTACCCATACGACGTACCTGATTACGCAGCAGCAGCAGCAATGCAGGCCGCTGGGCACCCAGAGCCCCTTGACAGCAGG
GGCTCCTTCTCCCTCCCCACGATGGGTGCCAACGTCTCTCAGGACAATGGCACTGGCCACAATGCCACCTTCTCCGAGCCA
CTGCCGTTCCTCTATGTGCTCCTGCCCGCCGTGTACTCCGGGATCTGTGCTGTGGGGCTGACTGGCAACACGGCCGTCATC
CTTGTAATCCTAAGGGCGCCCAAGATGAAGACGGTGACCAACGTGTTCATCCTGAACCTGGCCGTCGCCGACGGGCTCTTC
ACGCTGGTACTGCCCGTCAACATCGCGGAGCACCTGCTGCAGTACTGGCCCTTCGGGGAGCTGCTCTGCAAGCTGGTGCTG
GCCGTCGACCACTACAACATCTTCTCCAGCATCTACTTCCTAGCCGTGATGAGCGTGGACCGATACCTGGTGGTGCTGGCC
ACCGTGAGGTCCCGCCACATGCCCTGGCGCACCTACCGGGGGGCGAAGGTCGCCAGCCTGTGTGTCTGGCTGGGCGTCACG
GTCCTGGTTCTGCCCTTCTTCTCTTTCGCTGGCGTCTACAGCAACGAGCTGCAGGTCCCAAGCTGTGGGCTGAGCTTCCCG
TGGCCCGAGCGGGTCTGGTTCAAGGCCAGCCGTGTCTACACTTTGGTCCTGGGCTTCGTGCTGCCCGTGTGCACCATCTGT
GTGCTCTACACAGACCTCCTGCGCAGGCTGCGGGCCGTGCGGCTCCGCTCTGGAGCCAAGGCTCTAGGCAAGGCCAGGCGG
AAGGTGACCGTCCTGGTCCTCGTCGTGCTGGCCGTGTGCCTCCTCTGCTGGACGCCCTTCCACCTGGCCTCTGTCGTGGCC
CTGACCACGGACCTGCCCCAGACCCCACTGGTCATCAGTATGTCCTACGTCATCACCAGCCTCAGCTACGCCAACTCGTGC
CTGAACCCCTTCCTCTACGCCTTTCTAGATGACAACTTCCGGAAGAACTTCCGCAGCATATTGCGGTGCGCGGCCGCACGG
GGACGCACCCCACCCAGCCTGGGTCCCCAAGATGAGTCCTGCACCACCGCCAGCTCCTCCCTGGCCAAGGACACTTCATCG
TGA

SEQ ID No:82

Figure 3Y

Amino Acid sequence of the wild-type hGPR22 ACCESSION NP_005286.1

MCFSPILEINMQSESNITVRDDIDDINTNMYQPLSYPLSFQVSLTGFLMLEIVLGLGSNLTVLVLYCMKSNLINSVSNII
TMNLHVLDVIICVGCIPLTIVILLLSLESNTALICCFHEACVSFASVSTAINVFAITLDRYDISVKPANRILTMGRAVML
MISIWIFSFFSFLIPFIEVNFFSLQSGNTWENKTLLCVSTNEYYTELGMYYHLLVQIPIFFFTVVVMLITYTKILQALNI
RIGTRFSTGQKKKARKKKTISLTTQHEATDMSQSSGGRNVVFGVRTSVSVIIALRRAVKRHRERRERQKRVFRMSLLIIS
TFLLCWTPISVLNTTILCLGPSDLLVKLRLCFLVMAYGTTIFHPLLYAFTRQKFQKVLKSKMKKRVVSIVEADPLPNNAV
IHNSWIDPKRNKKITFEDSEIREKCLVPQVVTD

SEQ ID No:83

Nucleotide sequence of the wild-type hGPR22 ACCESSION NM_ 005295

ATGTGTTTTTCTCCCATTCTGGAAATCAACATGCAGTCTGAATCTAACATTACAGTGCGAGATGACATTGATGACATCAA
CACCAATATGTACCAACCACTATCATATCCGTTAAGCTTTCAAGTGTCTCTCACCGGATTTCTTATGTTAGAAATTGTGT
TGGGACTTGGCAGCAACCTCACTGTATTGGTACTTTACTGCATGAAATCCAACTTAATCAACTCTGTCAGTAACATTATT
ACAATGAATCTTCATGTACTTGATGTAATAATTTGTGTGGGATGTATTCCTCTAACTATAGTTATCCTTCTGCTTTCACT
GGAGAGTAACACTGCTCTCATTTGCTGTTTCCATGAGGCTTGTGTATCTTTTGCAAGTGTCTCAACAGCAATCAACGTTT
TTGCTATCACTTTGGACAGATATGACATCTCTGTAAAACCTGCAAACCGAATTCTGACAATGGGCAGAGCTGTAATGTTA
ATGATATCCATTTGGATTTTTTCTTTTTTCTCTTTCCTGATTCCTTTTATTGAGGTAAATTTTTTCAGTCTTCAAAGTGG
AAATACCTGGGAAAACAAGACACTTTTATGTGTCAGTACAAATGAATACTACACTGAACTGGGAATGTATTATCACCTGT
TAGTACAGATCCCAATATTCTTTTTCACTGTTGTAGTAATGTTAATCACATACACCAAAATACTTCAGGCTCTTAATATT
CGAATAGGCACAAGATTTTCAACAGGGCAGAAGAAGAAAGCAAGAAAGAAAAAGACAATTTCTCTAACCACACAACATGA
GGCTACAGACATGTCACAAAGCAGTGGTGGGGAGAAATGTAGTCTTTGGTGTAAGAACTTCAGTTTCTGTAATAATTGCCC
TCCGGCGAGCTGTGAAACGACACCGTGAACGACGAGAAAGACAAAAGAGAGTCTTCAGGATGTCTTTATTGATTATTTCT
ACATTTCTTCTCTGCTGGACACCAATTTCTGTTTTAAATACCACCATTTTATGTTTAGGCCCAAGTGACCTTTTAGTAAA
ATTAAGATTGTGTTTTTTAGTCATGGCTTATGGAACAACTATATTTCACCCTCTATTATATGCATTCACTAGACAAAAAT
TTCAAAAGGTCTTGAAAAGTAAAATGAAAAAGCGAGTTGTTTCTATAGTAGAAGCTGATCCCCTGCCTAATAATGCTGTA
ATACACAACTCTTGGATAGATCCTAAAAGAAACAAAAAAATTACCTTTGAAGATAGTGAAATAAGAGAAAAATGTTTAGT
GCCTCAGGTTGTCACAGACTAG

SEQ ID No:84

Figure 3Z
Amino Acid sequence of the HA tagged wild-type hGPR22

MYPYDVPDYAAAAAMCFSPILEINMQSESNITVRDDIDDINTNMYQPLSYPLSFQVSLTGFLMLEIVLGLGSNLTVLVLY
CMKSNLINSVSNIITMNLHVLDVIICVGCIPLTIVILLLSLESNTALICCFHEACVSFASVSTAINVFAITLDRYDISVK
PANRILTMGRAVMLMISIWIFSFFSFLIPFIEVNFFSLQSGNTWENKTLLCVSTNEYYTELGMYYHLLVQIPIFFFTVVV
MLITYTKILQALNIRIGTRFSTGQKKKARKKKTISLTTQHEATDMSQSSGGRNVVFGVRTSVSVIIALRRAVKRHRERRE
RQKRVFRMSLLIISTFLLCWTPISVLNTTILCLGPSDLLVKLRLCFLVMAYGTTIFHPLLYAFTRQKFQKVLKSKMKKRV
VSIVEADPLPNNAVIHNSWIDPKRNKKITFEDSEIREKCLVPQVVTD

SEQ ID No:85

Nucleotide sequence of the HA tagged wild-type hGPR22

ATGTACCCATACGACGTACCTGATTACGCAGCAGCAGCAGCAATGTGTTTTTCTCCCATTCTGGAAATCAACATGCAGTC
TGAATCTAACATTACAGTGCGAGATGACATTGATGACATCAACACCAATATGTACCAACCACTATCATATCCGTTAAGCT
TTCAAGTGTCTCTCACCGGATTTCTTATGTTAGAAATTGTGTTGGGACTTGGCAGCAACCTCACTGTATTGGTACTTTAC
TGCATGAAATCCAACTTAATCAACTCTGTCAGTAACATTATTACAATGAATCTTCATGTACTTGATGTAATAATTTGTGT
GGGATGTATTCCTCTAACTATAGTTATCCTTCTGCTTTCACTGGAGAGTAACACTGCTCTCATTTGCTGTTTCCATGAGG
CTTGTGTATCTTTTGCAAGTGTCTCAACAGCAATCAACGTTTTTGCTATCACTTTGGACAGATATGACATCTCTGTAAAA
CCTGCAAACCGAATTCTGACAATGGGCAGAGCTGTAATGTTAATGATATCCATTTGGATTTTTTCTTTTTTCTCTTTCCT
GATTCCTTTTATTGAGGTAAATTTTTTCAGTCTTCAAAGTGGAAATACCTGGGAAAACAAGACACTTTTATGTGTCAGTA
CAAATGAATACTACACTGAACTGGGAATGTATTATCACCTGTTAGTACAGATCCCAATATTCTTTTTCACTGTTGTAGTA
ATGTTAATCACATACACCAAAATACTTCAGGCTCTTAATATTCGAATAGGCACAAGATTTTCAACAGGGCAGAAGAAGAA
AGCAAGAAAGAAAAAGACAATTTCTCTAACCACACAACATGAGGCTACAGACATGTCACAAAGCAGTGGTGGGAGAAATG
TAGTCTTTGGTGTAAGAACTTCAGTTTCTGTAATAATTGCCCTCCGGCGAGCTGTGAAACGACACCGTGAACGACGAGAA
AGACAAAAGAGAGTCTTCAGGATGTCTTTATTGATTATTTCTACATTTCTTCTCTGCTGGACACCAATTTCTGTTTTAAA
TACCACCATTTTATGTTTAGGCCCAAGTGACCTTTTAGTAAAATTAAGATTGTGTTTTTTAGTCATGGCTTATGGAACAA
CTATATTTCACCCTCTATTATATGCATTCACTAGACAAAAATTTCAAAAGGTCTTGAAAAGTAAAATGAAAAAGCGAGTT
GTTTCTATAGTAGAAGCTGATCCCCTGCCTAATAATGCTGTAATACACAACTCTTGGATAGATCCTAAAAGAAACAAAAA
AATTACCTTTGAAGATAGTGAAATAAGAGAAAAATGTTTAGTGCCTCAGGTTGTCACAGACTAG

SEQ ID No:86

Figure 3AA

Amino Acid sequence of the hGPR22-Enhanced Receptor

MCFSPILEINMQSESNITVRDDIDDINTNMYQPLSYPLSFQVSLTGFLMLEIVLGLGSNLTVLVLYCMKSNLINSVSNII
TMNLHVLDVIICVGCIPLTIVILLLSLESNTALICCFHEACVSFASVSTAINVFAITLDRYDISVKPANRILTMGRAVML
MISIWIFSFFSFLIPFIEVNFFSLQSGNTWENKTLLCVSTNEYYTELGMYYHLLVQIPIFFFTVVVMLITYTKILQALNI
RIGTRFSTGQKKKARKKKTISLTTQHEATDMSQSSGGRNVVFGVRTSVSVIIALRRAVKRHRERRERQKRVFRMSLLIIS
TFLLCWTPISVLNTTILCLGPSDLLVKLRLCFLVMAYGTTIFHPLLYAFTRQKFQKVLKSKMKKRVVCAAARGRTPPSLG
PQDESCTTASSSLAKDTSS

SEQ ID No:87

Nucleotide sequence of the hGPR22-Enhanced Receptor

ATGTGTTTTTCTCCcaTTCTGGAAATCAACATGCAGTCTGAATCTAACATTACAGTGCGAGATGACATTGATGACATCAA
CACCAATATGTACCAACCACTATCATATCCGTTAAGCTTTCAAGTGTCTCTCACCGGATTTCTTATGTTAGAAATTGTGT
TGGGACTTGGCAGCAACCTCACTGTATTGGTACTTTACTGCATGAAATCCAACTTAATCAACTCTGTCAGTAACATTATT
ACAATGAATCTTCATGTACTTGATGTAATAATTTGTGTGGGATGTATTCCTCTAACTATAGTTATCCTTCTGCTTTCACT
GGAGAGTAACACTGCTCTCATTTGCTGTTTCCATGAGGCTTGTGTATCTTTTGCAAGTGTCTCAACAGCAATCAACGTTT
TTGCTATCACTTTGGACAGATATGACATCTCTGTAAAACCTGCAAACCGAATTCTGACAATGGGCAGAGCTGTAATGTTA
ATGATATCCATTTGGATTTTTTCTTTTTTCTCTTTCCTGATTCCTTTTATTGAGGTAAATTTTTTCAGTCTTCAAAGTGG
AAATACCTGGGAAAACAAGACACTTTTATGTGTCAGTACAAATGAATACTACACTGAACTGGGAATGTATTATCACCTGT
TAGTACAGATCCCAATATTCTTTTTCACTGTTGTAGTAATGTTAATCACATACACCAAAATACTTCAGGCTCTTAATATT
CGAATAGGCACAAGATTTTCAACAGGGCAGAAGAAGAAAGCAAGAAAGAAAAAGACAATTTCTCTAACCACACAACATGA
GGCTACAGACATGTCACAAAGCAGTGGTGGGAGAAATGTAGTCTTTGGTGTAAGAACTTCAGTTTCTGTAATAATTGCCC
TCCGGCGAGCTGTGAAACGACACCGTGAACGACGAGAAAGACAAAAGAGAGTCTTCAGGATGTCTTTATTGATTATTTCT
ACATTTCTTCTCTGCTGGACACCAATTTCTGTTTTAAATACCACCATTTTATGTTTAGGCCCAAGTGACCTTTTAGTAAA
ATTAAGATTGTGTTTTTTAGTCATGGCTTATGGAACAACTATATTTCACCCTCTATTATATGCATTCACTAGACAAAAAT
TTCAAAAGGTCTTGAAAAGTAAAATGAAAAAGCGAGTTGTTTGTGCGGCCGCACGGGGACGCACCCCACCCAGCCTGGGT
CCCCAAGATGAGTCCTGCACCACCGCCAGCTCCTCCCTGGCCAAGGACACTTCATCGTGA

SEQ ID No:88

Figure 3BB

Amino Acid sequence of the HA tagged hGPR22- Enhanced Receptor

MYPYDVPDYAAAAAMCFSPILEINMQSESNITVRDDIDDINTNMYQPLSYPLSFQVSLTGFLMLEIVLGLGSNLTVLVLY
CMKSNLINSVSNIITMNLHVLDVIICVGCIPLTIVILLLSLESNTALICCFHEACVSFASVSTAINVFAITLDRYDISVK
PANRILTMGRAVMLMISIWIFSFFSFLIPFIEVNFFSLQSGNTWENKTLLCVSTNEYYTELGMYYHLLVQIPIFFFTVVV
MLITYTKILQALNIRIGTRFSTGQKKKARKKKTISLTTQHEATDMSQSSGGRNVVFGVRTSVSVIIALRRAVKRHRERRE
RQKRVFRMSLLIISTFLLCWTPISVLNTTILCLGPSDLLVKLRLCFLVMAYGTTIFHPLLYAFTRQKFQKVLKSKMKKRV
VCAAARGRTPPSLGPQDESCTTASSSLAKDTSS

SEQ ID No:89

Nucleotide sequence of the HA tagged hGPR22-Enhanced Receptor

ATGTACCCATACGACGTACCTGATTACGCAGCAGCAGCAGCAATGTGTTTTCTCCcaTTCTGGAAATCAACATGCAGTCT
GAATCTAACATTACAGTGCGAGATGACATTGATGACATCAACACCAATATGTACCAACCACTATCATATCCGTTAAGCTTT
CAAGTGTCTCTCACCGGATTTCTTATGTTAGAAATTGTGTTGGGACTTGGCAGCAACCTCACTGTATTGGTACTTTACTGC
ATGAAATCCAACTTAATCAACTCTGTCAGTAACATTATTACAATGAATCTTCATGTACTTGATGTAATAATTTGTGTGGGA
TGTATTCCTCTAACTATAGTTATCCTTCTGCTTTCACTGGAGAGTAACACTGCTCTCATTTGCTGTTTCCATGAGGCTTGT
GTATCTTTTGCAAGTGTCTCAACAGCAATCAACGTTTTTGCTATCACTTTGGACAGATATGACATCTCTGTAAAACCTGCA
AACCGAATTCTGACAATGGGCAGAGCTGTAATGTTAATGATATCCATTTGGATTTTTTCTTTTTTCTCTTTCCTGATTCCT
TTTATTGAGGTAAATTTTTTCAGTCTTCAAAGTGGAAATACCTGGGAAAACAAGACACTTTTATGTGTCAGTACAAATGAA
TACTACACTGAACTGGGAATGTATTATCACCTGTTAGTACAGATCCCAATATTCTTTTTCACTGTTGTAGTAATGTTAATC
ACATACACCAAAATACTTCAGGCTCTTAATATTCGAATAGGCACAAGATTTTCAACAGGGCAGAAGAAGAAAGCAAGAAAG
AAAAAGACAATTTCTCTAACCACACAACATGAGGCTACAGACATGTCACAAAGCAGTGGTGGGAGAAATGTAGTCTTTGGT
GTAAGAACTTCAGTTTCTGTAATAATTGCCCTCCGGCGAGCTGTGAAACGACACCGTGAACGACGAGAAAGACAAAAGAGA
GTCTTCAGGATGTCTTTATTGATTATTTCTACATTTCTTCTCTGCTGGACACCAATTTCTGTTTTAAATACCACCATTTTA
TGTTTAGGCCCAAGTGACCTTTTAGTAAAATTAAGATTGTGTTTTTTAGTCATGGCTTATGGAACAACTATATTTCACCCT
CTATTATATGCATTCACTAGACAAAAATTTCAAAAGGTCTTGAAAAGTAAAATGAAAAAGCGAGTTGTTTGTGCGGCCGCA
CGGGGACGCACCCCACCCAGCCTGGGTCCCCAAGATGAGTCCTGCACCACCGCCAGCTCCTCCCTGGCCAAGGACACTTCA
TCGTGA

SEQ ID No:90

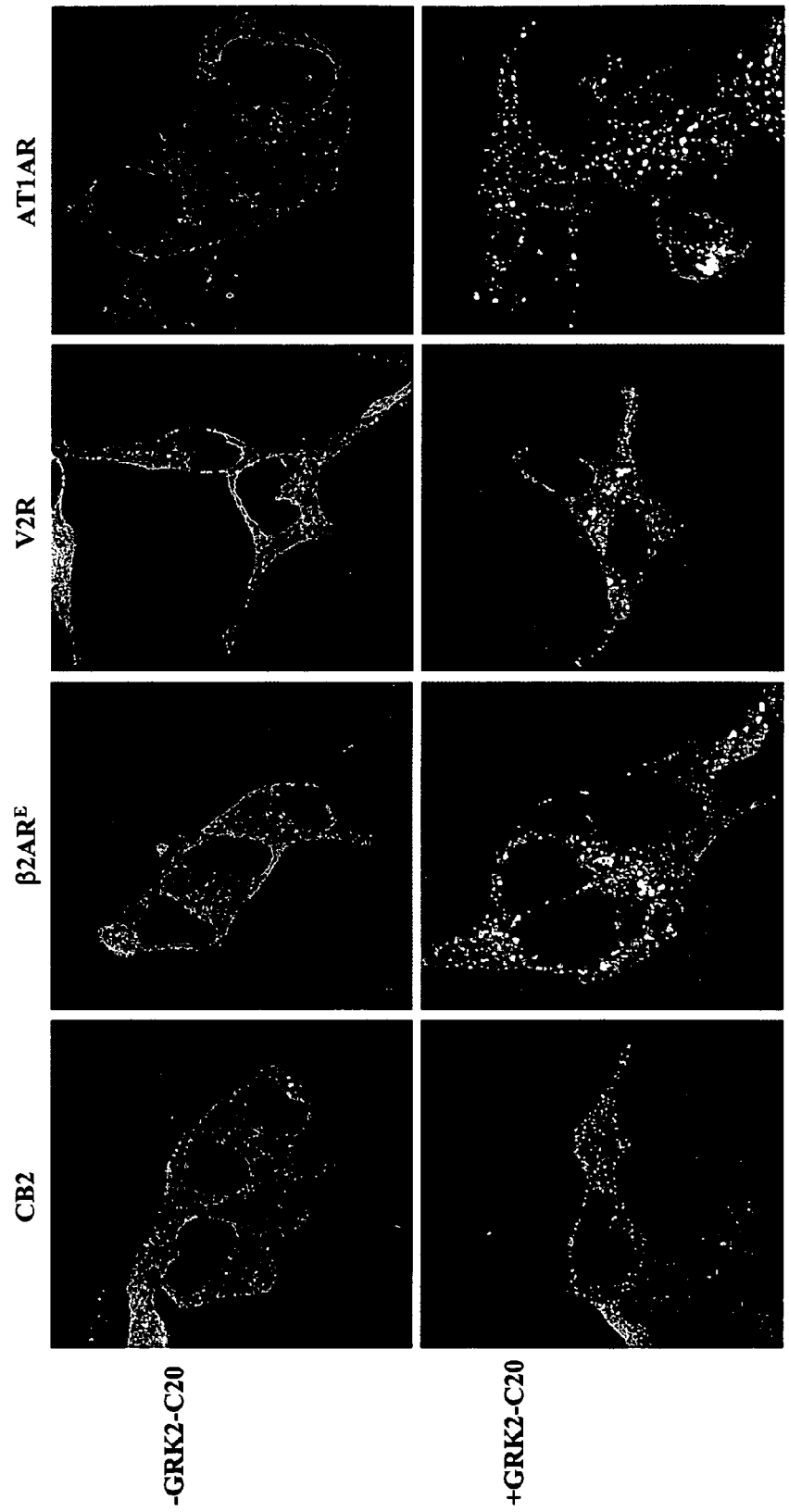

Agonist-Independent Translocation of Arrestin-GFP to GPCRs in the Presence of GRK2-C20

SEQUENCE LISTING

```
<160> NUMBER OF SEQ ID NOS: 94

<210> SEQ ID NO 1
<211> LENGTH: 689
<212> TYPE: PRT
<213> ORGANISM: Bos taurus

<400> SEQUENCE: 1

Met Ala Asp Leu Glu Ala Val Leu Ala Asp Val Ser Tyr Leu Met Ala
 1               5                  10                  15

Met Glu Lys Ser Lys Ala Thr Pro Ala Ala Arg Ala Ser Lys Lys Ile
            20                  25                  30

Leu Leu Pro Glu Pro Ser Ile Arg Ser Val Met Gln Lys Tyr Leu Glu
        35                  40                  45

Asp Arg Gly Glu Val Thr Phe Glu Lys Ile Phe Ser Gln Lys Leu Gly
    50                  55                  60

Tyr Leu Leu Phe Arg Asp Phe Cys Leu Lys His Leu Glu Glu Ala Lys
65                  70                  75                  80

Pro Leu Val Glu Phe Tyr Glu Glu Ile Lys Lys Tyr Glu Lys Leu Glu
```

-continued

```
                85                  90                  95
Thr Glu Glu Arg Leu Val Cys Ser Arg Glu Ile Phe Asp Thr Tyr
            100                 105                 110
Ile Met Lys Glu Leu Leu Ala Cys Ser His Pro Phe Ser Lys Ser Ala
            115                 120                 125
Ile Glu His Val Gln Gly His Leu Val Lys Lys Gln Val Pro Pro Asp
            130                 135                 140
Leu Phe Gln Pro Tyr Ile Glu Glu Ile Cys Gln Asn Leu Arg Gly Asp
145                 150                 155                 160
Val Phe Gln Lys Phe Ile Glu Ser Asp Lys Phe Thr Arg Phe Cys Gln
            165                 170                 175
Trp Lys Asn Val Glu Leu Asn Ile His Leu Thr Met Asn Asp Phe Ser
            180                 185                 190
Val His Arg Ile Ile Gly Arg Gly Gly Phe Gly Glu Val Tyr Gly Cys
            195                 200                 205
Arg Lys Ala Asp Thr Gly Lys Met Tyr Ala Met Lys Cys Leu Asp Lys
            210                 215                 220
Lys Arg Ile Lys Met Lys Gln Gly Glu Thr Leu Ala Leu Asn Glu Arg
225                 230                 235                 240
Ile Met Leu Ser Leu Val Ser Thr Gly Asp Cys Pro Phe Ile Val Cys
            245                 250                 255
Met Ser Tyr Ala Phe His Thr Pro Asp Lys Leu Ser Phe Ile Leu Asp
            260                 265                 270
Leu Met Asn Gly Gly Asp Leu His Tyr His Leu Ser Gln His Gly Val
            275                 280                 285
Phe Ser Glu Ala Asp Met Arg Phe Tyr Ala Ala Glu Ile Ile Leu Gly
            290                 295                 300
Leu Glu His Met His Asn Arg Phe Val Val Tyr Arg Asp Leu Lys Pro
305                 310                 315                 320
Ala Asn Ile Leu Leu Asp Glu His Gly His Val Arg Ile Ser Asp Leu
            325                 330                 335
Gly Leu Ala Cys Asp Phe Ser Lys Lys Lys Pro His Ala Ser Val Gly
            340                 345                 350
Thr His Gly Tyr Met Ala Pro Glu Val Leu Gln Lys Gly Val Ala Tyr
            355                 360                 365
Asp Ser Ser Ala Asp Trp Phe Ser Leu Gly Cys Met Leu Phe Lys Leu
            370                 375                 380
Leu Arg Gly His Ser Pro Phe Arg Gln His Lys Thr Lys Asp Lys His
385                 390                 395                 400
Glu Ile Asp Arg Met Thr Leu Thr Met Ala Val Glu Leu Pro Asp Ser
            405                 410                 415
Phe Ser Pro Glu Leu Arg Ser Leu Leu Glu Gly Leu Leu Gln Arg Asp
            420                 425                 430
Val Asn Arg Arg Leu Gly Cys Leu Gly Arg Gly Ala Gln Glu Val Lys
            435                 440                 445
Glu Ser Pro Phe Phe Arg Ser Leu Asp Trp Gln Met Val Phe Leu Gln
            450                 455                 460
Lys Tyr Pro Pro Pro Leu Ile Pro Pro Arg Gly Glu Val Asn Ala Ala
465                 470                 475                 480
Asp Ala Phe Asp Ile Gly Ser Phe Asp Glu Asp Thr Lys Gly Ile
            485                 490                 495
Lys Leu Leu Asp Ser Asp Gln Glu Leu Tyr Arg Asn Phe Pro Leu Thr
            500                 505                 510
```

```
Ile Ser Glu Arg Trp Gln Gln Glu Val Ala Glu Thr Val Phe Asp Thr
        515                 520                 525

Ile Asn Ala Glu Thr Asp Arg Leu Glu Ala Arg Lys Lys Thr Lys Asn
    530                 535                 540

Lys Gln Leu Gly His Glu Asp Tyr Ala Leu Gly Lys Asp Cys Ile
545                 550                 555                 560

Met His Gly Tyr Met Ser Lys Gly Asn Pro Phe Leu Thr Gln Trp
                565                 570                 575

Gln Arg Arg Tyr Phe Tyr Leu Phe Pro Asn Arg Leu Glu Trp Arg Gly
            580                 585                 590

Glu Gly Glu Ala Pro Gln Ser Leu Leu Thr Met Glu Glu Ile Gln Ser
        595                 600                 605

Val Glu Thr Gln Ile Lys Glu Arg Lys Cys Leu Leu Lys Ile
    610                 615                 620

Arg Gly Gly Lys Gln Phe Val Leu Gln Cys Asp Ser Asp Pro Glu Leu
625                 630                 635                 640

Val Gln Trp Lys Lys Glu Leu Arg Asp Ala Tyr Arg Glu Ala Gln Gln
                645                 650                 655

Leu Val Gln Arg Val Pro Lys Met Lys Asn Lys Pro Arg Ser Pro Val
            660                 665                 670

Val Glu Leu Ser Lys Val Pro Leu Ile Gln Arg Gly Ser Cys Val Leu
        675                 680                 685

Leu

<210> SEQ ID NO 2
<211> LENGTH: 2070
<212> TYPE: DNA
<213> ORGANISM: Bos taurus

<400> SEQUENCE: 2
atggcggacc tggaggcggt gctggccgac gtgagctacc tgatggccat ggagaagagc      60
aaggccacgc cggcggcgcg cgccagcaag aagatcctgc tgcccgagcc agcatccgc     120 agcgtcatgc agaagtacct ggaggaccgg ggcgaggtga cttttgagaa gatcttctcc     180
cagaagctgg ggtacctgct tttccgagac ttctgcctga gcacctggag ggaggccaag     240
cccttggtag agttctacga ggagatcaag aaatacgaga agctggagac agaggaggag     300
cgcctggtct gcagccgaga gatcttcgac acgtacatca tgaaggagct gctggcctgc     360
tcacatcctt tctcgaagag cgccattgag acgtccagg gccatctggt gaagaagcag     420
gtgcctccgg atctcttcca gccatatatt gaagaaattt gccagaacct ccgaggagac     480
gtgttccaga aattcatcga gagcgataaa ttcacacgat tttgccagtg aagaatgta      540 gagctcaaca tccacctgac catgaacgac ttcagtgtgc accgcatcat cgggcgaggc     600
ggcttcggtg aggtctacgg ctgccggaag gccgacacgg gcaagatgta cgccatgaag     660
tgtctggaca agaagcgcat caagatgaag caaggggaga ctctggccct gaatgagcgc     720
atcatgctgt cgctcgtcag caccggggac tgcccgttca tcgtctgcat gtcatacgcc     780
ttccacacac cggacaagct cagcttcatc ctggatctca tgaacggcgg ggacctgcac     840
taccacctgt cccagcacgg ggtcttctcc gaggccgaca tgcgtttcta cgccgccgag     900
atcatcctgg gcctggagca catgcacaac cgcttcgtgg tctaccggga cctgaagccg     960
gccaacatcc tgctgacgga gcacggccac gtgcgcatct cagacctggg cctggccctgt    1020 gacttctcca agaagaagcc tcacgccagt gtgggcaccc acgggtacat ggctcccgag    1080
```

```
gttctacaga agggtgtggc ctacgacagc agcgccgact ggttctccct gggctgcatg    1140
ctcttcaagc tgctgcgagg gcatagccct tccggcagc acaagaccaa agacaagcat     1200
gagatcgaca gaatgacatt gacaatggct gtggagctgc ctgactcctt ctcccctgag    1260
ctccgctcct tgctggaggg gctgctgcag agggatgtca accggaggct aggctgcctg    1320
ggccgagggg cccaggaggt gaaggagagc cccttcttcc gttccctgga ctggcagatg    1380 gtcttttac aaaagtaccc tcccccgttg atcccccac gaggggaggt gaatgcagcc      1440
gacgcctttg acattggctc cttcgatgag gaggacacaa aaggaatcaa gctactggac    1500
agtgaccagg agctctaccg caacttcccc ctgaccatct cggagcggtg gcagcaggag    1560
gtagcagaga ctgtctttga caccatcaat gctgagacgg accggctgga ggcccgcaag    1620
aaaaccaaaa acaagcagtt gggccacgag gaagactacg ccctgggcaa ggactgcatc    1680
atgcatggct acatgtccaa gatgggcaac cccttcctga cccagtggca gcggcggtac    1740
ttctacctgt tccctaaccg gctcgagtgg cggggcgagg gcgaggcccc gcagagcctg    1800
ctgaccatgg aggagatcca gtcggtggag gagacgcaga tcaaggagcg aaagtgcctc    1860
ctcctcaaga tccgaggtgg caagcagttt gtcctgcagt gcgatagtga cccagagctg    1920
gtgcagtgga agaaggagct tcgagacgcc taccgcgagg cccagcagct agtgcagcgg    1980
gtgcccaaga tgaagaacaa gccgcgctcg cccgtcgtgg agctgagcaa ggtgccactg    2040
atccagcgcg gcagttgtgt gcttctttag                                     2070
```

<210> SEQ ID NO 3
<211> LENGTH: 689
<212> TYPE: PRT
<213> ORGANISM: Homo sapiens

<400> SEQUENCE: 3

```
Met Ala Asp Leu Glu Ala Val Leu Ala Asp Val Ser Tyr Leu Met Ala
  1               5                  10                  15

Met Glu Lys Ser Lys Ala Thr Pro Ala Ala Arg Ala Ser Lys Lys Ile
                 20                  25                  30

Leu Leu Pro Glu Pro Ser Ile Arg Ser Val Met Gln Lys Tyr Leu Glu
             35                  40                  45

Asp Arg Gly Glu Val Thr Phe Glu Lys Ile Phe Ser Gln Lys Leu Gly
         50                  55                  60

Tyr Leu Leu Phe Arg Asp Phe Cys Leu Asn His Leu Glu Glu Ala Arg
 65                  70                  75                  80

Pro Leu Val Glu Phe Tyr Glu Glu Ile Lys Lys Tyr Glu Lys Leu Glu
                 85                  90                  95

Thr Glu Glu Glu Arg Val Ala Arg Ser Arg Glu Ile Phe Asp Ser Tyr
            100                 105                 110

Ile Met Lys Glu Leu Leu Ala Cys Ser His Pro Phe Ser Lys Ser Ala
        115                 120                 125

Thr Glu His Val Gln Gly His Leu Gly Lys Lys Gln Val Pro Pro Asp
    130                 135                 140

Leu Phe Gln Pro Tyr Ile Glu Glu Ile Cys Gln Asn Leu Arg Gly Asp
145                 150                 155                 160

Val Phe Gln Lys Phe Ile Glu Ser Asp Lys Phe Thr Arg Phe Cys Gln
                165                 170                 175

Trp Lys Asn Val Glu Leu Asn Ile His Leu Thr Met Asn Asp Phe Ser
            180                 185                 190
```

```
Val His Arg Ile Ile Gly Arg Gly Gly Phe Gly Glu Val Tyr Gly Cys
        195                 200                 205

Arg Lys Ala Asp Thr Gly Lys Met Tyr Ala Met Lys Cys Leu Asp Lys
        210                 215                 220

Lys Arg Ile Lys Met Lys Gln Gly Glu Thr Leu Ala Leu Asn Glu Arg
225                 230                 235                 240

Ile Met Leu Ser Leu Val Ser Thr Gly Asp Cys Pro Phe Ile Val Cys
                245                 250                 255

Met Ser Tyr Ala Phe His Thr Pro Asp Lys Leu Ser Phe Ile Leu Asp
            260                 265                 270

Leu Met Asn Gly Gly Asp Leu His Tyr His Leu Ser Gln His Gly Val
        275                 280                 285

Phe Ser Glu Ala Asp Met Arg Phe Tyr Ala Ala Glu Ile Ile Leu Gly
        290                 295                 300

Leu Glu His Met His Asn Arg Phe Val Val Tyr Arg Asp Leu Lys Pro
305                 310                 315                 320

Ala Asn Ile Leu Leu Asp Glu His Gly His Val Arg Ile Ser Asp Leu
                325                 330                 335

Gly Leu Ala Cys Asp Phe Ser Lys Lys Lys Pro His Ala Ser Val Gly
            340                 345                 350

Thr His Gly Tyr Met Ala Pro Glu Val Leu Gln Lys Gly Val Ala Tyr
        355                 360                 365

Asp Ser Ser Ala Asp Trp Phe Ser Leu Gly Cys Met Leu Phe Lys Leu
        370                 375                 380

Leu Arg Gly His Ser Pro Phe Arg Gln His Lys Thr Lys Asp Lys His
385                 390                 395                 400

Glu Ile Asp Arg Met Thr Leu Thr Met Ala Val Glu Leu Pro Asp Ser
                405                 410                 415

Phe Ser Pro Glu Leu Arg Ser Leu Leu Glu Gly Leu Leu Gln Arg Asp
            420                 425                 430

Val Asn Arg Arg Leu Gly Cys Leu Gly Arg Gly Ala Gln Glu Val Lys
        435                 440                 445

Glu Ser Pro Phe Phe Arg Ser Leu Asp Trp Gln Met Val Phe Leu Gln
        450                 455                 460

Lys Tyr Pro Pro Pro Leu Ile Pro Pro Arg Gly Glu Val Asn Ala Ala
465                 470                 475                 480

Asp Ala Phe Asp Ile Gly Ser Phe Asp Glu Glu Asp Thr Lys Gly Ile
                485                 490                 495

Lys Leu Leu Asp Ser Asp Gln Glu Leu Tyr Arg Asn Phe Pro Leu Thr
            500                 505                 510

Ile Ser Glu Arg Trp Gln Gln Glu Val Ala Glu Thr Val Phe Asp Thr
        515                 520                 525

Ile Asn Ala Glu Thr Asp Arg Leu Glu Ala Arg Lys Lys Ala Lys Asn
        530                 535                 540

Lys Gln Leu Gly His Glu Glu Asp Tyr Ala Leu Gly Lys Asp Cys Ile
545                 550                 555                 560

Met His Gly Tyr Met Ser Lys Met Gly Asn Pro Phe Leu Thr Gln Trp
                565                 570                 575

Gln Arg Arg Tyr Phe Tyr Leu Phe Pro Asn Arg Leu Glu Trp Arg Gly
            580                 585                 590

Glu Gly Glu Ala Pro Gln Ser Leu Leu Thr Met Glu Glu Ile Gln Ser
        595                 600                 605

Val Glu Glu Thr Gln Ile Lys Glu Arg Lys Cys Leu Leu Leu Lys Ile
```

```
                610             615             620
Arg Gly Gly Lys Gln Phe Ile Leu Gln Cys Asp Ser Asp Pro Glu Leu
625             630                 635                 640

Val Gln Trp Lys Lys Glu Leu Arg Asp Ala Tyr Arg Glu Ala Gln Gln
                645                 650                 655

Leu Val Gln Arg Val Pro Lys Met Lys Asn Lys Pro Arg Ser Pro Val
            660                 665                 670

Val Glu Leu Ser Lys Val Pro Leu Val Gln Arg Gly Ser Ala Asn Gly
                675                 680             685

Leu

<210> SEQ ID NO 4
<211> LENGTH: 2070
<212> TYPE: DNA
<213> ORGANISM: Homo sapiens

<400> SEQUENCE: 4
atggcggacc tggaggcggt gctggccgac gtgagctacc tgatggccat ggagaagagc      60
aaggccacgc cggccgcgcg cgccagcaag aagatactgc tgcccgagcc agcatccgc     120
agtgtcatgc agaagtacct ggaggaccgg ggcgaggtga cctttgagaa gatcttttcc     180
cagaagctgg ggtacctgct cttccgagac ttctgcctga ccacctgga ggaggccagg     240
cccttggtgg aattctatga ggagatcaag aagtacgaga gctggagac ggaggaggag     300
cgtgtggccc gcagccggga gatcttcgac tcatacatca tgaaggagct gctggcctgc     360
tcgcatccct tctcgaagag tgccactgag catgtccaag gccacctggg gaagaagcag     420
gtgcctccgg atctcttcca gccatacatc gaagagattt gtcaaaacct ccaggggac     480
gtgttccaga aattcattga gagcgataag ttcacacggt tttgccagtg aagaatgtg     540
gagctcaaca tccacctgac catgaatgac ttcagcgtgc atcgcatcat gggcgcggg     600
ggctttggcg aggtctatgg gtgccggaag gctgacacag gcaagatgta cgccatgaag     660
tgcctggaca aaaagcgcat caagatgaag caggggaga ccctggccct gaacgagcgc     720
atcatgctct cgctcgtcag cactggggac tgcccattca ttgtctgcat gtcatacgcg     780
ttccacacgc cagacaagct cagcttcatc ctggacctca tgaacggtgg ggacctgcac     840
taccacctct cccagcacgg ggtcttctca gaggctgaca tgcgcttcta tgcggccgag     900
atcatcctgg gcctggagca catgcacaac cgcttcgtgg tctaccggga cctgaagcca     960
gccaacatcc ttctggacga gcatggccac gtgcggatct cggacctggg cctggcctgt    1020
gacttctcca agaagaagcc ccatgccagc gtgggcaccc acgggtacat ggctccggag    1080
gtcctgcaga agggcgtggc ctacgacagc agtgccgact ggttctctct ggggtgcatg    1140
ctcttcaagt tgctgcgggg gcacagcccc ttccggcagc acaagaccaa agacaagcat    1200
gagatcgacc gcatgacgct gacgatggcc gtggagctgc ccgactcctt ctcccctgaa    1260
ctacgctccc tgctggaggg gttgctgcag agggatgtca accggagatt gggctgcctg    1320
ggccgagggg ctcaggaggt gaagagagc ccctttttcc gctcccctgga ctggcagatg    1380
gtcttcttgc agaagtaccc tcccccgctg atccccccac gagggaggt gaacgcggcc    1440
gacgccttcg acattggctc cttcgatgag gaggacacaa aaggaatcaa gttactggac    1500
agtgatcagg agctctaccg caacttcccc ctcaccatct cggagcggtg gcagcaggag    1560
gtggcagaga ctgtcttcga caccatcaac gctgagacag accggctgga ggctcgcaag    1620
aaagccaaga acaagcagct gggccatgag gaagactacg ccctgggcaa ggactgcatc    1680
```

-continued

```
atgcatggct acatgtccaa gatgggcaac cccttcctga cccagtggca gcggcggtac    1740
ttctacctgt tccccaaccg cctcgagtgg cggggcgagg gcgaggcccc gcagagcctg    1800
ctgaccatgg aggagatcca gtcggtggag gagacgcaga tcaaggagcg caagtgcctg    1860
ctcctcaaga tccgcggtgg gaaacagttc attttgcagt gcgatagcga ccctgagctg    1920
gtgcagtgga agaaggagct gcgcgacgcc taccgcgagg cccagcagct ggtgcagcgg    1980
gtgcccaaga tgaagaacaa gccgcgctcg cccgtggtgg agctgagcaa ggtgccgctg    2040
gtccagcgcg gcagtgccaa cggcctctga                                    2070
```

<210> SEQ ID NO 5
<211> LENGTH: 589
<212> TYPE: PRT
<213> ORGANISM: Homo sapiens

<400> SEQUENCE: 5

```
Met Glu Leu Glu Asn Ile Val Ala Asn Thr Val Leu Leu Lys Ala Arg
 1               5                  10                  15

Glu Gly Gly Gly Gly Asn Arg Lys Gly Lys Ser Lys Lys Trp Arg Gln
            20                  25                  30

Met Leu Gln Phe Pro His Ile Ser Gln Cys Glu Glu Leu Arg Leu Ser
        35                  40                  45

Leu Glu Arg Asp Tyr His Ser Leu Cys Glu Arg Gln Pro Ile Gly Arg
    50                  55                  60

Leu Leu Phe Arg Glu Phe Cys Ala Thr Arg Pro Glu Leu Ser Arg Cys
65                  70                  75                  80

Val Ala Phe Leu Asp Gly Val Ala Glu Tyr Glu Val Thr Pro Asp Asp
                85                  90                  95

Lys Arg Lys Ala Cys Gly Arg Gln Leu Thr Gln Asn Phe Leu Ser His
            100                 105                 110

Thr Gly Pro Asp Leu Ile Pro Glu Val Pro Arg Gln Leu Val Thr Asn
        115                 120                 125

Cys Thr Gln Arg Leu Glu Gln Gly Pro Cys Lys Asp Leu Phe Gln Glu
    130                 135                 140

Leu Thr Arg Leu Thr His Glu Tyr Leu Ser Val Ala Pro Phe Ala Asp
145                 150                 155                 160

Tyr Leu Asp Ser Ile Tyr Phe Asn Arg Phe Leu Gln Trp Lys Trp Leu
                165                 170                 175

Glu Arg Gln Pro Val Thr Lys Asn Thr Phe Arg Gln Tyr Arg Val Leu
            180                 185                 190

Gly Lys Gly Gly Phe Gly Glu Val Cys Ala Cys Gln Val Arg Ala Thr
        195                 200                 205

Gly Lys Met Tyr Ala Cys Lys Lys Leu Glu Lys Lys Arg Ile Lys Lys
    210                 215                 220

Arg Lys Gly Glu Ala Met Ala Leu Asn Glu Lys Gln Ile Leu Glu Lys
225                 230                 235                 240

Val Asn Ser Arg Phe Val Val Ser Leu Ala Tyr Ala Tyr Glu Thr Lys
                245                 250                 255

Asp Ala Leu Cys Leu Val Leu Thr Leu Met Asn Gly Gly Asp Leu Lys
            260                 265                 270

Phe His Ile Tyr His Met Gly Gln Ala Gly Phe Pro Glu Ala Arg Ala
        275                 280                 285

Val Phe Tyr Ala Ala Glu Ile Cys Cys Gly Leu Glu Asp Leu His Arg
    290                 295                 300
```

```
Glu Arg Ile Val Tyr Arg Asp Leu Lys Pro Glu Asn Ile Leu Leu Asp
305                 310                 315                 320

Asp His Gly His Ile Arg Ile Ser Asp Leu Gly Leu Ala Val His Val
                325                 330                 335

Pro Glu Gly Gln Thr Ile Lys Gly Arg Val Gly Thr Val Gly Tyr Met
                340                 345                 350

Ala Pro Glu Val Val Lys Asn Glu Arg Tyr Thr Phe Ser Pro Asp Trp
            355                 360                 365

Trp Ala Leu Gly Cys Leu Leu Tyr Glu Met Ile Ala Gly Gln Ser Pro
370                 375                 380

Phe Gln Gln Arg Lys Lys Ile Lys Arg Glu Glu Val Glu Arg Leu
385                 390                 395                 400

Val Lys Glu Val Pro Glu Glu Tyr Ser Glu Arg Phe Ser Pro Gln Ala
                405                 410                 415

Arg Ser Leu Cys Ser Gln Leu Leu Cys Lys Asp Pro Ala Glu Arg Leu
            420                 425                 430

Gly Cys Arg Gly Gly Ser Ala Arg Glu Val Lys Glu His Pro Leu Phe
        435                 440                 445

Lys Lys Leu Asn Phe Lys Arg Leu Gly Ala Gly Met Leu Glu Pro Pro
450                 455                 460

Phe Lys Pro Asp Pro Gln Ala Ile Tyr Cys Lys Asp Val Leu Asp Ile
465                 470                 475                 480

Glu Gln Phe Ser Thr Val Lys Gly Val Glu Leu Glu Pro Thr Asp Gln
                485                 490                 495

Asp Phe Tyr Gln Lys Phe Ala Thr Gly Ser Val Pro Ile Pro Trp Gln
            500                 505                 510

Asn Glu Met Val Glu Thr Glu Cys Phe Gln Glu Leu Asn Val Phe Gly
        515                 520                 525

Leu Asp Gly Ser Val Pro Pro Asp Leu Asp Trp Lys Gly Gln Pro Pro
530                 535                 540

Ala Pro Pro Lys Lys Gly Leu Leu Gln Arg Leu Phe Ser Arg Gln Arg
545                 550                 555                 560

Ile Ala Val Glu Thr Ala Ala Thr Ala Arg Lys Ser Ser Pro Ala
                565                 570                 575

Ser Ser Pro Gln Pro Glu Ala Pro Thr Ser Ser Trp Arg
            580                 585
```

<210> SEQ ID NO 6
<211> LENGTH: 1770
<212> TYPE: DNA
<213> ORGANISM: Homo sapiens

<400> SEQUENCE: 6

```
atggagctcg agaacatcgt agcgaacacg gtgctactca aggcccggga aggtggcggt    60
ggaaatcgca aaggcaaaag caagaaatgg cggcagatgc tccagttccc tcacatcagc   120
cagtgcgaag agctgcggct cagcctcgag cgtgactatc acagcctgtg cgagcggcag   180
cccattgggc gcctgctgtt ccgagagttc tgtgccacga ggccggagct gagccgctgc   240
gtcgccttcc tggatgggt ggccgagtat gaagtgaccc cggatgacaa gcggaaggca   300
tgtgggcggc agctaacgca gaattttctg agccacacgg tcctgacct catccctgag   360
gtcccccggc agctggtgac gaactgcacc cagcggctgg agcagggtcc ctgcaaagac   420
cttttccagg aactcacccg gctgacccac gagtacctga gcgtggcccc ttttgccgac   480
```

```
tacctcgaca gcatctactt caaccgtttc ctgcagtgga agtggctgga aaggcagcca    540
gtgaccaaaa acaccttcag gcaataccga gtcctgggca aggtggcttt ggggaggtg     600
tgcgcctgcc aggtgcgggc cacaggtaag atgtatgcct gcaagaagct agagaaaaag    660
cggatcaaga agcggaaagg ggaggccatg gcgctgaacg agaagcagat cctggagaaa    720
gtgaacagta ggtttgtagt gagcttggcc tacgcctatg agaccaagga cgcgctgtgc    780
ctggtgctga cactgatgaa cggggcgac ctcaagttcc acatctacca catgggccag     840
gctggcttcc ccgaagcgcg ggccgtcttc tacgccgccg agatctgctg tggcctggag    900
gacctgcacc gggagcgcat cgtgtacagg gacctgaagc ccgagaacat cttgctggat    960
gaccacggcc acatccgcat ctctgacctg gactagctg tgcatgtgcc cgagggccag    1020
accatcaaag ggcgtgtggg caccgtgggt tacatggctc cggaggtggt gaagaatgaa   1080
cggtacacgt tcagccctga ctggtgggcg ctcggctgcc tcctgtacga gatgatcgca   1140
ggccagtcgc ccttccagca gaggaagaag aagatcaagc gggaggaggt ggagcggctg   1200
gtgaaggagg tccccgagga gtattccgag cgcttttccc cgcaggcccg ctcactttgc   1260
tcacagctcc tctgcaagga ccctgccgaa cgcctggggt gtcgtggggg cagtgcccgc   1320
gaggtgaagg agcaccccct ctttaagaag ctgaacttca gcggctggg agctggcatg    1380
ctggagccgc cgttcaagcc tgacccccag gccatttact gcaaggatgt tctggacatt   1440
gaacagttct ctacggtcaa gggcgtggag ctggagccta ccgaccagga cttctaccag   1500
aagtttgcca caggcagtgt gcccatcccc tggcagaacg agatggtgga gaccgagtgc   1560
ttccaagagc tgaatgtctt tgggctggat ggctcagttc ccccagacct ggactggaag   1620
ggccagccac ctgcacctcc taaaaaggga ctgctgcaga gactcttcag tcgccaaagg   1680
attgctgtgg aaactgcagc gacagcgagg aagagctccc cacccgcctc tagcccccag   1740
cccgaggccc ccaccagcag ttggcggtag                                    1770
```

<210> SEQ ID NO 7
<211> LENGTH: 560
<212> TYPE: PRT
<213> ORGANISM: Homo sapiens

<400> SEQUENCE: 7

```
Met Glu Leu Glu Asn Ile Val Ala Asn Thr Val Leu Leu Lys Ala Arg
 1               5                  10                  15

Glu Gly Gly Gly Gly Asn Arg Lys Gly Lys Ser Lys Lys Trp Arg Gln
             20                  25                  30

Met Leu Gln Phe Pro His Ile Ser Gln Cys Glu Glu Leu Arg Leu Ser
         35                  40                  45

Leu Glu Arg Asp Tyr His Ser Leu Cys Glu Arg Gln Pro Ile Gly Arg
     50                  55                  60

Leu Leu Phe Arg Glu Phe Cys Ala Thr Arg Pro Glu Leu Ser Arg Cys
 65                  70                  75                  80

Val Ala Phe Leu Asp Gly Val Ala Glu Tyr Glu Val Thr Pro Asp Asp
                 85                  90                  95

Lys Arg Lys Ala Cys Gly Arg Gln Leu Thr Gln Asn Phe Leu Ser His
            100                 105                 110

Thr Gly Pro Asp Leu Ile Pro Glu Val Pro Arg Gln Leu Val Thr Asn
        115                 120                 125

Cys Thr Gln Arg Leu Glu Gln Gly Pro Cys Lys Asp Leu Phe Gln Glu
    130                 135                 140
```

```
Leu Thr Arg Leu Thr His Glu Tyr Leu Ser Val Ala Pro Phe Ala Asp
145                 150                 155                 160

Tyr Leu Asp Ser Ile Tyr Phe Asn Arg Phe Leu Gln Trp Lys Trp Leu
                165                 170                 175

Glu Arg Gln Pro Val Thr Lys Asn Thr Phe Arg Gln Tyr Arg Val Leu
            180                 185                 190

Gly Lys Gly Gly Phe Gly Glu Val Cys Ala Cys Gln Val Arg Ala Thr
        195                 200                 205

Gly Lys Met Tyr Ala Cys Lys Lys Leu Glu Lys Lys Arg Ile Lys Lys
    210                 215                 220

Arg Lys Gly Glu Ala Met Ala Leu Asn Glu Lys Gln Ile Leu Glu Lys
225                 230                 235                 240

Val Asn Ser Arg Phe Val Val Ser Leu Ala Tyr Ala Tyr Glu Thr Lys
                245                 250                 255

Asp Ala Leu Cys Leu Val Leu Thr Leu Met Asn Gly Gly Asp Leu Lys
            260                 265                 270

Phe His Ile Tyr His Met Gly Gln Ala Gly Phe Pro Glu Ala Arg Ala
        275                 280                 285

Val Phe Tyr Ala Ala Glu Ile Cys Cys Gly Leu Glu Asp Leu His Arg
    290                 295                 300

Glu Arg Ile Val Tyr Arg Asp Leu Lys Pro Glu Asn Ile Leu Leu Asp
305                 310                 315                 320

Asp His Gly His Ile Arg Ile Ser Asp Leu Gly Leu Ala Val His Val
                325                 330                 335

Pro Glu Gly Gln Thr Ile Lys Gly Arg Val Gly Thr Val Gly Tyr Met
            340                 345                 350

Ala Pro Glu Val Val Lys Asn Glu Arg Tyr Thr Phe Ser Pro Asp Trp
        355                 360                 365

Trp Ala Leu Gly Cys Leu Leu Tyr Glu Met Ile Ala Gly Gln Ser Pro
    370                 375                 380

Phe Gln Gln Arg Lys Lys Lys Ile Lys Arg Glu Glu Val Glu Arg Leu
385                 390                 395                 400

Val Lys Glu Val Pro Glu Glu Tyr Ser Glu Arg Phe Ser Pro Gln Ala
                405                 410                 415

Arg Ser Leu Cys Ser Gln Leu Leu Cys Lys Asp Pro Ala Glu Arg Leu
            420                 425                 430

Gly Cys Arg Gly Gly Ser Ala Arg Glu Val Lys Glu His Pro Leu Phe
        435                 440                 445

Lys Lys Leu Asn Phe Lys Arg Leu Gly Ala Gly Met Leu Glu Pro Pro
    450                 455                 460

Phe Lys Pro Asp Pro Gln Ala Ile Tyr Cys Lys Asp Val Leu Asp Ile
465                 470                 475                 480

Glu Gln Phe Ser Thr Val Lys Gly Val Glu Leu Glu Pro Thr Asp Gln
                485                 490                 495

Asp Phe Tyr Gln Lys Phe Ala Thr Gly Ser Val Pro Ile Pro Trp Gln
            500                 505                 510

Asn Glu Met Val Glu Thr Glu Cys Phe Gln Glu Leu Asn Val Phe Gly
        515                 520                 525

Leu Asp Gly Ser Val Pro Pro Asp Leu Asp Trp Lys Gly Gln Pro Pro
    530                 535                 540

Ala Pro Pro Lys Lys Gly Leu Leu Gln Arg Leu Phe Ser Arg Gln Arg
545                 550                 555                 560
```

<210> SEQ ID NO 8
<211> LENGTH: 1683
<212> TYPE: DNA
<213> ORGANISM: Homo sapiens

<400> SEQUENCE: 8

```
atggagctcg agaacatcgt agcgaacacg gtgctactca aggcccggga aggtggcggt    60
ggaaatcgca aaggcaaaag caagaaatgg cggcagatgc tccagttccc tcacatcagc   120
cagtgcgaag agctgcggct cagcctcgag cgtgactatc acagcctgtg cgagcggcag   180
cccattgggc gcctgctgtt ccgagagttc tgtgccacga ggccgagct gagccgctgc   240
gtcgccttcc tggatggggt ggccgagtat gaagtgaccc cggatgacaa gcggaaggca   300
tgtgggcggc agctaacgca gaattttctg agccacacgg tcctgacct catccctgag   360
gtcccccggc agctggtgac gaactgcacc cagcggctgg agcagggtcc ctgcaaagac   420
cttttccagg aactcacccg gctgacccac gagtacctga gcgtggcccc ttttgccgac   480
tacctcgaca gcatctactt caaccgtttc ctgcagtgga agtggctgga aaggcagcca   540
gtgaccaaaa acaccttcag gcaataccga gtcctgggca aggtggctt tggggaggtg   600
tgcgcctgcc aggtgcgggc cacaggtaag atgtatgcct gcaagaagct agagaaaaag   660
cggatcaaga gcggaaagg ggaggccatg gcgctgaacg agaagcagat cctggagaaa   720
gtgaacagta ggtttgtagt gagcttggcc tacgcctatg agaccaagga cgcgctgtgc   780
ctggtgctga cactgatgaa cggggcgac ctcaagttcc acatctacca catgggccag   840
gctggcttcc ccgaagcgcg ggccgtcttc tacgccgccg agatctgctg tggcctggag   900
gacctgcacc gggagcgcat cgtgtacagg gacctgaagc ccgagaacat cttgctggat   960
gaccacggcc acatccgcat ctctgacctg ggactagctg tgcatgtgcc cgagggccag  1020
accatcaaag gcgtgtgggg caccgtgggt tacatggctc cggaggtggt gaagaatgaa  1080
cggtacacgt tcagccctga ctggtgggcg ctcggctgcc tcctgtacga gatgatcgca  1140
ggccagtcgc ccttccagca gaggaagaag aagatcaagc gggaggaggt ggagcggctg  1200
gtgaaggagg tccccgagga gtattccgag cgcttttccc cgcaggcccg ctcactttgc  1260
tcacagctcc tctgcaagga ccctgccgaa cgcctggggt gtcgtggggg cagtgcccgc  1320
gaggtgaagg agcacccccct ctttaagaag ctgaacttca gcggctggg agctggcatg  1380
ctggagccgc cgttcaagcc tgaccccag gccatttact gcaaggatgt tctggacatt  1440
gaacagttct ctacggtcaa gggcgtggag ctggagccta ccgaccagga cttctaccag  1500
aagtttgcca caggcagtgt gcccatcccc tggcagaacg agatggtgga gaccgagtgc  1560
ttccaagagc tgaatgtctt tgggctggat ggctcagttc ccccagacct ggactggaag  1620
ggccagccac ctgcacctcc taaaaaggga ctgctgcaga gactcttcag tcgccaaagg  1680
tga                                                                1683
```

<210> SEQ ID NO 9
<211> LENGTH: 576
<212> TYPE: PRT
<213> ORGANISM: Homo sapiens

<400> SEQUENCE: 9

Met Glu Leu Glu Asn Ile Val Ala Asn Thr Val Leu Leu Lys Ala Arg
  1               5                  10                  15

Glu Gly Gly Gly Gly Asn Arg Lys Gly Lys Ser Lys Lys Trp Arg Gln
             20                  25                  30

-continued

```
Met Leu Gln Phe Pro His Ile Ser Gln Cys Glu Glu Leu Arg Leu Ser
         35                  40                  45
Leu Glu Arg Asp Tyr His Ser Leu Cys Glu Arg His Ala Ile Gly Arg
     50                  55                  60
Leu Leu Phe Arg Glu Phe Cys Ala Thr Arg Pro Glu Leu Ser Arg Cys
 65                  70                  75                  80
Val Ala Phe Leu Asp Gly Val Ala Glu Tyr Glu Val Thr Pro Asp Asp
                 85                  90                  95
Lys Arg Lys Ala Cys Gly Arg His Val Thr Gln Asn Phe Leu Ser His
            100                 105                 110
Thr Gly Pro Asp Leu Ile Pro Glu Val Pro Arg Gln Leu Val Thr Asn
        115                 120                 125
Cys Thr Gln Arg Leu Glu Gln Gly Pro Cys Lys Asp Leu Phe Gln Glu
    130                 135                 140
Leu Thr Arg Leu Thr His Glu Tyr Leu Ser Val Ala Pro Phe Ala Asp
145                 150                 155                 160
Tyr Leu Asp Ser Ile Tyr Phe Asn Arg Phe Leu Gln Trp Lys Trp Leu
                165                 170                 175
Glu Arg Gln Pro Val Thr Lys Asn Thr Phe Arg Gln Tyr Arg Val Leu
            180                 185                 190
Gly Lys Gly Gly Phe Gly Glu Val Cys Ala Cys Gln Val Arg Ala Thr
        195                 200                 205
Gly Lys Met Tyr Ala Cys Lys Lys Leu Glu Lys Lys Arg Ile Lys Lys
    210                 215                 220
Arg Lys Gly Glu Ala Met Ala Leu Asn Glu Lys Gln Ile Leu Glu Lys
225                 230                 235                 240
Val Asn Ser Arg Phe Val Val Ser Leu Ala Tyr Ala Tyr Glu Thr Lys
                245                 250                 255
Asp Ala Leu Cys Leu Val Leu Thr Leu Met Asn Gly Gly Asp Leu Lys
            260                 265                 270
Phe His Ile Tyr His Met Gly Gln Ala Gly Phe Pro Glu Ala Arg Ala
        275                 280                 285
Val Phe Tyr Ala Ala Glu Ile Cys Cys Gly Leu Glu Asp Leu His Arg
    290                 295                 300
Glu Arg Ile Val Tyr Arg Asp Leu Lys Pro Glu Asn Ile Leu Leu Asp
305                 310                 315                 320
Asp His Gly His Ile Arg Ile Ser Asp Leu Gly Leu Ala Val His Val
                325                 330                 335
Pro Glu Gly Gln Thr Ile Lys Gly Arg Val Gly Thr Val Gly Tyr Met
            340                 345                 350
Ala Pro Glu Val Val Lys Asn Glu Arg Tyr Thr Phe Ser Pro Asp Trp
        355                 360                 365
Trp Ala Leu Gly Cys Leu Leu Tyr Glu Met Ile Ala Gly Gln Ser Pro
    370                 375                 380
Phe Gln Gln Arg Lys Lys Lys Ile Lys Arg Glu Glu Val Glu Arg Leu
385                 390                 395                 400
Val Lys Glu Val Pro Glu Glu Tyr Ser Glu Arg Phe Ser Pro Gln Ala
                405                 410                 415
Arg Ser Leu Cys Ser Gln Leu Leu Cys Lys Asp Pro Ala Glu Arg Leu
            420                 425                 430
Gly Cys Arg Gly Gly Ser Ala Arg Glu Val Lys Glu His Pro Leu Phe
        435                 440                 445
Lys Lys Leu Asn Phe Lys Arg Leu Gly Ala Gly Met Leu Glu Pro Pro
```

|   |   |   |   |   |   |   |   |   |   |   |
|---|---|---|---|---|---|---|---|---|---|---|
| | | 450 | | | | 455 | | | 460 | |
| Phe | Lys | Pro | Asp | Pro | Gln | Ala | Ile | Tyr | Cys | Lys | Asp | Val | Leu | Asp | Ile |
| 465 | | | | 470 | | | | | 475 | | | | | 480 |

Phe Lys Pro Asp Pro Gln Ala Ile Tyr Cys Lys Asp Val Leu Asp Ile
465                 470                 475                 480

Glu Gln Phe Ser Thr Val Lys Gly Val Glu Leu Glu Pro Thr Asp Gln
                485                 490                 495

Asp Phe Tyr Gln Lys Phe Ala Thr Gly Ser Val Pro Ile Pro Trp Gln
            500                 505                 510

Asn Glu Met Val Glu Thr Glu Cys Phe Gln Glu Leu Asn Val Phe Gly
        515                 520                 525

Leu Asp Gly Ser Val Pro Pro Asp Leu Asp Trp Lys Gly Gln Pro Pro
530                 535                 540

Ala Pro Pro Lys Lys Gly Leu Leu Gln Arg Leu Phe Ser Arg Gln Asp
545                 550                 555                 560

Cys Cys Gly Asn Cys Ser Asp Ser Glu Glu Glu Leu Pro Thr Arg Leu
                565                 570                 575

<210> SEQ ID NO 10
<211> LENGTH: 1738
<212> TYPE: DNA
<213> ORGANISM: Homo sapiens

<400> SEQUENCE: 10

```
atggagctcg agaacatcgt agcgaacacg gtgctactca aggcccggga aggtggcggt      60
ggaaatcgca aaggcaaaag caagaaatgg cggcagatgc tccagttccc tcacatcagc     120
cagtgcgaag agctgcggct cagcctcgag cgtgactatc acagcctgtg cgagcggcac     180
gccattgggc gcctgctgtt ccgagagttc tgtgccacga ggccggagct gagccgctgc     240
gtcgccttcc tggatggggt ggccgagtat gaagtgaccc cggatgacaa gcggaaggca     300
tgtgggcggc acgtaacgca gaattttctg agccacacgg tcctgacct catccctgag     360
gtcccccggc agctggtgac gaactgcacc cagcggctgg agcagggtcc ctgcaaagac     420
cttttccagg aactcacccg gctgacccac gagtacctga gcgtggcccc ttttgccgac     480
tacctcgaca gcatctactt caaccgtttc ctgcagtgga gtggctgga aaggcagcca     540
gtgaccaaaa acaccttcag gcaataccga gtcctgggca aggtggctt ggggaggtg     600
tgcgcctgcc aggtgcgggc cacaggtaag atgtatgcct gcaagaagct agagaaaaag     660
cggatcaaga agcggaaagg ggaggccatg gcgctgaacg agaagcagat cctggagaaa     720
gtgaacagta ggtttgtagt gagcttggcc tacgcctatg agaccaagga cgcgctgtgc     780
ctggtgctga cactgatgaa cggggggcgac ctcaagttcc acatctacca catgggccag     840
gctggcttcc ccgaagcgcg ggccgtcttc tacgccgccg agatctgctg tggcctggag     900
gacctgcacc gggagcgcat cgtgtacagg gacctgaagc ccgagaacat cttgctggat     960
gaccacggcc acatccgcat ctctgacctg ggactagctg tgcatgtgcc cgagggccag    1020
accatcaaag ggcgtgtggg caccgtgggt tacatggctc cggaggtggt gaagaatgaa    1080
cggtacacgt tcagccctga ctggtgggcg ctcggctgcc tcctgtacga gatgatcgca    1140
ggccagtcgc ccttccagca gaggaagaag aagatcaagc gggaggaggt ggagcggctg    1200
gtgaaggagg tccccgagga gtattccgag cgcttttccc cgcaggcccg ctcactttgc    1260
tcacagctcc tctgcaagga ccctgccgaa cgcctggggg tcgtgggggg cagtgcccgc    1320
gaggtgaagg agcacccct cttaagaag ctgaacttca gcggctggg agctggcatg    1380
ctggagccgc cgttcaagcc tgaccccag gccatttact gcaaggatgt tctggacatt    1440
```

-continued

```
gaacagttct ctacggtcaa gggcgtggag ctggagccta ccgaccagga cttctaccag   1500
aagtttgcca caggcagtgt gcccatcccc tggcagaacg agatggtgga gaccgagtgc   1560
ttccaagagc tgaatgtctt tgggctggat ggctcagttc ccccagacct ggactggaag   1620
ggccagccac ctgcacctcc taaaaaggga ctgctgcaga gactcttcag tcgccaagat   1680
tgctgtggaa actgcagcga cagcgaggaa gagctcccca cccgcctcta gcccccag    1738
```

<210> SEQ ID NO 11
<211> LENGTH: 590
<212> TYPE: PRT
<213> ORGANISM: Homo sapiens

<400> SEQUENCE: 11

```
Met Glu Leu Glu Asn Ile Val Ala Asn Thr Val Leu Leu Lys Ala Arg
  1               5                  10                  15

Glu Gly Gly Gly Gly Lys Arg Lys Gly Lys Ser Lys Lys Trp Lys Glu
             20                  25                  30

Ile Leu Lys Phe Pro His Ile Ser Gln Cys Glu Asp Leu Arg Arg Thr
         35                  40                  45

Ile Asp Arg Asp Tyr Cys Ser Leu Cys Asp Lys Gln Pro Ile Gly Arg
     50                  55                  60

Leu Leu Phe Arg Gln Phe Cys Glu Thr Arg Pro Gly Leu Glu Cys Tyr
 65                  70                  75                  80

Ile Gln Phe Leu Asp Ser Val Ala Glu Tyr Glu Val Thr Pro Asp Glu
                 85                  90                  95

Lys Leu Gly Glu Lys Gly Lys Glu Ile Met Thr Lys Tyr Leu Thr Pro
            100                 105                 110

Lys Ser Pro Val Phe Ile Ala Gln Val Gly Gln Asp Leu Val Ser Gln
        115                 120                 125

Thr Glu Glu Lys Leu Leu Gln Lys Pro Cys Lys Glu Leu Phe Ser Ala
    130                 135                 140

Cys Ala Gln Ser Val His Glu Tyr Leu Arg Gly Glu Pro Phe His Glu
145                 150                 155                 160

Tyr Leu Asp Ser Met Phe Phe Asp Arg Phe Leu Gln Trp Lys Trp Leu
                165                 170                 175

Glu Arg Gln Pro Val Thr Lys Asn Thr Phe Arg Gln Tyr Arg Val Leu
            180                 185                 190

Gly Lys Gly Gly Phe Gly Glu Val Cys Ala Cys Gln Val Arg Ala Thr
        195                 200                 205

Gly Lys Met Tyr Ala Cys Lys Arg Leu Glu Lys Lys Arg Ile Lys Lys
    210                 215                 220

Arg Lys Gly Glu Ser Met Ala Leu Asn Glu Lys Gln Ile Leu Glu Lys
225                 230                 235                 240

Val Asn Ser Gln Phe Val Val Asn Leu Ala Tyr Ala Tyr Glu Thr Lys
                245                 250                 255

Asp Ala Leu Cys Leu Val Leu Thr Ile Met Asn Gly Gly Asp Leu Lys
            260                 265                 270

Phe His Ile Tyr Asn Met Gly Asn Pro Gly Phe Glu Glu Glu Arg Ala
        275                 280                 285

Leu Phe Tyr Ala Ala Glu Ile Leu Cys Gly Leu Glu Asp Leu His Arg
    290                 295                 300

Glu Asn Thr Val Tyr Arg Asp Leu Lys Pro Glu Asn Ile Leu Leu Asp
305                 310                 315                 320

Asp Tyr Gly His Ile Arg Ile Ser Asp Leu Gly Leu Ala Val Lys Ile
```

```
                    325                 330                 335
Pro Glu Gly Asp Leu Ile Arg Gly Arg Val Gly Thr Val Gly Tyr Met
                340                 345                 350

Ala Pro Glu Val Leu Asn Asn Gln Arg Tyr Gly Leu Ser Pro Asp Tyr
            355                 360                 365

Trp Gly Leu Gly Cys Leu Ile Tyr Glu Met Ile Glu Gly Gln Ser Pro
        370                 375                 380

Phe Arg Gly Arg Lys Glu Lys Val Lys Arg Glu Val Asp Arg Arg
385                 390                 395                 400

Val Leu Glu Thr Glu Glu Val Tyr Ser His Lys Phe Ser Glu Glu Ala
                405                 410                 415

Lys Ser Ile Cys Lys Met Leu Leu Thr Lys Asp Ala Lys Gln Arg Leu
            420                 425                 430

Gly Cys Gln Glu Glu Gly Ala Ala Glu Val Lys Arg His Pro Phe Phe
        435                 440                 445

Arg Asn Met Asn Phe Lys Arg Leu Glu Ala Gly Met Leu Asp Pro Pro
    450                 455                 460

Phe Val Pro Asp Pro Arg Ala Val Tyr Cys Lys Asp Val Leu Asp Ile
465                 470                 475                 480

Glu Gln Phe Ser Thr Val Lys Gly Val Asn Leu Asp His Thr Asp Asp
                485                 490                 495

Asp Phe Tyr Ser Lys Phe Ser Thr Gly Ser Val Ser Ile Pro Trp Gln
            500                 505                 510

Asn Glu Met Ile Glu Thr Glu Cys Phe Lys Glu Leu Asn Val Phe Gly
        515                 520                 525

Pro Asn Gly Thr Leu Pro Pro Asp Leu Asn Arg Asn His Pro Pro Glu
    530                 535                 540

Pro Pro Lys Lys Gly Leu Leu Gln Arg Leu Phe Lys Arg Gln His Gln
545                 550                 555                 560

Asn Asn Ser Lys Ser Ser Pro Ser Ser Lys Thr Ser Phe Asn His His
                565                 570                 575

Ile Asn Ser Asn His Val Ser Ser Asn Ser Thr Gly Ser Ser
            580                 585                 590

<210> SEQ ID NO 12
<211> LENGTH: 1773
<212> TYPE: DNA
<213> ORGANISM: Homo sapiens

<400> SEQUENCE: 12
atggagctgg aaaacatcgt ggccaacacg gtcttgctga agccaggga aggggcgga      60 ggaaagcgca aagggaaaag caagaagtgg aaagaaatcc tgaagttccc tcacattagc    120
cagtgtgaag acctccgaag gaccatagac agagattact gcagtttatg tgacaagcag    180
ccaatcggga ggctgctttt ccggcagttt tgtgaaacca ggcctgggct ggagtgttac    240
attcagttcc tggactccgt ggcagaatat gaagttactc cagatgaaaa actgggagag    300
aaagggaagg aaattatgac caagtacctc accccaaagt cccctgtttt catagcccaa    360
gttggccaag acctggtctc ccagacggag gagaagctcc tacagaagcc gtgcaaagaa    420
ctcttttctg cctgtgcaca gtctgtccac gagtacctga gggagaaacc attccacgaa    480
tatctggaca gcatgttttt tgaccgcttt ctccagtgga agtggttgga aaggcaaccg    540
gtgaccaaaa acactttcag gcagtatcga gtgctaggaa aggggggctt cggggaggtc    600
tgtgcctgcc aggttcgggc cacgggtaaa atgtatgcct gcaagcgctt ggagaagaag    660
```

-continued

```
aggatcaaaa agaggaaagg ggagtccatg gccctcaatg agaagcagat cctcgagaag    720
gtcaacagtc agtttgtggt caacctggcc tatgcctacg agaccaagga tgcactgtgc    780
ttggtcctga ccatcatgaa tgggggtgac ctgaagttcc acatctacaa catgggcaac    840
cctggcttcg aggaggagcg ggccttgttt tatgcggcag agatcctctg cggcttagaa    900
gacctccacc gtgagaacac cgtctaccga gatctgaaac ctgaaaacat cctgttagat    960
gattatggcc acattaggat ctcagacctg gcttggctg tgaagatccc cgagggagac    1020
ctgatccgcg gccgggtggg cactgttggc tacatggctc cagaggtcct gaacaaccag    1080
aggtacggcc tgagccccga ctactgggggc cttggctgcc tcatctatga gatgatcgag    1140
ggccagtcgc cgttccgcgg ccgcaaggag aaggtgaagc gggaggaggt ggaccgccgg    1200
gtcctggaga cggaggaggt gtactcccac aagttctccg aggaggccaa gtccatctgc    1260
aagatgctgc tcacgaaaga tgcgaagcag aggctgggct gccaggagga gggggctgca    1320
gaggtcaaga gacacccctt cttcaggaac atgaacttca gcgcttaga agccgggatg    1380 ttggaccctc ccttcgttcc agaccccgc gctgtgtact gtaaggacgt gctggacatc    1440
gagcagttct ccactgtgaa gggcgtcaat ctggaccaca cagacgacga cttctactcc    1500
aagttctcca cgggctctgt gtccatccca tggcaaaacg agatgataga aacagaatgc    1560
tttaaggagc tgaacgtgtt tggacctaat ggtaccctcc cgccagatct gaacagaaac    1620
caccctccgg aaccgcccaa gaaagggctg ctccagagac tcttcaagcg gcagcatcag    1680
aacaattcca gagttcgcc cagctccaag accagtttta accaccacat aaactcaaac    1740
catgtcagct cgaactccac cggaagcagc tag    1773
```

<210> SEQ ID NO 13
<211> LENGTH: 500
<212> TYPE: PRT
<213> ORGANISM: Homo sapiens

<400> SEQUENCE: 13

```
Met Glu Leu Glu Asn Ile Val Ala Asn Ser Leu Leu Lys Ala Arg
  1               5                  10                  15

Gln Glu Lys Asp Tyr Ser Ser Leu Cys Asp Lys Gln Pro Ile Gly Arg
                 20                  25                  30

Arg Leu Phe Arg Gln Phe Cys Asp Thr Lys Pro Thr Leu Lys Arg His
                 35                  40                  45

Ile Glu Phe Leu Asp Ala Val Ala Glu Tyr Glu Val Ala Asp Asp Glu
                 50                  55                  60

Asp Arg Ser Asp Cys Gly Leu Ser Ile Leu Asp Arg Phe Phe Asn Asp
 65                  70                  75                  80

Lys Leu Ala Ala Pro Leu Pro Glu Ile Pro Pro Asp Val Val Thr Glu
                 85                  90                  95

Cys Arg Leu Gly Leu Lys Glu Glu Asn Pro Ser Lys Lys Ala Phe Glu
                100                 105                 110

Glu Cys Thr Arg Val Ala His Asn Tyr Leu Arg Gly Glu Pro Phe Glu
                115                 120                 125

Glu Tyr Gln Glu Ser Ser Tyr Phe Ser Gln Phe Leu Gln Trp Lys Trp
                130                 135                 140

Leu Glu Arg Gln Pro Val Thr Lys Asn Thr Phe Arg His Tyr Arg Val
145                 150                 155                 160

Leu Gly Lys Gly Gly Phe Gly Glu Val Cys Ala Cys Gln Val Arg Ala
                165                 170                 175
```

Thr Gly Lys Met Tyr Ala Cys Lys Lys Leu Gln Lys Lys Arg Ile Lys
            180                 185                 190

Lys Arg Lys Gly Glu Ala Met Ala Leu Asn Glu Lys Arg Ile Leu Glu
        195                 200                 205

Lys Val Gln Ser Arg Phe Val Val Ser Leu Ala Tyr Ala Tyr Glu Thr
    210                 215                 220

Lys Asp Ala Leu Cys Leu Val Leu Thr Ile Met Asn Gly Gly Asp Leu
225                 230                 235                 240

Lys Phe His Ile Tyr Asn Leu Gly Asn Pro Gly Phe Asp Gln Arg
            245                 250                 255

Ala Val Phe Tyr Ala Ala Glu Leu Cys Cys Gly Leu Glu Asp Leu Gln
            260                 265                 270

Arg Glu Arg Ile Val Tyr Arg Asp Leu Lys Pro Glu Asn Ile Leu Leu
        275                 280                 285

Asp Asp Arg Gly His Ile Arg Ile Ser Asp Leu Gly Leu Ala Thr Glu
    290                 295                 300

Ile Pro Glu Gly Gln Arg Val Arg Gly Arg Val Gly Thr Val Gly Tyr
305                 310                 315                 320

Met Ala Pro Glu Val Val Asn Asn Glu Lys Tyr Thr Phe Ser Pro Asp
            325                 330                 335

Trp Trp Gly Leu Gly Cys Leu Ile Tyr Glu Met Ile Gln Gly His Ser
            340                 345                 350

Pro Phe Lys Lys Tyr Lys Glu Lys Val Lys Trp Glu Glu Val Asp Gln
        355                 360                 365

Arg Ile Lys Asn Asp Thr Glu Glu Tyr Ser Glu Lys Phe Ser Glu Asp
    370                 375                 380

Ala Lys Ser Ile Cys Arg Met Leu Leu Thr Lys Asn Pro Ser Lys Arg
385                 390                 395                 400

Leu Gly Cys Arg Gly Glu Gly Ala Ala Gly Val Lys Gln His Pro Val
            405                 410                 415

Phe Lys Asp Ile Asn Phe Arg Arg Leu Glu Ala Asn Met Leu Glu Pro
            420                 425                 430

Pro Phe Cys Pro Asp Pro His Ala Val Tyr Cys Lys Asp Val Leu Asp
        435                 440                 445

Ile Glu Gln Phe Ser Ala Val Lys Gly Ile Tyr Leu Asp Thr Ala Asp
    450                 455                 460

Glu Asp Phe Tyr Ala Arg Phe Ala Thr Gly Cys Val Ser Ile Pro Trp
465                 470                 475                 480

Gln Asn Glu Asp Cys Leu Thr Met Val Pro Ser Glu Lys Glu Val Glu
            485                 490                 495

Pro Lys Gln Cys
            500

<210> SEQ ID NO 14
<211> LENGTH: 1503
<212> TYPE: DNA
<213> ORGANISM: Homo sapiens

<400> SEQUENCE: 14
atggagctcg agaacatcgt ggccaactcg ctgctgctga agcgcgtca agaaaaggat      60 tatagcagtc tttgtgacaa gcaaccgata ggaagacgtc tcttcaggca gttctgtgat     120
accaaaccca ctctaaagag gcacattgaa ttcttggatg cagtggcaga atatgaagtt     180
gccgatgatg aggaccgaag tgattgtgga ctgtcaatct tagatagatt cttcaatgat     240

-continued

```
aagttggcag ccccttttacc agaaatacct ccagatgttg tgacagaatg tagattggga    300
ctgaaggagg agaacccttc caaaaaagcc tttgaggaat gtactagagt tgcccataac    360
tacctaagag gggaaccatt tgaagaatac caagaaagct catatttttc tcagttttta    420
caatggaaat ggctggaaag gcaacccgta acaaagaaca catttagaca ttacagagtt    480
ctaggaaaag gcggatttgg agaggtttgc gcctgtcaag tgcgagccac aggaaaaatg    540
tatgcctgca aaaagctaca aaaaaaaga ataagaaga ggaaggtga agctatggct       600 ctaaatgaga aaagaattct ggagaaagtg caaagtagat tcgtagttag tttagcctac    660
gcttatgaaa ccaaagatgc cttgtgcttg gtgctcacca ttatgaatgg agggatttg     720 aagtttcaca tttacaacct gggcaatccc ggctttgatg agcagagagc cgttttctat    780
gctgcagagc tgtgttgcgg cttggaagat ttacagaggg aaagaattgt atacagagac    840
ttgaagcctg agaatattct ccttgatgat cgtggacaca tccggatttc agacctcggt    900
ttggccacag agatcccaga aggacagagg gttcgaggaa gagttggaac agtcggctac    960
atggcacctg aagttgtcaa taatgaaaag tatacgttta gtcccgattg gtggggactt   1020
ggctgtctga tctatgaaat gattcaggga cattctccat tcaaaaaata caaagagaaa   1080
gtcaaatggg aggaggtcga tcaaagaatc aagaatgata ccgaggagta ttctgagaag   1140
ttttcagagg atgccaaatc tatctgcagg atgttactca ccaagaatcc aagcaagcgg   1200
ctgggctgca ggggcgaggg agcggctggg gtgaagcagc accccgtgtt caaggacatc   1260
aacttcagga ggctggaggc aaacatgctg gagccccctt tctgtcctga tcctcatgcc   1320
gtttactgta aggacgtcct ggatatcgag cagttctcgg cggtgaaagg gatctacctg   1380
gacaccgcag atgaagactt ctatgctcgg tttgctaccg ggtgtgtctc catcccctgg   1440
cagaatgagg actgcctgac catggtcccc agtgagaagg aagtggaacc caagcaatgc   1500
tga                                                                 1503
```

<210> SEQ ID NO 15
<211> LENGTH: 546
<212> TYPE: PRT
<213> ORGANISM: Homo sapiens

<400> SEQUENCE: 15

```
Met Glu Leu Glu Asn Ile Val Ala Asn Ser Leu Leu Leu Lys Ala Arg
 1               5                  10                  15

Gln Glu Lys Asp Tyr Ser Ser Leu Cys Asp Lys Gln Pro Ile Gly Arg
            20                  25                  30

Arg Leu Phe Arg Gln Phe Cys Asp Thr Lys Pro Thr Leu Lys Arg His
        35                  40                  45

Ile Glu Phe Leu Asp Ala Val Ala Glu Tyr Glu Val Ala Asp Asp Glu
    50                  55                  60

Asp Arg Ser Asp Cys Gly Leu Ser Ile Leu Asp Arg Phe Phe Asn Asp
65                  70                  75                  80

Lys Leu Ala Ala Pro Leu Pro Glu Ile Pro Pro Asp Val Val Thr Glu
                85                  90                  95

Cys Arg Leu Gly Leu Lys Glu Glu Asn Pro Ser Lys Lys Ala Phe Glu
            100                 105                 110

Glu Cys Thr Arg Val Ala His Asn Tyr Leu Arg Gly Glu Pro Phe Glu
        115                 120                 125

Glu Tyr Gln Glu Ser Ser Tyr Phe Ser Gln Phe Leu Gln Trp Lys Trp
    130                 135                 140
```

-continued

```
Leu Glu Arg Gln Pro Val Thr Lys Asn Thr Phe Arg His Tyr Arg Val
145                 150                 155                 160

Leu Gly Lys Gly Gly Phe Gly Glu Val Cys Ala Cys Gln Val Arg Ala
                165                 170                 175

Thr Gly Lys Met Tyr Ala Cys Lys Lys Leu Gln Lys Lys Arg Ile Lys
                180                 185                 190

Lys Arg Lys Gly Glu Ala Met Ala Leu Asn Glu Lys Arg Ile Leu Glu
                195                 200                 205

Lys Val Gln Ser Arg Phe Val Val Ser Leu Ala Tyr Ala Tyr Glu Thr
                210                 215                 220

Lys Asp Ala Leu Cys Leu Val Leu Thr Ile Met Asn Gly Gly Asp Leu
225                 230                 235                 240

Lys Phe His Ile Tyr Asn Leu Gly Asn Pro Gly Phe Asp Glu Gln Arg
                245                 250                 255

Ala Val Phe Tyr Ala Ala Glu Leu Cys Cys Gly Leu Glu Asp Leu Gln
                260                 265                 270

Arg Glu Arg Ile Val Tyr Arg Asp Leu Lys Pro Glu Asn Ile Leu Leu
                275                 280                 285

Asp Asp Arg Gly His Ile Arg Ile Ser Asp Leu Gly Leu Ala Thr Glu
                290                 295                 300

Ile Pro Glu Gly Gln Arg Val Arg Gly Arg Val Gly Thr Val Gly Tyr
305                 310                 315                 320

Met Ala Pro Glu Val Val Asn Asn Glu Lys Tyr Thr Phe Ser Pro Asp
                325                 330                 335

Trp Trp Gly Leu Gly Cys Leu Ile Tyr Glu Met Ile Gln Gly His Ser
                340                 345                 350

Pro Phe Lys Lys Tyr Lys Glu Lys Val Lys Trp Glu Glu Val Asp Gln
                355                 360                 365

Arg Ile Lys Asn Asp Thr Glu Glu Tyr Ser Glu Lys Phe Ser Glu Asp
                370                 375                 380

Ala Lys Ser Ile Cys Arg Met Leu Leu Thr Lys Asn Pro Ser Lys Arg
385                 390                 395                 400

Leu Gly Cys Arg Gly Glu Gly Ala Ala Gly Val Lys Gln His Pro Val
                405                 410                 415

Phe Lys Asp Ile Asn Phe Arg Arg Leu Glu Ala Asn Met Leu Glu Pro
                420                 425                 430

Pro Phe Cys Pro Asp Pro His Ala Val Tyr Cys Lys Asp Val Leu Asp
                435                 440                 445

Ile Glu Gln Phe Ser Ala Val Lys Gly Ile Tyr Leu Asp Thr Ala Asp
                450                 455                 460

Glu Asp Phe Tyr Ala Arg Phe Ala Thr Gly Cys Val Ser Ile Pro Trp
465                 470                 475                 480

Gln Asn Glu Met Ile Glu Ser Gly Cys Phe Lys Asp Ile Asn Lys Ser
                485                 490                 495

Glu Ser Glu Glu Ala Leu Pro Leu Asp Leu Asp Lys Asn Ile His Thr
                500                 505                 510

Pro Val Ser Arg Pro Asn Arg Gly Phe Phe Tyr Arg Leu Phe Arg Arg
                515                 520                 525

Gly Gly Cys Leu Thr Met Val Pro Ser Glu Lys Glu Val Glu Pro Lys
                530                 535                 540

Gln Cys
545
```

<210> SEQ ID NO 16
<211> LENGTH: 1641
<212> TYPE: DNA
<213> ORGANISM: Homo sapiens

<400> SEQUENCE: 16

| | | | | | |
|---|---|---|---|---|---|
| atggagctcg | agaacatcgt | ggccaactcg | ctgctgctga | aagcgcgtca | agaaaaggat | 60 |
| tatagcagtc | tttgtgacaa | gcaaccgata | ggaagacgtc | tcttcaggca | gttctgtgat | 120 |
| accaaaccca | ctctaaagag | gcacattgaa | ttcttggatg | cagtggcaga | atatgaagtt | 180 |
| gccgatgatg | aggaccgaag | tgattgtgga | ctgtcaatct | tagatagatt | cttcaatgat | 240 |
| aagttggcag | cccctttacc | agaaatacct | ccagatgttg | tgacagaatg | tagattggga | 300 |
| ctgaaggagg | agaacccttc | caaaaaagcc | tttgaggaat | gtactagagt | tgcccataac | 360 |
| tacctaagag | gggaaccatt | tgaagaatac | aagaaagct | catattttc | tcagttttta | 420 |
| caatggaaat | ggctggaaag | gcaacccgta | acaaagaaca | catttagaca | ttacagagtt | 480 |
| ctaggaaaag | gcggatttgg | agaggtttgc | gcctgtcaag | tgcgagccac | aggaaaaatg | 540 |
| tatgcctgca | aaagctaca | aaaaaaaga | ataagaaga | ggaaaggtga | agctatggct | 600 |
| ctaaatgaga | aagaattct | ggagaaagtg | caaagtagat | tcgtagttag | tttagcctac | 660 |
| gcttatgaaa | ccaaagatgc | cttgtgcttg | gtgctcacca | ttatgaatgg | aggggatttg | 720 |
| aagtttcaca | tttacaacct | gggcaatccc | ggctttgatg | agcagagagc | cgttttctat | 780 |
| gctgcagagc | tgtgttgcgg | cttggaagat | ttacagaggg | aaagaattgt | atacagagac | 840 |
| ttgaagcctg | agaatattct | ccttgatgat | cgtggacaca | tccggatttc | agacctcggt | 900 |
| ttggccacag | atcccaga | aggacagagg | gttcgaggaa | gagttggaac | agtcggctac | 960 |
| atggcacctg | aagttgtcaa | taatgaaaag | tatacgttta | gtcccgattg | gtggggactt | 1020 |
| ggctgtctga | tctatgaaat | gattcaggga | cattctccat | tcaaaaaata | caaagagaaa | 1080 |
| gtcaaatggg | aggaggtcga | tcaaagaatc | aagaatgata | ccgaggagta | ttctgagaag | 1140 |
| ttttcagagg | atgccaaatc | tatctgcagg | atgttactca | ccaagaatcc | aagcaagcgg | 1200 |
| ctgggctgca | ggggcgaggg | agcggctggg | gtgaagcagc | accccgtgtt | caaggacatc | 1260 |
| aacttcagga | ggctggaggc | aaacatgctg | gagccccctt | tctgtcctga | tcctcatgcc | 1320 |
| gtttactgta | aggacgtcct | ggatatcgag | cagttctcgg | cggtgaaagg | gatctacctg | 1380 |
| gacaccgcag | atgaagactt | ctatgctcgg | tttgctaccg | ggtgtgtctc | atcccctgg | 1440 |
| cagaatgaga | tgatcgaatc | cgggtgtttc | aaagacatca | acaaaagtga | aagtgaggaa | 1500 |
| gctttgccat | tagatctaga | caagaacata | catccccgg | tttccagacc | aaacagaggc | 1560 |
| ttcttctata | gactcttcag | aagaggggc | tgcctgacca | tggtccccag | tgagaaggaa | 1620 |
| gtggaaccca | agcaatgctg | a | | | | 1641 |

<210> SEQ ID NO 17
<211> LENGTH: 578
<212> TYPE: PRT
<213> ORGANISM: Homo sapiens

<400> SEQUENCE: 17

Met Glu Leu Glu Asn Ile Val Ala Asn Ser Leu Leu Lys Ala Arg
 1               5                  10                  15

Gln Gly Gly Tyr Gly Lys Lys Ser Gly Arg Ser Lys Lys Trp Lys Glu
                20                  25                  30

Ile Leu Thr Leu Pro Pro Val Ser Gln Cys Ser Glu Leu Arg His Ser

-continued

```
                35                  40                  45
Ile Glu Lys Asp Tyr Ser Ser Leu Cys Asp Lys Gln Pro Ile Gly Arg
            50                  55                  60

Arg Leu Phe Arg Gln Phe Cys Asp Thr Lys Pro Thr Leu Lys Arg His
 65                  70                  75                  80

Ile Glu Phe Leu Asp Ala Val Ala Glu Tyr Glu Val Ala Asp Asp Glu
                85                  90                  95

Asp Arg Ser Asp Cys Gly Leu Ser Ile Leu Asp Arg Phe Phe Asn Asp
            100                 105                 110

Lys Leu Ala Ala Pro Leu Pro Glu Ile Pro Pro Asp Val Val Thr Glu
            115                 120                 125

Cys Arg Leu Gly Leu Lys Glu Glu Asn Pro Ser Lys Lys Ala Phe Glu
            130                 135                 140

Glu Cys Thr Arg Val Ala His Asn Tyr Leu Arg Gly Glu Pro Phe Glu
145                 150                 155                 160

Glu Tyr Gln Glu Ser Ser Tyr Phe Ser Gln Phe Leu Gln Trp Lys Trp
                165                 170                 175

Leu Glu Arg Gln Pro Val Thr Lys Asn Thr Phe Arg His Tyr Arg Val
            180                 185                 190

Leu Gly Lys Gly Gly Phe Gly Glu Val Cys Ala Cys Gln Val Arg Ala
            195                 200                 205

Thr Gly Lys Met Tyr Ala Cys Lys Lys Leu Gln Lys Lys Arg Ile Lys
            210                 215                 220

Lys Arg Lys Gly Glu Ala Met Ala Leu Asn Glu Lys Arg Ile Leu Glu
225                 230                 235                 240

Lys Val Gln Ser Arg Phe Val Val Ser Leu Ala Tyr Ala Tyr Glu Thr
            245                 250                 255

Lys Asp Ala Leu Cys Leu Val Leu Thr Ile Met Asn Gly Gly Asp Leu
            260                 265                 270

Lys Phe His Ile Tyr Asn Leu Gly Asn Pro Gly Phe Asp Glu Gln Arg
            275                 280                 285

Ala Val Phe Tyr Ala Ala Glu Leu Cys Cys Gly Leu Glu Asp Leu Gln
            290                 295                 300

Arg Glu Arg Ile Val Tyr Arg Asp Leu Lys Pro Glu Asn Ile Leu Leu
305                 310                 315                 320

Asp Asp Arg Gly His Ile Arg Ile Ser Asp Leu Gly Leu Ala Thr Glu
            325                 330                 335

Ile Pro Glu Gly Gln Arg Val Arg Gly Arg Val Gly Thr Val Gly Tyr
            340                 345                 350

Met Ala Pro Glu Val Val Asn Asn Glu Lys Tyr Thr Phe Ser Pro Asp
            355                 360                 365

Trp Trp Gly Leu Gly Cys Leu Ile Tyr Glu Met Ile Gln Gly His Ser
            370                 375                 380

Pro Phe Lys Lys Tyr Lys Glu Lys Val Lys Trp Glu Glu Val Asp Gln
385                 390                 395                 400

Arg Ile Lys Asn Asp Thr Glu Glu Tyr Ser Glu Lys Phe Ser Glu Asp
            405                 410                 415

Ala Lys Ser Ile Cys Arg Met Leu Leu Thr Lys Asn Pro Ser Lys Arg
            420                 425                 430

Leu Gly Cys Arg Gly Glu Gly Ala Ala Gly Val Lys Gln His Pro Val
            435                 440                 445

Phe Lys Asp Ile Asn Phe Arg Arg Leu Glu Ala Asn Met Leu Glu Pro
            450                 455                 460
```

```
Pro Phe Cys Pro Asp Pro His Ala Val Tyr Cys Lys Asp Val Leu Asp
465                 470                 475                 480

Ile Glu Gln Phe Ser Ala Val Lys Gly Ile Tyr Leu Asp Thr Ala Asp
                485                 490                 495

Glu Asp Phe Tyr Ala Arg Phe Ala Thr Gly Cys Val Ser Ile Pro Trp
                500                 505                 510

Gln Asn Glu Met Ile Glu Ser Gly Cys Phe Lys Asp Ile Asn Lys Ser
            515                 520                 525

Glu Ser Glu Glu Ala Leu Pro Leu Asp Leu Asp Lys Asn Ile His Thr
        530                 535                 540

Pro Val Ser Arg Pro Asn Arg Gly Phe Phe Tyr Arg Leu Phe Arg Arg
545                 550                 555                 560

Gly Gly Cys Leu Thr Met Val Pro Ser Glu Lys Glu Val Glu Pro Lys
                565                 570                 575

Gln Cys

<210> SEQ ID NO 18
<211> LENGTH: 1737
<212> TYPE: DNA
<213> ORGANISM: Homo sapiens

<400> SEQUENCE: 18
atggagctcg agaacatcgt ggccaactcg ctgctgctga agcgcgtca aggaggatat      60 ggcaaaaaaa gtggtcgtag taaaaaatgg aaggagatac tgacactgcc tcctgtcagc    120
cagtgcagtg agcttagaca ttccattgaa aaggattata gcagtctttg tgacaagcaa    180
ccgataggaa gacgtctctt caggcagttc tgtgatacca aacccactct aaagaggcac    240
attgaattct ggatgcagt ggcagaatat gaagttgccg atgatgagga ccgaagtgat     300
tgtggactgt caatcttaga tagattcttc aatgataagt tggcagcccc tttaccagaa    360
atacctccag atgttgtgac agaatgtaga ttgggactga aggaggagaa cccttccaaa    420
aaagcctttg aggaatgtac tagagttgcc cataactacc taagagggga accatttgaa    480
gaataccaag aaagctcata ttttttctcag ttttacaat ggaaatggct ggaaaggcaa     540
cccgtaacaa agaacacatt tagacattac agagttctag aaaaggcgg atttggagag    600 gtttgcgcct gtcaagtgcg agccacagga aaaatgtatg cctgcaaaaa gctacaaaaa    660 aaagaataa agaagaggaa aggtgaagct atggctctaa atgagaaaag aattctggag     720
aaagtgcaaa gtagattcgt agttagttta gcctacgctt atgaaaccaa agatgccttg    780
tgcttggtgc tcaccattat gaatggaggg gatttgaagt tcacattta caacctgggc     840 aatcccggct tgatgagca gagagccgtt ttctatgctg cagagctgtg ttgcggcttg    900
gaagatttac agaggaaag aattgtatac agagacttga gcctgagaa tattctcctt     960 gatgatcgtg acacatccg gatttcagac ctcggtttgg ccacagagat cccagaagga   1020
cagagggttc gaggaagagt tggaacagtc ggctacatgg cacctgaagt tgtcaataat   1080
gaaaagtata cgtttagtcc cgattggtgg ggacttggct gtctgatcta tgaaatgatt   1140
cagggacatt ctccattcaa aaaatacaaa gagaaagtca atgggagga ggtcgatcaa   1200 agaatcaaga tgataccga ggagtattct gagaagtttt cagaggatgc aaatctatc    1260 tgcaggatgt tactcaccaa gaatccaagc aagcggctgg gctgcagggg cgaggagcg    1320 gctggggtga agcagcaccc cgtgttcaag gacatcaact tcaggaggct ggaggcaaac   1380
atgctggagc ccccttctg tcctgatcct catgccgttt actgtaagga cgtcctggat   1440
```

-continued

```
atcgagcagt tctcggcggt gaaagggatc tacctggaca ccgcagatga agacttctat    1500
gctcggtttg ctaccgggtg tgtctccatc ccctggcaga atgagatgat cgaatccggg    1560
tgtttcaaag acatcaacaa aagtgaaagt gaggaagctt tgccattaga tctagacaag    1620
aacatacata ccccggtttc cagaccaaac agaggcttct tctatagact cttcagaaga    1680 ggggctgcc tgaccatggt ccccagtgag aaggaagtgg aacccaagca atgctga        1737
```

<210> SEQ ID NO 19
<211> LENGTH: 532
<212> TYPE: PRT
<213> ORGANISM: Homo sapiens

<400> SEQUENCE: 19

```
Met Glu Leu Glu Asn Ile Val Ala Asn Ser Leu Leu Lys Ala Arg
 1               5                  10                  15

Gln Gly Gly Tyr Gly Lys Lys Ser Gly Arg Ser Lys Lys Trp Lys Glu
                20                  25                  30

Ile Leu Thr Leu Pro Pro Val Ser Gln Cys Ser Glu Leu Arg His Ser
            35                  40                  45

Ile Glu Lys Asp Tyr Ser Ser Leu Cys Asp Lys Gln Pro Ile Gly Arg
        50                  55                  60

Arg Leu Phe Arg Gln Phe Cys Asp Thr Lys Pro Thr Leu Lys Arg His
    65                  70                  75                  80

Ile Glu Phe Leu Asp Ala Val Ala Glu Tyr Glu Val Ala Asp Asp Glu
                85                  90                  95

Asp Arg Ser Asp Cys Gly Leu Ser Ile Leu Asp Arg Phe Phe Asn Asp
                100                 105                 110

Lys Leu Ala Ala Pro Leu Pro Glu Ile Pro Pro Asp Val Val Thr Glu
            115                 120                 125

Cys Arg Leu Gly Leu Lys Glu Glu Asn Pro Ser Lys Lys Ala Phe Glu
        130                 135                 140

Glu Cys Thr Arg Val Ala His Asn Tyr Leu Arg Gly Glu Pro Phe Glu
145                 150                 155                 160

Glu Tyr Gln Glu Ser Ser Tyr Phe Ser Gln Phe Leu Gln Trp Lys Trp
                165                 170                 175

Leu Glu Arg Gln Pro Val Thr Lys Asn Thr Phe Arg His Tyr Arg Val
            180                 185                 190

Leu Gly Lys Gly Gly Phe Gly Glu Val Cys Ala Cys Gln Val Arg Ala
        195                 200                 205

Thr Gly Lys Met Tyr Ala Cys Lys Lys Leu Gln Lys Lys Arg Ile Lys
    210                 215                 220

Lys Arg Lys Gly Glu Ala Met Ala Leu Asn Glu Lys Arg Ile Leu Glu
225                 230                 235                 240

Lys Val Gln Ser Arg Phe Val Val Ser Leu Ala Tyr Ala Tyr Glu Thr
                245                 250                 255

Lys Asp Ala Leu Cys Leu Val Leu Thr Ile Met Asn Gly Gly Asp Leu
            260                 265                 270

Lys Phe His Ile Tyr Asn Leu Gly Asn Pro Gly Phe Asp Glu Gln Arg
        275                 280                 285

Ala Val Phe Tyr Ala Ala Glu Leu Cys Cys Gly Leu Glu Asp Leu Gln
    290                 295                 300

Arg Glu Arg Ile Val Tyr Arg Asp Leu Lys Pro Glu Asn Ile Leu Leu
305                 310                 315                 320
```

```
Asp Asp Arg Gly His Ile Arg Ile Ser Asp Leu Gly Leu Ala Thr Glu
            325                 330                 335

Ile Pro Glu Gly Gln Arg Val Arg Gly Arg Val Gly Thr Val Gly Tyr
            340                 345                 350

Met Ala Pro Glu Val Val Asn Asn Glu Lys Tyr Thr Phe Ser Pro Asp
            355                 360                 365

Trp Trp Gly Leu Gly Cys Leu Ile Tyr Glu Met Ile Gln Gly His Ser
        370                 375                 380

Pro Phe Lys Lys Tyr Lys Glu Lys Val Lys Trp Glu Glu Val Asp Gln
385                 390                 395                 400

Arg Ile Lys Asn Asp Thr Glu Glu Tyr Ser Glu Lys Phe Ser Glu Asp
                405                 410                 415

Ala Lys Ser Ile Cys Arg Met Leu Leu Thr Lys Asn Pro Ser Lys Arg
            420                 425                 430

Leu Gly Cys Arg Gly Glu Gly Ala Ala Gly Val Lys Gln His Pro Val
        435                 440                 445

Phe Lys Asp Ile Asn Phe Arg Arg Leu Glu Ala Asn Met Leu Glu Pro
    450                 455                 460

Pro Phe Cys Pro Asp Pro His Ala Val Tyr Cys Lys Asp Val Leu Asp
465                 470                 475                 480

Ile Glu Gln Phe Ser Ala Val Lys Gly Ile Tyr Leu Asp Thr Ala Asp
                485                 490                 495

Glu Asp Phe Tyr Ala Arg Phe Ala Thr Gly Cys Val Ser Ile Pro Trp
            500                 505                 510

Gln Asn Glu Gly Cys Leu Thr Met Val Pro Ser Glu Lys Glu Val Glu
        515                 520                 525

Pro Lys Gln Cys
    530

<210> SEQ ID NO 20
<211> LENGTH: 1599
<212> TYPE: DNA
<213> ORGANISM: Homo sapiens

<400> SEQUENCE: 20
atggagctcg agaacatcgt ggccaactcg ctgctgctga agcgcgtca aggaggatat        60 ggcaaaaaaa gtggtcgtag taaaaaatgg aaggagatac tgacactgcc tcctgtcagc     120
cagtgcagtg agcttagaca ttccattgaa aaggattata gcagtctttg tgacaagcaa     180
ccgataggaa gacgtctctt caggcagttc tgtgatacca aacccactct aaagaggcac     240
attgaattct ggatgcagt ggcagaatat gaagttgccg atgatgagga ccgaagtgat     300
tgtggactgt caatcttaga tagattcttc aatgataagt tggcagcccc tttaccagaa     360
atacctccag atgttgtgac agaatgtaga ttgggactga aggaggagaa cccttccaaa     420
aaagcctttg aggaatgtac tagagttgcc ataactacc taagggggga accatttgaa     480
gaataccaag aaagctcata tttttctcag tttttacaat ggaaatggct ggaaaggcaa     540
cccgtaacaa agaacacatt tagacattac agagttctag aaaaggcgg atttggagag     600 gtttgcgcct gtcaagtgcg agccacagga aaaatgtatg cctgcaaaaa gctacaaaaa     660
aaaagaataa agaagaggaa aggtgaagct atggctctaa atgagaaaag aattctggag     720
aaagtgcaaa gtagattcgt agttagttta gcctacgctt atgaaaccaa agatgccttg     780
tgcttggtgc tcaccattat gaatggaggg gatttgaagt tcacattta caacctgggc     840 aatcccggct tgatgagca gagagccgtt ttctatgctg cagagctgtg ttgcggcttg     900
```

```
gaagatttac agagggaaag aattgtatac agagacttga agcctgagaa tattctcctt    960
gatgatcgtg gacacatccg gatttcagac ctcggtttgg ccacagagat cccagaagga   1020
cagagggttc gaggaagagt tggaacagtc ggctacatgg cacctgaagt tgtcaataat   1080
gaaaagtata cgtttagtcc cgattggtgg ggacttggct gtctgatcta tgaaatgatt   1140
cagggacatt ctccattcaa aaaatacaaa gagaaagtca atgggagga ggtcgatcaa    1200 agaatcaaga atgataccga ggagtattct gagaagtttt cagaggatgc caaatctatc   1260
tgcaggatgt tactcaccaa gaatccaagc aagcggctgg gctgcagggg cgagggagcg   1320
gctggggtga agcagcaccc cgtgttcaag gacatcaact tcaggaggct ggaggcaaac   1380
atgctggagc ccccttttctg tcctgatcct catgccgttt actgtaagga cgtcctggat   1440
atcgagcagt tctcggcggt gaaagggatc tacctggaca ccgcagatga agacttctat   1500
gctcggtttg ctaccgggtg tgtctccatc ccctggcaga atgagggctg cctgaccatg   1560
gtccccagtg agaaggaagt ggaacccaag caatgctga                          1599
```

<210> SEQ ID NO 21
<211> LENGTH: 553
<212> TYPE: PRT
<213> ORGANISM: Homo sapiens

<400> SEQUENCE: 21

```
Met Val Asp Met Gly Ala Leu Asp Asn Leu Ile Ala Asn Thr Ala Tyr
  1               5                  10                  15

Leu Gln Ala Arg Lys Pro Ser Asp Cys Asp Ser Lys Glu Leu Gln Arg
             20                  25                  30

Arg Arg Arg Ser Leu Ala Leu Pro Gly Leu Gln Gly Cys Ala Glu Leu
         35                  40                  45

Arg Gln Lys Leu Ser Leu Asn Phe His Ser Leu Cys Glu Gln Gln Pro
     50                  55                  60

Ile Gly Arg Arg Leu Phe Arg Asp Phe Leu Ala Thr Val Pro Thr Phe
 65                  70                  75                  80

Arg Lys Ala Ala Thr Phe Leu Glu Asp Val Gln Asn Trp Glu Leu Ala
                 85                  90                  95

Glu Glu Gly Pro Thr Lys Asp Ser Ala Leu Gln Gly Leu Val Ala Thr
            100                 105                 110

Cys Ala Ser Ala Pro Ala Pro Gly Asn Pro Gln Pro Phe Leu Ser Gln
        115                 120                 125

Ala Val Ala Thr Lys Cys Gln Ala Thr Thr Glu Glu Glu Arg Val
    130                 135                 140

Ala Ala Val Thr Leu Ala Lys Ala Glu Ala Met Ala Phe Leu Gln Glu
145                 150                 155                 160

Gln Pro Phe Lys Asp Phe Val Thr Ser Ala Phe Tyr Asp Lys Phe Leu
                165                 170                 175

Gln Trp Lys Leu Phe Glu Met Gln Pro Val Ser Asp Lys Tyr Phe Thr
            180                 185                 190

Glu Phe Arg Val Leu Gly Lys Gly Phe Gly Glu Val Cys Ala Val
        195                 200                 205

Gln Val Lys Asn Thr Gly Lys Met Tyr Ala Cys Lys Lys Leu Asp Lys
    210                 215                 220

Lys Arg Leu Lys Lys Lys Gly Gly Glu Lys Met Ala Leu Leu Glu Lys
225                 230                 235                 240

Glu Ile Leu Glu Lys Val Ser Ser Pro Phe Ile Val Ser Leu Ala Tyr
```

```
                245                 250                 255
Ala Phe Glu Ser Lys Thr His Leu Cys Leu Val Met Ser Leu Met Asn
            260                 265                 270

Gly Gly Asp Leu Lys Phe His Ile Tyr Asn Val Gly Thr Arg Gly Leu
            275                 280                 285

Asp Met Ser Arg Val Ile Phe Tyr Ser Ala Gln Ile Ala Cys Gly Met
            290                 295                 300

Leu His Leu His Glu Leu Gly Ile Val Tyr Arg Asp Met Lys Pro Glu
305                 310                 315                 320

Asn Val Leu Leu Asp Asp Leu Gly Asn Cys Arg Leu Ser Asp Leu Gly
                325                 330                 335

Leu Ala Val Glu Met Lys Gly Gly Lys Pro Ile Thr Gln Arg Ala Gly
            340                 345                 350

Thr Asn Gly Tyr Met Ala Pro Glu Ile Leu Met Glu Lys Val Ser Tyr
                355                 360                 365

Ser Tyr Pro Val Asp Trp Phe Ala Met Gly Cys Ser Ile Tyr Glu Met
370                 375                 380

Val Ala Gly Arg Thr Pro Phe Lys Asp Tyr Lys Glu Lys Val Ser Lys
385                 390                 395                 400

Glu Asp Leu Lys Gln Arg Thr Leu Gln Asp Glu Val Lys Phe Gln His
                405                 410                 415

Asp Asn Phe Thr Glu Glu Ala Lys Asp Ile Cys Arg Leu Phe Leu Ala
                420                 425                 430

Lys Lys Pro Glu Gln Arg Leu Gly Ser Arg Glu Lys Ser Asp Asp Pro
            435                 440                 445

Arg Lys His His Phe Phe Lys Thr Ile Asn Phe Pro Arg Leu Glu Ala
450                 455                 460

Gly Leu Ile Glu Pro Pro Phe Val Pro Asp Pro Ser Val Val Tyr Ala
465                 470                 475                 480

Lys Asp Ile Ala Glu Ile Asp Asp Phe Ser Glu Val Arg Gly Val Glu
                485                 490                 495

Phe Asp Asp Lys Asp Lys Gln Phe Phe Lys Asn Phe Ala Thr Gly Ala
            500                 505                 510

Val Pro Ile Ala Trp Gln Glu Ile Ile Glu Thr Gly Leu Phe Glu
            515                 520                 525

Glu Leu Asn Asp Pro Asn Arg Pro Thr Gly Cys Glu Glu Gly Asn Ser
530                 535                 540

Ser Lys Ser Gly Val Cys Leu Leu Leu
545                 550

<210> SEQ ID NO 22
<211> LENGTH: 1662
<212> TYPE: DNA
<213> ORGANISM: Homo sapiens

<400> SEQUENCE: 22
atggtggaca tggggggccct ggacaacctg atcgccaaca ccgcctacct gcaggcccgg      60
aagccctcgg actgcgacag caaagagctg cagcggcggc ggcgtagcct ggccctgccc     120
gggctgcagg gctgcgcgga gctccgccag aagctgtccc tgaacttcca cagcctgtgt     180
gagcagcagc ccatcggtcg ccgcctcttc cgtgacttcc tagccacagt gcccacgttc     240
cgcaaggcgg caaccttcct agaggacgtg cagaactggg agctggccga ggagggaccc     300
accaaagaca gcgcgctgca ggggctggtg gccacttgtg cgagtgcccc tgccccgggg     360
```

```
aacccgcaac ccttcctcag ccaggccgtg gccaccaagt gccaagcagc caccactgag     420
gaagagcgag tggctgcagt gacgctggcc aaggctgagg ccatggcttt cttgcaagag     480 cagccctta aggatttcgt gaccagcgcc ttctacgaca gtttctgca gtggaaactc       540 ttcgagatgc aaccagtgtc agacaagtac ttcactgagt tcagagtgct ggggaaaggt    600
ggttttgggg aggtatgtgc cgtccaggtg aaaaacactg ggaagatgta tgcctgtaag    660
aaactggaca agaagcggct gaagaagaaa ggtggcgaga gatggctct cttggaaaag     720 gaaatcttgg agaaggtcag cagccctttc attgtctctc tggcctatgc ctttgagagc    780
aagacccatc tctgccttgt catgagcctg atgaatgggg agacctcaa gttccacatc     840 tacaacgtgg gcacgcgtgg cctggacatg agccgggtga tcttttactc ggcccagata    900
gcctgtggga tgctgcacct ccatgaactc ggcatcgtct atcgggacat gaagcctgag    960
aatgtgcttc tggatgacct cggcaactgc aggttatctg acctggggct ggccgtggag   1020
atgaagggtg gcaagcccat cacccagagg gctggaacca atggttacat ggctcctgag   1080
atcctaatgg aaaaggtaag ttattcctat cctgtggact ggtttgccat gggatgcagc   1140
atttatgaaa tggttgctgg acgaacacca ttcaaagatt acaaggaaaa ggtcagtaaa   1200
gaggatctga agcaaagaac tctgcaagac gaggtcaaat ccagcatga taacttcaca    1260 gaggaagcaa aagatatttg caggctcttc ttggctaaga aaccagagca acgcttagga   1320
agcagagaaa agtctgatga tcccaggaaa catcatttct ttaaaacgat caactttcct   1380
cgcctggaag ctggcctaat tgaaccccca tttgtgccag acccttcagt ggtttatgcc   1440
aaagacatcg ctgaaattga tgatttctct gaggttcggg gggtggaatt tgatgacaaa   1500
gataagcagt tcttcaaaaa ctttgcgaca ggtgctgttc ctatagcatg gcaggaagaa   1560
attatagaaa cgggactgtt tgaggaactg aatgacccca acagacctac gggttgtgag   1620
gagggtaatt catccaagtc tggcgtgtgt ttgttattgt aa                       1662
```

<210> SEQ ID NO 23
<211> LENGTH: 563
<212> TYPE: PRT
<213> ORGANISM: Homo sapiens

<400> SEQUENCE: 23

```
Met Asp Phe Gly Ser Leu Glu Thr Val Val Ala Asn Ser Ala Phe Ile
  1               5                  10                  15

Ala Ala Arg Gly Ser Phe Asp Gly Ser Ser Gln Pro Ser Arg Asp
                 20                  25                  30

Lys Lys Tyr Leu Ala Lys Leu Lys Leu Pro Pro Leu Ser Lys Cys Glu
             35                  40                  45

Ser Leu Arg Asp Ser Leu Ser Leu Glu Phe Glu Ser Val Cys Leu Glu
         50                  55                  60

Gln Pro Ile Gly Lys Lys Leu Phe Gln Gln Phe Leu Gln Ser Ala Glu
 65                  70                  75                  80

Lys His Leu Pro Ala Leu Glu Leu Trp Lys Asp Ile Glu Asp Tyr Asp
                 85                  90                  95

Thr Ala Asp Asn Asp Leu Gln Pro Gln Lys Ala Gln Thr Ile Leu Ala
            100                 105                 110

Gln Tyr Leu Asp Pro Gln Ala Lys Leu Phe Cys Ser Phe Leu Asp Glu
        115                 120                 125

Gly Ile Val Ala Lys Phe Lys Glu Gly Pro Val Glu Ile Gln Asp Gly
    130                 135                 140
```

```
Leu Phe Gln Pro Leu Leu Gln Ala Thr Leu Ala His Leu Gly Gln Ala
145                 150                 155                 160

Pro Phe Gln Glu Tyr Leu Gly Ser Leu Tyr Phe Leu Arg Phe Leu Gln
            165                 170                 175

Trp Lys Trp Leu Glu Ala Gln Pro Met Gly Glu Asp Trp Phe Leu Asp
        180                 185                 190

Phe Arg Val Leu Gly Lys Gly Gly Phe Gly Glu Val Ser Ala Cys Gln
                195                 200                 205

Met Lys Ala Thr Gly Lys Leu Tyr Ala Cys Lys Lys Leu Asn Lys Lys
        210                 215                 220

Arg Leu Lys Lys Arg Lys Gly Tyr Gln Gly Ala Met Val Glu Lys Lys
225                 230                 235                 240

Ile Leu Met Lys Val His Ser Arg Phe Ile Val Ser Leu Ala Tyr Ala
                245                 250                 255

Phe Glu Thr Lys Ala Asp Leu Cys Leu Val Met Thr Ile Met Asn Gly
            260                 265                 270

Gly Asp Ile Arg Tyr His Ile Tyr Asn Val Asn Glu Glu Asn Pro Gly
                275                 280                 285

Phe Pro Glu Pro Arg Ala Leu Phe Tyr Thr Ala Gln Ile Ile Cys Gly
290                 295                 300

Leu Glu His Leu His Gln Arg Ile Val Tyr Arg Asp Leu Lys Pro
305                 310                 315                 320

Glu Asn Val Leu Leu Asp Asn Asp Gly Asn Val Arg Ile Ser Asp Leu
                325                 330                 335

Gly Leu Ala Val Glu Leu Leu Asp Gly Gln Ser Lys Thr Lys Gly Tyr
                340                 345                 350

Ala Gly Thr Pro Gly Phe Met Ala Pro Glu Leu Leu Gln Gly Glu Glu
        355                 360                 365

Tyr Asp Phe Ser Val Asp Tyr Phe Ala Leu Gly Val Thr Leu Tyr Glu
        370                 375                 380

Met Ile Ala Ala Arg Gly Pro Phe Arg Ala Arg Gly Glu Lys Val Glu
385                 390                 395                 400

Asn Lys Glu Leu Lys His Arg Ile Ile Ser Glu Pro Val Lys Tyr Pro
                405                 410                 415

Asp Lys Phe Ser Gln Ala Ser Lys Asp Phe Cys Glu Ala Leu Leu Glu
                420                 425                 430

Lys Asp Pro Glu Lys Arg Leu Gly Phe Arg Asp Glu Thr Cys Asp Lys
            435                 440                 445

Leu Arg Ala His Pro Leu Phe Lys Asp Leu Asn Trp Arg Gln Leu Glu
450                 455                 460

Ala Gly Met Leu Met Pro Pro Phe Ile Pro Asp Ser Lys Thr Val Tyr
465                 470                 475                 480

Ala Lys Asp Ile Gln Asp Val Gly Ala Phe Ser Thr Val Lys Gly Val
                485                 490                 495

Ala Phe Asp Lys Thr Asp Thr Glu Phe Phe Gln Glu Phe Ala Thr Gly
            500                 505                 510

Asn Cys Pro Ile Pro Trp Gln Glu Glu Met Ile Glu Thr Gly Ile Phe
        515                 520                 525

Gly Glu Leu Asn Val Trp Arg Ser Asp Gly Gln Met Pro Asp Asp Met
530                 535                 540

Lys Gly Ile Ser Gly Gly Ser Ser Ser Ser Lys Ser Gly Met Cys
545                 550                 555                 560

Leu Val Ser
```

<210> SEQ ID NO 24
<211> LENGTH: 1692
<212> TYPE: DNA
<213> ORGANISM: Homo sapiens

<400> SEQUENCE: 24

| | | | | | |
|---|---|---|---|---|---|
| atggatttcg | ggtctttgga | gaccgtggtg | gccaactctg | ccttcatcgc | cgcccgaggc | 60 |
| agctttgacg | gcagcagctc | ccaaccctcc | cgggacaaga | agtacctggc | caagctcaag | 120 |
| ctgcccccgc | tgtccaagtg | tgagtccctc | cgcgacagcc | tcagcctgga | gtttgagagt | 180 |
| gtgtgcttgg | agcagcccat | cggcaagaag | ctctttcagc | agttcctaca | atcggcagag | 240 |
| aagcacctgc | cggccctgga | gctctggaaa | gacatcgagg | actatgacac | ggcagacaat | 300 |
| gacctccagc | cacagaaggc | ccagaccatc | ctggcccagt | acctggaccc | ccaggccaaa | 360 |
| ctcttctgca | gcttcctgga | tgaggggata | gtggcgaagt | taaggaggg | gcctgtggag | 420 |
| atccaggacg | ggctcttcca | gcccctgctg | caggccaccc | tggcacacct | gggccaagcc | 480 |
| cccttccagg | agtacctggg | cagcctgtac | ttcctgaggt | tcctgcagtg | gaagtggctg | 540 |
| gaagcccagc | ccatggggga | ggactggttc | ctggacttca | gggtcctggg | aaagggggc | 600 |
| ttcggggagg | tgtcggcctg | ccagatgaag | gcgaccggca | agctgtatgc | ctgcaagaag | 660 |
| ctgaacaaga | gcggctgaa | gagaggaag | ggctaccagg | gtgctatggt | ggagaagaag | 720 |
| attctgatga | agtacacag | caggttcatc | gtgtctctgg | cctatgcgtt | tgaaaccaaa | 780 |
| gccgacctct | gtctggtgat | gaccatcatg | aacggaggtg | acatcaggta | ccacatctac | 840 |
| aacgtgaatg | aggagaaccc | tggcttcccg | gagccgcgcg | ccctcttcta | cacggcgcag | 900 |
| atcatctgcg | gcctggagca | cctgcaccag | aggcggatcg | tctaccgcga | cctcaagccc | 960 |
| gagaacgtgc | tgctggacaa | tgacggcaat | gtccggatct | ctgaccttgg | gctggccgtg | 1020 |
| gagctgctgg | acggacagag | caagaccaag | ggctacgcag | ggaccccagg | tttcatggcc | 1080 |
| cccgagctcc | tgcagggcga | ggagtacgac | ttctccgtgg | actactttgc | cctgggggtc | 1140 |
| accctgtatg | agatgattgc | ggccagagga | ccctttccgag | cccgtggaga | gaaggtggag | 1200 |
| aacaaggagc | tgaagcaccg | gatcatctca | gagcccgtga | agtaccctga | taagttcagc | 1260 |
| caggccagca | aggacttctg | cgaggcgctg | ctggagaagg | accggagaa | cgcctgggg | 1320 |
| ttcagagatg | agacctgcga | caagctccgt | gcccaccccc | tcttcaagga | ccttaactgg | 1380 |
| aggcagctgg | aggctgggat | gctgatgcc | cctttcatcc | cagactccaa | aactgtctac | 1440 |
| gcaaaggata | ttcaggacgt | gggtgccttt | tccaccgtca | aggtgtggc | ctttgacaaa | 1500 |
| acagacacag | aattctttca | ggaatttgcc | actggcaact | gccccatccc | ctggcaggag | 1560 |
| gagatgatcg | agacgggcat | cttggcgag | ctgaacgtgt | ggcgctcgga | cggtcagatg | 1620 |
| ccggacgaca | tgaagggcat | ctccgggggc | tccagctcct | cgtccaagtc | agggatgtgt | 1680 |
| ctggtttcct | ag | | | | | 1692 |

<210> SEQ ID NO 25
<211> LENGTH: 688
<212> TYPE: PRT
<213> ORGANISM: Homo sapiens

<400> SEQUENCE: 25

Met Ala Asp Leu Glu Ala Val Leu Ala Asp Val Ser Tyr Leu Met Ala
 1               5                  10                  15

Met Glu Lys Ser Lys Ala Thr Pro Ala Ala Arg Ala Ser Lys Arg Ile

-continued

```
                20                  25                  30
Val Leu Pro Glu Pro Ser Ile Arg Ser Val Met Gln Lys Tyr Leu Ala
             35                  40                  45
Glu Arg Asn Glu Ile Thr Phe Asp Lys Ile Phe Asn Gln Lys Ile Gly
 50                  55                  60
Phe Leu Phe Lys Asp Phe Cys Leu Asn Glu Ile Asn Glu Ala Val
 65                  70                  75                  80
Pro Gln Val Lys Phe Tyr Glu Glu Ile Lys Glu Tyr Glu Lys Leu Asp
                 85                  90                  95
Asn Glu Glu Asp Arg Leu Cys Arg Ser Arg Gln Ile Tyr Asp Ala Tyr
                100                 105                 110
Ile Met Lys Glu Leu Leu Ser Cys Ser His Pro Phe Ser Lys Gln Ala
                115                 120                 125
Val Glu His Val Gln Ser His Leu Ser Lys Lys Gln Val Thr Ser Thr
                130                 135                 140
Leu Phe Gln Pro Tyr Ile Glu Glu Ile Cys Glu Ser Leu Arg Gly Asp
145                 150                 155                 160
Ile Phe Gln Lys Phe Met Glu Ser Asp Lys Phe Thr Arg Phe Cys Gln
                165                 170                 175
Trp Lys Asn Val Glu Leu Asn Ile His Leu Thr Met Asn Glu Phe Ser
                180                 185                 190
Val His Arg Ile Ile Gly Arg Gly Gly Phe Gly Glu Val Tyr Gly Cys
                195                 200                 205
Arg Lys Ala Asp Thr Gly Lys Met Tyr Ala Met Lys Cys Leu Asp Lys
                210                 215                 220
Lys Arg Ile Lys Met Lys Gln Gly Glu Thr Leu Ala Leu Asn Glu Arg
225                 230                 235                 240
Ile Met Leu Ser Leu Val Ser Thr Gly Asp Cys Pro Phe Ile Val Cys
                245                 250                 255
Met Thr Tyr Ala Phe His Thr Pro Asp Lys Leu Cys Phe Ile Leu Asp
                260                 265                 270
Leu Met Asn Gly Gly Asp Leu His Tyr His Leu Ser Gln His Gly Val
                275                 280                 285
Phe Ser Glu Lys Glu Met Arg Phe Tyr Ala Thr Glu Ile Ile Leu Gly
                290                 295                 300
Leu Glu His Met His Asn Arg Phe Val Val Tyr Arg Asp Leu Lys Pro
305                 310                 315                 320
Ala Asn Ile Leu Leu Asp Glu His Gly His Ala Arg Ile Ser Asp Leu
                325                 330                 335
Gly Leu Ala Cys Asp Phe Ser Lys Lys Lys Pro His Ala Ser Val Gly
                340                 345                 350
Thr His Gly Tyr Met Ala Pro Glu Val Leu Gln Lys Gly Thr Ala Tyr
                355                 360                 365
Asp Ser Ser Ala Asp Trp Phe Ser Leu Gly Cys Met Leu Phe Lys Leu
                370                 375                 380
Leu Arg Gly His Ser Pro Phe Arg Gln His Lys Thr Lys Asp Lys His
385                 390                 395                 400
Glu Ile Asp Arg Met Thr Leu Thr Val Asn Val Glu Leu Pro Asp Thr
                405                 410                 415
Phe Ser Pro Glu Leu Lys Ser Leu Leu Glu Gly Leu Leu Gln Arg Asp
                420                 425                 430
Val Ser Lys Arg Leu Gly Cys His Gly Gly Gly Ser Gln Glu Val Lys
                435                 440                 445
```

```
Glu His Ser Phe Phe Lys Gly Val Asp Trp Gln His Val Tyr Leu Gln
        450                 455                 460
Lys Tyr Pro Pro Leu Ile Pro Pro Arg Gly Glu Val Asn Ala Ala
465                 470                 475                 480
Asp Ala Phe Asp Ile Gly Ser Phe Asp Glu Asp Thr Lys Gly Ile
            485                 490                 495
Lys Leu Leu Asp Cys Asp Gln Glu Leu Tyr Lys Asn Phe Pro Leu Val
                500                 505                 510
Ile Ser Glu Arg Trp Gln Gln Glu Val Thr Glu Thr Val Tyr Glu Ala
            515                 520                 525
Val Asn Ala Asp Thr Asp Lys Ile Glu Ala Arg Lys Arg Ala Lys Asn
    530                 535                 540
Lys Gln Leu Gly His Glu Glu Asp Tyr Ala Leu Gly Lys Asp Cys Ile
545                 550                 555                 560
Met His Gly Tyr Met Leu Lys Leu Gly Asn Pro Phe Leu Thr Gln Trp
                565                 570                 575
Gln Arg Arg Tyr Phe Tyr Leu Phe Pro Asn Arg Leu Glu Trp Arg Gly
            580                 585                 590
Glu Gly Glu Ser Arg Gln Asn Leu Leu Thr Met Glu Gln Ile Leu Ser
        595                 600                 605
Val Glu Glu Thr Gln Ile Lys Asp Lys Lys Cys Ile Leu Phe Arg Ile
    610                 615                 620
Lys Gly Gly Lys Gln Phe Val Leu Gln Cys Glu Ser Asp Pro Glu Phe
625                 630                 635                 640
Val Gln Trp Lys Lys Glu Leu Asn Glu Thr Phe Lys Glu Ala Gln Arg
                645                 650                 655
Leu Leu Arg Arg Ala Pro Lys Phe Leu Asn Lys Pro Arg Ser Gly Thr
            660                 665                 670
Val Glu Leu Pro Lys Pro Ser Leu Cys His Arg Asn Ser Asn Gly Leu
        675                 680                 685

<210> SEQ ID NO 26
<211> LENGTH: 2067
<212> TYPE: DNA
<213> ORGANISM: Homo sapiens

<400> SEQUENCE: 26
atggcggacc tggaggctgt gctggccgat gtcagttacc tgatggccat ggagaagagc      60
aaggcgaccc cggccgcccg cgccagcaag aggatcgtcc tgccggagcc cagtatccgg     120
agtgtgatgc agaagtacct tgcagagaga aatgaaataa cctttgacaa gattttcaat     180
cagaaaattg gttcttgct atttaaagat ttttgtttga atgaaattaa tgaagctgta     240
cctcaggtga gttttatga agagataaag gaatatgaaa acttgataa tgaggaagac     300
cgcctttgca gaagtcgaca aatttatgat gcctacatca tgaaggaact tctttcctgt     360
tcacatcctt tctcaaagca agctgtagaa cacgtacaaa gtcatttatc caagaaacaa     420
gtgacatcaa ctcttttttca gccatacata gaagaaattt gtgaaagcct tcgaggtgac     480
atttttcaaa aatttatgga aagtgacaag ttcactagat tttgtcagtg aaaaacgtt     540
gaattaaata tccatttgac catgaatgag ttcagtgtgc ataggattat ggacgagga     600
ggattcgggg aagtttatgg ttgcaggaaa gcagacactg gaaaaatgta tgcaatgaaa     660
tgcttagata gaagaggat caaaatgaaa caggagaaaa cattagcctt aaatgaaga     720
atcatgttgt ctcttgtcag cacaggagac tgtcctttca ttgtatgtat gacctatgcc     780
```

-continued

```
ttccataccc cagataaact ctgcttcatc ctggatctga tgaacggggg cgatttgcac      840 taccacctttt cacaacacgg tgtgttctct gagaaggaga tgcggtttta tgccactgaa     900
atcattctgg gtctggaaca catgcacaat cggtttgttg tctacagaga tttgaagcca     960
gcaaatattc tcttggatga acatggacac gcaagaatat cagatcttgg tcttgcctgc     1020 gattttttcca aaagaagcc tcatgcgagt gttggcaccc atgggtacat ggctcccgag     1080
gtgctgcaga aggggacggc ctatgacagc agtgccgact ggttctccct gggctgcatg     1140 ctttttcaaac ttctgagagg tcacagccct tcagacaac ataaaaccaa agacaagcat     1200
gaaattgacc gaatgacact caccgtgaat gtggaacttc agacaccttt ctctcctgaa     1260
ctgaagtccc ttttggaggg cttgcttcag cgagacgtta gcaagcggct gggctgtcac     1320
ggaggcggct cacaggaagt aaaagagcac agcttttttca aggtgttga ctggcagcat     1380 gtctacttac aaaagtaccc accaccctttg attcctcccc ggggagaagt caatgctgct     1440
gatgcctttg atattggctc atttgatgaa gaggatacca aagggattaa gctacttgat     1500
tgcgaccaag aactctacaa gaacttccct ttggtcatct ctgaacgctg cagcaagaa      1560 gtaacggaaa cagtttatga agcagtaaat gcagacacag ataaaatcga ggccaggaag     1620
agagctaaaa ataagcaact tggccacgaa gaagattacg ctctggggaa ggactgtatt     1680
atgcacgggt acatgctgaa actgggaaac ccatttctga ctcagtggca gcgtcgctat     1740 tttttacctct ttccaaatag acttgaatgg agaggagagg gagagtcccg gcaaaattta     1800
ctgacaatgg aacagattct ctctgtggaa gaaactcaaa ttaaagacaa aaatgcatt      1860 ttgttcagaa taaaggagg gaaacaattt gtcttgcaat gtgagagtga tccagagttt     1920
gtgcagtgga agaaagagtt gaacgaaacc ttcaaggagg cccagcggct attgcgtcgt     1980
gccccgaagt tcctcaacaa acctcggtca ggtactgtgg agctcccaaa gccatccctc     2040
tgtcacagaa acagcaacgg cctctag                                         2067
```

<210> SEQ ID NO 27
<211> LENGTH: 688
<212> TYPE: PRT
<213> ORGANISM: Bos taurus

<400> SEQUENCE: 27

```
Met Ala Asp Leu Glu Ala Val Leu Ala Asp Val Ser Tyr Leu Met Ala
 1               5                  10                  15

Met Glu Lys Ser Lys Ala Thr Pro Ala Ala Arg Ala Ser Lys Lys Ile
            20                  25                  30

Val Leu Pro Glu Pro Ser Ile Arg Ser Val Met Gln Lys Tyr Leu Glu
        35                  40                  45

Glu Arg His Glu Ile Thr Phe Asp Lys Ile Phe Asn Gln Arg Ile Gly
    50                  55                  60

Phe Leu Leu Phe Lys Asp Phe Cys Leu Asn Glu Ile Asn Glu Ala Val
65                  70                  75                  80

Pro Gln Val Lys Phe Tyr Glu Glu Ile Lys Glu Tyr Glu Lys Leu Glu
                85                  90                  95

Asn Glu Glu Asp Arg Leu Cys Arg Ser Arg Gln Ile Tyr Asp Thr Tyr
            100                 105                 110

Ile Met Lys Glu Leu Leu Ser Cys Ser His Pro Phe Ser Lys Gln Ala
        115                 120                 125

Val Glu His Val Gln Ser His Leu Ser Lys Lys Gln Val Thr Ser Thr
    130                 135                 140
```

```
Leu Phe Gln Pro Tyr Ile Glu Glu Ile Cys Glu Ser Leu Arg Gly Ser
145                 150                 155                 160

Ile Phe Gln Lys Phe Met Glu Ser Asp Lys Phe Thr Arg Phe Cys Gln
                165                 170                 175

Trp Lys Asn Val Glu Leu Asn Ile His Leu Thr Met Asn Asp Phe Ser
            180                 185                 190

Val His Arg Ile Ile Gly Arg Gly Gly Phe Gly Glu Val Tyr Gly Cys
        195                 200                 205

Arg Lys Ala Asp Thr Gly Lys Met Tyr Ala Met Lys Cys Leu Asp Lys
    210                 215                 220

Lys Arg Ile Lys Met Lys Gln Gly Glu Thr Leu Ala Leu Asn Glu Arg
225                 230                 235                 240

Ile Met Leu Ser Leu Val Ser Thr Gly Asp Cys Pro Phe Ile Val Cys
                245                 250                 255

Met Thr Tyr Ala Phe His Thr Pro Asp Lys Leu Cys Phe Ile Leu Asp
                260                 265                 270

Leu Met Asn Gly Gly Asp Leu His Tyr His Leu Ser Gln His Gly Val
            275                 280                 285

Phe Ser Glu Lys Glu Met Arg Phe Tyr Ala Thr Glu Ile Ile Leu Gly
        290                 295                 300

Leu Glu His Met His Asn Arg Phe Val Val Tyr Arg Asp Leu Lys Pro
305                 310                 315                 320

Ala Asn Ile Leu Leu Asp Glu His Gly His Val Arg Ile Ser Asp Leu
                325                 330                 335

Gly Leu Ala Cys Asp Phe Ser Lys Lys Lys Pro His Ala Ser Val Gly
            340                 345                 350

Thr His Gly Tyr Met Ala Pro Glu Val Leu Gln Lys Gly Thr Ala Tyr
        355                 360                 365

Asp Ser Ser Ala Asp Trp Phe Ser Leu Gly Cys Met Leu Phe Lys Leu
    370                 375                 380

Leu Arg Gly His Ser Pro Phe Arg Gln His Lys Thr Lys Asp Lys His
385                 390                 395                 400

Glu Ile Asp Arg Met Thr Leu Thr Met Asn Val Glu Leu Pro Asp Val
                405                 410                 415

Phe Ser Pro Glu Leu Lys Ser Leu Leu Glu Gly Leu Leu Gln Arg Asp
                420                 425                 430

Val Ser Lys Arg Leu Gly Cys His Gly Gly Ser Ala Gln Glu Leu Lys
            435                 440                 445

Thr His Asp Phe Phe Arg Gly Ile Asp Trp Gln His Val Tyr Leu Gln
    450                 455                 460

Lys Tyr Pro Pro Pro Leu Ile Pro Pro Arg Gly Glu Val Asn Ala Ala
465                 470                 475                 480

Asp Ala Phe Asp Ile Gly Ser Phe Asp Glu Asp Thr Lys Gly Ile
                485                 490                 495

Lys Leu Leu Asp Cys Asp Gln Glu Leu Tyr Lys Asn Phe Pro Leu Val
            500                 505                 510

Ile Ser Glu Arg Trp Gln Gln Glu Val Ala Glu Thr Val Tyr Glu Ala
        515                 520                 525

Val Asn Ala Asp Thr Asp Lys Ile Glu Ala Arg Lys Arg Ala Lys Asn
    530                 535                 540

Lys Gln Leu Gly His Glu Glu Asp Tyr Ala Leu Gly Arg Asp Cys Ile
545                 550                 555                 560
```

```
Val His Gly Tyr Met Leu Lys Leu Gly Asn Pro Phe Leu Thr Gln Trp
            565                 570                 575

Gln Arg Arg Tyr Phe Tyr Leu Phe Pro Asn Arg Leu Glu Trp Arg Gly
        580                 585                 590

Glu Gly Glu Ser Arg Gln Ser Leu Leu Thr Met Glu Gln Ile Val Ser
    595                 600                 605

Val Glu Glu Thr Gln Ile Lys Asp Lys Lys Cys Ile Leu Leu Arg Ile
610                 615                 620

Lys Gly Gly Lys Gln Phe Val Leu Gln Cys Glu Ser Asp Pro Glu Phe
625                 630                 635                 640

Val Gln Trp Lys Lys Glu Leu Thr Glu Thr Phe Met Glu Ala Gln Arg
            645                 650                 655

Leu Leu Arg Arg Ala Pro Lys Phe Leu Asn Lys Ser Arg Ser Ala Val
        660                 665                 670

Val Glu Leu Ser Lys Pro Pro Leu Cys His Arg Asn Ser Asn Gly Leu
    675                 680                 685

<210> SEQ ID NO 28
<211> LENGTH: 2067
<212> TYPE: DNA
<213> ORGANISM: Bos taurus

<400> SEQUENCE: 28
atggcggacc tggaggccgt gctggccgat gtcagctacc tgatggcgat ggagaagagc      60
aaggcgaccc cggccgcccg cgccagcaag aagatcgtcc tgcccgagcc cagtatccgg     120
agcgtgatgc agaagtatct tgaggagaga cacgaaatca cctttgacaa gattttttaat    180 cagagaattg gtttcttgct atttaaagat ttttgtttga atgaaattaa tgaagctgta     240
cctcaggtga agtttttatga agatataaaa gaatatgaaa gcttgagaa tgaggaagat     300 cgcctttgta gaagtcgaca gatttatgac acttacatca tgaaggagct gctgtcgtgt     360
tcacatccat tctcaaagca agccgtagaa cacgtacaaa gtcatctgtc caagaaacaa     420
gtgacatcaa ctctttttca gccatacata gaagaaattt gtgaaagtct ccgaggcagc     480
atttttcaaa aattcatgga aagtgacaag tttactagat tttgtcagtg gaaaaacgtg     540
gaattaaata tccatttgac catgaatgat ttcagcgtgc atcggatcat ggacgagga      600 ggattcggtg aagtatacgg ttgcaggaaa gcagacactg gaaagatgta tgcaatgaaa     660
tgcttggata gaagagaat caagatgaaa caggagaaa ccttagcctt aaatgaaagg       720
atcatgttgt ccctggtgag cacaggagat tgcccttca tcgtctgtat gacctatgcc      780
ttccacactc cagataaact gtgcttcatc ttggatctga tgaacggggg tgacctgcac     840
tatcaccttt cgcagcacgg ggtgttttct gagaaggaga tgcggtttta cgccacagaa     900
atcatcctgg ggctggaaca catgcacaat cggtttgttg tttacagaga cttgaagccc     960
gccaatatcc tcctggatga gcacggacat gtgaggtat cagaccttgg tcttgcctgc    1020 gattttttcca aaagaagcc gcacgcgagc gtgggcaccc acgggtacat ggcgcccgaa    1080
gttctgcaga aggggaccgc ctacgacagc agtgccgact ggttctccct gggctgtatg    1140 ctttttcaaac ttctgagagg tcacagccct tcagacaac ataaaaccaa agataagcat     1200
gagatagacc gaatgactct caccatgaac gtggaacttc cagacgtctt ctccctgag     1260 ctcaagtccc ttctggaagg cctgcttcag cgagatgtca gtaagcgcct cggctgccat    1320
ggaggcagcg cacaggagct aaaaacgcac gacttcttca gaggcatcga ctggcagcac    1380
gtctacctgc agaagtaccc tccacccttg atccctcccc gaggggaagt caatgcagcc    1440
```

-continued

```
gacgccttttg acatcggctc atttgatgaa gaggatacca aaggcatcaa gcttcttgat   1500
tgcgaccaag aactctacaa gaacttccct ctggtgatct ctgagcgctg gcagcaggaa   1560
gtggcggaaa cagtttatga agcagtaaat gcagacacgg ataaaatcga ggccaggaag   1620
agagctaaaa ataagcagct tggccacgaa gaagattacg ccctgggaag agactgcatc   1680
gtgcacgggt acatgctgaa gctggggaac ccttttcctga cccagtggca cgccgctat   1740 ttttacctct ttccgaacag acttgagtgg agaggagaag gcgagtcgcg acaaagttta   1800
ctgacaatgg aacagattgt gtccgtggaa gaaactcaga ttaaagacaa aaagtgcatt   1860
ttgttgagaa taaaggagg gaagcagttc gttttgcagt gtgagagtga cccagagttt   1920
gtgcagtgga agaaagagct gacggagaca ttcatggagg cccagcggct gctacggcga   1980
gcccccaagt tcctcaacaa atcccgctca gccgtcgtgg aactctcaaa gcctcccctc   2040
tgccatagga acagcaacgg cctctga                                       2067
```

<210> SEQ ID NO 29
<211> LENGTH: 689
<212> TYPE: PRT
<213> ORGANISM: Homo sapiens

<400> SEQUENCE: 29

```
Met Ala Asp Leu Glu Ala Val Leu Ala Asp Val Ser Tyr Leu Met Ala
  1               5                  10                  15

Met Glu Lys Ser Lys Ala Thr Pro Ala Ala Arg Ala Ser Lys Lys Ile
                 20                  25                  30

Leu Leu Pro Glu Pro Ser Ile Arg Ser Val Met Gln Lys Tyr Leu Glu
             35                  40                  45

Asp Arg Gly Glu Val Thr Phe Glu Lys Ile Phe Ser Gln Lys Leu Gly
         50                  55                  60

Tyr Leu Leu Phe Arg Asp Phe Cys Leu Asn His Leu Glu Glu Ala Arg
 65                  70                  75                  80

Pro Leu Val Glu Phe Tyr Glu Glu Ile Lys Lys Tyr Glu Lys Leu Glu
                 85                  90                  95

Thr Glu Glu Glu Arg Val Ala Arg Ser Arg Glu Ile Phe Asp Ser Tyr
            100                 105                 110

Ile Met Lys Glu Leu Leu Ala Cys Ser His Pro Phe Ser Lys Ser Ala
            115                 120                 125

Thr Glu His Val Gln Gly His Leu Gly Lys Lys Gln Val Pro Pro Asp
        130                 135                 140

Leu Phe Gln Pro Tyr Ile Glu Glu Ile Cys Gln Asn Leu Arg Gly Asp
145                 150                 155                 160

Val Phe Gln Lys Phe Ile Glu Ser Asp Lys Phe Thr Arg Phe Cys Gln
                165                 170                 175

Trp Lys Asn Val Glu Leu Asn Ile His Leu Thr Met Asn Asp Phe Ser
            180                 185                 190

Val His Arg Ile Ile Gly Arg Gly Gly Phe Gly Glu Val Tyr Gly Cys
        195                 200                 205

Arg Lys Ala Asp Thr Gly Lys Met Tyr Ala Met Lys Cys Leu Asp Lys
    210                 215                 220

Lys Arg Ile Lys Met Lys Gln Gly Glu Thr Leu Ala Leu Asn Glu Arg
225                 230                 235                 240

Ile Met Leu Ser Leu Val Ser Thr Gly Asp Cys Pro Phe Ile Val Cys
                245                 250                 255
```

-continued

```
Met Ser Tyr Ala Phe His Thr Pro Asp Lys Leu Ser Phe Ile Leu Asp
            260                 265                 270

Leu Met Asn Gly Gly Asp Leu His Tyr His Leu Ser Gln His Gly Val
        275                 280                 285

Phe Ser Glu Ala Asp Met Arg Phe Tyr Ala Ala Glu Ile Ile Leu Gly
        290                 295                 300

Leu Glu His Met His Asn Arg Phe Val Val Tyr Arg Asp Leu Lys Pro
305             310                 315                 320

Ala Asn Ile Leu Leu Asp Glu His Gly His Val Arg Ile Ser Asp Leu
                325                 330                 335

Gly Leu Ala Cys Asp Phe Ser Lys Lys Lys Pro His Ala Ser Val Gly
                340                 345                 350

Thr His Gly Tyr Met Ala Pro Glu Val Leu Gln Lys Gly Val Ala Tyr
            355                 360                 365

Asp Ser Ser Ala Asp Trp Phe Ser Leu Gly Cys Met Leu Phe Lys Leu
        370                 375                 380

Leu Arg Gly His Ser Pro Phe Arg Gln His Lys Thr Lys Asp Lys His
385             390                 395                 400

Glu Ile Asp Arg Met Thr Leu Thr Met Ala Val Glu Leu Pro Asp Ser
                405                 410                 415

Phe Ser Pro Glu Leu Arg Ser Leu Leu Glu Gly Leu Leu Gln Arg Asp
            420                 425                 430

Val Asn Arg Arg Leu Gly Cys Leu Gly Arg Gly Ala Gln Glu Val Lys
        435                 440                 445

Glu Ser Pro Phe Phe Arg Ser Leu Asp Trp Gln Met Val Phe Leu Gln
    450                 455                 460

Lys Tyr Pro Pro Pro Leu Ile Pro Pro Arg Gly Glu Val Asn Ala Ala
465                 470                 475                 480

Asp Ala Phe Asp Ile Gly Ser Phe Asp Glu Glu Asp Thr Lys Gly Ile
                485                 490                 495

Lys Leu Leu Asp Ser Asp Gln Glu Leu Tyr Arg Asn Phe Pro Leu Thr
                500                 505                 510

Ile Ser Glu Arg Trp Gln Gln Glu Val Ala Glu Thr Val Phe Asp Thr
            515                 520                 525

Ile Asn Ala Glu Thr Asp Arg Leu Glu Ala Arg Lys Lys Ala Lys Asn
        530                 535                 540

Lys Gln Leu Gly His Glu Glu Asp Tyr Ala Leu Gly Lys Asp Cys Ile
545                 550                 555                 560

Met His Gly Tyr Met Ser Lys Met Gly Asn Pro Phe Leu Thr Gln Trp
                565                 570                 575

Gln Arg Arg Tyr Phe Tyr Leu Phe Pro Asn Arg Leu Glu Trp Arg Gly
            580                 585                 590

Glu Gly Glu Ala Pro Gln Ser Leu Leu Thr Met Glu Glu Ile Gln Ser
        595                 600                 605

Val Glu Glu Thr Gln Ile Lys Glu Arg Lys Cys Leu Leu Leu Lys Ile
    610                 615                 620

Arg Gly Gly Lys Gln Phe Ile Leu Gln Cys Asp Ser Asp Pro Glu Leu
625                 630                 635                 640

Val Gln Trp Lys Lys Glu Leu Arg Asp Ala Tyr Arg Glu Ala Gln Gln
                645                 650                 655

Leu Val Gln Arg Val Pro Lys Met Lys Asn Lys Pro Arg Ser Pro Val
            660                 665                 670

Val Glu Leu Ser Lys Val Pro Leu Val Gln Arg Gly Ser Ala Asn Gly
```

|   | 675 |   | 680 |   | 685 |   |

Leu

<210> SEQ ID NO 30
<211> LENGTH: 2070
<212> TYPE: DNA
<213> ORGANISM: Homo sapiens

<400> SEQUENCE: 30

| atggcggacc tggaggcggt gctggccgac gtgagctacc tgatggccat ggagaagagc | 60 |
| aaggccacgc cggccgcgcg cgccagcaag aagatactgc tgcccgagcc cagcatccgc | 120 |
| agtgtcatgc agaagtacct ggaggaccgg ggcgaggtga cctttgagaa gatcttttcc | 180 |
| cagaagctgg ggtacctgct cttccgagac ttctgcctga accacctgga ggaggccagg | 240 |
| cccttggtgg aattctatga ggagatcaag aagtacgaga gctggagac ggaggaggag | 300 |
| cgtgtggccc gcagccggga gatcttcgac tcatacatca tgaaggagct gctggcctgc | 360 |
| tcgcatccct tctcgaagag tgccactgag catgtccaag ccacctggg gaagaagcag | 420 |
| gtgcctccgg atctcttcca gccatacatc gaagagattt gtcaaaacct ccaggggac | 480 |
| gtgttccaga aattcattga gagcgataag ttcacacggt tttgccagtg aagaatgtg | 540 |
| gagctcaaca tccacctgac catgaatgac ttcagcgtgc atcgcatcat gggcgcggg | 600 |
| ggctttggcg aggtctatgg ggtgccggaag gctgacacag gcaagatgta cgccatgaag | 660 |
| tgcctggaca aaaagcgcat caagatgaag caggggaga ccctggccct gaacgagcgc | 720 |
| atcatgctct cgctcgtcag cactggggac tgcccattca ttgtctgcat gtcatacgcg | 780 |
| ttccacacgc cagacaagct cagcttcatc ctggacctca tgaacggtgg ggacctgcac | 840 |
| taccacctct cccagcacgg ggtcttctca gaggctgaca tgcgcttcta tgcggccgag | 900 |
| atcatcctgg gcctggagca catgcacaac cgcttcgtgg tctaccggga cctgaagcca | 960 |
| gccaacatcc ttctggacga gcatggccac gtgcggatct cggacctggg cctggcctgt | 1020 |
| gacttctcca gaagaagcc ccatgccagc gtgggcaccc acgggtacat ggctccggag | 1080 |
| gtcctgcaga agggcgtggc ctacgacagc agtgccgact ggttctctct ggggtgcatg | 1140 |
| ctcttcaagt gctgcgggg gcacagcccc ttccggcagc acaagaccaa agacaagcat | 1200 |
| gagatcgacc gcatgacgct gacgatggcc gtggagctgc ccgactcctt ctcccctgaa | 1260 |
| ctacgctccc tgctggaggg gttgctgcag agggatgtca accggagatt gggctgcctg | 1320 |
| ggccgagggg ctcaggaggt gaaagagagc ccctttttcc gctccctgga ctggcagatg | 1380 |
| gtcttcttgc agaagtaccc tccccgctg atccccccac gaggggaggt gaacgcggcc | 1440 |
| gacgccttcg acattggctc cttcgatgag gaggacacaa aaggaatcaa gttactggac | 1500 |
| agtgatcagg agctctaccg caacttcccc ctcaccatct cggagcggtg gcagcaggag | 1560 |
| gtggcagaga ctgtcttcga caccatcaac gctgagacag accggctgga ggctcgcaag | 1620 |
| aaagccaaga caagcagct gggccatgag gaagactacg ccctgggcaa ggactgcatc | 1680 |
| atgcatggct acatgtccaa gatgggcaac cccttcctga cccagtggca gcggcggtac | 1740 |
| ttctacctgt tccccaaccg cctcgagtgg cggggcgagg gcgaggcccc gcagagcctg | 1800 |
| ctgaccatgg aggagatcca gtcggtggag agacgcagag tcaaggagcg caagtgcctg | 1860 |
| ctcctcaaga tccgcggtgg gaaacagttc attttgcagt gcgatagcga ccctgagctg | 1920 |
| gtgcagtgga agaaggagct gcgcgacgcc taccgcgagg cccagcagct ggtgcagcgg | 1980 |
| gtgcccaaga tgaagaacaa gccgcgctcg cccgtggtgg agctgagcaa ggtgccgctg | 2040 | gtccagcgcg gcagtgccaa cggcctctga 2070

<210> SEQ ID NO 31
<211> LENGTH: 689
<212> TYPE: PRT
<213> ORGANISM: Homo sapiens

<400> SEQUENCE: 31

```
Met Ala Asp Leu Glu Ala Val Leu Ala Asp Val Ser Tyr Leu Met Ala
  1               5                  10                  15

Met Glu Lys Ser Lys Ala Thr Pro Ala Ala Arg Ala Ser Lys Lys Ile
             20                  25                  30

Leu Leu Pro Glu Pro Ser Ile Arg Ser Val Met Gln Lys Tyr Leu Glu
         35                  40                  45

Asp Arg Gly Glu Val Thr Phe Glu Lys Ile Phe Ser Gln Lys Leu Gly
     50                  55                  60

Tyr Leu Leu Phe Arg Asp Phe Cys Leu Asn His Leu Glu Glu Ala Arg
 65                  70                  75                  80

Pro Leu Val Glu Phe Tyr Glu Glu Ile Lys Lys Tyr Glu Lys Leu Glu
                 85                  90                  95

Thr Glu Glu Arg Val Ala Arg Ser Arg Glu Ile Phe Asp Ser Tyr
            100                 105                 110

Ile Met Lys Glu Leu Leu Ala Cys Ser His Pro Phe Ser Lys Ser Ala
        115                 120                 125

Thr Glu His Val Gln Gly His Leu Gly Lys Lys Gln Val Pro Pro Asp
    130                 135                 140

Leu Phe Gln Pro Tyr Ile Glu Glu Ile Cys Gln Asn Leu Arg Gly Asp
145                 150                 155                 160

Val Phe Gln Lys Phe Ile Glu Ser Asp Lys Phe Thr Arg Phe Cys Gln
                165                 170                 175

Trp Lys Asn Val Glu Leu Asn Ile His Leu Thr Met Asn Asp Phe Ser
            180                 185                 190

Val His Arg Ile Ile Gly Arg Gly Gly Phe Gly Glu Val Tyr Gly Cys
        195                 200                 205

Arg Lys Ala Asp Thr Gly Lys Met Tyr Ala Met Lys Cys Leu Asp Lys
    210                 215                 220

Lys Arg Ile Lys Met Lys Gln Gly Glu Thr Leu Ala Leu Asn Glu Arg
225                 230                 235                 240

Ile Met Leu Ser Leu Val Ser Thr Gly Asp Cys Pro Phe Ile Val Cys
                245                 250                 255

Met Ser Tyr Ala Phe His Thr Pro Asp Lys Leu Ser Phe Ile Leu Asp
            260                 265                 270

Leu Met Asn Gly Gly Asp Leu His Tyr His Leu Ser Gln His Gly Val
        275                 280                 285

Phe Ser Glu Ala Asp Met Arg Phe Tyr Ala Ala Glu Ile Ile Leu Gly
    290                 295                 300

Leu Glu His Met His Asn Arg Phe Val Val Tyr Arg Asp Leu Lys Pro
305                 310                 315                 320

Ala Asn Ile Leu Leu Asp Glu His Gly His Val Arg Ile Ser Asp Leu
                325                 330                 335

Gly Leu Ala Cys Asp Phe Ser Lys Lys Lys Pro His Ala Ser Val Gly
            340                 345                 350

Thr His Gly Tyr Met Ala Pro Glu Val Leu Gln Lys Gly Val Ala Tyr
        355                 360                 365
```

```
Asp Ser Ser Ala Asp Trp Phe Ser Leu Gly Cys Met Leu Phe Lys Leu
    370                 375                 380

Leu Arg Gly His Ser Pro Phe Arg Gln His Lys Thr Lys Asp Lys His
385                 390                 395                 400

Glu Ile Asp Arg Met Thr Leu Thr Met Ala Val Glu Leu Pro Asp Ser
                405                 410                 415

Phe Ser Pro Glu Leu Arg Ser Leu Leu Glu Gly Leu Leu Gln Arg Asp
            420                 425                 430

Val Asn Arg Arg Leu Gly Cys Leu Gly Arg Gly Ala Gln Glu Val Lys
        435                 440                 445

Glu Ser Pro Phe Phe Arg Ser Leu Asp Trp Gln Met Val Phe Leu Gln
    450                 455                 460

Lys Tyr Pro Pro Pro Leu Ile Pro Pro Arg Gly Glu Val Asn Ala Ala
465                 470                 475                 480

Asp Ala Phe Asp Ile Gly Ser Phe Asp Glu Glu Asp Thr Lys Gly Ile
                485                 490                 495

Lys Leu Leu Asp Ser Asp Gln Glu Leu Tyr Arg Asn Phe Pro Leu Thr
            500                 505                 510

Ile Ser Glu Arg Trp Gln Gln Glu Val Ala Glu Thr Val Phe Asp Thr
        515                 520                 525

Ile Asn Ala Glu Thr Asp Arg Leu Glu Ala Arg Lys Lys Ala Lys Asn
    530                 535                 540

Lys Gln Leu Gly His Glu Glu Asp Tyr Ala Leu Gly Lys Asp Cys Ile
545                 550                 555                 560

Met His Gly Tyr Met Ser Lys Met Gly Asn Pro Phe Leu Thr Gln Trp
                565                 570                 575

Gln Arg Arg Tyr Phe Tyr Leu Phe Pro Asn Arg Leu Glu Trp Arg Gly
            580                 585                 590

Glu Gly Glu Ala Pro Gln Ser Leu Leu Thr Met Glu Glu Ile Gln Ser
        595                 600                 605

Val Glu Glu Thr Gln Ile Lys Glu Arg Lys Cys Leu Leu Leu Lys Ile
    610                 615                 620

Arg Gly Gly Lys Gln Phe Ile Leu Gln Cys Asp Ser Asp Pro Glu Leu
625                 630                 635                 640

Val Gln Trp Lys Lys Glu Leu Arg Asp Ala Tyr Arg Glu Ala Gln Gln
                645                 650                 655

Leu Val Gln Arg Val Pro Lys Met Lys Asn Lys Pro Arg Ser Pro Val
            660                 665                 670

Val Glu Leu Ser Lys Val Pro Leu Val Gln Arg Gly Ser Cys Val Leu
        675                 680                 685

Leu

<210> SEQ ID NO 32
<211> LENGTH: 2070
<212> TYPE: DNA
<213> ORGANISM: Homo sapiens

<400> SEQUENCE: 32
atggcggacc tggaggcggt gctggccgac gtgagctacc tgatggccat ggagaagagc    60
aaggccacgc cggccgcgcg cgccagcaag aagatactgc tgcccgagcc agcatccgc   120 agtgtcatgc agaagtacct ggaggaccgg ggcgaggtga cctttgagaa gatcttttcc   180
cagaagctgg ggtacctgct cttccgagac ttctgcctga accacctgga ggaggccagg   240
```

```
ccccttggtgg aattctatga ggagatcaag aagtacgaga agctggagac ggaggaggag    300
cgtgtggccc gcagccggga gatcttcgac tcatacatca tgaaggagct gctggcctgc    360
tcgcatccct tctcgaagag tgccactgag catgtccaag gccacctggg aagaagcag     420 gtgcctccgg atctcttcca gccatacatc gaagagattt gtcaaaacct ccgaggggac    480
gtgttccaga aattcattga gagcgataag ttcacacggt tttgccagtg aagaatgtg     540 gagctcaaca tccacctgac catgaatgac ttcagcgtgc atcgcatcat tgggcgcggg    600
ggctttggcg aggtctatgg gtgccggaag gctgacacag gcaagatgta cgccatgaag    660
tgcctggaca aaaagcgcat caagatgaag caggggggaga ccctggcccct gaacgagcgc   720 atcatgctct cgctcgtcag cactggggac tgcccattca ttgtctgcat gtcatacgcg    780
ttccacacgc cagacaagct cagcttcatc ctggacctca tgaacggtgg ggacctgcac    840
taccacctct cccagcacgg ggtcttctca gaggctgaca tgcgcttcta tgcggccgag    900
atcatcctgg gcctggagca catgcacaac cgcttcgtgg tctaccggga cctgaagcca    960
gccaacatcc ttctggacga gcatggccac gtgcggatct cggacctggg cctggcctgt   1020
gacttctcca agaagaagcc ccatgccagc gtgggcaccc acgggtacat ggctccggag   1080
gtcctgcaga agggcgtggc ctacgacagc agtgccgact ggttctctct ggggtgcatg   1140
ctcttcaagt gctgcggggg gcacagcccc ttccggcagc acaagaccaa agacaagcat   1200
gagatcgacc gcatgacgct gacgatggcc gtggagctgc ccgactcctt ctcccctgaa   1260
ctacgctccc tgctggaggg gttgctgcag agggatgtca accggagatt gggctgcctg   1320
ggccgagggg ctcaggaggt gaaagagagc ccctttttcc gctccctgga ctggcagatg   1380
gtcttcttgc agaagtaccc tccccgctg atccccccac gaggggaggt gaacgcggcc    1440
gacgccttcg acattggctc cttcgatgag gaggacacaa aaggaatcaa gttactggac   1500
agtgatcagg agctctaccg caacttcccc ctcaccatct cggagcggtg gcagcaggag   1560
gtggcagaga ctgtcttcga caccatcaac gctgagacag accggctgga ggctcgcaag   1620
aaagccaaga caagcagct gggccatgag gaagactacg ccctgggcaa ggactgcatc   1680
atgcatggct acatgtccaa gatgggcaac cccttcctga cccagtggca gcggcggtac   1740
ttctacctgt tccccaaccg cctcgagtgg cggggcgagg gcgaggcccc gcagagcctg   1800
ctgaccatgg aggagatcca gtcggtggag gagacgcaga tcaaggagcg caagtgcctg   1860
ctcctcaaga tccgcggtgg gaaacagttc attttgcagt gcgatagcga ccctgagctg   1920
gtgcagtgga agaaggagct gcgcgacgcc taccgcgagg cccagcagct ggtgcagcgg   1980
gtgcccaaga tgaagaacaa gccgcgctcg cccgtggtgg agctgagcaa ggtgccgctg   2040
gtccagcgcg gcagttgtgt gcttctttag                                    2070
```

<210> SEQ ID NO 33
<211> LENGTH: 689
<212> TYPE: PRT
<213> ORGANISM: Bos taurus

<400> SEQUENCE: 33

Met Ala Asp Leu Glu Ala Val Leu Ala Asp Val Ser Tyr Leu Met Ala
1               5                   10                  15

Met Glu Lys Ser Lys Ala Thr Pro Ala Ala Arg Ala Ser Lys Lys Ile
            20                  25                  30

Leu Leu Pro Glu Pro Ser Ile Arg Ser Val Met Gln Lys Tyr Leu Glu
        35                  40                  45

-continued

```
Asp Arg Gly Glu Val Thr Phe Glu Lys Ile Phe Ser Gln Lys Leu Gly
     50                  55                  60

Tyr Leu Leu Phe Arg Asp Phe Cys Leu Lys His Leu Glu Glu Ala Lys
 65                  70                  75                  80

Pro Leu Val Glu Phe Tyr Glu Glu Ile Lys Lys Tyr Glu Lys Leu Glu
                 85                  90                  95

Thr Glu Glu Glu Arg Leu Val Cys Ser Arg Glu Ile Phe Asp Thr Tyr
             100                 105                 110

Ile Met Lys Glu Leu Leu Ala Cys Ser His Pro Phe Ser Lys Ser Ala
         115                 120                 125

Ile Glu His Val Gln Gly His Leu Val Lys Lys Gln Val Pro Pro Asp
     130                 135                 140

Leu Phe Gln Pro Tyr Ile Glu Glu Ile Cys Gln Asn Leu Arg Gly Asp
145                 150                 155                 160

Val Phe Gln Lys Phe Ile Glu Ser Asp Lys Phe Thr Arg Phe Cys Gln
                165                 170                 175

Trp Lys Asn Val Glu Leu Asn Ile His Leu Thr Met Asn Asp Phe Ser
            180                 185                 190

Val His Arg Ile Ile Gly Arg Gly Gly Phe Gly Glu Val Tyr Gly Cys
        195                 200                 205

Arg Lys Ala Asp Thr Gly Lys Met Tyr Ala Met Lys Cys Leu Asp Lys
    210                 215                 220

Lys Arg Ile Lys Met Lys Gln Gly Glu Thr Leu Ala Leu Asn Glu Arg
225                 230                 235                 240

Ile Met Leu Ser Leu Val Ser Thr Gly Asp Cys Pro Phe Ile Val Cys
                245                 250                 255

Met Ser Tyr Ala Phe His Thr Pro Asp Lys Leu Ser Phe Ile Leu Asp
            260                 265                 270

Leu Met Asn Gly Gly Asp Leu His Tyr His Leu Ser Gln His Gly Val
        275                 280                 285

Phe Ser Glu Ala Asp Met Arg Phe Tyr Ala Ala Glu Ile Ile Leu Gly
    290                 295                 300

Leu Glu His Met His Asn Arg Phe Val Val Tyr Arg Asp Leu Lys Pro
305                 310                 315                 320

Ala Asn Ile Leu Leu Asp Glu His Gly His Val Arg Ile Ser Asp Leu
                325                 330                 335

Gly Leu Ala Cys Asp Phe Ser Lys Lys Pro His Ala Ser Val Gly
            340                 345                 350

Thr His Gly Tyr Met Ala Pro Glu Val Leu Gln Lys Gly Val Ala Tyr
        355                 360                 365

Asp Ser Ser Ala Asp Trp Phe Ser Leu Gly Cys Met Leu Phe Lys Leu
    370                 375                 380

Leu Arg Gly His Ser Pro Phe Arg Gln His Lys Thr Lys Asp Lys His
385                 390                 395                 400

Glu Ile Asp Arg Met Thr Leu Thr Met Ala Val Glu Leu Pro Asp Ser
                405                 410                 415

Phe Ser Pro Glu Leu Arg Ser Leu Leu Glu Gly Leu Leu Gln Arg Asp
            420                 425                 430

Val Asn Arg Arg Leu Gly Cys Leu Gly Arg Gly Ala Gln Glu Val Lys
        435                 440                 445

Glu Ser Pro Phe Phe Arg Ser Leu Asp Trp Gln Met Val Phe Leu Gln
    450                 455                 460

Lys Tyr Pro Pro Pro Leu Ile Pro Pro Arg Gly Glu Val Asn Ala Ala
```

```
                465                 470                 475                 480
Asp Ala Phe Asp Ile Gly Ser Phe Asp Glu Glu Asp Thr Lys Gly Ile
                    485                 490                 495
Lys Leu Leu Asp Ser Asp Gln Glu Leu Tyr Arg Asn Phe Pro Leu Thr
                500                 505                 510
Ile Ser Glu Arg Trp Gln Gln Glu Val Ala Glu Thr Val Phe Asp Thr
            515                 520                 525
Ile Asn Ala Glu Thr Asp Arg Leu Glu Ala Arg Lys Lys Thr Lys Asn
        530                 535                 540
Lys Gln Leu Gly His Glu Glu Asp Tyr Ala Leu Gly Lys Asp Cys Ile
545                 550                 555                 560
Met His Gly Tyr Met Ser Lys Met Gly Asn Pro Phe Leu Thr Gln Trp
                565                 570                 575
Gln Arg Arg Tyr Phe Tyr Leu Phe Pro Asn Arg Leu Glu Trp Arg Gly
                580                 585                 590
Glu Gly Glu Ala Pro Gln Ser Leu Leu Thr Met Glu Glu Ile Gln Ser
                595                 600                 605
Val Glu Glu Thr Gln Ile Lys Glu Arg Lys Cys Leu Leu Leu Lys Ile
            610                 615                 620
Arg Gly Gly Lys Gln Phe Val Leu Gln Cys Asp Ser Asp Pro Glu Leu
625                 630                 635                 640
Val Gln Trp Lys Lys Glu Leu Arg Asp Ala Tyr Arg Glu Ala Gln Gln
                645                 650                 655
Leu Val Gln Arg Val Pro Lys Met Lys Asn Lys Pro Arg Ser Pro Val
            660                 665                 670
Val Glu Leu Ser Lys Val Pro Leu Ile Gln Arg Gly Ser Ala Asn Gly
        675                 680                 685
Leu

<210> SEQ ID NO 34
<211> LENGTH: 2070
<212> TYPE: DNA
<213> ORGANISM: Bos taurus

<400> SEQUENCE: 34
atggcggacc tggaggcggt gctggccgac gtgagctacc tgatggccat ggagaagagc    60
aaggccacgc cggcggcgcg cgccagcaag aagatcctgc tgcccgagcc cagcatccgc   120
agcgtcatgc agaagtacct ggaggaccgg ggcgaggtga cttttgagaa gatcttctcc   180
cagaagctgg ggtacctgct tttccgagac ttctgcctga agcacctgga ggaggccaag   240
cccttggtag agttctacga ggagatcaag aaatacgaga agctggagac agaggaggag   300
cgcctggtct gcagccgaga gatcttcgac acgtacatca tgaaggagct gctggcctgc   360
tcacatcctt tctcgaagag cgccattgag cacgtccagg ccatctggt gaagaagcag   420
gtgcctccgg atctcttcca gccatatatt gaagaaattt gccagaacct ccgaggagac   480
gtgttccaga aattcatcga gagcgataaa ttcacacgat tttgccagtg aagaatgta   540
gagctcaaca tccacctgac catgaacgac ttcagtgtgc accgcatcat cgggcgaggc   600
ggcttcggtg aggtctacgg ctgccggaag gccgacacgg gcaagatgta cgccatgaag   660
tgtctggaca agaagcgcat caagatgaag caaggggaga ctctggccct gaatgagcgc   720
atcatgctgt cgctcgtcag caccggggac tgcccgttca tcgtctgcat gtcatacgcc   780
ttccacacac cggacaagct cagcttcatc ctggatctca tgaacggcgg ggaccctgca c  840
```

```
taccacctgt cccagcacgg ggtcttctcc gaggccgaca tgcgtttcta cgccgccgag    900
atcatcctgg gcctggagca catgcacaac cgcttcgtgg tctaccggga cctgaagccg    960
gccaacatcc tgctggacga gcacggccac gtgcgcatct cagacctggg cctggcctgt   1020
gacttctcca agaagaagcc tcacgccagt gtgggcaccc acgggtacat ggctcccgag   1080
gttctacaga agggtgtggc ctacgacagc agcgccgact ggttctccct gggctgcatg   1140
ctcttcaagc tgctgcgagg gcatagccct tccggcagc acaagaccaa agacaagcat    1200
gagatcgaca gaatgacatt gacaatggct gtggagctgc ctgactcctt ctcccctgag   1260
ctccgctcct tgctggaggg gctgctgcag agggatgtca accggaggct aggctgcctg   1320
ggccgagggg cccaggaggt gaaggagagc cccttcttcc gttccctgga ctggcagatg   1380 gtcttttac aaaagtaccc tcccccgttg atcccccac gaggggaggt gaatgcagcc    1440
gacgcctttg acattggctc cttcgatgag gaggacacaa aaggaatcaa gctactggac   1500
agtgaccagg agctctaccg caacttcccc ctgaccatct cggagcggtg gcagcaggag   1560
gtagcagaga ctgtctttga caccatcaat gctgagacgg accggctgga ggcccgcaag   1620
aaaaccaaaa acaagcagtt gggccacgag gaagactacg ccctgggcaa ggactgcatc   1680
atgcatggct acatgtccaa gatgggcaac cccttcctga cccagtggca gcggcggtac   1740
ttctacctgt tccctaaccg gctcgagtgg cggggcgagg cgaggcccc gcagagcctg   1800 ctgaccatgg aggagatcca gtcggtggag gagacgcaga tcaaggagcg aaagtgcctc   1860
ctcctcaaga tccgaggtgg caagcagttt gtcctgcagt gcgatagtga cccagagctg   1920
gtgcagtgga agaaggagct tcgagacgcc taccgcgagg cccagcagct agtgcagcgg   1980
gtgcccaaga tgaagaacaa gccgcgctcg cccgtcgtgg agctgagcaa ggtgccactg   2040
atccagcgcg gcagtgccaa cggcctctga                                    2070
```

<210> SEQ ID NO 35
<211> LENGTH: 330
<212> TYPE: PRT
<213> ORGANISM: Homo sapiens

<400> SEQUENCE: 35

```
Met Met Trp Gly Ala Gly Ser Pro Leu Ala Trp Leu Ser Ala Gly Ser
 1               5                   10                  15

Gly Asn Val Asn Val Ser Ser Val Gly Pro Ala Glu Gly Pro Thr Gly
                20                  25                  30

Pro Ala Ala Pro Leu Pro Ser Pro Lys Ala Trp Asp Val Val Leu Cys
            35                  40                  45

Ile Ser Gly Thr Leu Val Ser Cys Glu Asn Ala Leu Val Val Ala Ile
        50                  55                  60

Ile Val Gly Thr Pro Ala Phe Arg Ala Pro Met Phe Leu Leu Val Gly
    65                  70                  75                  80

Ser Leu Ala Val Ala Asp Leu Leu Ala Gly Leu Val Leu His
                85                  90                  95

Phe Ala Ala Val Phe Cys Ile Gly Ser Ala Glu Met Ser Leu Val Leu
            100                 105                 110

Val Gly Val Leu Ala Met Ala Phe Thr Ala Ser Ile Gly Ser Leu Leu
        115                 120                 125

Ala Ile Thr Val Asp Arg Tyr Leu Ser Leu Tyr Asn Ala Leu Thr Tyr
    130                 135                 140

Tyr Ser Glu Thr Thr Val Thr Arg Thr Tyr Val Met Leu Ala Leu Val
145                 150                 155                 160
```

-continued

```
Trp Gly Gly Ala Leu Gly Leu Gly Leu Leu Pro Val Leu Ala Trp Asn
            165                 170                 175

Cys Leu Asp Gly Leu Thr Thr Cys Gly Val Val Tyr Pro Leu Ser Lys
            180                 185                 190

Asn His Leu Val Val Leu Ala Ile Ala Phe Phe Met Val Phe Gly Ile
            195                 200                 205

Met Leu Gln Leu Tyr Ala Gln Ile Cys Arg Ile Val Cys Arg His Ala
        210                 215                 220

Gln Gln Ile Ala Leu Gln Arg His Leu Leu Pro Ala Ser His Tyr Val
225                 230                 235                 240

Ala Thr Arg Lys Gly Ile Ala Thr Leu Ala Val Val Leu Gly Ala Phe
            245                 250                 255

Ala Ala Cys Trp Leu Pro Phe Thr Val Tyr Cys Leu Leu Gly Asp Ala
            260                 265                 270

His Ser Pro Pro Leu Tyr Thr Tyr Leu Thr Leu Leu Pro Ala Thr Tyr
        275                 280                 285

Asn Ser Met Ile Asn Pro Ile Ile Tyr Ala Phe Arg Asn Gln Asp Val
    290                 295                 300

Gln Lys Val Leu Trp Ala Val Cys Cys Cys Ser Ser Ser Lys Ile
305                 310                 315                 320

Pro Phe Arg Ser Arg Ser Pro Ser Asp Val
            325                 330
```

<210> SEQ ID NO 36
<211> LENGTH: 993
<212> TYPE: DNA
<213> ORGANISM: Homo sapiens

<400> SEQUENCE: 36

```
atgatgtggg gtgcaggcag ccctctggcc tggctctcag ctggctcagg caacgtgaat      60
gtaagcagcg tgggcccagc agaggggccc acaggtccag ccgcaccact gccctcgcct     120
aaggcctggg atgtggtgct ctgcatctca ggcaccctgg tgtcctgcga gaatgcgcta     180
gtggtggcca tcatcgtggg cactcctgcc ttccgtgccc ccatgttcct gctggtgggc     240
agcctggccg tggcagacct gctggcaggc ctgggcctgg tcctgcactt tgctgctgtc     300
ttctgcatcg gctcagcgga gatgagcctg gtgctggttg gcgtgctggc aatgcctttt     360
accgccagca tcggcagtct actggccatc actgtcgacc gctacctttc tctgtacaat     420
gccctcacct actattcaga gacaacagtg acacggacct atgtgatgct ggccttagtg     480
tggggaggtg ccctgggcct ggggctgctg cctgtgctgg cctggaactg cctggatggc     540
ctgaccacat gtggcgtggt ttatccactc tccaagaacc atctggtagt tctggccatt     600
gccttcttca tggtgtttgg catcatgctg cagctctacg cccaaatctg ccgcatcgtc     660
tgccgccatg cccagcagat tgcccttcag cggcacctgc tgcctgcctc ccactatgtg     720
gccacccgca agggcattgc cacactggcc gtggtgcttg gagcctttgc cgcctgctgg     780
ttgcccttca ctgtctactg cctgctgggt gatgcccact ctccacctct ctacacctat     840
cttaccttgc tccctgccac ctacaactcc atgatcaacc ctatcatcta cgccttccgc     900
aaccaggatg tgcagaaagt gctgtgggct gtctgctgct gctgttcctc ttccaagatc     960
cccttccgat cccgctcccc cagtgatgtc tag                                  993
```

<210> SEQ ID NO 37
<211> LENGTH: 344

```
<212> TYPE: PRT
<213> ORGANISM: Homo sapiens

<400> SEQUENCE: 37

Met Tyr Pro Tyr Asp Val Pro Asp Tyr Ala Ala Ala Ala Met Met
 1               5                  10                  15

Trp Gly Ala Gly Ser Pro Leu Ala Trp Leu Ser Ala Gly Ser Gly Asn
                20                  25                  30

Val Asn Val Ser Ser Val Gly Pro Ala Glu Gly Pro Thr Gly Pro Ala
            35                  40                  45

Ala Pro Leu Pro Ser Pro Lys Ala Trp Asp Val Val Leu Cys Ile Ser
        50                  55                  60

Gly Thr Leu Val Ser Cys Glu Asn Ala Leu Val Ala Ile Ile Val
 65                  70                  75                  80

Gly Thr Pro Ala Phe Arg Ala Pro Met Phe Leu Val Gly Ser Leu
                85                  90                  95

Ala Val Ala Asp Leu Leu Ala Gly Leu Gly Leu Val Leu His Phe Ala
                100                 105                 110

Ala Val Phe Cys Ile Gly Ser Ala Glu Met Ser Leu Val Leu Val Gly
                115                 120                 125

Val Leu Ala Met Ala Phe Thr Ala Ser Ile Gly Ser Leu Leu Ala Ile
130                 135                 140

Thr Val Asp Arg Tyr Leu Ser Leu Tyr Asn Ala Leu Thr Tyr Tyr Ser
145                 150                 155                 160

Glu Thr Thr Val Thr Arg Thr Tyr Val Met Leu Ala Leu Val Trp Gly
                165                 170                 175

Gly Ala Leu Gly Leu Gly Leu Leu Pro Val Leu Ala Trp Asn Cys Leu
                180                 185                 190

Asp Gly Leu Thr Thr Cys Gly Val Val Tyr Pro Leu Ser Lys Asn His
            195                 200                 205

Leu Val Val Leu Ala Ile Ala Phe Phe Met Val Phe Gly Ile Met Leu
        210                 215                 220

Gln Leu Tyr Ala Gln Ile Cys Arg Ile Val Cys Arg His Ala Gln Gln
225                 230                 235                 240

Ile Ala Leu Gln Arg His Leu Leu Pro Ala Ser His Tyr Val Ala Thr
                245                 250                 255

Arg Lys Gly Ile Ala Thr Leu Ala Val Val Leu Gly Ala Phe Ala Ala
                260                 265                 270

Cys Trp Leu Pro Phe Thr Val Tyr Cys Leu Leu Gly Asp Ala His Ser
            275                 280                 285

Pro Pro Leu Tyr Thr Tyr Leu Thr Leu Leu Pro Ala Thr Tyr Asn Ser
        290                 295                 300

Met Ile Asn Pro Ile Ile Tyr Ala Phe Arg Asn Gln Asp Val Gln Lys
305                 310                 315                 320

Val Leu Trp Ala Val Cys Cys Cys Ser Ser Lys Ile Pro Phe
                325                 330                 335

Arg Ser Arg Ser Pro Ser Asp Val
            340

<210> SEQ ID NO 38
<211> LENGTH: 1035
<212> TYPE: DNA
<213> ORGANISM: Homo sapiens

<400> SEQUENCE: 38
```

```
atgtacccat acgacgtacc tgattacgca gcagcagcag caatgatgtg gggtgcaggc    60
agccctctgg cctggctctc agctggctca ggcaacgtga atgtaagcag cgtgggccca   120
gcagaggggc ccacaggtcc agccgcacca ctgccctcgc ctaaggcctg ggatgtggtg   180
ctctgcatct caggcaccct ggtgtcctgc gagaatgcgc tagtggtggc catcatcgtg   240
ggcactcctg ccttccgtgc ccccatgttc ctgctggtgg gcagcctggc cgtggcagac   300
ctgctggcag gctgggcct ggtcctgcac tttgctgctg tcttctgcat cggctcagcg   360
gagatgagcc tggtgctggt tggcgtgctg gcaatggcct ttaccgccag catcggcagt   420
ctactggcca tcactgtcga ccgctacctt tctctgtaca atgccctcac ctactattca   480
gagacaacag tgacacggac ctatgtgatg ctggccttag tgtggggagg tgccctgggc   540
ctggggctgc tgcctgtgct ggcctggaac tgcctggatg gcctgaccac atgtggcgtg   600
gtttatccac tctccaagaa ccatctggta gttctggcca ttgccttctt catggtgttt   660
ggcatcatgc tgcagctcta cgcccaaatc tgccgcatcg tctgccgcca tgcccagcag   720
attgccctc agcggcacct gctgcctgcc tcccactatg tggccacccg caagggcatt   780
gccacactgg ccgtggtgct ggagcctt gccgctgct ggttgcct cactgtctac   840
tgcctgctgg gtgatgccca ctctccacct ctctacacct atcttacctt gctccctgcc   900
acctacaact ccatgatcaa ccctatcatc tacgccttcc gcaaccagga tgtgcagaaa   960
gtgctgtggg ctgtctgctg ctgctgttcc tcttccaaga tccccttccg atcccgctcc  1020
cccagtgatg tctag                                                    1035
```

<210> SEQ ID NO 39
<211> LENGTH: 346
<212> TYPE: PRT
<213> ORGANISM: Homo sapiens

<400> SEQUENCE: 39

```
Met Met Trp Gly Ala Gly Ser Pro Leu Ala Trp Leu Ser Ala Gly Ser
  1               5                  10                  15

Gly Asn Val Asn Val Ser Ser Val Gly Pro Ala Glu Gly Pro Thr Gly
                 20                  25                  30

Pro Ala Ala Pro Leu Pro Ser Pro Lys Ala Trp Asp Val Val Leu Cys
             35                  40                  45

Ile Ser Gly Thr Leu Val Ser Cys Glu Asn Ala Leu Val Val Ala Ile
         50                  55                  60

Ile Val Gly Thr Pro Ala Phe Arg Ala Pro Met Phe Leu Leu Val Gly
     65                  70                  75                  80

Ser Leu Ala Val Ala Asp Leu Leu Ala Gly Leu Gly Leu Val Leu His
                 85                  90                  95

Phe Ala Ala Val Phe Cys Ile Gly Ser Ala Glu Met Ser Leu Val Leu
                100                 105                 110

Val Gly Val Leu Ala Met Ala Phe Thr Ala Ser Ile Gly Ser Leu Leu
            115                 120                 125

Ala Ile Thr Val Asp Arg Tyr Leu Ser Leu Tyr Asn Ala Leu Thr Tyr
        130                 135                 140

Tyr Ser Glu Thr Thr Val Thr Arg Thr Tyr Val Met Leu Ala Leu Val
145                 150                 155                 160

Trp Gly Gly Ala Leu Gly Leu Gly Leu Leu Pro Val Leu Ala Trp Asn
                165                 170                 175

Cys Leu Asp Gly Leu Thr Thr Cys Gly Val Val Tyr Pro Leu Ser Lys
            180                 185                 190
```

Asn His Leu Val Val Leu Ala Ile Ala Phe Phe Met Val Phe Gly Ile
                195                 200                 205

Met Leu Gln Leu Tyr Ala Gln Ile Cys Arg Ile Val Cys Arg His Ala
            210                 215                 220

Gln Gln Ile Ala Leu Gln Arg His Leu Leu Pro Ala Ser His Tyr Val
225                 230                 235                 240

Ala Thr Arg Lys Gly Ile Ala Thr Leu Ala Val Val Leu Gly Ala Phe
                245                 250                 255

Ala Ala Cys Trp Leu Pro Phe Thr Val Tyr Cys Leu Leu Gly Asp Ala
            260                 265                 270

His Ser Pro Pro Leu Tyr Thr Tyr Leu Thr Leu Leu Pro Ala Thr Tyr
            275                 280                 285

Asn Ser Met Ile Asn Pro Ile Ile Tyr Ala Phe Arg Asn Gln Asp Val
                290                 295                 300

Gln Lys Val Leu Trp Ala Val Cys Cys Cys Ala Ala Ala Arg Gly
305                 310                 315                 320

Arg Thr Pro Pro Ser Leu Gly Pro Gln Asp Glu Ser Cys Thr Thr Ala
                325                 330                 335

Ser Ser Ser Leu Ala Lys Asp Thr Ser Ser
                340                 345

<210> SEQ ID NO 40
<211> LENGTH: 1041
<212> TYPE: DNA
<213> ORGANISM: Homo sapiens

<400> SEQUENCE: 40
atgatgtggg gtgcaggcag ccctctggcc tggctctcag ctggctcagg caacgtgaat      60
gtaagcagcg tgggcccagc agaggggccc acaggtccag ccgcaccact gccctcgcct     120
aaggcctggg atgtggtgct ctgcatctca ggcaccctgg tgtcctgcga aatgcgcta     180
gtggtggcca tcatcgtggg cactcctgcc ttccgtgccc ccatgttcct gctggtgggc     240
agcctggccg tggcagacct gctggcaggc ctgggcctgg tcctgcactt tgctgctgtc     300
ttctgcatcg gctcagcgga gatgagcctg gtgctggttg gcgtgctggc aatggccttt     360
acygccagca tcggcagtct actggccatc actgtcgacc gctaccttc tctgtacaat     420
gccctcacct actattcaga gacaacagtg acacggacct atgtgatgct ggccttagtg     480
tggggaggtg ccctgggcct ggggctgctg cctgtgctgg cctggaactg cctggatggc     540
ctgaccacat gtggcgtggt ttatccactc tccaagaacc atctggtagt tctggccatt     600
gccttcttca tggtgtttgg catcatgctg cagctctacg cccaaatctg ccgcatcgtc     660
tgccgccatg cccagcagat tgcccttcag cggcacctgc tgcctgcctc ccactatgtg     720
gccacccgca agggcattgc cacactggcc gtggtgcttg gagcctttgc cgcctgctgg     780
ttgcccttca ctgtctactg cctgctgggt gatgcccact ctccacctct ctacacctat     840
cttaccttgc tccctgccac ctacaactcc atgatcaacc ctatcatcta cgccttccgc     900
aaccaggatg tgcagaaagt gctgtgggct gtctgctgct gctgtgcggc cgcacgggga     960
cgcacccaca ccagcctggg tccccaagat gagtcctgca ccaccgccag ctcctccctg    1020
gccaaggaca cttcatcgtg a                                               1041

<210> SEQ ID NO 41
<211> LENGTH: 360
<212> TYPE: PRT

<213> ORGANISM: Homo sapiens

<400> SEQUENCE: 41

```
Met Tyr Pro Tyr Asp Val Pro Asp Tyr Ala Ala Ala Ala Met Met
 1               5                  10                  15

Trp Gly Ala Gly Ser Pro Leu Ala Trp Leu Ser Ala Gly Ser Gly Asn
                20                  25                  30

Val Asn Val Ser Ser Val Gly Pro Ala Glu Gly Pro Thr Gly Pro Ala
            35                  40                  45

Ala Pro Leu Pro Ser Pro Lys Ala Trp Asp Val Val Leu Cys Ile Ser
        50                  55                  60

Gly Thr Leu Val Ser Cys Glu Asn Ala Leu Val Val Ala Ile Ile Val
 65                 70                  75                  80

Gly Thr Pro Ala Phe Arg Ala Pro Met Phe Leu Leu Val Gly Ser Leu
                85                  90                  95

Ala Val Ala Asp Leu Leu Ala Gly Leu Gly Leu Val Leu His Phe Ala
            100                 105                 110

Ala Val Phe Cys Ile Gly Ser Ala Glu Met Ser Leu Val Leu Val Gly
        115                 120                 125

Val Leu Ala Met Ala Phe Thr Ala Ser Ile Gly Ser Leu Leu Ala Ile
130                 135                 140

Thr Val Asp Arg Tyr Leu Ser Leu Tyr Asn Ala Leu Thr Tyr Tyr Ser
145                 150                 155                 160

Glu Thr Thr Val Thr Arg Thr Tyr Val Met Leu Ala Leu Val Trp Gly
                165                 170                 175

Gly Ala Leu Gly Leu Gly Leu Leu Pro Val Leu Ala Trp Asn Cys Leu
            180                 185                 190

Asp Gly Leu Thr Thr Cys Gly Val Val Tyr Pro Leu Ser Lys Asn His
        195                 200                 205

Leu Val Val Leu Ala Ile Ala Phe Phe Met Val Phe Gly Ile Met Leu
    210                 215                 220

Gln Leu Tyr Ala Gln Ile Cys Arg Ile Val Cys Arg His Ala Gln Gln
225                 230                 235                 240

Ile Ala Leu Gln Arg His Leu Leu Pro Ala Ser His Tyr Val Ala Thr
                245                 250                 255

Arg Lys Gly Ile Ala Thr Leu Ala Val Val Leu Gly Ala Phe Ala Ala
            260                 265                 270

Cys Trp Leu Pro Phe Thr Val Tyr Cys Leu Leu Gly Asp Ala His Ser
        275                 280                 285

Pro Pro Leu Tyr Thr Tyr Leu Thr Leu Leu Pro Ala Thr Tyr Asn Ser
    290                 295                 300

Met Ile Asn Pro Ile Ile Tyr Ala Phe Arg Asn Gln Asp Val Gln Lys
305                 310                 315                 320

Val Leu Trp Ala Val Cys Cys Cys Ala Ala Arg Gly Arg Thr
                325                 330                 335

Pro Pro Ser Leu Gly Pro Gln Asp Glu Ser Cys Thr Thr Ala Ser Ser
            340                 345                 350

Ser Leu Ala Lys Asp Thr Ser Ser
        355                 360
```

<210> SEQ ID NO 42
<211> LENGTH: 1083
<212> TYPE: DNA
<213> ORGANISM: Homo sapiens -continued

```
<400> SEQUENCE: 42
atgtacccat acgacgtacc tgattacgca gcagcagcag caatgatgtg gggtgcaggc      60
agccctctgg cctggctctc agctggctca ggcaacgtga atgtaagcag cgtgggccca     120
gcagaggggc ccacaggtcc agccgcacca ctgccctcgc ctaaggcctg ggatgtggtg     180
ctctgcatct caggcaccct ggtgtcctgc gagaatgcgc tagtggtggc catcatcgtg     240
ggcactcctg ccttccgtgc ccccatgttc ctgctggtgg gcagcctggc cgtggcagac     300
ctgctggcag gcctgggcct ggtcctgcac tttgctgctg tcttctgcat cggctcagcg     360
gagatgagcc tggtgctggt tggcgtgctg caatggcct ttactgccag catcggcagt      420
ctactggcca tcactgtcga ccgctacctt tctctgtaca atgccctcac ctactattca     480
gagacaacag tgcacggac ctatgtgatg ctggccttag tgtggggagg tgccctgggc      540
ctggggctgc tgcctgtgct ggcctggaac tgcctggatg gcctgaccac atgtggcgtg     600
gtttatccac tctccaagaa ccatctggta gttctggcca ttgccttctt catggtgttt     660
ggcatcatgc tgcagctcta cgcccaaatc tgccgcatcg tctgccgcca tgcccagcag     720
attgcccttc agcggcacct gctgcctgcc tcccactatg tggccacccg caagggcatt     780
gccacactgg ccgtggtgct ggagcctttt gccgcctgct ggttgccctt cactgtctac     840
tgcctgctgg gtgatgccca ctctccacct ctctacacct atcttacctt gctccctgcc     900
acctacaact ccatgatcaa ccctatcatc tacgccttcc gcaaccagga tgtgcagaaa     960
gtgctgtggg ctgtctgctg ctgctgtgcg gccgcacggg gacgcacccc acccagcctg    1020
ggtccccaag atgagtcctg caccaccgcc agctcctccc tggccaagga cacttcatcg    1080
tga                                                                  1083

<210> SEQ ID NO 43
<211> LENGTH: 362
<212> TYPE: PRT
<213> ORGANISM: Homo sapiens

<400> SEQUENCE: 43

Met Asn Ala Ser Ala Ala Ser Leu Asn Asp Ser Gln Val Val Val
  1               5                   10                  15

Ala Ala Glu Gly Ala Ala Ala Ala Thr Ala Ala Gly Gly Pro Asp
                 20                  25                  30

Thr Gly Glu Trp Gly Pro Pro Ala Ala Ala Leu Gly Ala Gly Gly
                 35                  40                  45

Gly Ala Asn Gly Ser Leu Glu Leu Ser Ser Gln Leu Ser Ala Gly Pro
 50                  55                  60

Pro Gly Leu Leu Leu Pro Ala Val Asn Pro Trp Asp Val Leu Leu Cys
 65                  70                  75                  80

Val Ser Gly Thr Val Ile Ala Gly Glu Asn Ala Leu Val Val Ala Leu
                 85                  90                  95

Ile Ala Ser Thr Pro Ala Leu Arg Thr Pro Met Phe Val Leu Val Gly
                100                 105                 110

Ser Leu Ala Thr Ala Asp Leu Leu Ala Gly Cys Gly Leu Ile Leu His
                115                 120                 125

Phe Val Phe Gln Tyr Leu Val Pro Ser Glu Thr Val Ser Leu Leu Thr
                130                 135                 140

Val Gly Phe Leu Val Ala Ser Phe Ala Ala Ser Val Ser Ser Leu Leu
145                 150                 155                 160

Ala Ile Thr Val Asp Arg Tyr Leu Ser Leu Tyr Asn Ala Leu Thr Tyr
```

```
                    165                 170                 175
Tyr Ser Arg Arg Thr Leu Leu Gly Val His Leu Leu Ala Ala Thr
            180                 185                 190

Trp Thr Val Ser Leu Gly Leu Gly Leu Leu Pro Val Leu Gly Trp Asn
            195                 200                 205

Cys Leu Ala Glu Arg Ala Ala Cys Ser Val Val Arg Pro Leu Ala Arg
            210                 215                 220

Ser His Val Ala Leu Leu Ser Ala Ala Phe Phe Met Val Phe Gly Ile
225                 230                 235                 240

Met Leu His Leu Tyr Val Arg Ile Cys Gln Val Val Trp Arg His Ala
                245                 250                 255

His Gln Ile Ala Leu Gln Gln His Cys Leu Ala Pro Pro His Leu Ala
            260                 265                 270

Ala Thr Arg Lys Gly Val Gly Thr Leu Ala Val Val Leu Gly Thr Phe
            275                 280                 285

Gly Ala Ser Trp Leu Pro Phe Ala Ile Tyr Cys Val Val Gly Ser His
            290                 295                 300

Glu Asp Pro Ala Val Tyr Thr Tyr Ala Thr Leu Leu Pro Ala Thr Tyr
305                 310                 315                 320

Asn Ser Met Ile Asn Pro Ile Ile Tyr Ala Phe Arg Asn Gln Glu Ile
                325                 330                 335

Gln Arg Ala Leu Trp Leu Leu Leu Cys Gly Cys Phe Gln Ser Lys Val
            340                 345                 350

Pro Phe Arg Ser Arg Ser Pro Ser Glu Val
            355                 360

<210> SEQ ID NO 44
<211> LENGTH: 1089
<212> TYPE: DNA
<213> ORGANISM: Homo sapiens

<400> SEQUENCE: 44
atgaacgcga gcgccgcctc gctcaacgac tcccaggtgg tggtagtggc ggccgaagga      60
gcggcggcgg cggccacagc agcagggggg ccggacacgg gcgaatgggg accccctgct     120
gcggcggctc taggagccgg cggcggagct aatgggtctc tggagctgtc ctcgcagctg     180
tcggctgggc caccgggact cctgctgcca gcggtgaatc cgtgggacgt gctcctgtgc     240
gtgtcgggga cagtgatcgc tggagaaaac gcgctggtgg tggcgctcat cgcgtccact     300
ccggcgctgc gcacgcccat gttcgtgctg gtaggcagcc tggccaccgc tgacctgttg     360
gcgggctgtg gcctcatctt gcactttgtg ttccagtact tggtgccctc ggagactgtg     420
agtctgctca cggtgggctt cctcgtggcc tccttcgccg cctctgtcag cagcctgctg     480
gccattacgg tggaccgcta cctgtccctg tataacgcgc tcacctatta ctcgcgccgg     540
accctgttgg gcgtgcacct cctgcttgcc gccacttgga ccgtgtccct aggcctgggg     600
ctgctgcccg tgctgggctg gaactgcctg gcagagcgcg ccgcctgcag cgtggtgcgc     660
ccgctggcgc gcagccacgt ggctctgctc tccgccgcct tcttcatggt cttcggcatc     720
atgctgcacc tgtacgtgcg catctgccag gtggtctggc gccacgcgca ccagatcgcg     780
ctgcagcagc actgcctggc gcacccccat ctcgctgcca ccagaaaggg tgtgggctac     840
ctggctgtgg tgctgggcac tttcggcgcc agctggctgc ccttcgccat ctattgcgtg     900
gtgggcagcc atgaggaccc ggcggtctac acttacgcca ccctgctgcc cgccacctac     960
aactccatga tcaatcccat catctatgcc ttccgcaacc aggagatcca gcgcgccctg    1020
```

```
tggctcctgc tctgtggctg tttccagtcc aaagtgccct ttcgttccag gtctcccagc    1080
gaggtctga                                                            1089
```

<210> SEQ ID NO 45
<211> LENGTH: 376
<212> TYPE: PRT
<213> ORGANISM: Homo sapiens

<400> SEQUENCE: 45

```
Met Tyr Pro Tyr Asp Val Pro Asp Tyr Ala Ala Ala Ala Met Asn
 1               5                  10                  15

Ala Ser Ala Ala Ser Leu Asn Asp Ser Gln Val Val Val Ala Ala
                20                  25                  30

Glu Gly Ala Ala Ala Ala Thr Ala Ala Gly Gly Pro Asp Thr Gly
            35                  40                  45

Glu Trp Gly Pro Pro Ala Ala Ala Leu Gly Ala Gly Gly Gly Ala
 50                  55                  60

Asn Gly Ser Leu Glu Leu Ser Ser Gln Leu Ser Ala Gly Pro Pro Gly
 65                  70                  75                  80

Leu Leu Leu Pro Ala Val Asn Pro Trp Asp Val Leu Leu Cys Val Ser
                 85                  90                  95

Gly Thr Val Ile Ala Gly Glu Asn Ala Leu Val Val Ala Leu Ile Ala
                100                 105                 110

Ser Thr Pro Ala Leu Arg Thr Pro Met Phe Val Leu Val Gly Ser Leu
                115                 120                 125

Ala Thr Ala Asp Leu Leu Ala Gly Cys Gly Leu Ile Leu His Phe Val
                130                 135                 140

Phe Gln Tyr Leu Val Pro Ser Glu Thr Val Ser Leu Leu Thr Val Gly
145                 150                 155                 160

Phe Leu Val Ala Ser Phe Ala Ala Ser Val Ser Ser Leu Leu Ala Ile
                165                 170                 175

Thr Val Asp Arg Tyr Leu Ser Leu Tyr Asn Ala Leu Thr Tyr Tyr Ser
                180                 185                 190

Arg Arg Thr Leu Leu Gly Val His Leu Leu Leu Ala Ala Thr Trp Thr
                195                 200                 205

Val Ser Leu Gly Leu Gly Leu Leu Pro Val Leu Gly Trp Asn Cys Leu
            210                 215                 220

Ala Glu Arg Ala Ala Cys Ser Val Val Arg Pro Leu Ala Arg Ser His
225                 230                 235                 240

Val Ala Leu Leu Ser Ala Ala Phe Phe Met Val Phe Gly Ile Met Leu
                245                 250                 255

His Leu Tyr Val Arg Ile Cys Gln Val Val Trp Arg His Ala His Gln
                260                 265                 270

Ile Ala Leu Gln Gln His Cys Leu Ala Pro Pro His Leu Ala Ala Thr
                275                 280                 285

Arg Lys Gly Val Gly Thr Leu Ala Val Val Leu Gly Thr Phe Gly Ala
            290                 295                 300

Ser Trp Leu Pro Phe Ala Ile Tyr Cys Val Val Gly Ser His Glu Asp
305                 310                 315                 320

Pro Ala Val Tyr Thr Tyr Ala Thr Leu Leu Pro Ala Thr Tyr Asn Ser
                325                 330                 335

Met Ile Asn Pro Ile Ile Tyr Ala Phe Arg Asn Gln Glu Ile Gln Arg
                340                 345                 350
```

```
Ala Leu Trp Leu Leu Cys Gly Cys Phe Gln Ser Lys Val Pro Phe
        355                 360                 365

Arg Ser Arg Ser Pro Ser Glu Val
    370                 375
```

<210> SEQ ID NO 46
<211> LENGTH: 1131
<212> TYPE: DNA
<213> ORGANISM: Homo sapiens

<400> SEQUENCE: 46

```
atgtacccat acgacgtacc tgattacgca gcagcagcag caatgaacgc gagcgccgcc      60
tcgctcaacg actcccaggt ggtggtagtg gcggccgaag gagcggcggc ggcggccaca     120
gcagcagggg ggccggacac gggcgaatgg gaccccctg ctgcggcggc tctaggagcc     180
ggcggcggag ctaatgggtc tctggagctg tcctcgcagc tgtcggctgg gccaccggga     240
ctcctgctgc cagcggtgaa tccgtgggac gtgctcctgt gcgtgtcggg acagtgatc     300
gctggagaaa acgcgctggt ggtggcgctc atcgcgtcca ctccggcgct gcgcacgccc     360
atgttcgtgc tggtaggcag cctggccacc gctgacctgt ggcgggctg tggcctcatc     420
ttgcactttg tgttccagta cttggtgccc tcggagactg tgagtctgct cacggtgggc     480
ttcctcgtgg cctccttcgc cgcctctgtc agcagcctgc tggccattac ggtggaccgc     540
tacctgtccc tgtataacgc gctcacctat tactcgcgcc ggaccctgtt gggcgtgcac     600
ctcctgcttg ccgccacttg gaccgtgtcc ctaggcctgg gctgctgcc cgtgctgggc     660
tggaactgcc tggcagagcg cgccgcctgc agcgtggtgc gcccgctggc gcgcagccac     720
gtggctctgc tctccgccgc cttcttcatg gtcttcggca tcatgctgca cctgtacgtg     780
cgcatctgcc aggtggtctg gcgccacgcg caccagatcg cgctgcagca gcactgcctg     840
gcgccacccc catctcgctgc caccagaaag ggtgtgggta cactggctgt ggtgctgggc     900
actttcggcg ccagctggct gcccttcgcc atctattgcg tggtgggcag ccatgaggac     960
ccggcggtct acacttacgc caccctgctg cccgccacct acaactccat gatcaatccc    1020
atcatctatg ccttccgcaa ccaggagatc cagcgcgccc tgtggctcct gctctgtggc    1080
tgtttccagt ccaaagtgcc ctttcgttcc aggtctccca gcgaggtctg a             1131
```

<210> SEQ ID NO 47
<211> LENGTH: 378
<212> TYPE: PRT
<213> ORGANISM: Homo sapiens

<400> SEQUENCE: 47

```
Met Asn Ala Ser Ala Ala Ser Leu Asn Asp Ser Gln Val Val Val
 1               5                  10                  15

Ala Ala Glu Gly Ala Ala Ala Ala Thr Ala Ala Gly Gly Pro Asp
                20                  25                  30

Thr Gly Glu Trp Gly Pro Pro Ala Ala Ala Leu Gly Ala Gly Gly
            35                  40                  45

Gly Ala Asn Gly Ser Leu Glu Leu Ser Ser Gln Leu Ser Ala Gly Pro
    50                  55                  60

Pro Gly Leu Leu Leu Pro Ala Val Asn Pro Trp Asp Val Leu Leu Cys
 65                  70                  75                  80

Val Ser Gly Thr Val Ile Ala Gly Glu Asn Ala Leu Val Val Ala Leu
                85                  90                  95

Ile Ala Ser Thr Pro Ala Leu Arg Thr Pro Met Phe Val Leu Val Gly
```

```
                100             105             110
Ser Leu Ala Thr Ala Asp Leu Leu Ala Gly Cys Gly Leu Ile Leu His
            115                 120                 125

Phe Val Phe Gln Tyr Leu Val Pro Ser Glu Thr Val Ser Leu Leu Thr
            130                 135                 140

Val Gly Phe Leu Val Ala Ser Phe Ala Ala Ser Val Ser Ser Leu Leu
145                 150                 155                 160

Ala Ile Thr Val Asp Arg Tyr Leu Ser Leu Tyr Asn Ala Leu Thr Tyr
                165                 170                 175

Tyr Ser Arg Arg Thr Leu Leu Gly Val His Leu Leu Leu Ala Ala Thr
            180                 185                 190

Trp Thr Val Ser Leu Gly Leu Gly Leu Leu Pro Val Leu Gly Trp Asn
            195                 200                 205

Cys Leu Ala Glu Arg Ala Ala Cys Ser Val Val Arg Pro Leu Ala Arg
            210                 215                 220

Ser His Val Ala Leu Leu Ser Ala Ala Phe Phe Met Val Phe Gly Ile
225                 230                 235                 240

Met Leu His Leu Tyr Val Arg Ile Cys Gln Val Val Trp Arg His Ala
                245                 250                 255

His Gln Ile Ala Leu Gln Gln His Cys Leu Ala Pro Pro His Leu Ala
                260                 265                 270

Ala Thr Arg Lys Gly Val Gly Thr Leu Ala Val Val Leu Gly Thr Phe
            275                 280                 285

Gly Ala Ser Trp Leu Pro Phe Ala Ile Tyr Cys Val Val Gly Ser His
            290                 295                 300

Glu Asp Pro Ala Val Tyr Thr Tyr Ala Thr Leu Leu Pro Ala Thr Tyr
305                 310                 315                 320

Asn Ser Met Ile Asn Pro Ile Ile Tyr Ala Phe Arg Asn Gln Glu Ile
                325                 330                 335

Gln Arg Ala Leu Trp Leu Leu Leu Cys Gly Cys Ala Ala Ala Arg Gly
            340                 345                 350

Arg Thr Pro Pro Ser Leu Gly Pro Gln Asp Glu Ser Cys Thr Thr Ala
            355                 360                 365

Ser Ser Ser Leu Ala Lys Asp Thr Ser Ser
            370                 375

<210> SEQ ID NO 48
<211> LENGTH: 1137
<212> TYPE: DNA
<213> ORGANISM: Homo sapiens

<400> SEQUENCE: 48
atgaacgcga gcgccgcctc gctcaacgac tcccaggtgg tggtagtggc ggccgaagga      60
gcggcggcgg cggccacagc agcagggggg ccggacacgg gcgaatgggg accccctgct     120
gcggcggctc taggagccgg cggcggagct aatgggtctc tggagctgtc ctcgcagctg     180
tcggctgggc caccgggact cctgctgcca gcggtgaatc cgtgggacgt gctcctgtgc     240
gtgtcgggga cagtgatcgc tggagaaaac gcgctggtgg tggcgctcat cgcgtccact     300
ccggcgctgc gcacgcccat gttcgtgctg gtaggcagcc tggccaccgc tgacctgttg     360
gcgggctgtg gcctcatctt gcactttgtg ttccagtact ggtgccctc ggagactgtg      420 agtctgctca cggtgggctt cctcgtggcc tccttcgccg cctctgtcag cagcctgctg     480
gccattacgg tggaccgcta cctgtccctg tataacgcgc tcacctatta ctcgcgccgg     540
```

```
accctgttgg gcgtgcacct cctgcttgcc gccacttgga ccgtgtccct aggcctgggg    600
ctgctgcccg tgctgggctg gaactgcctg gcagagcgcg ccgcctgcag cgtggtgcgc    660
ccgctggcgc gcagccacgt ggctctgctc tccgccgcct tcttcatggt cttcggcatc    720
atgctgcacc tgtacgtgcg catctgccag gtggtctggc gccacgcgca ccagatcgcg    780
ctgcagcagc actgcctggc gccacccat ctcgctgcca ccagaaaggg tgtgggtaca    840
ctggctgtgg tgctgggcac tttcggcgcc agctggctgc ccttcgccat ctattgcgtg    900
gtgggcagcc atgaggaccc ggcggtctac acttacgcca ccctgctgcc cgccacctac    960
aactccatga tcaatcccat catctatgcc ttccgcaacc aggagatcca gcgcgccctg   1020
tggctcctgc tctgtggctg tgcggccgca cggggacgca ccccacccag cctgggtccc   1080
caagatgagt cctgcaccac cgccagctcc tccctggcca aggacacttc atcgtga      1137
```

<210> SEQ ID NO 49  
<211> LENGTH: 392  
<212> TYPE: PRT  
<213> ORGANISM: Homo sapiens

<400> SEQUENCE: 49

```
Met Tyr Pro Tyr Asp Val Pro Asp Tyr Ala Ala Ala Ala Met Asn
  1               5                  10                  15

Ala Ser Ala Ala Ser Leu Asn Asp Ser Gln Val Val Val Ala Ala
                 20                  25                  30

Glu Gly Ala Ala Ala Ala Thr Ala Ala Gly Gly Pro Asp Thr Gly
             35                  40                  45

Glu Trp Gly Pro Pro Ala Ala Ala Leu Gly Ala Gly Gly Gly Ala
         50                  55                  60

Asn Gly Ser Leu Glu Leu Ser Ser Gln Leu Ser Ala Gly Pro Pro Gly
 65                  70                  75                  80

Leu Leu Leu Pro Ala Val Asn Pro Trp Asp Val Leu Cys Val Ser
                 85                  90                  95

Gly Thr Val Ile Ala Gly Glu Asn Ala Leu Val Ala Leu Ile Ala
                100                 105                 110

Ser Thr Pro Ala Leu Arg Thr Pro Met Phe Val Leu Gly Ser Leu
            115                 120                 125

Ala Thr Ala Asp Leu Leu Ala Gly Cys Gly Leu Ile Leu His Phe Val
        130                 135                 140

Phe Gln Tyr Leu Val Pro Ser Glu Thr Val Ser Leu Leu Thr Val Gly
145                 150                 155                 160

Phe Leu Val Ala Ser Phe Ala Ala Ser Val Ser Ser Leu Leu Ala Ile
                165                 170                 175

Thr Val Asp Arg Tyr Leu Ser Leu Tyr Asn Ala Leu Thr Tyr Tyr Ser
            180                 185                 190

Arg Arg Thr Leu Leu Gly Val His Leu Leu Leu Ala Ala Thr Trp Thr
        195                 200                 205

Val Ser Leu Gly Leu Gly Leu Leu Pro Val Leu Gly Trp Asn Cys Leu
    210                 215                 220

Ala Glu Arg Ala Ala Cys Ser Val Val Arg Pro Leu Ala Arg Ser His
225                 230                 235                 240

Val Ala Leu Leu Ser Ala Ala Phe Phe Met Val Phe Gly Ile Met Leu
                245                 250                 255

His Leu Tyr Val Arg Ile Cys Gln Val Val Trp Arg His Ala His Gln
            260                 265                 270
```

```
Ile Ala Leu Gln Gln His Cys Leu Ala Pro Pro His Leu Ala Ala Thr
            275                 280                 285

Arg Lys Gly Val Gly Thr Leu Ala Val Val Leu Gly Thr Phe Gly Ala
        290                 295                 300

Ser Trp Leu Pro Phe Ala Ile Tyr Cys Val Val Gly Ser His Glu Asp
305                 310                 315                 320

Pro Ala Val Tyr Thr Tyr Ala Thr Leu Leu Pro Ala Thr Tyr Asn Ser
                325                 330                 335

Met Ile Asn Pro Ile Ile Tyr Ala Phe Arg Asn Gln Glu Ile Gln Arg
                340                 345                 350

Ala Leu Trp Leu Leu Leu Cys Gly Cys Ala Ala Ala Arg Gly Arg Thr
                355                 360                 365

Pro Pro Ser Leu Gly Pro Gln Asp Glu Ser Cys Thr Thr Ala Ser Ser
            370                 375                 380

Ser Leu Ala Lys Asp Thr Ser Ser
385                 390

<210> SEQ ID NO 50
<211> LENGTH: 1179
<212> TYPE: DNA
<213> ORGANISM: Homo sapiens

<400> SEQUENCE: 50
atgtacccat acgacgtacc tgattacgca gcagcagcag caatgaacgc gagcgccgcc      60
tcgctcaacg actcccaggt ggtggtagtg gcggccgaag gagcggcggc ggcggccaca     120
gcagcagggg ggccggacac gggcgaatgg ggaccccctg ctgcggcggc tctaggagcc     180
ggcggcggag ctaatgggtc tctggagctg tcctcgcagc cgtcggctgg gccaccggga     240
ctcctgctgc cagcggtgaa tccgtgggac gtgctcctgt gcgtgtcggg gacagtgatc     300
gctggagaaa acgcgctggt ggtggcgctc atcgcgtcca ctccggcgct gcgcacgccc     360
atgttcgtgc tggtaggcag cctggccacc gctgacctgt ggcgggctg tggcctcatc     420 ttgcactttg tgttccagta cttggtgccc tcggagactg tgagtctgct cacggtgggc     480
ttcctcgtgg cctccttcgc cgcctctgtc agcagcctgc tggccattac ggtggaccgc     540
tacctgtccc tgtataacgc gctcacctat tactcgcgcc ggaccctgtt gggcgtgcac     600
ctcctgcttg ccgccacttg gaccgtgtcc ctaggcctgg ggctgctgcc cgtgctgggc     660
tggaactgcc tggcagagcg cgccgcctgc agcgtggtgc gccgctggc gcgcagccac     720 gtggctctgc tctccgccgc cttcttcatg gtcttcggca tcatgctgca cctgtacgtg     780
cgcatctgcc aggtggtctg cgccacgcg caccagatcg cgctgcagca gcactgcctg     840
gcgccacccc atctcgctgc caccagaaag ggtgtgggta cactggctgt ggtgctgggc     900
actttcggcg ccagctggct gcccttcgcc atctattgcg tggtgggcag ccatgaggac     960
ccggcggtct acacttacgc cacctgctg ccgccaccct acaactccat gatcaatccc    1020
atcatctatg ccttccgcaa ccaggagatc cagcgcgccc tgtggctcct gctctgtggc    1080
tgtgcggccg cacggggacg cacccccacc agcctgggtc cccaagatga gtcctgcacc    1140
accgccagct cctccctggc caaggacact tcatcgtga                           1179

<210> SEQ ID NO 51
<211> LENGTH: 334
<212> TYPE: PRT
<213> ORGANISM: Homo sapiens

<400> SEQUENCE: 51
```

-continued

```
Met Asn Glu Asp Leu Lys Val Asn Leu Ser Gly Leu Pro Arg Asp Tyr
  1               5                  10                  15

Leu Asp Ala Ala Ala Glu Asn Ile Ser Ala Val Ser Ser Arg
             20                  25                  30

Val Pro Ala Val Glu Pro Pro Glu Leu Val Val Asn Pro Trp Asp
             35                  40                  45

Ile Val Leu Cys Thr Ser Gly Thr Leu Ile Ser Cys Glu Asn Ala Ile
     50                  55                  60

Val Val Leu Ile Ile Phe His Asn Pro Ser Leu Arg Ala Pro Met Phe
 65                  70                  75                  80

Leu Leu Ile Gly Ser Leu Ala Leu Ala Asp Leu Leu Ala Gly Ile Gly
                 85                  90                  95

Leu Ile Thr Asn Phe Val Phe Ala Tyr Leu Leu Gln Ser Glu Ala Thr
                100                 105                 110

Lys Leu Val Thr Ile Gly Leu Ile Val Ala Ser Phe Ser Ala Ser Val
             115                 120                 125

Cys Ser Leu Leu Ala Ile Thr Val Asp Arg Tyr Leu Ser Leu Tyr Tyr
 130                 135                 140

Ala Leu Thr Tyr His Ser Glu Arg Thr Val Thr Phe Thr Tyr Val Met
145                 150                 155                 160

Leu Val Met Leu Trp Gly Thr Ser Ile Cys Leu Gly Leu Leu Pro Val
                165                 170                 175

Met Gly Trp Asn Cys Leu Arg Asp Glu Ser Thr Cys Ser Val Val Arg
                180                 185                 190

Pro Leu Thr Lys Asn Asn Ala Ala Ile Leu Ser Val Ser Phe Leu Phe
             195                 200                 205

Met Phe Ala Leu Met Leu Gln Leu Tyr Ile Gln Ile Cys Lys Ile Val
 210                 215                 220

Met Arg His Ala His Gln Ile Ala Leu Gln His His Phe Leu Ala Thr
225                 230                 235                 240

Ser His Tyr Val Thr Thr Arg Lys Gly Val Ser Thr Leu Ala Ile Ile
                245                 250                 255

Leu Gly Thr Phe Ala Ala Cys Trp Met Pro Phe Thr Leu Tyr Ser Leu
                260                 265                 270

Ile Ala Asp Tyr Thr Tyr Pro Ser Ile Tyr Thr Tyr Ala Thr Leu Leu
             275                 280                 285

Pro Ala Thr Tyr Asn Ser Ile Ile Asn Pro Val Ile Tyr Ala Phe Arg
 290                 295                 300

Asn Gln Glu Ile Gln Lys Ala Leu Cys Leu Ile Cys Cys Gly Cys Ile
305                 310                 315                 320

Pro Ser Ser Leu Ala Gln Arg Ala Arg Ser Pro Ser Asp Val
                325                 330
```

<210> SEQ ID NO 52
<211> LENGTH: 1005
<212> TYPE: DNA
<213> ORGANISM: Homo sapiens

<400> SEQUENCE: 52

```
atgaatgaag acctgaaggt caatttaagc gggctgcctc gggattattt agatgccgct      60
gctgcggaga acatctcggc tgctgtctcc tcccggggttc ctgccgtaga gccagagcct    120
gagctcgtag tcaaccccctg gacattgtc ttgtgtacct cgggaaccct catctcctgt    180
gaaaatgcca ttgtggtcct tatcatcttc cacaacccca gcctgcgagc acccatgttc    240
```

-continued

```
ctgctaatag gcagcctggc tcttgcagac ctgctggccg gcattggact catcaccaat    300 tttgttttg cctacctgct tcagtcagaa gccaccaagc tggtcacgat cggcctcatt    360
gtcgcctctt tctctgcctc tgtctgcagc ttgctggcta tcactgttga ccgctacctc    420
tcactgtact acgctctgac gtaccattcg gagaggacgg tcacgtttac ctatgtcatg    480
ctcgtcatgc tctgggggac ctccatctgc tggggctgc tgcccgtcat gggctggaac    540
tgcctccgag acgagtccac ctgcagcgtg gtcagaccgc tcaccaagaa caacgcggcc    600
atcctctcgg tgtccttcct cttcatgttt gcgctcatgc ttcagctcta catccagatc    660
tgtaagattg tgatgaggca cgcccatcag atagccctgc agcaccactt cctggccacg    720
tcgcactatg tgaccacccg gaaagggtc tccaccctgg ctatcatcct ggggacgttt    780
gctgcttgct ggatgccttt caccctctat tccttgatag cggattacac ctaccccctcc    840 atctatacct acgccaccct cctgcccgcc acctacaatt ccatcatcaa ccctgtcata    900
tatgctttca gaaaccaaga gatccagaaa gcgctctgtc tcatttgctg cggctgcatc    960
ccgtccagtc tcgcccagag agcgcgctcg cccagtgatg tgtag                    1005
```

<210> SEQ ID NO 53
<211> LENGTH: 348
<212> TYPE: PRT
<213> ORGANISM: Homo sapiens

<400> SEQUENCE: 53

```
Met Tyr Pro Tyr Asp Val Pro Asp Tyr Ala Ala Ala Ala Met Asn
 1               5                  10                  15

Glu Asp Leu Lys Val Asn Leu Ser Gly Leu Pro Arg Asp Tyr Leu Asp
            20                  25                  30

Ala Ala Ala Glu Asn Ile Ser Ala Ala Val Ser Ser Arg Val Pro
        35                  40                  45

Ala Val Glu Pro Glu Pro Glu Leu Val Val Asn Pro Trp Asp Ile Val
    50                  55                  60

Leu Cys Thr Ser Gly Thr Leu Ile Ser Cys Glu Asn Ala Ile Val Val
65                  70                  75                  80

Leu Ile Ile Phe His Asn Pro Ser Leu Arg Ala Pro Met Phe Leu Leu
                85                  90                  95

Ile Gly Ser Leu Ala Leu Ala Asp Leu Leu Ala Gly Ile Gly Leu Ile
            100                 105                 110

Thr Asn Phe Val Phe Ala Tyr Leu Leu Gln Ser Glu Ala Thr Lys Leu
        115                 120                 125

Val Thr Ile Gly Leu Ile Val Ala Ser Phe Ser Ala Ser Val Cys Ser
    130                 135                 140

Leu Leu Ala Ile Thr Val Asp Arg Tyr Leu Ser Leu Tyr Tyr Ala Leu
145                 150                 155                 160

Thr Tyr His Ser Glu Arg Thr Val Thr Phe Thr Tyr Val Met Leu Val
                165                 170                 175

Met Leu Trp Gly Thr Ser Ile Cys Leu Gly Leu Leu Pro Val Met Gly
            180                 185                 190

Trp Asn Cys Leu Arg Asp Glu Ser Thr Cys Ser Val Val Arg Pro Leu
        195                 200                 205

Thr Lys Asn Asn Ala Ala Ile Leu Ser Val Ser Phe Leu Phe Met Phe
    210                 215                 220

Ala Leu Met Leu Gln Leu Tyr Ile Gln Ile Cys Lys Ile Val Met Arg
225                 230                 235                 240
```

```
His Ala His Gln Ile Ala Leu Gln His His Phe Leu Ala Thr Ser His
            245                 250                 255

Tyr Val Thr Thr Arg Lys Gly Val Ser Thr Leu Ala Ile Ile Leu Gly
            260                 265                 270

Thr Phe Ala Ala Cys Trp Met Pro Phe Thr Leu Tyr Ser Leu Ile Ala
            275                 280                 285

Asp Tyr Thr Tyr Pro Ser Ile Tyr Thr Tyr Ala Thr Leu Leu Pro Ala
            290                 295                 300

Thr Tyr Asn Ser Ile Ile Asn Pro Val Ile Tyr Ala Phe Arg Asn Gln
305                 310                 315                 320

Glu Ile Gln Lys Ala Leu Cys Leu Ile Cys Cys Gly Cys Ile Pro Ser
                325                 330                 335

Ser Leu Ala Gln Arg Ala Arg Ser Pro Ser Asp Val
            340                 345

<210> SEQ ID NO 54
<211> LENGTH: 1047
<212> TYPE: DNA
<213> ORGANISM: Homo sapiens

<400> SEQUENCE: 54
atgtacccat acgacgtacc tgattacgca gcagcagcag caatgaatga agacctgaag      60
gtcaatttaa gcgggctgcc tcgggattat ttagatgccg ctgctgcgga gaacatctcg     120
gctgctgtct cctcccgggt tcctgccgta gagccagagc tgagctcgt agtcaacccc      180
tgggacattg tcttgtgtac ctcgggaacc ctcatctcct gtgaaaatgc cattgtggtc     240
cttatcatct tccacaaccc cagcctgcga gcacccatgt tcctgctaat aggcagcctg     300
gctcttgcag acctgctggc cggcattgga ctcatcacca ttttgttttt tgcctacctg     360
cttcagtcag aagccaccaa gctggtcacg atcggcctca ttgtcgcctc tttctctgcc     420
tctgtctgca gcttgctggc tatcactgtt gaccgctacc tctcactgta ctacgctctg     480
acgtaccatt cggagaggac ggtcacgttt acctatgtca tgctcgtcat gctctggggg     540
acctccatct gcctggggct gctgcccgtc atgggctgga actgcctccg agacgagtcc     600
acctgcagcg tggtcagacc gctcaccaag aacaacgcgg ccatcctctc ggtgtccttc     660
ctcttcatgt ttgcgctcat gcttcagctc tacatccaga tctgtaagat tgtgatgagg     720
cacgcccatc agatagccct gcagcaccac ttcctggcca cgtcgcacta tgtgaccacc     780
cggaaagggg tctccaccct ggctatcatc ctggggacgt ttgctgcttg ctggatgcct     840
ttcaccctct attccttgat agcggattac acctacccct ccatctatac ctacgccacc     900
ctcctgcccg ccacctacaa ttccatcatc aaccctgtca tatatgcttt cagaaaccaa     960
gagatccaga aagcgctctg tctcatttgc tgcggctgca tcccgtccag tctcgcccag    1020
agagcgcgct cgcccagtga tgtgtag                                        1047

<210> SEQ ID NO 55
<211> LENGTH: 350
<212> TYPE: PRT
<213> ORGANISM: Homo sapiens

<400> SEQUENCE: 55

Met Asn Glu Asp Leu Lys Val Asn Leu Ser Gly Leu Pro Arg Asp Tyr
  1               5                  10                  15

Leu Asp Ala Ala Ala Ala Glu Asn Ile Ser Ala Ala Val Ser Ser Arg
             20                  25                  30
```

```
Val Pro Ala Val Glu Pro Glu Pro Glu Leu Val Val Asn Pro Trp Asp
         35                  40                  45

Ile Val Leu Cys Thr Ser Gly Thr Leu Ile Ser Cys Glu Asn Ala Ile
     50                  55                  60

Val Val Leu Ile Ile Phe His Asn Pro Ser Leu Arg Ala Pro Met Phe
 65                  70                  75                  80

Leu Leu Ile Gly Ser Leu Ala Leu Ala Asp Leu Leu Ala Gly Ile Gly
                 85                  90                  95

Leu Ile Thr Asn Phe Val Phe Ala Tyr Leu Leu Gln Ser Glu Ala Thr
                100                 105                 110

Lys Leu Val Thr Ile Gly Leu Ile Val Ala Ser Phe Ser Ala Ser Val
            115                 120                 125

Cys Ser Leu Leu Ala Ile Thr Val Asp Arg Tyr Leu Ser Leu Tyr Tyr
    130                 135                 140

Ala Leu Thr Tyr His Ser Glu Arg Thr Val Thr Phe Thr Tyr Val Met
145                 150                 155                 160

Leu Val Met Leu Trp Gly Thr Ser Ile Cys Leu Gly Leu Leu Pro Val
                165                 170                 175

Met Gly Trp Asn Cys Leu Arg Asp Glu Ser Thr Cys Ser Val Val Arg
                180                 185                 190

Pro Leu Thr Lys Asn Asn Ala Ala Ile Leu Ser Val Ser Phe Leu Phe
            195                 200                 205

Met Phe Ala Leu Met Leu Gln Leu Tyr Ile Gln Ile Cys Lys Ile Val
    210                 215                 220

Met Arg His Ala His Gln Ile Ala Leu Gln His His Phe Leu Ala Thr
225                 230                 235                 240

Ser His Tyr Val Thr Thr Arg Lys Gly Val Ser Thr Leu Ala Ile Ile
                245                 250                 255

Leu Gly Thr Phe Ala Ala Cys Trp Met Pro Phe Thr Leu Tyr Ser Leu
                260                 265                 270

Ile Ala Asp Tyr Thr Tyr Pro Ser Ile Tyr Thr Tyr Ala Thr Leu Leu
            275                 280                 285

Pro Ala Thr Tyr Asn Ser Ile Ile Asn Pro Val Ile Tyr Ala Phe Arg
    290                 295                 300

Asn Gln Glu Ile Gln Lys Ala Leu Cys Leu Ile Cys Cys Gly Cys Ala
305                 310                 315                 320

Ala Ala Arg Gly Arg Thr Pro Pro Ser Leu Gly Pro Gln Asp Glu Ser
                325                 330                 335

Cys Thr Thr Ala Ser Ser Ser Leu Ala Lys Asp Thr Ser Ser
            340                 345                 350

<210> SEQ ID NO 56
<211> LENGTH: 1053
<212> TYPE: DNA
<213> ORGANISM: Homo sapiens

<400> SEQUENCE: 56
atgaatgaag aacctgaaggt caatttaagc gggctgcctc gggattattt agatgccgct      60
gctgcggaga acatctcggc tgctgtctcc tcccgggttc ctgccgtaga gccagagcct     120
gagctcgtag tcaaccccctg ggacattgtc ttgtgtacct cgggaaccct catctcctgt     180
gaaaatgcca ttgtggtcct tatcatcttc cacaacccca gcctgcgagc acccatgttc     240
ctgctaatag gcagcctggc tcttgcagac ctgctggccg gcattggact catcaccaat     300
```

```
tttgttttg cctacctgct tcagtcagaa gccaccaagc tggtcacgat cggcctcatt      360
gtcgcctctt tctctgcctc tgtctgcagc ttgctggcta tcactgttga ccgctacctc      420
tcactgtact acgctctgac gtaccattcg gagaggacgg tcacgtttac ctatgtcatg      480
ctcgtcatgc tctggggac ctccatctgc ctggggctgc tgcccgtcat gggctggaac      540
tgcctccgag acgagtccac ctgcagcgtg gtcagaccgc tcaccaagaa caacgcggcc      600
atcctctcgg tgtccttcct cttcatgttt gcgctcatgc ttcagctcta catccagatc      660
tgtaagattg tgatgaggca cgcccatcag atagccctgc agcaccactt cctggccacg      720
tcgcactatg tgaccacccg gaaagggtc tccaccctgg ctatcatcct ggggacgttt      780
gctgcttgct ggatgccttt caccctctat tccttgatag cggattacac ctacccctcc      840
atctataccct acgccaccct cctgcccgcc acctacaatt ccatcatcaa ccctgtcata      900
tatgctttca gaaaccaaga gatccagaaa gcgctctgtc tcatttgctg cggctgcgcg      960
gccgcacggg gacgcacccc acccagcctg ggtccccaag atgagtcctg caccaccgcc     1020
agctcctccc tggccaagga cacttcatcg tga                                   1053
```

<210> SEQ ID NO 57
<211> LENGTH: 364
<212> TYPE: PRT
<213> ORGANISM: Homo sapiens

<400> SEQUENCE: 57

```
Met Tyr Pro Tyr Asp Val Pro Asp Tyr Ala Ala Ala Ala Met Asn
  1               5                  10                  15

Glu Asp Leu Lys Val Asn Leu Ser Gly Leu Pro Arg Asp Tyr Leu Asp
             20                  25                  30

Ala Ala Ala Ala Glu Asn Ile Ser Ala Ala Val Ser Ser Arg Val Pro
         35                  40                  45

Ala Val Glu Pro Glu Pro Glu Leu Val Val Asn Pro Trp Asp Ile Val
     50                  55                  60

Leu Cys Thr Ser Gly Thr Leu Ile Ser Cys Glu Asn Ala Ile Val Val
 65                  70                  75                  80

Leu Ile Ile Phe His Asn Pro Ser Leu Arg Ala Pro Met Phe Leu Leu
                 85                  90                  95

Ile Gly Ser Leu Ala Leu Ala Asp Leu Leu Ala Gly Ile Gly Leu Ile
            100                 105                 110

Thr Asn Phe Val Phe Ala Tyr Leu Leu Gln Ser Glu Ala Thr Lys Leu
        115                 120                 125

Val Thr Ile Gly Leu Ile Val Ala Ser Phe Ser Ala Ser Val Cys Ser
    130                 135                 140

Leu Leu Ala Ile Thr Val Asp Arg Tyr Leu Ser Leu Tyr Tyr Ala Leu
145                 150                 155                 160

Thr Tyr His Ser Glu Arg Thr Val Thr Phe Thr Tyr Val Met Leu Val
                165                 170                 175

Met Leu Trp Gly Thr Ser Ile Cys Leu Gly Leu Leu Pro Val Met Gly
            180                 185                 190

Trp Asn Cys Leu Arg Asp Glu Ser Thr Cys Ser Val Val Arg Pro Leu
        195                 200                 205

Thr Lys Asn Asn Ala Ala Ile Leu Ser Val Ser Phe Leu Phe Met Phe
    210                 215                 220

Ala Leu Met Leu Gln Leu Tyr Ile Gln Ile Cys Lys Ile Val Met Arg
225                 230                 235                 240
```

```
His Ala His Gln Ile Ala Leu Gln His His Phe Leu Ala Thr Ser His
                245                 250                 255

Tyr Val Thr Thr Arg Lys Gly Val Ser Thr Leu Ala Ile Ile Leu Gly
            260                 265                 270

Thr Phe Ala Ala Cys Trp Met Pro Phe Thr Leu Tyr Ser Leu Ile Ala
        275                 280                 285

Asp Tyr Thr Tyr Pro Ser Ile Tyr Thr Tyr Ala Thr Leu Leu Pro Ala
    290                 295                 300

Thr Tyr Asn Ser Ile Ile Asn Pro Val Ile Tyr Ala Phe Arg Asn Gln
305                 310                 315                 320

Glu Ile Gln Lys Ala Leu Cys Leu Ile Cys Cys Gly Cys Ala Ala Ala
                325                 330                 335

Arg Gly Arg Thr Pro Pro Ser Leu Gly Pro Gln Asp Glu Ser Cys Thr
            340                 345                 350

Thr Ala Ser Ser Ser Leu Ala Lys Asp Thr Ser Ser
        355                 360
```

<210> SEQ ID NO 58
<211> LENGTH: 1095
<212> TYPE: DNA
<213> ORGANISM: Homo sapiens

<400> SEQUENCE: 58

```
atgtacccat acgacgtacc tgattacgca gcagcagcag caatgaatga agacctgaag      60
gtcaatttaa gcgggctgcc tcgggattat ttagatgccg ctgctgcgga gaacatctcg     120
gctgctgtct cctcccgggt tcctgccgta gagccagagc tgagctcgt agtcaacccc      180
tgggacattg tcttgtgtac ctcgggaacc ctcatctcct gtgaaaatgc cattgtggtc     240
cttatcatct tccacaaccc cagcctgcga gcacccatgt tcctgctaat aggcagcctg     300
gctcttgcag acctgctggc cggcattgga ctcatcacca atttttgtttt tgcctacctg     360
cttcagtcag aagccaccaa gctggtcacg atcggcctca ttgtcgcctc tttctctgcc     420
tctgtctgca gcttgctggc tatcactgtt gaccgctacc tctcactgta ctacgctctg     480
acgtaccatt cggagaggac ggtcacgttt acctatgtca tgctcgtcat gctctggggg     540
acctccatct gcctggggct gctgcccgtc atgggctgga actgcctccg agacgagtcc     600
acctgcagcg tggtcagacc gctcaccaag aacaacgcgg ccatcctctc ggtgtccttc     660
ctcttcatgt ttgcgctcat gcttcagctc tacatccaga tctgtaagat tgtgatgagg     720
cacgcccatc agatagccct gcagcaccac ttcctggcca cgtcgcacta tgtgaccacc     780
cggaaagggg tctccaccct ggctatcatc ctggggacgt tgctgcttg ctggatgcct     840
ttcaccctct attccttgat agcggattac acctaccct ccatctatac ctacgccacc     900
ctcctgcccg ccacctacaa ttccatcatc aaccctgtca tatatgcttt cagaaaccaa     960
gagatccaga aagcgctctg tctcatttgc tgcggctgcg cggccgcacg gggacgcacc    1020
ccacccagcc tgggtcccca agatgagtcc tgcaccaccg ccagctcctc cctggccaag    1080
gacacttcat cgtga                                                    1095
```

<210> SEQ ID NO 59
<211> LENGTH: 373
<212> TYPE: PRT
<213> ORGANISM: Homo sapiens

<400> SEQUENCE: 59

Met Ala Asn Thr Thr Gly Glu Pro Glu Glu Val Ser Gly Ala Leu Ser

```
            1               5                  10                 15
Pro Pro Ser Ala Ser Ala Tyr Val Lys Leu Val Leu Leu Gly Leu Ile
                20                 25                 30

Met Cys Val Ser Leu Ala Gly Asn Ala Ile Leu Ser Leu Leu Val Leu
        35                 40                 45

Lys Glu Arg Ala Leu His Lys Ala Pro Tyr Tyr Phe Leu Leu Asp Leu
        50                 55                 60

Cys Leu Ala Asp Gly Ile Arg Ser Ala Val Cys Phe Pro Phe Val Leu
65                  70                 75                 80

Ala Ser Val Arg His Gly Ser Ser Trp Thr Phe Ser Ala Leu Ser Cys
                85                 90                 95

Lys Ile Val Ala Phe Met Ala Val Leu Phe Cys Phe His Ala Ala Phe
                100                105                110

Met Leu Phe Cys Ile Ser Val Thr Arg Tyr Met Ala Ile Ala His His
        115                120                125

Arg Phe Tyr Ala Lys Arg Met Thr Leu Trp Thr Cys Ala Ala Val Ile
    130                135                140

Cys Met Ala Trp Thr Leu Ser Val Ala Met Ala Phe Pro Pro Val Phe
145                 150                155                160

Asp Val Gly Thr Tyr Lys Phe Ile Arg Glu Glu Asp Gln Cys Ile Phe
                165                170                175

Glu His Arg Tyr Phe Lys Ala Asn Asp Thr Leu Gly Phe Met Leu Met
            180                185                190

Leu Ala Val Leu Met Ala Ala Thr His Ala Val Tyr Gly Lys Leu Leu
        195                200                205

Leu Phe Glu Tyr Arg His Arg Lys Met Lys Pro Val Gln Met Val Pro
    210                215                220

Ala Ile Ser Gln Asn Trp Thr Phe His Gly Pro Gly Ala Thr Gly Gln
225                 230                235                240

Ala Ala Ala Asn Trp Ile Ala Gly Phe Gly Arg Gly Pro Met Pro Pro
                245                250                255

Thr Leu Leu Gly Ile Arg Gln Asn Gly His Ala Ala Ser Arg Arg Leu
            260                265                270

Leu Gly Met Asp Glu Val Lys Gly Glu Lys Gln Leu Gly Arg Met Phe
        275                280                285

Tyr Ala Ile Thr Leu Leu Phe Leu Leu Leu Trp Ser Pro Tyr Ile Val
    290                295                300

Ala Cys Tyr Trp Arg Val Phe Val Lys Ala Cys Ala Val Pro His Arg
305                 310                315                320

Tyr Leu Ala Thr Ala Val Trp Met Ser Phe Ala Gln Ala Ala Val Asn
                325                330                335

Pro Ile Val Cys Phe Leu Leu Asn Lys Asp Leu Lys Lys Cys Leu Arg
            340                345                350

Thr His Ala Pro Cys Trp Gly Thr Gly Gly Ala Pro Ala Pro Arg Glu
        355                360                365

Pro Tyr Cys Val Met
    370

<210> SEQ ID NO 60
<211> LENGTH: 1122
<212> TYPE: DNA
<213> ORGANISM: Homo sapiens

<400> SEQUENCE: 60
```

-continued

```
atggccaaca ctaccggaga gcctgaggag gtgagcggcg ctctgtcccc accgtccgca      60
tcagcttatg tgaagctggt actgctggga ctgattatgt gcgtgagcct ggcgggtaac     120
gccatcttgt ccctgctggt gctcaaggag cgtgccctgc acaaggctcc ttactacttc     180
ctgctggacc tgtgcctggc cgatggcata cgctctgccg tctgcttccc ctttgtgctg     240
gcttctgtgc gccacggctc ttcatggacc ttcagtgcac tcagctgcaa gattgtggcc     300
tttatggccg tgctcttttg cttccatgcg gccttcatgc tgttctgcat cagcgtcacc     360
cgctacatgg ccatcgccca ccaccgcttc tacgccaagc gcatgacact ctggacatgc     420
gcggctgtca tctgcatggc ctggaccctg tctgtggcca tggccttccc acctgtcttt     480
gacgtgggca cctacaagtt tattcgggag gaggaccagt gcatctttga gcatcgctac     540
ttcaaggcca atgacacgct gggcttcatg cttatgttgg ctgtgctcat ggcagctacc     600
catgctgtct acggcaagct gctcctcttc gagtatcgtc accgcaagat gaagccagtg     660
cagatggtgc cagccatcag ccagaactgg acattccatg gtcccggggc caccggccag     720
gctgctgcca actggatcgc cggctttggc cgtgggccca tgccaccaac cctgctgggt     780
atccggcaga tgggcatgc agccagccgg cggctactgg gcatggacga ggtcaagggt     840
gaaaagcagc tgggccgcat gttctacgcg atcacactgc tctttctgct cctctggtca     900
ccctacatcg tggcctgcta ctggcgagtg tttgtgaaag cctgtgctgt gccccaccgc     960
tacctggcca ctgctgtttg atgagcttc gcccaggctg ccgtcaaccc aattgtctgc    1020
ttcctgctca acaaggacct caagaagtgc ctgaggactc acgcccctg ctggggcaca    1080
ggaggtgccc cggctcccag agaaccctac tgtgtcatgt ga                      1122
```

<210> SEQ ID NO 61
<211> LENGTH: 387
<212> TYPE: PRT
<213> ORGANISM: Homo sapiens

<400> SEQUENCE: 61

```
Met Tyr Pro Tyr Asp Val Pro Asp Tyr Ala Ala Ala Ala Met Ala
 1               5                  10                  15

Asn Thr Thr Gly Glu Pro Glu Glu Val Ser Gly Ala Leu Ser Pro Pro
            20                  25                  30

Ser Ala Ser Ala Tyr Val Lys Leu Val Leu Gly Leu Ile Met Cys
         35                  40                  45

Val Ser Leu Ala Gly Asn Ala Ile Leu Ser Leu Leu Val Leu Lys Glu
     50                  55                  60

Arg Ala Leu His Lys Ala Pro Tyr Tyr Phe Leu Leu Asp Leu Cys Leu
 65                  70                  75                  80

Ala Asp Gly Ile Arg Ser Ala Val Cys Phe Pro Phe Val Leu Ala Ser
                 85                  90                  95

Val Arg His Gly Ser Ser Trp Thr Phe Ser Ala Leu Ser Cys Lys Ile
            100                 105                 110

Val Ala Phe Met Ala Val Leu Phe Cys Phe His Ala Ala Phe Met Leu
         115                 120                 125

Phe Cys Ile Ser Val Thr Arg Tyr Met Ala Ile Ala His His Arg Phe
     130                 135                 140

Tyr Ala Lys Arg Met Thr Leu Trp Thr Cys Ala Ala Val Ile Cys Met
145                 150                 155                 160

Ala Trp Thr Leu Ser Val Ala Met Ala Phe Pro Pro Val Phe Asp Val
                165                 170                 175
```

```
Gly Thr Tyr Lys Phe Ile Arg Glu Glu Asp Gln Cys Ile Phe Glu His
                180                 185                 190
Arg Tyr Phe Lys Ala Asn Asp Thr Leu Gly Phe Met Leu Met Leu Ala
            195                 200                 205
Val Leu Met Ala Ala Thr His Ala Val Tyr Gly Lys Leu Leu Leu Phe
        210                 215                 220
Glu Tyr Arg His Arg Lys Met Lys Pro Val Gln Met Val Pro Ala Ile
225                 230                 235                 240
Ser Gln Asn Trp Thr Phe His Gly Pro Gly Ala Thr Gly Gln Ala Ala
                245                 250                 255
Ala Asn Trp Ile Ala Gly Phe Gly Arg Gly Pro Met Pro Pro Thr Leu
            260                 265                 270
Leu Gly Ile Arg Gln Asn Gly His Ala Ala Ser Arg Arg Leu Leu Gly
        275                 280                 285
Met Asp Glu Val Lys Gly Glu Lys Gln Leu Gly Arg Met Phe Tyr Ala
290                 295                 300
Ile Thr Leu Leu Phe Leu Leu Leu Trp Ser Pro Tyr Ile Val Ala Cys
305                 310                 315                 320
Tyr Trp Arg Val Phe Val Lys Ala Cys Ala Val Pro His Arg Tyr Leu
                325                 330                 335
Ala Thr Ala Val Trp Met Ser Phe Ala Gln Ala Ala Val Asn Pro Ile
            340                 345                 350
Val Cys Phe Leu Leu Asn Lys Asp Leu Lys Lys Cys Leu Arg Thr His
        355                 360                 365
Ala Pro Cys Trp Gly Thr Gly Gly Ala Pro Ala Pro Arg Glu Pro Tyr
    370                 375                 380
Cys Val Met
385

<210> SEQ ID NO 62
<211> LENGTH: 1164
<212> TYPE: DNA
<213> ORGANISM: Homo sapiens

<400> SEQUENCE: 62
atgtacccat acgacgtacc tgattacgca gcagcagcag caatggccaa cactaccgga      60
gagcctgagg aggtgagcgg cgctctgtcc ccaccgtccg catcagctta tgtgaagctg     120
gtactgctgg gactgattat gtgcgtgagc ctggcgggta acgccatctt gtccctgctg     180
gtgctcaagg agcgtgccct gcacaaggct ccttactact tcctgctgga cctgtgcctg     240
gccgatggca tacgtctgc cgtctgcttc ccctttgtgc tggcttctgt gcgccacggc     300
tcttcatgga ccttcagtgc actcagctgc aagattgtgg cctttatggc cgtgctcttt     360
tgcttccatg cggccttcat gctgttctgc atcagcgtca cccgctacat ggccatcgcc     420
caccaccgct tctacgccaa gcgcatgaca ctctggacat gcgcggctgt catctgcatg     480
gcctggaccc tgtctgtggc catggccttc ccacctgtct tgacgtggga cctacaag     540 tttattcggg aggaggacca gtgcatcttt gagcatcgct acttcaaggc caatgacacg     600
ctgggcttca tgcttatgtt ggctgtgctc atggcagcta cccatgctgt ctacggcaag     660 ctgctccctct tcgagtatcg tcaccgcaag atgaagccag tgcagatggt gccagccatc     720
agccagaact ggacattcca tggtcccggg gccaccggcc aggctgctgc caactggatc     780
gccggctttg gccgtgggcc catgccacca accctgctgg gtatccggca gaatgggcat     840
gcagccagcc ggcggctact gggcatggac gaggtcaagg gtgaaaagca gctgggccgc     900
```

-continued

```
atgttctacg cgatcacact gctctttctg ctcctctggt caccctacat cgtggcctgc     960
tactggcgag tgtttgtgaa agcctgtgct gtgccccacc gctacctggc cactgctgtt    1020
tggatgagct tcgcccaggc tgccgtcaac ccaattgtct gcttcctgct caacaaggac    1080
ctcaagaagt gcctgaggac tcacgccccc tgctggggca caggaggtgc cccggctccc    1140
agagaaccct actgtgtcat gtga                                           1164
```

<210> SEQ ID NO 63
<211> LENGTH: 388
<212> TYPE: PRT
<213> ORGANISM: Homo sapiens

<400> SEQUENCE: 63

```
Met Ala Asn Thr Thr Gly Glu Pro Glu Val Ser Gly Ala Leu Ser
  1               5                  10                  15

Pro Pro Ser Ala Ser Ala Tyr Val Lys Leu Val Leu Gly Leu Ile
                 20                  25                  30

Met Cys Val Ser Leu Ala Gly Asn Ala Ile Leu Ser Leu Val Leu
             35                  40                  45

Lys Glu Arg Ala Leu His Lys Ala Pro Tyr Tyr Phe Leu Leu Asp Leu
         50                  55                  60

Cys Leu Ala Asp Gly Ile Arg Ser Ala Val Cys Phe Pro Phe Val Leu
 65                  70                  75                  80

Ala Ser Val Arg His Gly Ser Ser Trp Thr Phe Ser Ala Leu Ser Cys
                 85                  90                  95

Lys Ile Val Ala Phe Met Ala Val Leu Phe Cys Phe His Ala Ala Phe
            100                 105                 110

Met Leu Phe Cys Ile Ser Val Thr Arg Tyr Met Ala Ile Ala His His
            115                 120                 125

Arg Phe Tyr Ala Lys Arg Met Thr Leu Trp Thr Cys Ala Ala Val Ile
        130                 135                 140

Cys Met Ala Trp Thr Leu Ser Val Ala Met Ala Phe Pro Pro Val Phe
145                 150                 155                 160

Asp Val Gly Thr Tyr Lys Phe Ile Arg Glu Glu Asp Gln Cys Ile Phe
                165                 170                 175

Glu His Arg Tyr Phe Lys Ala Asn Asp Thr Leu Gly Phe Met Leu Met
            180                 185                 190

Leu Ala Val Leu Met Ala Ala Thr His Ala Val Tyr Gly Lys Leu Leu
        195                 200                 205

Leu Phe Glu Tyr Arg His Arg Lys Met Lys Pro Val Gln Met Val Pro
    210                 215                 220

Ala Ile Ser Gln Asn Trp Thr Phe His Gly Pro Gly Ala Thr Gly Gln
225                 230                 235                 240

Ala Ala Ala Asn Trp Ile Ala Gly Phe Gly Arg Gly Pro Met Pro Pro
                245                 250                 255

Thr Leu Leu Gly Ile Arg Gln Asn Gly His Ala Ala Ser Arg Arg Leu
            260                 265                 270

Leu Gly Met Asp Glu Val Lys Gly Glu Lys Gln Leu Gly Arg Met Phe
        275                 280                 285

Tyr Ala Ile Thr Leu Leu Phe Leu Leu Leu Trp Ser Pro Tyr Ile Val
    290                 295                 300

Ala Cys Tyr Trp Arg Val Phe Val Lys Ala Cys Ala Val Pro His Arg
305                 310                 315                 320
```

```
Tyr Leu Ala Thr Ala Val Trp Met Ser Phe Ala Gln Ala Ala Val Asn
                325                 330                 335

Pro Ile Val Cys Phe Leu Leu Asn Lys Asp Leu Lys Lys Cys Leu Arg
            340                 345                 350

Thr His Ala Pro Cys Ala Ala Ala Arg Gly Arg Thr Pro Pro Ser Leu
        355                 360                 365

Gly Pro Gln Asp Glu Ser Cys Thr Thr Ala Ser Ser Ser Leu Ala Lys
    370                 375                 380

Asp Thr Ser Ser
385

<210> SEQ ID NO 64
<211> LENGTH: 1167
<212> TYPE: DNA
<213> ORGANISM: Homo sapiens

<400> SEQUENCE: 64
atggccaaca ctaccggaga gcctgaggag gtgagcggcg ctctgtcccc accgtccgca      60
tcagcttatg tgaagctggt actgctggga ctgattatgt gcgtgagcct ggcgggtaac     120
gccatcttgt ccctgctggt gctcaaggag cgtgccctgc acaaggctcc ttactacttc     180
ctgctggacc tgtgcctggc cgatggcata cgctctgccg tctgcttccc ctttgtgctg     240
gcttctgtgc gccacggctc ttcatggacc ttcagtgcac tcagctgcaa gattgtggcc     300
tttatggccg tgctcttttg cttccatgcg gccttcatgc tgttctgcat cagcgtcacc     360
cgctacatgg ccatcgccca ccaccgcttc tacgccaagc gcatgacact ctggacatgc     420
gcggctgtca tctgcatggc ctggaccctg tctgtggcca tggccttccc acctgtcttt     480
gacgtgggca cctacaagtt tattcgggag gaggaccagt gcatctttga gcatcgctac     540
ttcaaggcca tgacacgct gggcttcatg cttatgttgg ctgtgctcat ggcagctacc     600
catgctgtct acggcaagct gctcctcttc gagtatcgtc accgcaagat gaagccagtg     660
cagatggtgc cagccatcag ccagaactgg acattccatg gtcccggggc caccggccag     720
gctgctgcca actggatcgc cggctttggc cgtgggccca tgccaccaac cctgctgggt     780
atccggcaga tgggcatgc agccagccgg cggctactgg gcatggacga ggtcaagggt     840
gaaaagcagc tgggccgcat gttctacgcg atcacactgc tctttctgct cctctggtca     900
ccctacatcg tggcctgcta ctggcgagtg tttgtgaaag cctgtgctgt gccccaccgc     960
tacctggcca ctgctgtttg gatgagcttc gcccaggctg ccgtcaaccc aattgtctgc    1020
ttcctgctca acaaggacct caagaagtgc ctgaggactc acgcccctg cgcggccgca    1080
cggggacgca cccacccag cctgggtccc aagatgagt cctgcaccac cgccagctcc    1140
tccctggcca aggacacttc atcgtga                                        1167

<210> SEQ ID NO 65
<211> LENGTH: 402
<212> TYPE: PRT
<213> ORGANISM: Homo sapiens

<400> SEQUENCE: 65

Met Tyr Pro Tyr Asp Val Pro Asp Tyr Ala Ala Ala Ala Met Ala
 1               5                  10                  15

Asn Thr Thr Gly Glu Pro Glu Glu Val Ser Gly Ala Leu Ser Pro Pro
                20                  25                  30

Ser Ala Ser Ala Tyr Val Lys Leu Val Leu Leu Gly Leu Ile Met Cys
            35                  40                  45
```

Val Ser Leu Ala Gly Asn Ala Ile Leu Ser Leu Leu Val Leu Lys Glu
                50                  55                  60

Arg Ala Leu His Lys Ala Pro Tyr Tyr Phe Leu Leu Asp Leu Cys Leu
 65                  70                  75                  80

Ala Asp Gly Ile Arg Ser Ala Val Cys Phe Pro Val Leu Ala Ser
                    85                  90                  95

Val Arg His Gly Ser Ser Trp Thr Phe Ser Ala Leu Ser Cys Lys Ile
                100                 105                 110

Val Ala Phe Met Ala Val Leu Phe Cys Phe His Ala Ala Phe Met Leu
                115                 120                 125

Phe Cys Ile Ser Val Thr Arg Tyr Met Ala Ile Ala His His Arg Phe
130                 135                 140

Tyr Ala Lys Arg Met Thr Leu Trp Thr Cys Ala Ala Val Ile Cys Met
145                 150                 155                 160

Ala Trp Thr Leu Ser Val Ala Met Ala Phe Pro Pro Val Phe Asp Val
                165                 170                 175

Gly Thr Tyr Lys Phe Ile Arg Glu Glu Asp Gln Cys Ile Phe Glu His
                180                 185                 190

Arg Tyr Phe Lys Ala Asn Asp Thr Leu Gly Phe Met Leu Met Leu Ala
                195                 200                 205

Val Leu Met Ala Ala Thr His Ala Val Tyr Gly Lys Leu Leu Leu Phe
210                 215                 220

Glu Tyr Arg His Arg Lys Met Lys Pro Val Gln Met Val Pro Ala Ile
225                 230                 235                 240

Ser Gln Asn Trp Thr Phe His Gly Pro Gly Ala Thr Gly Gln Ala Ala
                245                 250                 255

Ala Asn Trp Ile Ala Gly Phe Gly Arg Gly Pro Met Pro Thr Leu
                260                 265                 270

Leu Gly Ile Arg Gln Asn Gly His Ala Ala Ser Arg Arg Leu Leu Gly
                275                 280                 285

Met Asp Glu Val Lys Gly Glu Lys Gln Leu Gly Arg Met Phe Tyr Ala
290                 295                 300

Ile Thr Leu Leu Phe Leu Leu Leu Trp Ser Pro Tyr Ile Val Ala Cys
305                 310                 315                 320

Tyr Trp Arg Val Phe Val Lys Ala Cys Ala Val Pro His Arg Tyr Leu
                325                 330                 335

Ala Thr Ala Val Trp Met Ser Phe Ala Gln Ala Ala Val Asn Pro Ile
                340                 345                 350

Val Cys Phe Leu Leu Asn Lys Asp Leu Lys Lys Cys Leu Arg Thr His
                355                 360                 365

Ala Pro Cys Ala Ala Ala Arg Gly Arg Thr Pro Pro Ser Leu Gly Pro
370                 375                 380

Gln Asp Glu Ser Cys Thr Thr Ala Ser Ser Leu Ala Lys Asp Thr
385                 390                 395                 400

Ser Ser

<210> SEQ ID NO 66
<211> LENGTH: 1209
<212> TYPE: DNA
<213> ORGANISM: Homo sapiens

<400> SEQUENCE: 66
atgtacccat acgacgtacc tgattacgca gcagcagcag caatggccaa cactaccgga        60

-continued

```
gagcctgagg aggtgagcgg cgctctgtcc ccaccgtccg catcagctta tgtgaagctg     120
gtactgctgg gactgattat gtgcgtgagc ctggcgggta acgccatctt gtccctgctg     180
gtgctcaagg agcgtgccct gcacaaggct ccttactact tcctgctgga cctgtgcctg     240
gccgatggca tacgctctgc cgtctgcttc ccctttgtgc tggcttctgt gcgccacggc     300
tcttcatgga ccttcagtgc actcagctga agattgtgg cctttatggc cgtgctcttt      360
tgcttccatg cggccttcat gctgttctgc atcagcgtca cccgctacat ggccatcgcc     420
caccaccgct tctacgccaa gcgcatgaca ctctggacat gcgcggctgt catctgcatg     480
gcctggaccc tgtctgtggc catggccttc ccacctgtct ttgacgtggg cacctacaag     540
tttattcggg aggaggacca gtgcatcttt gagcatcgct acttcaaggc caatgacacg     600
ctgggcttca tgcttatgtt ggctgtgctc atggcagcta cccatgctgt ctacggcaag     660
ctgctcctct tcgagtatcg tcaccgcaag atgaagccag tgcagatggt gccagccatc     720
agccagaact ggacattcca tggtcccggg gccaccggcc aggctgctgc caactggatc     780
gccggctttg ccgtgggcc catgccacca accctgctgg gtatccggca gaatgggcat      840
gcagccagcc ggcggctact gggcatggac gaggtcaagg gtgaaaagca gctgggccgc     900
atgttctacg cgatcacact gctctttctg ctcctctggt caccctacat cgtggcctgc     960
tactggcgag tgtttgtgaa agcctgtgct gtgcccacc gctacctggc cactgctgtt      1020
tggatgagct tcgcccaggc tgccgtcaac ccaattgtct gcttcctgct caacaaggac     1080
ctcaagaagt gcctgaggac tcacgccccc tgcgcggccg cacggggacg cacccccaccc    1140 agcctgggtc cccaagatga gtcctgcacc accgccagct cctccctggc caaggacact    1200
tcatcgtga                                                              1209
```

<210> SEQ ID NO 67
<211> LENGTH: 370
<212> TYPE: PRT
<213> ORGANISM: Homo sapiens

<400> SEQUENCE: 67

```
Met Ala Asn Tyr Ser His Ala Ala Asp Asn Ile Leu Gln Asn Leu Ser
  1               5                  10                  15

Pro Leu Thr Ala Phe Leu Lys Leu Thr Ser Leu Gly Phe Ile Ile Gly
                 20                  25                  30

Val Ser Val Val Gly Asn Leu Leu Ile Ser Ile Leu Leu Val Lys Asp
             35                  40                  45

Lys Thr Leu His Arg Ala Pro Tyr Tyr Phe Leu Leu Asp Leu Cys Cys
         50                  55                  60

Ser Asp Ile Leu Arg Ser Ala Ile Cys Phe Pro Phe Val Phe Asn Ser
 65                  70                  75                  80

Val Lys Asn Gly Ser Thr Trp Thr Tyr Gly Thr Leu Thr Cys Lys Val
                 85                  90                  95

Ile Ala Phe Leu Gly Val Leu Ser Cys Phe His Thr Ala Phe Met Leu
                100                 105                 110

Phe Cys Ile Ser Val Thr Arg Tyr Leu Ala Ile Ala His His Arg Phe
            115                 120                 125

Tyr Thr Lys Arg Leu Thr Phe Trp Thr Cys Leu Ala Val Ile Cys Met
        130                 135                 140

Val Trp Thr Leu Ser Val Ala Met Ala Phe Pro Pro Val Leu Asp Val
145                 150                 155                 160

Gly Thr Tyr Ser Phe Ile Arg Glu Glu Asp Gln Cys Thr Phe Gln His
```

```
                     165                 170                 175
Arg Ser Phe Arg Ala Asn Asp Ser Leu Gly Phe Met Leu Leu Ala
                180                 185                 190
Leu Ile Leu Leu Ala Thr Gln Leu Val Tyr Leu Lys Leu Ile Phe Phe
            195                 200                 205
Val His Asp Arg Arg Lys Met Lys Pro Val Gln Phe Ala Ala Val
        210                 215                 220
Ser Gln Asn Trp Thr Phe His Gly Pro Gly Ala Ser Gly Gln Ala Ala
225                 230                 235                 240
Ala Asn Trp Leu Ala Gly Phe Gly Arg Gly Pro Thr Pro Pro Thr Leu
                245                 250                 255
Leu Gly Ile Arg Gln Asn Ala Asn Thr Thr Gly Arg Arg Leu Leu
            260                 265                 270
Val Leu Asp Glu Phe Lys Met Glu Lys Arg Ile Ser Arg Met Phe Tyr
        275                 280                 285
Ile Met Thr Phe Leu Phe Thr Leu Trp Gly Pro Tyr Leu Val Ala
                290                 295                 300
Cys Tyr Trp Arg Val Phe Ala Arg Gly Pro Val Val Pro Gly Gly Phe
305                 310                 315                 320
Leu Thr Ala Ala Val Trp Met Ser Phe Ala Gln Ala Gly Ile Asn Pro
                325                 330                 335
Phe Val Cys Ile Phe Ser Asn Arg Glu Leu Arg Arg Cys Phe Ser Thr
                340                 345                 350
Thr Leu Leu Tyr Cys Arg Lys Ser Arg Leu Pro Arg Glu Pro Tyr Cys
            355                 360                 365
Val Ile
    370

<210> SEQ ID NO 68
<211> LENGTH: 1113
<212> TYPE: DNA
<213> ORGANISM: Homo sapiens

<400> SEQUENCE: 68
atggcgaact atagccatgc agctgacaac attttgcaaa atctctcgcc tctaacagcc      60
tttctgaaac tgacttcctt gggtttcata ataggagtca gcgtggtggg caacctcctg     120
atctccattt tgctagtgaa agataagacc ttgcatagag caccttacta cttcctgttg     180
gatctttgct gttcagatat cctcagatct gcaatttgtt tcccatttgt gttcaactct     240
gtcaaaaatg gctctacctg gacttatggg actctgactt gcaaagtgat tgcctttctg     300
ggggttttgt cctgtttcca cactgctttc atgctcttct gcatcagtgt caccagatac     360
ttagctatcg cccatcaccg cttctataca aagaggctga cctttggac gtgtctggct     420
gtgatctgta tggtgtggac tctgtctgtg ccatggcat ttccccggt tttagacgtg     480
ggcacttact cattcattag ggaggaagat caatgcacct ccaacaccg ctccttcagg     540
gctaatgatt ccttaggatt tatgctgctt cttgctctca tcctcctagc cacacagctt     600
gtctacctca agctgatatt tttcgtccac gatcgaagaa aaatgaagcc agtccagttt     660
gtagcagcag tcagccagaa ctggactttt catggtcctg gagccagtgg ccaggcagct     720
gccaattggc tagcaggatt tggaaggggt cccacaccac ccaccttgct gggcatcagg     780
caaaatgcaa acaccacagg cagaagaagg ctattggtct tagacgagtt caaaatggag     840
aaaagaatca gcagaatgtt ctatataatg acttttctgt ttctaacctt gtggggcccc     900
```

```
tacctggtgg cctgttattg gagagttttt gcaagagggc ctgtagtacc aggggggattt    960 ctaacagctg ctgtctggat gagttttgcc caagcaggaa tcaatccttt tgtctgcatt   1020
ttctcaaaca gggagctgag gcgctgtttc agcacaaccc ttctttactg cagaaaatcc   1080
aggttaccaa gggaaccttta ctgtgttata tga                               1113
```

<210> SEQ ID NO 69
<211> LENGTH: 384
<212> TYPE: PRT
<213> ORGANISM: Homo sapiens

<400> SEQUENCE: 69

```
Met Tyr Pro Tyr Asp Val Pro Asp Tyr Ala Ala Ala Ala Met Ala
 1               5                  10                  15

Asn Tyr Ser His Ala Ala Asp Asn Ile Leu Gln Asn Leu Ser Pro Leu
                20                  25                  30

Thr Ala Phe Leu Lys Leu Thr Ser Leu Gly Phe Ile Ile Gly Val Ser
            35                  40                  45

Val Val Gly Asn Leu Leu Ile Ser Ile Leu Leu Val Lys Asp Lys Thr
     50                  55                  60

Leu His Arg Ala Pro Tyr Tyr Phe Leu Leu Asp Leu Cys Cys Ser Asp
 65                  70                  75                  80

Ile Leu Arg Ser Ala Ile Cys Phe Pro Phe Val Phe Asn Ser Val Lys
                 85                  90                  95

Asn Gly Ser Thr Trp Thr Tyr Gly Thr Leu Thr Cys Lys Val Ile Ala
            100                 105                 110

Phe Leu Gly Val Leu Ser Cys Phe His Thr Ala Phe Met Leu Phe Cys
        115                 120                 125

Ile Ser Val Thr Arg Tyr Leu Ala Ile Ala His His Arg Phe Tyr Thr
    130                 135                 140

Lys Arg Leu Thr Phe Trp Thr Cys Leu Ala Val Ile Cys Met Val Trp
145                 150                 155                 160

Thr Leu Ser Val Ala Met Ala Phe Pro Pro Val Leu Asp Val Gly Thr
                165                 170                 175

Tyr Ser Phe Ile Arg Glu Glu Asp Gln Cys Thr Phe Gln His Arg Ser
            180                 185                 190

Phe Arg Ala Asn Asp Ser Leu Gly Phe Met Leu Leu Leu Ala Leu Ile
        195                 200                 205

Leu Leu Ala Thr Gln Leu Val Tyr Leu Lys Leu Ile Phe Phe Val His
    210                 215                 220

Asp Arg Arg Lys Met Lys Pro Val Gln Phe Val Ala Ala Val Ser Gln
225                 230                 235                 240

Asn Trp Thr Phe His Gly Pro Gly Ala Ser Gly Gln Ala Ala Ala Asn
                245                 250                 255

Trp Leu Ala Gly Phe Gly Arg Gly Pro Thr Pro Thr Leu Leu Gly
            260                 265                 270

Ile Arg Gln Asn Ala Asn Thr Thr Gly Arg Arg Leu Leu Val Leu
        275                 280                 285

Asp Glu Phe Lys Met Glu Lys Arg Ile Ser Arg Met Phe Tyr Ile Met
    290                 295                 300

Thr Phe Leu Phe Leu Thr Leu Trp Gly Pro Tyr Leu Val Ala Cys Tyr
305                 310                 315                 320

Trp Arg Val Phe Ala Arg Gly Pro Val Val Pro Gly Gly Phe Leu Thr
                325                 330                 335
```

```
Ala Ala Val Trp Met Ser Phe Ala Gln Ala Gly Ile Asn Pro Phe Val
            340                 345                 350

Cys Ile Phe Ser Asn Arg Glu Leu Arg Arg Cys Phe Ser Thr Thr Leu
        355                 360                 365

Leu Tyr Cys Arg Lys Ser Arg Leu Pro Arg Glu Pro Tyr Cys Val Ile
    370                 375                 380

<210> SEQ ID NO 70
<211> LENGTH: 1155
<212> TYPE: DNA
<213> ORGANISM: Homo sapiens

<400> SEQUENCE: 70
atgtacccat acgacgtacc tgattacgca gcagcagcag caatggcgaa ctatagccat      60
gcagctgaca acattttgca aaatctctcg cctctaacag cctttctgaa actgacttcc     120
ttgggtttca taataggagt cagcgtggtg ggcaacctcc tgatctccat tttgctagtg     180
aaagataaga ccttgcatag agcaccttac tacttcctgt tggatctttg ctgttcagat     240
atcctcagat ctgcaatttg tttcccattt gtgttcaact ctgtcaaaaa tggctctacc     300
tggacttatg ggactctgac ttgcaaagtg attgcctttc gggggttttt gtcctgtttc     360
cacactgctt tcatgctctt ctgcatcagt gtcaccagat acttagctat cgcccatcac     420
cgcttctata caaagaggct gacctttggg acgtgtctgg ctgtgatctg tatggtgtgg     480
actctgtctg tggccatggc atttcccccg gttttagacg tgggcactta ctcattcatt     540
agggaggaag atcaatgcac cttccaacac cgctccttca gggctaatga ttccttagga     600
tttatgctgc tcttgctct catcctccta gccacacagc ttgtctacct caagctgata     660
ttttttcgtcc acgatcgaag aaaaatgaag ccagtccagt ttgtagcagc agtcagccag     720
aactggactt tcatggtcc tggagccagt ggccaggcag ctgccaattg gctagcagga     780
tttggaaggg gtcccacacc acccaccttg ctgggcatca ggcaaaatgc aaacaccaca     840
ggcagaagaa ggctattggt cttagacgag ttcaaaatgg agaaaagaat cagcagaatg     900
ttctatataa tgacttttct gtttctaacc ttgtggggcc cctacctggt ggcctgttat     960
tggagagttt ttgcaagagg gcctgtagta ccaggggat tctaacagc tgctgtctgg    1020
atgagttttg cccaagcagg aatcaatcct tttgtctgca ttttctcaaa caggagctg    1080
aggcgctgtt tcagcacaac ccttctttac tgcagaaaat ccaggttacc aagggaacct    1140
tactgtgtta tatga                                                    1155

<210> SEQ ID NO 71
<211> LENGTH: 388
<212> TYPE: PRT
<213> ORGANISM: Homo sapiens

<400> SEQUENCE: 71

Met Ala Asn Tyr Ser His Ala Ala Asp Asn Ile Leu Gln Asn Leu Ser
 1               5                  10                  15

Pro Leu Thr Ala Phe Leu Lys Leu Thr Ser Leu Gly Phe Ile Ile Gly
            20                  25                  30

Val Ser Val Val Gly Asn Leu Leu Ile Ser Ile Leu Leu Val Lys Asp
        35                  40                  45

Lys Thr Leu His Arg Ala Pro Tyr Tyr Phe Leu Leu Asp Leu Cys Cys
    50                  55                  60

Ser Asp Ile Leu Arg Ser Ala Ile Cys Phe Pro Phe Val Phe Asn Ser
65                  70                  75                  80
```

Val Lys Asn Gly Ser Thr Trp Thr Tyr Gly Thr Leu Thr Cys Lys Val
                 85                  90                  95

Ile Ala Phe Leu Gly Val Leu Ser Cys Phe His Thr Ala Phe Met Leu
            100                 105                 110

Phe Cys Ile Ser Val Thr Arg Tyr Leu Ala Ile Ala His His Arg Phe
        115                 120                 125

Tyr Thr Lys Arg Leu Thr Phe Trp Thr Cys Leu Ala Val Ile Cys Met
    130                 135                 140

Val Trp Thr Leu Ser Val Ala Met Ala Phe Pro Pro Val Leu Asp Val
145                 150                 155                 160

Gly Thr Tyr Ser Phe Ile Arg Glu Glu Asp Gln Cys Thr Phe Gln His
                165                 170                 175

Arg Ser Phe Arg Ala Asn Asp Ser Leu Gly Phe Met Leu Leu Leu Ala
            180                 185                 190

Leu Ile Leu Leu Ala Thr Gln Leu Val Tyr Leu Lys Leu Ile Phe Phe
        195                 200                 205

Val His Asp Arg Arg Lys Met Lys Pro Val Gln Phe Val Ala Ala Val
    210                 215                 220

Ser Gln Asn Trp Thr Phe His Gly Pro Gly Ala Ser Gly Gln Ala Ala
225                 230                 235                 240

Ala Asn Trp Leu Ala Gly Phe Gly Arg Gly Pro Thr Pro Pro Thr Leu
                245                 250                 255

Leu Gly Ile Arg Gln Asn Ala Asn Thr Thr Gly Arg Arg Leu Leu
            260                 265                 270

Val Leu Asp Glu Phe Lys Met Glu Lys Arg Ile Ser Arg Met Phe Tyr
        275                 280                 285

Ile Met Thr Phe Leu Phe Leu Thr Leu Trp Gly Pro Tyr Leu Val Ala
    290                 295                 300

Cys Tyr Trp Arg Val Phe Ala Arg Gly Pro Val Val Pro Gly Gly Phe
305                 310                 315                 320

Leu Thr Ala Ala Val Trp Met Ser Phe Ala Gln Ala Gly Ile Asn Pro
                325                 330                 335

Phe Val Cys Ile Phe Ser Asn Arg Glu Leu Arg Arg Cys Phe Ser Thr
            340                 345                 350

Thr Leu Leu Tyr Cys Ala Ala Ala Arg Gly Arg Thr Pro Pro Ser Leu
        355                 360                 365

Gly Pro Gln Asp Glu Ser Cys Thr Thr Ala Ser Ser Leu Ala Lys
    370                 375                 380

Asp Thr Ser Ser
385

<210> SEQ ID NO 72
<211> LENGTH: 1167
<212> TYPE: DNA
<213> ORGANISM: Homo sapiens

<400> SEQUENCE: 72
atggcgaact atagccatgc agctgacaac attttgcaaa atctctcgcc tctaacagcc    60
tttctgaaac tgacttcctt gggtttcata ataggagtca gcgtggtggg caacctcctg   120
atctccattt tgctagtgaa agataagacc ttgcatagag cacccactac cttcctgttg   180
gatctttgct gttcagatat cctcagatct gcaatttgtt tcccattgt gttcaactct   240 gtcaaaaatg gctctacctg gacttatggg actctgactt gcaaagtgat tgcctttctg   300

-continued

```
ggggttttgt cctgtttcca cactgctttc atgctcttct gcatcagtgt caccagatac    360
ttagctatcg cccatcaccg cttctataca aagaggctga ccttttggac gtgtctggct    420
gtgatctgta tggtgtggac tctgtctgtg gccatggcat tccccccggt tttagacgtg    480
ggcacttact cattcattag ggaggaagat caatgcacct ccaacaccg ctccttcagg     540 gctaatgatt ccttaggatt tatgctgctt cttgctctca tcctcctagc cacacagctt    600
gtctacctca agctgatatt tttcgtccac gatcgaagaa aaatgaagcc agtccagttt    660
gtagcagcag tcagccagaa ctggactttt catggtcctg gagccagtgg ccaggcagct    720
gccaattggc tagcaggatt tggaaggggt cccacaccac ccaccttgct gggcatcagg    780
caaaatgcaa acaccacagg cagaagaagg ctattggtct tagacgagtt caaaatggag    840
aaaagaatca gcagaatgtt ctatataatg acttttctgt ttctaacctt gtggggcccc    900
tacctggtgg cctgttattg gagagttttt gcaagagggc tgtagtacc aggggattt      960 ctaacagctg ctgtctggat gagttttgcc caagcaggaa tcaatccttt tgtctgcatt   1020
ttctcaaaca gggagctgag gcgctgtttc agcacaaccc ttctttactg cgcggccgca   1080
cggggacgca ccccacccag cctgggtccc caagatgagt cctgcaccac cgccagctcc   1140
tccctggcca aggacacttc atcgtga                                       1167
```

<210> SEQ ID NO 73
<211> LENGTH: 402
<212> TYPE: PRT
<213> ORGANISM: Homo sapiens

<400> SEQUENCE: 73

```
Met Tyr Pro Tyr Asp Val Pro Asp Tyr Ala Ala Ala Ala Met Ala
 1               5                   10                  15

Asn Tyr Ser His Ala Ala Asp Asn Ile Leu Gln Asn Leu Ser Pro Leu
                20                  25                  30

Thr Ala Phe Leu Lys Leu Thr Ser Leu Gly Phe Ile Ile Gly Val Ser
            35                  40                  45

Val Val Gly Asn Leu Leu Ile Ser Ile Leu Leu Val Lys Asp Lys Thr
        50                  55                  60

Leu His Arg Ala Pro Tyr Tyr Phe Leu Leu Asp Leu Cys Cys Ser Asp
65                  70                  75                  80

Ile Leu Arg Ser Ala Ile Cys Phe Pro Phe Val Phe Asn Ser Val Lys
                85                  90                  95

Asn Gly Ser Thr Trp Thr Tyr Gly Thr Leu Thr Cys Lys Val Ile Ala
            100                 105                 110

Phe Leu Gly Val Leu Ser Cys Phe His Thr Ala Phe Met Leu Phe Cys
        115                 120                 125

Ile Ser Val Thr Arg Tyr Leu Ala Ile Ala His His Arg Phe Tyr Thr
    130                 135                 140

Lys Arg Leu Thr Phe Trp Thr Cys Leu Ala Val Ile Cys Met Val Trp
145                 150                 155                 160

Thr Leu Ser Val Ala Met Ala Phe Pro Pro Val Leu Asp Val Gly Thr
                165                 170                 175

Tyr Ser Phe Ile Arg Glu Glu Asp Gln Cys Thr Phe Gln His Arg Ser
            180                 185                 190

Phe Arg Ala Asn Asp Ser Leu Gly Phe Met Leu Leu Leu Ala Leu Ile
        195                 200                 205

Leu Leu Ala Thr Gln Leu Val Tyr Leu Lys Leu Ile Phe Phe Val His
    210                 215                 220
```

```
Asp Arg Arg Lys Met Lys Pro Val Gln Phe Val Ala Ala Val Ser Gln
225                 230                 235                 240

Asn Trp Thr Phe His Gly Pro Ala Ser Gly Gln Ala Ala Ala Asn
                245                 250                 255

Trp Leu Ala Gly Phe Gly Arg Gly Pro Thr Pro Thr Leu Leu Gly
                260                 265                 270

Ile Arg Gln Asn Ala Asn Thr Thr Gly Arg Arg Leu Leu Val Leu
                275                 280                 285

Asp Glu Phe Lys Met Glu Lys Arg Ile Ser Arg Met Phe Tyr Ile Met
290                 295                 300

Thr Phe Leu Phe Leu Thr Leu Trp Gly Pro Tyr Leu Val Ala Cys Tyr
305                 310                 315                 320

Trp Arg Val Phe Ala Arg Gly Pro Val Val Pro Gly Gly Phe Leu Thr
                325                 330                 335

Ala Ala Val Trp Met Ser Phe Ala Gln Ala Gly Ile Asn Pro Phe Val
                340                 345                 350

Cys Ile Phe Ser Asn Arg Glu Leu Arg Arg Cys Phe Ser Thr Thr Leu
                355                 360                 365

Leu Tyr Cys Ala Ala Ala Arg Gly Arg Thr Pro Pro Ser Leu Gly Pro
370                 375                 380

Gln Asp Glu Ser Cys Thr Thr Ala Ser Ser Ser Leu Ala Lys Asp Thr
385                 390                 395                 400

Ser Ser

<210> SEQ ID NO 74
<211> LENGTH: 1209
<212> TYPE: DNA
<213> ORGANISM: Homo sapiens

<400> SEQUENCE: 74
atgtacccat acgacgtacc tgattacgca gcagcagcag caatggcgaa ctatagccat      60
gcagctgaca acattttgca aaatctctcg cctctaacag cctttctgaa actgacttcc     120
ttgggtttca taataggagt cagcgtggtg ggcaaccctc tgatctccat tttgctagtg     180
aaagataaga ccttgcatag agcaccttac tacttcctgt tggatctttg ctgttcagat     240
atcctcagat ctgcaatttg tttcccattt gtgttcaact ctgtcaaaaa tggctctacc     300
tggacttatg ggactctgac ttgcaaagtg attgcctttc tgggggtttt gtcctgtttc     360
cacactgctt tcatgctctt ctgcatcagt gtcaccagat acttagctat cgcccatcac     420
cgcttctata caaagaggct gacccttttgg acgtgtctgg ctgtgatctg tatggtgtgg     480
actctgtctg tggccatggc atttcccccg gttttagacg tgggcactta ctcattcatt     540
agggaggaag atcaatgcac cttccaacac cgctccttca gggctaatga ttccttagga     600
tttatgctgc ttcttgctct catcctccta gccacacagc ttgtctacct caagctgata     660 ttttcgtcc acgatcgaag aaaaatgaag ccagtccagt tgtagcagc agtcagccag      720 aactggactt tcatggtcc tggagccagt ggccaggcag ctgccaattg ctagcagga     780 tttggaaggg gtcccacacc acccaccttg ctgggcatca ggcaaaatgc aaacaccaca     840
ggcagaagaa ggctattggt cttagacgag ttcaaaatgg agaaaagaat cagcagaatg     900
ttctatataa tgacttttct gtttctaacc ttgtggggcc cctacctggt ggcctgttat     960
tggagagttt ttgcaagagg gcctgtagta ccagggggat tctaacagc tgctgtctgg    1020 atgagttttg cccaagcagg aatcaatcct tttgtctgca ttttctcaaa cagggagctg    1080
```

```
aggcgctgtt tcagcacaac ccttctttac tgcgcggccg cacggggacg caccccaccc      1140
agcctgggtc cccaagatga gtcctgcacc accgccagct cctccctggc caaggacact      1200
tcatcgtga                                                              1209
```

<210> SEQ ID NO 75
<211> LENGTH: 333
<212> TYPE: PRT
<213> ORGANISM: Homo sapiens
<220> FEATURE:
<221> NAME/KEY: MOD_RES
<222> LOCATION: (305)
<223> OTHER INFORMATION: Variable amino acid

<400> SEQUENCE: 75

```
Met Gln Ala Ala Gly His Pro Glu Pro Leu Asp Ser Arg Gly Ser Phe
 1               5                  10                  15

Ser Leu Pro Thr Met Gly Ala Asn Val Ser Gln Asp Asn Gly Thr Gly
                20                  25                  30

His Asn Ala Thr Phe Ser Glu Pro Leu Pro Phe Leu Tyr Val Leu Leu
            35                  40                  45

Pro Ala Val Tyr Ser Gly Ile Cys Ala Val Gly Leu Thr Gly Asn Thr
        50                  55                  60

Ala Val Ile Leu Val Ile Leu Arg Ala Pro Lys Met Lys Thr Val Thr
 65                  70                  75                  80

Asn Val Phe Ile Leu Asn Leu Ala Val Ala Asp Gly Leu Phe Thr Leu
                85                  90                  95

Val Leu Pro Val Asn Ile Ala Glu His Leu Leu Gln Tyr Trp Pro Phe
            100                 105                 110

Gly Glu Leu Leu Cys Lys Leu Val Leu Ala Val Asp His Tyr Asn Ile
        115                 120                 125

Phe Ser Ser Ile Tyr Phe Leu Ala Val Met Ser Val Asp Arg Tyr Leu
    130                 135                 140

Val Val Leu Ala Thr Val Arg Ser Arg His Met Pro Trp Arg Thr Tyr
145                 150                 155                 160

Arg Gly Ala Lys Val Ala Ser Leu Cys Val Trp Leu Gly Val Thr Val
                165                 170                 175

Leu Val Leu Pro Phe Phe Ser Phe Ala Gly Val Tyr Ser Asn Glu Leu
            180                 185                 190

Gln Val Pro Ser Cys Gly Leu Ser Phe Pro Trp Pro Glu Arg Val Trp
        195                 200                 205

Phe Lys Ala Ser Arg Val Tyr Thr Leu Val Leu Gly Phe Val Leu Pro
    210                 215                 220

Val Cys Thr Ile Cys Val Leu Tyr Thr Asp Leu Leu Arg Arg Leu Arg
225                 230                 235                 240

Ala Val Arg Leu Arg Ser Gly Ala Lys Ala Leu Gly Lys Ala Arg Arg
                245                 250                 255

Lys Val Thr Val Leu Val Leu Val Val Leu Ala Val Cys Leu Leu Cys
            260                 265                 270

Trp Thr Pro Phe His Leu Ala Ser Val Val Ala Leu Thr Thr Asp Leu
        275                 280                 285

Pro Gln Thr Pro Leu Val Ile Ser Met Ser Tyr Val Ile Thr Ser Leu
    290                 295                 300

Xaa Tyr Ala Asn Ser Cys Leu Asn Pro Phe Leu Tyr Ala Phe Leu Asp
305                 310                 315                 320
```

```
Asp Asn Phe Arg Lys Asn Phe Arg Ser Ile Leu Arg Cys
            325                 330
```

```
<210> SEQ ID NO 76
<211> LENGTH: 1002
<212> TYPE: DNA
<213> ORGANISM: Homo sapiens

<400> SEQUENCE: 76
atgcaggccg ctgggcaccc agagcccctt gacagcaggg gctccttctc cctccccacg      60
atgggtgcca acgtctctca ggacaatggc actggccaca atgccacctt ctccgagcca     120
ctgccgttcc tctatgtgct cctgcccgcc gtgtactccg gatctgtgc tgtggggctg      180
actggcaaca cggccgtcat ccttgtaatc ctaagggcgc ccaagatgaa gacggtgacc     240
aacgtgttca tcctgaacct ggccgtcgcc gacgggctct tcacgctggt actgccgtc     300
aacatcgcgg agcacctgct gcagtactgg cccttcgggg agctgctctg caagctggtg    360
ctggccgtcg accactacaa catcttctcc agcatctact cctagccgt gatgagcgtg     420
gaccgatacc tggtggtgct ggccaccgtg aggtcccgcc acatgccctg cgcacctac     480
cggggggcga aggtcgccag cctgtgtgtc tggctgggcg tcacggtcct ggttctgccc    540
ttcttctctt cgctggcgt ctacagcaac gagctgcagg tcccaagctg tgggctgagc    600
ttcccgtggc ccgagcgggt ctggttcaag gccagccgtg tctacacttt ggtcctgggc    660
ttcgtgctgc ccgtgtgcac catctgtgtg ctctacacag acctcctgcg caggctgcgg    720
gccgtgcggc tccgctctgg agccaaggct ctaggcaagg ccaggcggaa ggtgaccgtc    780
ctggtcctcg tcgtgctggc cgtgtgcctc ctctgctgga cgcccttcca cctggcctct    840
gtcgtggccc tgaccacgga cctgcccag accccactgg tcatcagtat gtcctacgtc    900
atcaccagcc tcasstacgc caactcgtgc ctgaaccct tcctctacgc ctttctagat     960
gacaacttcc ggaagaactt ccgcagcata ttgcggtgct ga                      1002
```

```
<210> SEQ ID NO 77
<211> LENGTH: 347
<212> TYPE: PRT
<213> ORGANISM: Homo sapiens
<220> FEATURE:
<221> NAME/KEY: MOD_RES
<222> LOCATION: (319)
<223> OTHER INFORMATION: Variable amino acid

<400> SEQUENCE: 77

Met Tyr Pro Tyr Asp Val Pro Asp Tyr Ala Ala Ala Ala Met Gln
  1               5                  10                  15

Ala Ala Gly His Pro Glu Pro Leu Asp Ser Arg Gly Ser Phe Ser Leu
                20                  25                  30

Pro Thr Met Gly Ala Asn Val Ser Gln Asp Asn Gly Thr Gly His Asn
         35                  40                  45

Ala Thr Phe Ser Glu Pro Leu Pro Phe Leu Tyr Val Leu Leu Pro Ala
     50                  55                  60

Val Tyr Ser Gly Ile Cys Ala Val Gly Leu Thr Gly Asn Thr Ala Val
 65                  70                  75                  80

Ile Leu Val Ile Leu Arg Ala Pro Lys Met Lys Thr Val Thr Asn Val
                 85                  90                  95

Phe Ile Leu Asn Leu Ala Val Ala Asp Gly Leu Phe Thr Leu Val Leu
            100                 105                 110

Pro Val Asn Ile Ala Glu His Leu Leu Gln Tyr Trp Pro Phe Gly Glu
```

```
                115                 120                 125
Leu Leu Cys Lys Leu Val Leu Ala Val Asp His Tyr Asn Ile Phe Ser
    130                 135                 140

Ser Ile Tyr Phe Leu Ala Val Met Ser Val Asp Arg Tyr Leu Val Val
145                 150                 155                 160

Leu Ala Thr Val Arg Ser Arg His Met Pro Trp Arg Thr Tyr Arg Gly
                165                 170                 175

Ala Lys Val Ala Ser Leu Cys Val Trp Leu Gly Val Thr Val Leu Val
                180                 185                 190

Leu Pro Phe Phe Ser Phe Ala Gly Val Tyr Ser Asn Glu Leu Gln Val
                195                 200                 205

Pro Ser Cys Gly Leu Ser Phe Pro Trp Pro Glu Arg Val Trp Phe Lys
    210                 215                 220

Ala Ser Arg Val Tyr Thr Leu Val Leu Gly Phe Val Leu Pro Val Cys
225                 230                 235                 240

Thr Ile Cys Val Leu Tyr Thr Asp Leu Leu Arg Arg Leu Arg Ala Val
                245                 250                 255

Arg Leu Arg Ser Gly Ala Lys Ala Leu Gly Lys Ala Arg Arg Lys Val
                260                 265                 270

Thr Val Leu Val Leu Val Val Leu Ala Val Cys Leu Leu Cys Trp Thr
    275                 280                 285

Pro Phe His Leu Ala Ser Val Val Ala Leu Thr Thr Asp Leu Pro Gln
    290                 295                 300

Thr Pro Leu Val Ile Ser Met Ser Tyr Val Ile Thr Ser Leu Xaa Tyr
305                 310                 315                 320

Ala Asn Ser Cys Leu Asn Pro Phe Leu Tyr Ala Phe Leu Asp Asp Asn
                325                 330                 335

Phe Arg Lys Asn Phe Arg Ser Ile Leu Arg Cys
                340                 345

<210> SEQ ID NO 78
<211> LENGTH: 1044
<212> TYPE: DNA
<213> ORGANISM: Homo sapiens

<400> SEQUENCE: 78
atgtacccat acgacgtacc tgattacgca gcagcagcag caatgcaggc cgctgggcac      60
ccagagcccc ttgacagcag gggctccttc tccctcccca cgatgggtgc caacgtctct     120
caggacaatg gcactggcca caatgccacc ttctccgagc cactgccgtt cctctatgtg     180
ctcctgcccg ccgtgtactc cgggatctgt gctgtggggc tgactggcaa cacggccgtc     240
atccttgtaa tcctaagggc gcccaagatg aagacggtga ccaacgtgtt catcctgaac     300
ctggccgtcg ccgacgggct cttcacgctg gtactgcccg tcaacatcgc ggagcacctg     360
ctgcagtact ggcccttcgg ggagctgctc tgcaagctgg tgctggccgt cgaccactac     420
aacatcttct ccagcatcta cttcctagcc gtgatgagcg tggaccgata cctggtggtg     480
ctggccaccg tgaggtcccg ccacatgccc tggcgcacct accgggggc gaaggtcgcc     540 agcctgtgtg tctggctggg cgtcacggtc ctggttctgc ccttcttctc tttcgctggc     600
gtctacagca acgagctgca agtcccaagc tgtgggctga gcttcccgtg gccgagcgg     660 gtctggttca aggccagccg tgtctacact ttggtcctgg gcttcgtgct gcccgtgtgc     720
accatctgtg tgctctacac agacctcctg cgcaggctgc gggccgtgcg gctccgctct     780
ggagccaagg ctctaggcaa ggccaggcgg aaggtgaccg tcctggtcct cgtcgtgctg     840
```

```
gccgtgtgcc tcctctgctg gacgcccttc cacctggcct ctgtcgtggc cctgaccacg      900
gacctgcccc agaccccact ggtcatcagt atgtcctacg tcatcaccag cctcasstac      960
gccaactcgt gcctgaaccc cttcctctac gcctttctag atgacaactt ccggaagaac     1020
ttccgcagca tattgcggtg ctga                                             1044
```

<210> SEQ ID NO 79
<211> LENGTH: 364
<212> TYPE: PRT
<213> ORGANISM: Homo sapiens

<400> SEQUENCE: 79

```
Met Gln Ala Ala Gly His Pro Glu Pro Leu Asp Ser Arg Gly Ser Phe
 1               5                   10                  15

Ser Leu Pro Thr Met Gly Ala Asn Val Ser Gln Asp Asn Gly Thr Gly
                20                  25                  30

His Asn Ala Thr Phe Ser Glu Pro Leu Pro Phe Leu Tyr Val Leu Leu
            35                  40                  45

Pro Ala Val Tyr Ser Gly Ile Cys Ala Val Gly Leu Thr Gly Asn Thr
        50                  55                  60

Ala Val Ile Leu Val Ile Leu Arg Ala Pro Lys Met Lys Thr Val Thr
65                  70                  75                  80

Asn Val Phe Ile Leu Asn Leu Ala Val Ala Asp Gly Leu Phe Thr Leu
                85                  90                  95

Val Leu Pro Val Asn Ile Ala Glu His Leu Leu Gln Tyr Trp Pro Phe
            100                 105                 110

Gly Glu Leu Leu Cys Lys Leu Val Leu Ala Val Asp His Tyr Asn Ile
        115                 120                 125

Phe Ser Ser Ile Tyr Phe Leu Ala Val Met Ser Val Asp Arg Tyr Leu
130                 135                 140

Val Val Leu Ala Thr Val Arg Ser Arg His Met Pro Trp Arg Thr Tyr
145                 150                 155                 160

Arg Gly Ala Lys Val Ala Ser Leu Cys Val Trp Leu Gly Val Thr Val
                165                 170                 175

Leu Val Leu Pro Phe Phe Ser Phe Ala Gly Val Tyr Ser Asn Glu Leu
            180                 185                 190

Gln Val Pro Ser Cys Gly Leu Ser Phe Pro Trp Pro Glu Arg Val Trp
        195                 200                 205

Phe Lys Ala Ser Arg Val Tyr Thr Leu Val Leu Gly Phe Val Leu Pro
        210                 215                 220

Val Cys Thr Ile Cys Val Leu Tyr Thr Asp Leu Leu Arg Arg Leu Arg
225                 230                 235                 240

Ala Val Arg Leu Arg Ser Gly Ala Lys Ala Leu Gly Lys Ala Arg Arg
                245                 250                 255

Lys Val Thr Val Leu Val Leu Val Leu Ala Val Cys Leu Leu Cys
            260                 265                 270

Trp Thr Pro Phe His Leu Ala Ser Val Val Ala Leu Thr Thr Asp Leu
        275                 280                 285

Pro Gln Thr Pro Leu Val Ile Ser Met Ser Tyr Val Ile Thr Ser Leu
    290                 295                 300

Ser Tyr Ala Asn Ser Cys Leu Asn Pro Phe Leu Tyr Ala Phe Leu Asp
305                 310                 315                 320

Asp Asn Phe Arg Lys Asn Phe Arg Ser Ile Leu Arg Cys Ala Ala Ala
                325                 330                 335
```

```
Arg Gly Arg Thr Pro Pro Ser Leu Gly Pro Gln Asp Glu Ser Cys Thr
            340                 345                 350

Thr Ala Ser Ser Ser Leu Ala Lys Asp Thr Ser Ser
        355                 360
```

<210> SEQ ID NO 80
<211> LENGTH: 1095
<212> TYPE: DNA
<213> ORGANISM: Homo sapiens

<400> SEQUENCE: 80

```
atgcaggccg ctgggcaccc agagcccctt gacagcaggg gctccttctc cctccccacg      60
atgggtgcca acgtctctca ggacaatggc actggccaca atgccacctt ctccgagcca     120
ctgccgttcc tctatgtgct cctgcccgcc gtgtactccg ggatctgtgc tgtggggctg     180
actggcaaca cggccgtcat ccttgtaatc ctaagggcgc ccaagatgaa gacggtgacc     240
aacgtgttca tcctgaacct ggccgtcgcc gacgggctct tcacgctggt actgccgtc      300
aacatcgcgg agcacctgct gcagtactgg cccttcgggg agctgctctg caagctggtg     360
ctggccgtcg accactacaa catcttctcc agcatctact tcctagccgt gatgagcgtg     420
gaccgatacc tggtggtgct ggccaccgtg aggtcccgcc acatgccctg cgcacctac      480
cgggggggcga aggtcgccag cctgtgtgtc tggctgggcg tcacggtcct ggttctgccc     540
ttcttctctt cgctggcgt ctacagcaac gagctgcagg tcccaagctg tgggctgagc      600
ttcccgtggc ccgagcgggt ctggttcaag gccagccgtg tctacacttt ggtcctgggc     660
ttcgtgctgc ccgtgtgcac catctgtgtg ctctacacag acctcctgcg caggctgcgg     720
gccgtgcggc tccgctctgg agccaaggct ctaggcaagg ccaggcggaa ggtgaccgtc     780
ctggtcctcg tcgtgctggc cgtgtgcctc ctctgctgga cgcccttcca cctggcctct     840
gtcgtggccc tgaccacgga cctgccccag acccccactgg tcatcagtat gtcctacgtc     900
atcaccagcc tcagctacgc caactcgtgc ctgaaccccct tcctctacgc ctttctagat     960
gacaacttcc ggaagaactt ccgcagcata ttgcggtgcg cggccgcacg gggacgcacc    1020
ccacccagcc tgggtcccca agatgagtcc tgcaccaccg ccagctcctc cctggccaag    1080
gacacttcat cgtga                                                     1095
```

<210> SEQ ID NO 81
<211> LENGTH: 378
<212> TYPE: PRT
<213> ORGANISM: Homo sapiens

<400> SEQUENCE: 81

```
Met Tyr Pro Tyr Asp Val Pro Asp Tyr Ala Ala Ala Ala Met Gln
  1               5                  10                  15

Ala Ala Gly His Pro Glu Pro Leu Asp Ser Arg Gly Ser Phe Ser Leu
            20                  25                  30

Pro Thr Met Gly Ala Asn Val Ser Gln Asp Asn Gly Thr Gly His Asn
        35                  40                  45

Ala Thr Phe Ser Glu Pro Leu Pro Phe Leu Tyr Val Leu Leu Pro Ala
    50                  55                  60

Val Tyr Ser Gly Ile Cys Ala Val Gly Leu Thr Gly Asn Thr Ala Val
 65                  70                  75                  80

Ile Leu Val Ile Leu Arg Ala Pro Lys Met Lys Thr Val Thr Asn Val
                85                  90                  95
```

```
Phe Ile Leu Asn Leu Ala Val Ala Asp Gly Leu Phe Thr Leu Val Leu
            100                 105                 110
Pro Val Asn Ile Ala Glu His Leu Leu Gln Tyr Trp Pro Phe Gly Glu
        115                 120                 125
Leu Leu Cys Lys Leu Val Leu Ala Val Asp His Tyr Asn Ile Phe Ser
    130                 135                 140
Ser Ile Tyr Phe Leu Ala Val Met Ser Val Asp Arg Tyr Leu Val Val
145                 150                 155                 160
Leu Ala Thr Val Arg Ser Arg His Met Pro Trp Arg Thr Tyr Arg Gly
                165                 170                 175
Ala Lys Val Ala Ser Leu Cys Val Trp Leu Gly Val Thr Val Leu Val
            180                 185                 190
Leu Pro Phe Phe Ser Phe Ala Gly Val Tyr Ser Asn Glu Leu Gln Val
        195                 200                 205
Pro Ser Cys Gly Leu Ser Phe Pro Trp Pro Glu Arg Val Trp Phe Lys
    210                 215                 220
Ala Ser Arg Val Tyr Thr Leu Val Leu Gly Phe Val Leu Pro Val Cys
225                 230                 235                 240
Thr Ile Cys Val Leu Tyr Thr Asp Leu Leu Arg Arg Leu Arg Ala Val
                245                 250                 255
Arg Leu Arg Ser Gly Ala Lys Ala Leu Gly Lys Ala Arg Arg Lys Val
            260                 265                 270
Thr Val Leu Val Leu Val Val Leu Ala Val Cys Leu Leu Cys Trp Thr
        275                 280                 285
Pro Phe His Leu Ala Ser Val Val Ala Leu Thr Thr Asp Leu Pro Gln
    290                 295                 300
Thr Pro Leu Val Ile Ser Met Ser Tyr Val Ile Thr Ser Leu Ser Tyr
305                 310                 315                 320
Ala Asn Ser Cys Leu Asn Pro Phe Leu Tyr Ala Phe Leu Asp Asp Asn
                325                 330                 335
Phe Arg Lys Asn Phe Arg Ser Ile Leu Arg Cys Ala Ala Ala Arg Gly
            340                 345                 350
Arg Thr Pro Pro Ser Leu Gly Pro Gln Asp Glu Ser Cys Thr Thr Ala
        355                 360                 365
Ser Ser Ser Leu Ala Lys Asp Thr Ser Ser
    370                 375

<210> SEQ ID NO 82
<211> LENGTH: 1137
<212> TYPE: DNA
<213> ORGANISM: Homo sapiens

<400> SEQUENCE: 82
atgtacccat acgacgtacc tgattacgca gcagcagcag caatgcaggc cgctgggcac      60
ccagagcccc ttgacagcag gggctccttc tccctcccca cgatgggtgc caacgtctct     120
caggacaatg gcactggcca caatgccacc ttctccgagc cactgccgtt cctctatgtg     180
ctcctgcccg ccgtgtactc cgggatctgt gctgtgggc tgactggcaa cacggccgtc     240
atccttgtaa tcctaagggc gcccaagatg aagacggtga ccaacgtgtt catcctgaac     300
ctggccgtcg ccgacgggct cttcacgctg gtactgcccg tcaacatcgc ggagcacctg     360
ctgcagtact ggcccttcgg ggagctgctc tgcaagctgg tgctggccgt cgaccactac     420
aacatcttct ccagcatcta cttcctagcc gtgatgagcg tggaccgata cctggtggtg     480
ctggccaccg tgaggtcccg ccacatgccc tggcgcacct accgggggc gaaggtcgcc     540
```

-continued

| | | | | | |
|---|---|---|---|---|---|
| agcctgtgtg | tctggctggg | cgtcacggtc | ctggttctgc | ccttcttctc | tttcgctggc | 600 |
| gtctacagca | acgagctgca | ggtcccaagc | tgtgggctga | gcttcccgtg | gcccgagcgg | 660 |
| gtctggttca | aggccagccg | tgtctacact | ttggtcctgg | gcttcgtgct | gcccgtgtgc | 720 |
| accatctgtg | tgctctacac | agacctcctg | cgcaggctgc | gggccgtgcg | gctccgctct | 780 |
| ggagccaagg | ctctaggcaa | ggccaggcgg | aaggtgaccg | tcctggtcct | cgtcgtgctg | 840 |
| gccgtgtgcc | tcctctgctg | gacgcccttc | cacctggcct | ctgtcgtggc | cctgaccacg | 900 |
| gacctgcccc | agaccccact | ggtcatcagt | atgtcctacg | tcatcaccag | cctcagctac | 960 |
| gccaactcgt | gcctgaaccc | cttcctctac | gcctttctag | atgacaactt | ccggaagaac | 1020 |
| ttccgcagca | tattgcggtg | cgcggccgca | cggggacgca | ccccacccag | cctgggtccc | 1080 |
| caagatgagt | cctgcaccac | cgccagctcc | tccctggcca | aggacacttc | atcgtga | 1137 |

<210> SEQ ID NO 83
<211> LENGTH: 433
<212> TYPE: PRT
<213> ORGANISM: Homo sapiens

<400> SEQUENCE: 83

Met Cys Phe Ser Pro Ile Leu Glu Ile Asn Met Gln Ser Glu Ser Asn
1               5                   10                  15

Ile Thr Val Arg Asp Asp Ile Asp Ile Asn Thr Asn Met Tyr Gln
            20                  25                  30

Pro Leu Ser Tyr Pro Leu Ser Phe Gln Val Ser Leu Thr Gly Phe Leu
        35                  40                  45

Met Leu Glu Ile Val Leu Gly Leu Gly Ser Asn Leu Thr Val Leu Val
    50                  55                  60

Leu Tyr Cys Met Lys Ser Asn Leu Ile Asn Ser Val Ser Asn Ile Ile
65                  70                  75                  80

Thr Met Asn Leu His Val Leu Asp Val Ile Cys Val Gly Cys Ile
                85                  90                  95

Pro Leu Thr Ile Val Ile Leu Leu Ser Leu Glu Ser Asn Thr Ala
            100                 105                 110

Leu Ile Cys Cys Phe His Glu Ala Cys Val Ser Phe Ala Ser Val Ser
        115                 120                 125

Thr Ala Ile Asn Val Phe Ala Ile Thr Leu Asp Arg Tyr Asp Ile Ser
    130                 135                 140

Val Lys Pro Ala Asn Arg Ile Leu Thr Met Gly Arg Ala Val Met Leu
145                 150                 155                 160

Met Ile Ser Ile Trp Ile Phe Ser Phe Ser Phe Leu Ile Pro Phe
                165                 170                 175

Ile Glu Val Asn Phe Phe Ser Leu Gln Ser Gly Asn Thr Trp Glu Asn
            180                 185                 190

Lys Thr Leu Leu Cys Val Ser Thr Asn Glu Tyr Tyr Thr Glu Leu Gly
        195                 200                 205

Met Tyr Tyr His Leu Leu Val Gln Ile Pro Ile Phe Phe Thr Val
    210                 215                 220

Val Val Met Leu Ile Thr Tyr Thr Lys Ile Leu Gln Ala Leu Asn Ile
225                 230                 235                 240

Arg Ile Gly Thr Arg Phe Ser Thr Gly Gln Lys Lys Ala Arg Lys
                245                 250                 255

Lys Lys Thr Ile Ser Leu Thr Thr Gln His Glu Ala Thr Asp Met Ser
            260                 265                 270

```
Gln Ser Ser Gly Gly Arg Asn Val Val Phe Gly Val Arg Thr Ser Val
            275                 280                 285
Ser Val Ile Ile Ala Leu Arg Arg Ala Val Lys Arg His Arg Glu Arg
        290                 295                 300
Arg Glu Arg Gln Lys Arg Val Phe Arg Met Ser Leu Leu Ile Ile Ser
305                 310                 315                 320
Thr Phe Leu Leu Cys Trp Thr Pro Ile Ser Val Leu Asn Thr Thr Ile
                325                 330                 335
Leu Cys Leu Gly Pro Ser Asp Leu Leu Val Lys Leu Arg Leu Cys Phe
            340                 345                 350
Leu Val Met Ala Tyr Gly Thr Thr Ile Phe His Pro Leu Leu Tyr Ala
        355                 360                 365
Phe Thr Arg Gln Lys Phe Gln Lys Val Leu Lys Ser Lys Met Lys Lys
    370                 375                 380
Arg Val Val Ser Ile Val Glu Ala Asp Pro Leu Pro Asn Asn Ala Val
385                 390                 395                 400
Ile His Asn Ser Trp Ile Asp Pro Lys Arg Asn Lys Lys Ile Thr Phe
                405                 410                 415
Glu Asp Ser Glu Ile Arg Glu Lys Cys Leu Val Pro Gln Val Val Thr
            420                 425                 430
Asp
```

<210> SEQ ID NO 84
<211> LENGTH: 1302
<212> TYPE: DNA
<213> ORGANISM: Homo sapiens

<400> SEQUENCE: 84

```
atgtgttttt ctcccattct ggaaatcaac atgcagtctg aatctaacat tacagtgcga    60
gatgacattg atgacatcaa caccaatatg taccaaccac tatcatatcc gttaagcttt   120
caagtgtctc tcaccggatt tcttatgtta gaaattgtgt tgggacttgg cagcaacctc   180
actgtattgg tactttactg catgaaatcc aacttaatca actctgtcag taacattatt   240
acaatgaatc ttcatgtact tgatgtaata atttgtgtgg gatgtattcc tctaactata   300
gttatccttc tgcttttcact ggagagtaac actgctctca tttgctgttt ccatgaggct   360
tgtgtatctt ttgcaagtgt ctcaacagca atcaacgttt tgctatcac tttggacaga   420
tatgacatct ctgtaaaacc tgcaaaccga attctgacaa tgggcagagc tgtaatgtta   480
atgatatcca tttggatttt tcttttttc tcttcctga ttccttttat tgaggtaaat   540
ttttcagtc ttcaaagtgg aaatacctgg gaaaacaaga cacttttatg tgtcagtaca   600
aatgaatact acactgaact gggaatgtat tatcacctgt tagtacagat cccaatattc   660
ttttcactg ttgtagtaat gttaatcaca tacaccaaaa tacttcaggc tcttaatatt   720
cgaataggca caagattttc aacagggcag aagaagaaag caagaaagaa aaagacaatt   780
tctctaacca cacaacatga ggctacagac atgtcacaaa gcagtggtgg agaaaatgta   840
gtctttggtg taagaacttc agtttctgta ataattgccc tccggcgagc tgtgaaacga   900
caccgtgaac gacgagaaag acaaaagaga gtcttcagga tgtctttatt gattatttct   960
acatttcttc tctgctggac accaatttct gttttaaata ccaccatttt atgtttaggc  1020
ccaagtgacc tttagtaaa attaagattg tgttttttag tcatggctta tggaacaact  1080
atatttcacc ctctattata tgcattcact agacaaaaat ttcaaaaggt cttgaaaagt  1140
```

-continued

```
aaaatgaaaa agcgagttgt ttctatagta gaagctgatc ccctgcctaa taatgctgta    1200
atacacaact cttggataga tcctaaaaga aacaaaaaaa ttacctttga agatagtgaa    1260
ataagagaaa aatgtttagt gcctcaggtt gtcacagact ag                      1302
```

<210> SEQ ID NO 85
<211> LENGTH: 447
<212> TYPE: PRT
<213> ORGANISM: Homo sapiens

<400> SEQUENCE: 85

```
Met Tyr Pro Tyr Asp Val Pro Asp Tyr Ala Ala Ala Ala Met Cys
 1               5                  10                  15

Phe Ser Pro Ile Leu Glu Ile Asn Met Gln Ser Glu Ser Asn Ile Thr
                20                  25                  30

Val Arg Asp Asp Ile Asp Asp Ile Asn Thr Asn Met Tyr Gln Pro Leu
            35                  40                  45

Ser Tyr Pro Leu Ser Phe Gln Val Ser Leu Thr Gly Phe Leu Met Leu
        50                  55                  60

Glu Ile Val Leu Gly Leu Gly Ser Asn Leu Thr Val Leu Val Leu Tyr
 65                  70                  75                  80

Cys Met Lys Ser Asn Leu Ile Asn Ser Val Ser Asn Ile Ile Thr Met
                85                  90                  95

Asn Leu His Val Leu Asp Val Ile Cys Val Gly Cys Ile Pro Leu
                100                 105                 110

Thr Ile Val Ile Leu Leu Ser Leu Glu Ser Asn Thr Ala Leu Ile
                115                 120                 125

Cys Cys Phe His Glu Ala Cys Val Ser Phe Ala Ser Val Ser Thr Ala
    130                 135                 140

Ile Asn Val Phe Ala Ile Thr Leu Asp Arg Tyr Asp Ile Ser Val Lys
145                 150                 155                 160

Pro Ala Asn Arg Ile Leu Thr Met Gly Arg Ala Val Met Leu Met Ile
                165                 170                 175

Ser Ile Trp Ile Phe Ser Phe Phe Ser Phe Leu Ile Pro Phe Ile Glu
                180                 185                 190

Val Asn Phe Phe Ser Leu Gln Ser Gly Asn Thr Trp Glu Asn Lys Thr
            195                 200                 205

Leu Leu Cys Val Ser Thr Asn Glu Tyr Tyr Thr Glu Leu Gly Met Tyr
    210                 215                 220

Tyr His Leu Leu Val Gln Ile Pro Ile Phe Phe Phe Thr Val Val Val
225                 230                 235                 240

Met Leu Ile Thr Tyr Thr Lys Ile Leu Gln Ala Leu Asn Ile Arg Ile
                245                 250                 255

Gly Thr Arg Phe Ser Thr Gly Gln Lys Lys Ala Arg Lys Lys Lys
                260                 265                 270

Thr Ile Ser Leu Thr Thr Gln His Glu Ala Thr Asp Met Ser Gln Ser
    275                 280                 285

Ser Gly Gly Arg Asn Val Val Phe Gly Val Arg Thr Ser Val Ser Val
    290                 295                 300

Ile Ile Ala Leu Arg Arg Ala Val Lys Arg His Arg Glu Arg Glu
305                 310                 315                 320

Arg Gln Lys Arg Val Phe Arg Met Ser Leu Leu Ile Ile Ser Thr Phe
                325                 330                 335

Leu Leu Cys Trp Thr Pro Ile Ser Val Leu Asn Thr Thr Ile Leu Cys
                340                 345                 350
```

```
Leu Gly Pro Ser Asp Leu Leu Val Lys Leu Arg Leu Cys Phe Leu Val
        355                 360                 365

Met Ala Tyr Gly Thr Thr Ile Phe His Pro Leu Leu Tyr Ala Phe Thr
370                 375                 380

Arg Gln Lys Phe Gln Lys Val Leu Lys Ser Lys Met Lys Lys Arg Val
385                 390                 395                 400

Val Ser Ile Val Glu Ala Asp Pro Leu Pro Asn Asn Ala Val Ile His
                405                 410                 415

Asn Ser Trp Ile Asp Pro Lys Arg Asn Lys Lys Ile Thr Phe Glu Asp
            420                 425                 430

Ser Glu Ile Arg Glu Lys Cys Leu Val Pro Gln Val Val Thr Asp
        435                 440                 445

<210> SEQ ID NO 86
<211> LENGTH: 1344
<212> TYPE: DNA
<213> ORGANISM: Homo sapiens

<400> SEQUENCE: 86
atgtacccat acgacgtacc tgattacgca gcagcagcag caatgtgttt ttctcccatt     60
ctggaaatca acatgcagtc tgaatctaac attacagtgc gagatgacat tgatgacatc    120
aacaccaata tgtaccaacc actatcatat ccgttaagct ttcaagtgtc tctcaccgga    180
tttcttatgt tagaaattgt gttgggactt ggcagcaacc tcactgtatt ggtactttac    240
tgcatgaaat ccaacttaat caactctgtc agtaacatta ttacaatgaa tcttcatgta    300
cttgatgtaa taatttgtgt gggatgtatt cctctaacta tagttatcct tctgctttca    360
ctggagagta acactgctct catttgctgt ttccatgagg cttgtgtatc ttttgcaagt    420
gtctcaacag caatcaacgt ttttgctatc actttggaca gatatgacat ctctgtaaaa    480
cctgcaaacc gaattctgac aatgggcaga gctgtaatgt taatgatatc catttggatt    540
ttttcttttt tctctttcct gattcctttt attgaggtaa atttttttcag tcttcaaagt    600 ggaaatacct gggaaaacaa gacactttta tgtgtcagta caaatgaata ctacactgaa    660
ctgggaatgt attatcacct gttagtacag atcccaatat tcttttttcac tgttgtagta    720 atgttaatca catacaccaa atacttcag gctcttaata ttcgaatagg cacaagattt    780
tcaacagggc agaagaagaa agcaagaaag aaaaagacaa tttctctaac cacacaacat    840
gaggctacag acatgtcaca aagcagtggt gggagaaatg tagtctttgg tgtaagaact    900
tcagtttctg taataattgc cctccggcga gctgtgaaac gacaccgtga acgacgagaa    960
agacaaaaga gagtcttcag gatgtcttta ttgattattt ctacatttct tctctgctgg   1020
acaccaattt ctgttttaaa taccaccatt ttatgtttag gcccaagtga ccttttagta   1080
aaattaagat tgtgtttttt agtcatggct tatggaacaa ctatatttca ccctctatta   1140
tatgcattca ctagacaaaa atttcaaaag gtcttgaaaa gtaaaatgaa aaagcgagtt   1200
gtttctatag tagaagctga tccccctgcct aataatgctg taatacacaa ctcttggata   1260
gatcctaaaa gaaacaaaaa aattacctttt gaagatagtg aaataagaga aaaatgttta   1320
gtgcctcagg ttgtcacaga ctag                                           1344
```

<210> SEQ ID NO 87
<211> LENGTH: 419
<212> TYPE: PRT
<213> ORGANISM: Homo sapiens

<400> SEQUENCE: 87

Met Cys Phe Ser Pro Ile Leu Glu Ile Asn Met Gln Ser Glu Ser Asn
1               5                   10                  15

Ile Thr Val Arg Asp Asp Ile Asp Ile Asn Thr Asn Met Tyr Gln
            20                  25                  30

Pro Leu Ser Tyr Pro Leu Ser Phe Gln Val Ser Leu Thr Gly Phe Leu
        35                  40                  45

Met Leu Glu Ile Val Leu Gly Leu Gly Ser Asn Leu Thr Val Leu Val
    50                  55                  60

Leu Tyr Cys Met Lys Ser Asn Leu Ile Asn Ser Val Ser Asn Ile Ile
65                  70                  75                  80

Thr Met Asn Leu His Val Leu Asp Val Ile Ile Cys Val Gly Cys Ile
                85                  90                  95

Pro Leu Thr Ile Val Ile Leu Leu Ser Leu Glu Ser Asn Thr Ala
            100                 105                 110

Leu Ile Cys Cys Phe His Glu Ala Cys Val Ser Phe Ala Ser Val Ser
        115                 120                 125

Thr Ala Ile Asn Val Phe Ala Ile Thr Leu Asp Arg Tyr Asp Ile Ser
    130                 135                 140

Val Lys Pro Ala Asn Arg Ile Leu Thr Met Gly Arg Ala Val Met Leu
145                 150                 155                 160

Met Ile Ser Ile Trp Ile Phe Ser Phe Ser Phe Leu Ile Pro Phe
                165                 170                 175

Ile Glu Val Asn Phe Phe Ser Leu Gln Ser Gly Asn Thr Trp Glu Asn
            180                 185                 190

Lys Thr Leu Leu Cys Val Ser Thr Asn Glu Tyr Tyr Thr Glu Leu Gly
        195                 200                 205

Met Tyr Tyr His Leu Leu Val Gln Ile Pro Ile Phe Phe Phe Thr Val
    210                 215                 220

Val Val Met Leu Ile Thr Tyr Thr Lys Ile Leu Gln Ala Leu Asn Ile
225                 230                 235                 240

Arg Ile Gly Thr Arg Phe Ser Thr Gly Gln Lys Lys Ala Arg Lys
                245                 250                 255

Lys Lys Thr Ile Ser Leu Thr Thr Gln His Glu Ala Thr Asp Met Ser
            260                 265                 270

Gln Ser Ser Gly Gly Arg Asn Val Val Phe Gly Val Arg Thr Ser Val
        275                 280                 285

Ser Val Ile Ile Ala Leu Arg Arg Ala Val Lys Arg His Arg Glu Arg
    290                 295                 300

Arg Glu Arg Gln Lys Arg Val Phe Arg Met Ser Leu Leu Ile Ile Ser
305                 310                 315                 320

Thr Phe Leu Leu Cys Trp Thr Pro Ile Ser Val Leu Asn Thr Thr Ile
                325                 330                 335

Leu Cys Leu Gly Pro Ser Asp Leu Leu Val Lys Leu Arg Leu Cys Phe
            340                 345                 350

Leu Val Met Ala Tyr Gly Thr Thr Ile Phe His Pro Leu Leu Tyr Ala
        355                 360                 365

Phe Thr Arg Gln Lys Phe Gln Lys Val Leu Lys Ser Lys Met Lys Lys

```
              370                 375                 380
Arg Val Val Cys Ala Ala Ala Arg Gly Arg Thr Pro Pro Ser Leu Gly
385                 390                 395                 400

Pro Gln Asp Glu Ser Cys Thr Thr Ala Ser Ser Ser Leu Ala Lys Asp
                405                 410                 415

Thr Ser Ser

<210> SEQ ID NO 88
<211> LENGTH: 1260
<212> TYPE: DNA
<213> ORGANISM: Homo sapiens

<400> SEQUENCE: 88
atgtgttttt ctcccattct ggaaatcaac atgcagtctg aatctaacat tacagtgcga    60
gatgacattg atgacatcaa caccaatatg taccaaccac tatcatatcc gttaagcttt   120
caagtgtctc tcaccggatt tcttatgtta gaaattgtgt gggacttgg cagcaacctc    180 actgtattgg tactttactg catgaaatcc aacttaatca actctgtcag taacattatt   240
acaatgaatc ttcatgtact tgatgtaata atttgtgtgg gatgtattcc tctaactata   300
gttatccttc tgctttcact ggagagtaac actgctctca tttgctgttt ccatgaggct   360
tgtgtatctt ttgcaagtgt ctcaacagca atcaacgttt tgctatcac tttggacaga    420 tatgacatct ctgtaaaacc tgcaaaccga attctgacaa tgggcagagc tgtaatgtta   480
atgatatcca tttggatttt ttcttttttc tctttcctga ttccttttat tgaggtaaat   540
tttttcagtc ttcaaagtgg aaatacctgg aaaacaaga cacttttatg tgtcagtaca    600
aatgaatact acactgaact gggaatgtat tatcacctgt tagtacagat cccaatattc   660
tttttcactg ttgtagtaat gttaatcaca tacaccaaaa tacttcaggc tcttaatatt   720
cgaataggca caagattttc aacagggcag aagaagaaag caagaaagaa aaagacaatt   780
tctctaacca cacaacatga ggctacagac atgtcacaaa gcagtggtgg gagaaatgta   840
gtctttggtg taagaacttc agtttctgta ataattgccc tccggcgagc tgtgaaacga   900
caccgtgaac gacgagaaag acaaaagaga gtcttcagga tgtctttatt gattatttct   960
acatttcttc tctgctggac accaatttct gttttaaata ccaccatttt atgtttaggc  1020
ccaagtgacc ttttagtaaa attaagattg tgttttttag tcatggctta tggaacaact  1080
atatttcacc ctctattata tgcattcact agacaaaaat ttcaaaaggt cttgaaaagt  1140
aaaatgaaaa agcgagttgt ttgtgcggcc gcacgggac gcaccccacc cagcctgggt   1200
ccccaagatg agtcctgcac caccgccagc tcctccctgg ccaaggacac ttcatcgtga  1260

<210> SEQ ID NO 89
<211> LENGTH: 433
<212> TYPE: PRT
<213> ORGANISM: Homo sapiens

<400> SEQUENCE: 89

Met Tyr Pro Tyr Asp Val Pro Asp Tyr Ala Ala Ala Ala Met Cys
  1               5                  10                  15

Phe Ser Pro Ile Leu Glu Ile Asn Met Gln Ser Glu Ser Asn Ile Thr
                 20                  25                  30

Val Arg Asp Asp Ile Asp Asp Ile Asn Thr Asn Met Tyr Gln Pro Leu
             35                  40                  45

Ser Tyr Pro Leu Ser Phe Gln Val Ser Leu Thr Gly Phe Leu Met Leu
         50                  55                  60
```

-continued

```
Glu Ile Val Leu Gly Leu Gly Ser Asn Leu Thr Val Leu Val Leu Tyr
 65                  70                  75                  80
Cys Met Lys Ser Asn Leu Ile Asn Ser Val Ser Asn Ile Ile Thr Met
                 85                  90                  95
Asn Leu His Val Leu Asp Val Ile Ile Cys Val Gly Cys Ile Pro Leu
            100                 105                 110
Thr Ile Val Ile Leu Leu Ser Leu Glu Ser Asn Thr Ala Leu Ile
        115                 120                 125
Cys Cys Phe His Glu Ala Cys Val Ser Phe Ala Ser Val Ser Thr Ala
130                 135                 140
Ile Asn Val Phe Ala Ile Thr Leu Asp Arg Tyr Asp Ile Ser Val Lys
145                 150                 155                 160
Pro Ala Asn Arg Ile Leu Thr Met Gly Arg Ala Val Met Leu Met Ile
                165                 170                 175
Ser Ile Trp Ile Phe Ser Phe Phe Ser Phe Leu Ile Pro Phe Ile Glu
            180                 185                 190
Val Asn Phe Phe Ser Leu Gln Ser Gly Asn Thr Trp Glu Asn Lys Thr
        195                 200                 205
Leu Leu Cys Val Ser Thr Asn Glu Tyr Tyr Thr Glu Leu Gly Met Tyr
210                 215                 220
Tyr His Leu Leu Val Gln Ile Pro Ile Phe Phe Phe Thr Val Val Val
225                 230                 235                 240
Met Leu Ile Thr Tyr Thr Lys Ile Leu Gln Ala Leu Asn Ile Arg Ile
                245                 250                 255
Gly Thr Arg Phe Ser Thr Gly Gln Lys Lys Ala Arg Lys Lys Lys
            260                 265                 270
Thr Ile Ser Leu Thr Thr Gln His Glu Ala Thr Asp Met Ser Gln Ser
        275                 280                 285
Ser Gly Gly Arg Asn Val Val Phe Gly Val Arg Thr Ser Val Ser Val
290                 295                 300
Ile Ile Ala Leu Arg Arg Ala Val Lys Arg His Arg Glu Arg Arg Glu
305                 310                 315                 320
Arg Gln Lys Arg Val Phe Arg Met Ser Leu Leu Ile Ile Ser Thr Phe
                325                 330                 335
Leu Leu Cys Trp Thr Pro Ile Ser Val Leu Asn Thr Thr Ile Leu Cys
            340                 345                 350
Leu Gly Pro Ser Asp Leu Leu Val Lys Leu Arg Leu Cys Phe Leu Val
        355                 360                 365
Met Ala Tyr Gly Thr Thr Ile Phe His Pro Leu Leu Tyr Ala Phe Thr
370                 375                 380
Arg Gln Lys Phe Gln Lys Val Leu Lys Ser Lys Met Lys Lys Arg Val
385                 390                 395                 400
Val Cys Ala Ala Ala Arg Gly Arg Thr Pro Pro Ser Leu Gly Pro Gln
                405                 410                 415
Asp Glu Ser Cys Thr Thr Ala Ser Ser Ser Leu Ala Lys Asp Thr Ser
            420                 425                 430
Ser
```

<210> SEQ ID NO 90
<211> LENGTH: 1302
<212> TYPE: DNA
<213> ORGANISM: Homo sapiens

<400> SEQUENCE: 90

```
atgtacccat acgacgtacc tgattacgca gcagcagcag caatgtgttt ttctcccatt      60
ctggaaatca acatgcagtc tgaatctaac attacagtgc gagatgacat tgatgacatc     120
aacaccaata tgtaccaacc actatcatat ccgttaagct ttcaagtgtc tctcaccgga     180
tttcttatgt tagaaattgt gttgggactt ggcagcaacc tcactgtatt ggtactttac     240
tgcatgaaat ccaacttaat caactctgtc agtaacatta ttacaatgaa tcttcatgta     300
cttgatgtaa taatttgtgt gggatgtatt cctctaacta tagttatcct tctgctttca     360
ctggagagta acactgctct catttgctgt ttccatgagg cttgtgtatc ttttgcaagt     420
gtctcaacag caatcaacgt ttttgctatc actttggaca gatatgacat ctctgtaaaa     480
cctgcaaacc gaattctgac aatgggcaga gctgtaatgt taatgatatc catttggatt     540
ttttcttttt tctctttcct gattccttt attgaggtaa atttttttcag tcttcaaagt     600 ggaaatacct gggaaaacaa gacactttta tgtgtcagta caaatgaata ctacactgaa     660
ctgggaatgt attatcacct gttagtacag atcccaatat tcttttttcac tgttgtagta     720 atgttaatca catacaccaa aatacttcag gctcttaata ttcgaatagg cacaagattt     780
tcaacagggc agaagaagaa agcaagaaag aaaaagacaa tttctctaac cacacaacat     840
gaggctacag acatgtcaca aagcagtggt gggagaaatg tagtctttgg tgtaagaact     900
tcagtttctg taataattgc cctccggcga gctgtgaaac gacaccgtga acgacgagaa     960
agacaaaaga gagtcttcag gatgtcttta ttgattattt ctacatttct tctctgctgg    1020
acaccaattt ctgttttaaa taccaccatt ttatgtttag gcccaagtga ccttttagta    1080
aaattaagat tgtgtttttt agtcatggct tatggaacaa ctatatttca ccctctatta    1140
tatgcattca ctagacaaaa atttcaaaag gtcttgaaaa gtaaaatgaa aaagcgagtt    1200
gtttgtgcgg ccgcacgggg acgcacccca cccagcctgg gtccccaaga tgagtcctgc    1260
accaccgcca gctcctccct ggccaaggac acttcatcgt ga                       1302
```

<210> SEQ ID NO 91
<211> LENGTH: 5
<212> TYPE: PRT
<213> ORGANISM: Homo sapiens

<400> SEQUENCE: 91

Ser Ser Leu Ser Thr
 1               5

<210> SEQ ID NO 92
<211> LENGTH: 4
<212> TYPE: PRT
<213> ORGANISM: Homo sapiens

<400> SEQUENCE: 92

Ser Thr Leu Ser
 1

<210> SEQ ID NO 93
<211> LENGTH: 5
<212> TYPE: PRT
<213> ORGANISM: Homo sapiens

<400> SEQUENCE: 93

Thr Thr Ile Ser Thr
 1               5

```
<210> SEQ ID NO 94
<211> LENGTH: 4
<212> TYPE: PRT
<213> ORGANISM: Homo sapiens

<400> SEQUENCE: 94

Cys Val Leu Leu
1
```

CONSTITUTIVELY TRANSLOCATING CELL LINE

The present application is a Continuation-In-Part application of International Application No. PCT/US03/14581, filed on May 12, 2003, which claims the benefit of U.S. Provisional Application No. 60/379,986 filed on May 13, 2002; and U.S. Provisional Application No. 60/401,698 filed on Aug. 7, 2002; which are hereby incorporated by reference in their entireties.

FIELD OF THE INVENTION

The present invention relates to methods of assaying GPCR desensitization in a agonist-independent manner, host cells useful in such methods, methods of the identification of compounds that alter GPCR desensitization, the compounds identified, and their use in disease treatment.

BACKGROUND

G protein-coupled receptors (GPCRs) are cell surface proteins that translate hormone or ligand binding into intracellular signals. GPCRs are found in all animals, insects, and plants. GPCR signaling plays a pivotal role in regulating various physiological functions including phototransduction, olfaction, neurotransmission, vascular tone, cardiac output, digestion, pain, and fluid and electrolyte balance. Although they are involved in numerous physiological functions, GPCRs share a number of common structural features. They contain seven membrane domains bridged by alternating intracellular and extracellular loops and an intracellular carboxyl-terminal tail of variable length.

GPCRs have been implicated in a number of disease states, including, but not limited to: cardiac indications such as angina pectoris, essential hypertension, myocardial infarction, supraventricular and ventricular arrhythmias, congestive heart failure, atherosclerosis, renal failure, diabetes, respiratory indications such as asthma, chronic bronchitis, bronchospasm, emphysema, airway obstruction, upper respiratory indications such as rhinitis, seasonal allergies, inflammatory disease, inflammation in response to injury, rheumatoid arthritis, chronic inflammatory bowel disease, glaucoma, hypergastrinemia, gastrointestinal indications such as acid/peptic disorder, erosive esophagitis, gastrointestinal hypersecretion, mastocytosis, gastrointestinal reflux, peptic ulcer, Zollinger-Ellison syndrome, pain, obesity, bulimia nervosa, depression, obsessive-compulsive disorder, organ malformations (for example, cardiac malformations), neurodegenerative diseases such as Parkinson's Disease and Alzheimer's Disease, multiple sclerosis, Epstein-Barr infection and cancer.

The magnitude of the physiological responses controlled by GPCRs is linked to the balance between GPCR signaling and signal termination. The signaling of GPCRs is controlled by a family of intracellular proteins called arrestins. Arrestins bind activated GPCRs, including those that have been agonist-activated and especially those that have been phosphorylated by G protein-coupled receptor kinases (GRKs).

Receptors, including GPCRs, have historically been targets for drug discovery and therapeutic agents because they bind ligands, hormones, and drugs with high specificity. Approximately fifty percent of the therapeutic drugs in use today target or interact directly with GPCRs. See e.g., Jurgen Drews, (2000) "Drug Discovery: A Historical Perspective," Science 287:1960-1964.

There is a need for accurate, easy to interpret methods of detecting G protein-coupled receptor activity and methods of assaying GPCR activity. One method, as disclosed in Barak et al., U.S. Pat. Nos. 5,891,646 and 6,110,693, uses a cell expressing a GPCR and a conjugate of an arrestin and a detectable molecule, the contents of which are incorporated by reference in their entirety.

Although only several hundred human GPCRs are known, it is estimated that upwards of a thousand GPCRs exist in the human genome. Of these known GPCRs, many are orphan receptors that have yet to be associated with a ligand.

The majority of the existing methods for identifying GPCR antagonists are dependent on the presence of agonist. Assays for identifying compounds that prevent the activation of GPCRs typically require that the GPCR is first activated in order to identify interfering compounds. For receptors with known agonists, these agonists are currently used to activate these receptors. However, many GPCRs are orphan receptors with no known ligand or agonist.

The agonist-dependence of GPCR assays continues to be a problem because antagonist discovery for orphan receptors is typically dependent on the prior discovery of agonist or ligand. Agonist-independent methods to screen for compounds that alter GPCR desensitization will (1) eliminate the step of agonist-addition in screening methods, and (2) enable identification of compounds that alter the desensitization of orphan receptors. Agonist-independent methods will eliminate the step of identifying an agonist of an orphan receptor prior to screening for compounds that alter desensitization of the orphan receptor.

SUMMARY

The present invention relates to methods of identifying compounds which alter GPCR internalization.

A first aspect of the present invention is a method of identifying a compound which alters GPCR internalization, including: (a) providing a cell including a GPCR, an arrestin, and a modified GRK, wherein said GPCR is at least partially internalized in an agonist-independent manner upon expression of said GRK; (b) exposing said cell to the compound(s); (c) determining the cellular distribution of the GPCR, arrestin, or modified GRK; and (d) monitoring a difference between (1) the distribution of the GPCR, arrestin, or modified GRK in the cell in the presence of the compound(s) and (2) the distribution of the GPCR, arrestin, or modified GRK in the cell in the absence of the compound(s). An agonist may not be provided in the above method. In the method, a difference between (1) and (2) of step (d) may indicate modulation of GPCR internalization.

The GRK may be over-expressed, its expression may be inducible, and it may include a CAAX motif. The GRK may be GRK1, GRK2, GRK3, GRK4, GRK5, GRK6, or a biologically active fragment thereof.

The GPCR may be modified to have enhanced phosphorylation by a GRK. The GPCR may be β$_2$AR(Y326A), a GPCR listed in FIG. 1A-1C, an orphan GPCR, a modified GPCR, a taste receptor, a Class A GPCR, a Class B GPCR, a mutant GPCR, or a biologically active fragment thereof.

The arrestin may be visual arrestin, cone arrestin, β-arrestin 1, β-arrestin-2, or a biologically active fragment thereof.

The GPCR, GRK, or arrestin may be detectably labeled. A molecule involved in desensitization may be detectably labeled, or a molecule that interacts with a molecule involved in desensitization may be detectably labeled.

In a further aspect, the present invention relates to a method of identifying a compound that alters GPCR phosphorylation, including: (a) providing a cell including a GPCR and a GRK; (b) exposing the cell to the compound(s); and (c) determining whether GRK phosphorylation of the GPCR is altered in the presence of the compound(s).

The cellular distribution of the GPCR or GRK may be determined. A difference may be monitored between (1) the distribution of the GPCR or GRK in the cell in the presence of the compound(s) and (2) the distribution of the GPCR or GRK in the cell in the absence of the compound(s). A difference may be correlated between (1) and (2) to the phosphorylation of the GPCR.

The GRK may not be located in the plasma membrane, indicating that GRK phosphorylation of the GPCR is altered. The phosphorylation state of the GPCR may be determined. The activity of the GRK may be determined. The ability of the GPCR to be internalized may be determined.

In an additional aspect, the present invention relates to a method of determining if a GPCR is expressed at the plasma membrane, including: (a) providing a cell including a GPCR, an arrestin, and a GRK, wherein the arrestin is detectably labeled; (b) determining the cellular distribution of the arrestin; and (c) correlating the cellular distribution of the arrestin to the ability of the GPCR to be expressed at the plasma membrane. The arrestin may be localized in vesicles, pits endosomes, or elsewhere in the desensitization pathway.

Additionally, the present invention relates to a further method of determining if a GPCR is expressed at the plasma membrane, including: (a) providing a cell including a GPCR and a GRK, wherein the GRK is detectably labeled; (b) determining the cellular distribution of the GRK, and (c) correlating the cellular distribution of the GRK to the ability of the GPCR to be expressed at the plasma membrane. The GRK may be localized at the plasma membrane.

In a further aspect, the present invention relates to a method of analyzing the ability of a GPCR to bind arrestin, including: (a) providing a cell including a GPCR, an arrestin, and a GRK, wherein the arrestin is detectably labeled; (b) determining the cellular distribution of the arrestin; and (c) correlating the cellular distribution of the arrestin to the ability of the GPCR to bind arrestin. The arrestin or the GPCR may be localized in vesicles, pits, or endosomes.

In an additional aspect, the present invention relates to a compound identified by a method of the present invention.

In a further aspect, the present invention is related to a method of treating a disease by modulating desensitization of a GPCR in a host cell, including: (a) providing a compound identified by a method of the present invention; and (b) administering the compound to a host.

Another aspect of the invention relates to a host cell including a GPCR and a modified GRK. The GRK may be inducible or over-expressed. The host cell may further include arrestin, wherein the arrestin may be detectably labeled. The GPCR, GRK or another molecule involved in desensitization, or a molecule that interacts with a molecule involved in desensitization may be detectably labeled.

A further aspect of the present invention relates to a method of modifying a nucleic acid encoding a GRK in which a GPCR is constitutively internalized, including: (a) providing a nucleic acid encoding a GRK; (b) mutating the nucleic acid encoding a GRK such that the encoded GRK includes a CAAX motif, wherein the modified GRK phosphorylates a GPCR in the absence of agonist; and (c) expressing the modified GRK in a cell. The nucleic acid encoding a GRK may include SEQ ID No: 2, 4, 6, 8, 10, 12, 14, 16, 18, 20, 22, 24, 26, 28, 30, 32, or 34.

The present invention also relates to a kit for identifying a compound that modulates the internalization of a GPCR, including a host cell including a GPCR and a modified GRK.

In a further aspect, the present invention relates to a modified GPCR including a NPXXY motif, and a carboxyl terminal tail, wherein the carboxyl terminal tail includes a putative site of palmitoylation and one or more clusters of phosphorylation, wherein the carboxyl terminal tail includes a retained portion of a carboxyl-terminus region of a first GPCR portion fused to a portion of a carboxyl-terminus from a second GPCR, and wherein the second GPCR includes the one or more clusters of phosphorylation and further includes a second putative site of palmitoylation approximately 10 to 25 amino acid residues downstream of a second NPXXY motif. The first GPCR may be a Class A receptor. The first GPCR may be hGPR3, hGPR6, hGPR12, hSREB2, hSREB3, hGPR8, or hGPR22. The second GPCR may be a Class B receptor. The Class B receptor may be selected from the group consisting of a vasopressin V2 receptor, a neurotensin-1 receptor, a substance P receptor, and an oxytocin receptor.

The present invention relates to a nucleic acid encoding a modified GPCR. Included in the present invention are nucleic acids selected from the group consisting of SEQ ID Nos: 36, 38, 40, 42, 44, 46, 48, 50, 52, 54, 56, 58, 60, 62, 64, 66, 68, 70, 72, 74, 76, 78, 80, 82, 84, 86, 88, and 90. Also included in the present invention are expression vectors including the nucleic acid. Host cells including the expression vector or the nucleic acid are also included.

In a further aspect, the present invention relates to a method of screening compounds for GPCR activity including the steps of: (a) providing a cell that expresses at least one modified GPCR, wherein the cell further includes arrestin conjugated to a detectable molecule; b) exposing the cell to the compound; (c) detecting location of the arrestin within the cell; (d) comparing the location of the arrestin within the cell in the presence of the compound to the location of the arrestin within the cell in the absence of the compound; and (e) correlating a difference between (1) the location of the arrestin within the cell in the presence of the compound and (2) the location of the arrestin within the cell in the absence of the compound. The arrestin may be detected in endosomes, endocytic vesicles, or pits.

A further aspect of the present invention is a kit for identifying a molecule that modulates the activity of a GPCR, including a cell that expresses at least one modified GPCR, wherein the cell further includes a molecule involved in desensitization conjugated to a detectable molecule.

BRIEF DESCRIPTION OF DRAWINGS

The objects and advantages of the invention will be understood by reading the following detailed description in conjunction with the drawings in which:

FIG. 1A-1C is a list of GPCRs that may be used with the present invention.

FIG. 2A-2Q is a list of GRKs that may be used with the present invention. Amino acid and nucleic acid sequences of certain GRKs are shown. The amino acid and nucleic acid sequences of GRK2-C20, a modified GRK, are shown.

FIG. 3A-3BB is a list of GPCRs that have been modified to have enhanced affinity for arrestin. The amino acid and nucleic acid sequences are shown.

FIG. 4 illustrates the agonist-independent translocation of arrestin-GFP to GPCRs in the presence of GRK2-C20.

DETAILED DESCRIPTION

Figure 5:
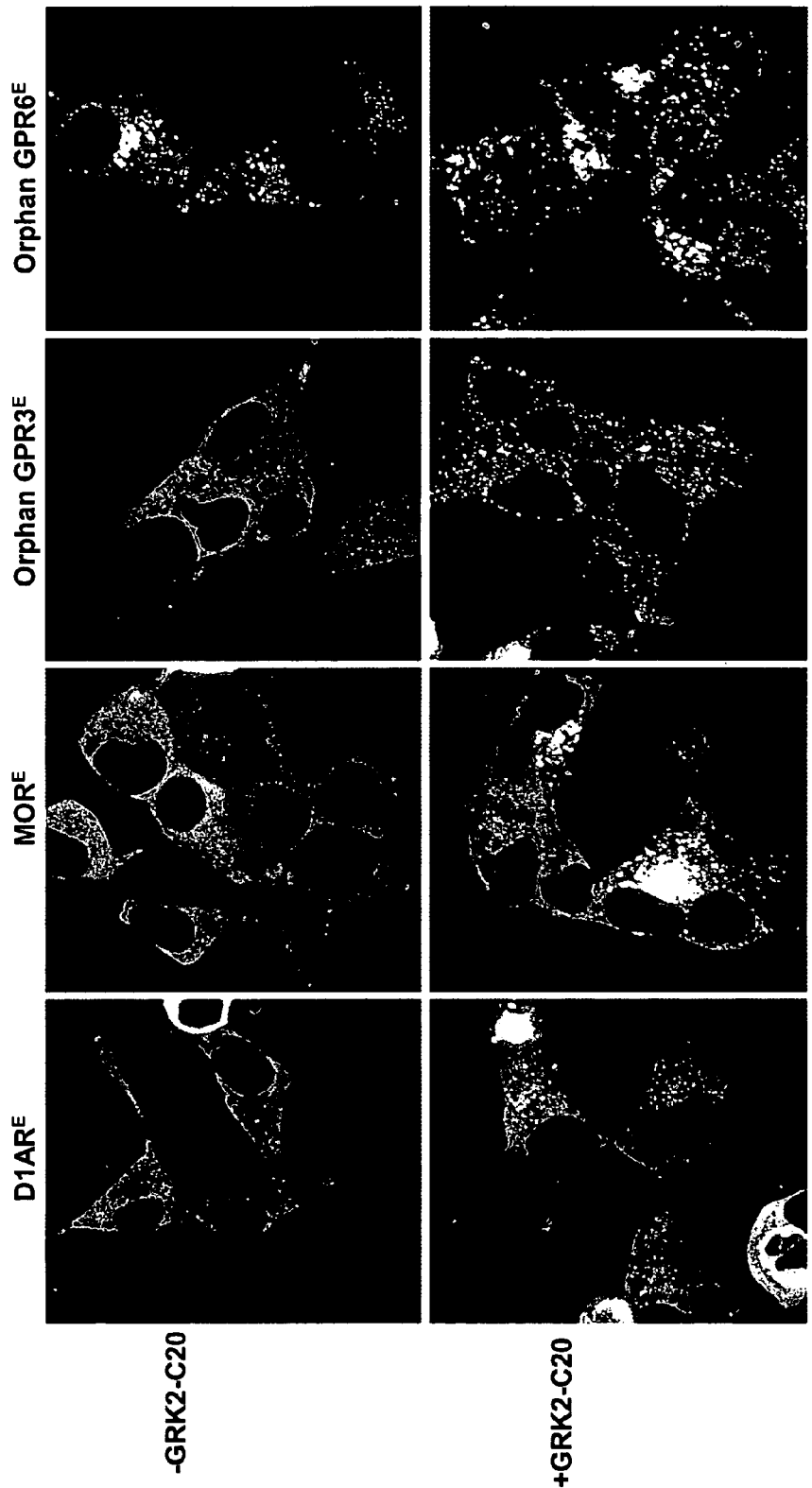
FIG. 5 illustrates the agonist-independent translocation of arrestin-GFP to GPCRs in the presence of GRK2-C20.
Figure 6:
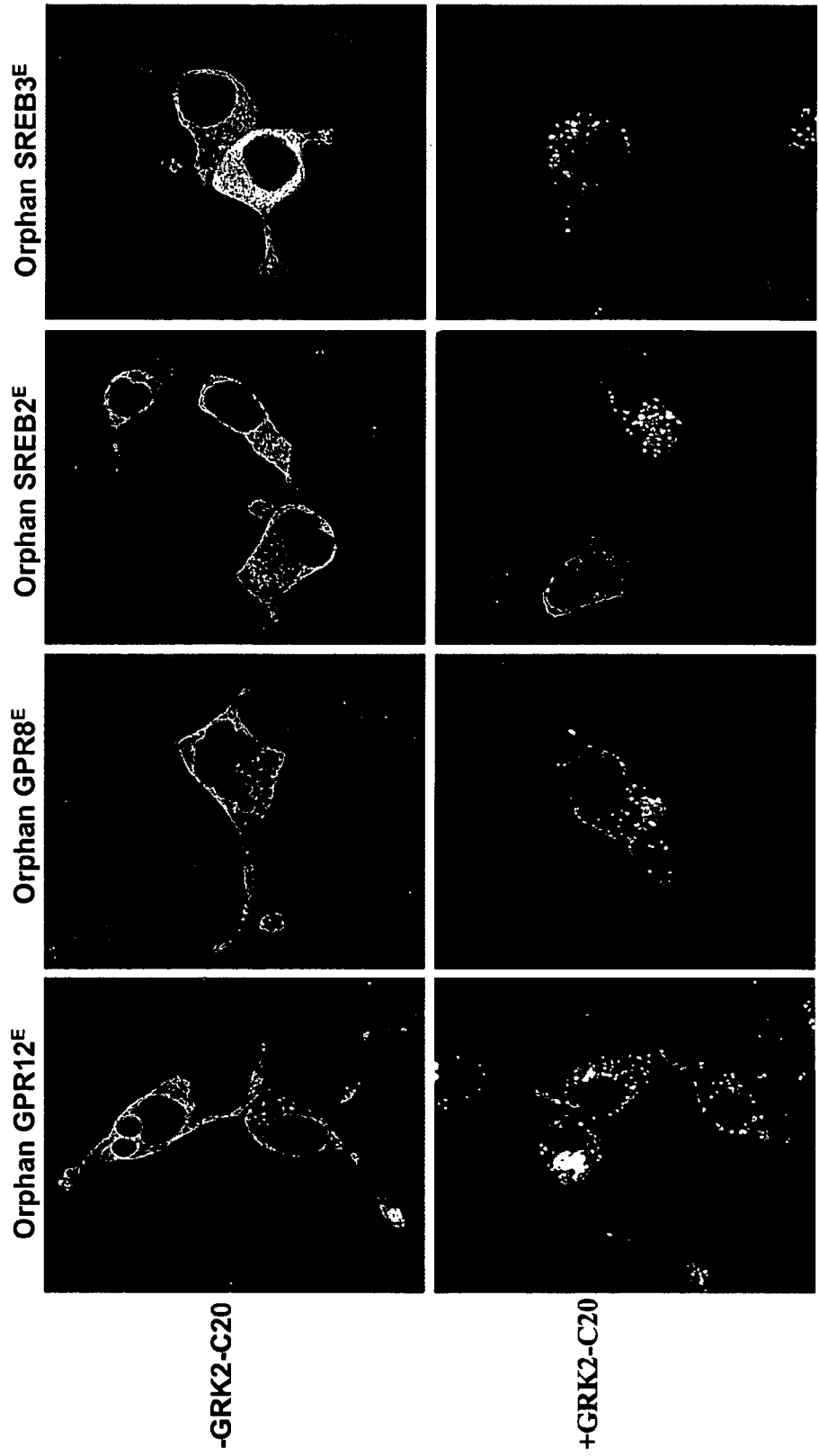
FIG. 6 illustrates the agonist-independent translocation of arrestin-GFP to GPCRs in the presence of GRK2-C20.

In accordance with the present invention there may be employed conventional molecular biology, microbiology, immunology, and recombinant DNA techniques within the skill of the art. Such techniques are explained fully in the literature. See, e.g., Sambrook et al, "Molecular Cloning: A Laboratory Manual" ($3^{rd}$ edition, 2001); "Current Protocols in Molecular Biology" Volumes I-IV [Ausubel, R. M., ed. (2002 and updated bimonthly)]; "Cell Biology: A Laboratory Handbook" Volumes I-III [J. E. Celis, ed. (1994)]; "Current Protocols in Immunology" Volumes I-IV [Coligan, J. E., ed. (2002 and updated bimonthly)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Culture of Animal Cells, $4^{th}$ edition" [R. I Freshney, ed. (2000)]; "Immobilized Cells And Enzymes" [IRL Press, (1986)]; B. Perbal, "A Practical Guide To Molecular Cloning" (1988); Using Antibodies: A Laboratory Manual: Portable Protocol No. I, Harlow, Ed and Lane, David (Cold Spring Harbor Press, 1998); Using Antibodies: A Laboratory Manual, Harlow, Ed and Lane, David (Cold Spring Harbor Press, 1999); "G Protein-Coupled Receptors" [T. Haga, et al., eds. (1999)].

Unless otherwise stated, the following terms used in the specification and claims have the meanings given below:

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in the initiation of DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

The expression of a coding sequence in a host cell may be inducible. By inducible, it is meant that the expression can be regulated. For example, the nucleic acid may be present in the cell, but it is not expressed until a necessary signal is provided. Typically, inducible expression of a protein is controlled by a promoter that requires a necessary signal to induce transcription of the protein. However, expression may also be induced by a process or sequence that increases the number of DNA sequences of interest in the cell. Such processes or sequences include origins of replication, as well as the physical addition of DNA to a cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 65% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding the same amino acid sequence as SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, and 89, but also those which are degenerate to SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, and 90. By "degenerate to" is meant that a different three-letter codon is used to specify a particular amino acid.

"Arrestin" means all types of naturally occurring and engineered variants of arrestin, including, but not limited to, visual arrestin (sometimes referred to as Arrestin 1), cone arrestin (sometimes referred to as arrestin-4), β-arrestin 1 (sometimes referred to as Arrestin 2), and β-arrestin 2 (sometimes referred to as Arrestin 3).

"βARK1" is a GRK termed β-adrenergic receptor kinase 1, also called GRK2.

"βAR" is a GPCR termed a β-adrenergic receptor.

"Internalization" of a GPCR is the translocation of a GPCR from the cell surface membrane to an intracellular vesicular membrane, where it may be inaccessible to substances remaining outside the cell.

"Carboxyl-terminal tail" means the carboxyl-terminal tail of a GPCR following membrane span 7. The carboxyl-terminal tail of many GPCRs begins shortly after the conserved NPXXY motif that marks the end of the seventh transmembrane domain (i.e. what follows the NPXXY motif is the carboxyl-terminal tail of the GPCR). The carboxyl-terminal tail may be relatively long (approximately tens to hundreds of amino acids), relatively short (approximately tens of amino acids), or virtually non-existent (less than approximately ten amino acids). As used herein, "carboxyl-terminal tail" shall mean all three variants (whether relatively long, relatively short, or virtually non-existent), and may or may not contain palmitoylated cysteine residue(s).

"Class A receptors" preferably do not translocate together with arrestin proteins to endocytic vesicles or endosomes in association with arrestin-GFP in HEK-293 cells.

"Class B receptors" preferably do translocate together with arrestin proteins to endocytic vesicles or endosomes associated with arrestin-GFP in HEK-293 cells.

"DACs" mean any desensitization active compounds. Desensitization active compounds are any compounds that influence the GPCR desensitization mechanism by either stimulating or inhibiting the process. DACs may influence the GPCR desensitization pathway by acting on any cellular component of the process, as well as any cellular structure implicated in the process, including but not limited to: arrestins, GRKs, GPCRs, phosphoinositide 3-kinase, AP-2 protein, clathrin, protein phosphatases, and the like. DACs may include, but are not limited to, compounds that inhibit arrestin translocating to a GPCR, compounds that inhibit arrestin binding to a GPCR, compounds that stimulate arrestin translocating to a GPCR, compounds that stimulate arrestin binding to a GPCR, compounds that inhibit GRK phosphorylation of a GPCR, compounds that stimulate GRK phosphorylation of a GPCR, compounds that stimulate or inhibit GRK binding to a GPCR, compounds that inhibit protein phosphatase dephosphorylation of a GPCR, compounds that stimulate protein phosphatase dephosphorylation of a GPCR, compounds that prevent GPCR internalization or recycling to the cell surface, compounds that regulate the release of arrestin from a GPCR, antagonists of a GPCR, inverse agonists and the like. DACs may inhibit or stimulate the GPCR desensitization process and may not bind to the same ligand binding site of the GPCR as traditional agonists and antagonists of the GPCR. DACs may act independently of the GPCR, i.e., they do not have high specificity for one particular GPCR or one particular type of GPCRs. DACs may bind the same site(s) as agonist or antagonist but do not desensitize the receptor (perhaps by not altering the receptor to be properly phosphorylated or bind to arrestin or any other protein). DACs may bind to allosteric sites on the receptor and inhibit or enhance desensitization.

"Detectable molecule" means any molecule capable of detection by spectroscopic, photochemical, biochemical, immunochemical, electrical, radioactive, and optical means, including but not limited to, fluorescence, phosphorescence, and bioluminescence and radioactive decay. Detectable molecules include, but are not limited to, GFP, luciferase, β-galactosidase, rhodamine-conjugated antibody, and the like. Detectable molecules include radioisotopes, epitope tags, affinity labels, enzymes, fluorescent groups, chemiluminescent groups, and the like. Detectable molecules include molecules which are directly or indirectly detected as a function of their interaction with other molecule(s).

"GFP" means Green Fluorescent Protein which refers to various naturally occurring forms of GFP which may be isolated from natural sources or genetically engineered, as well as artificially modified GFPs. GFPs are well known in the art. See, for example, U.S. Pat. Nos. 5,625,048; 5,777, 079; and 6,066,476. It is well understood in the art that GFP is readily interchangeable with other fluorescent proteins, isolated from natural sources or genetically engineered, including but not limited to, yellow fluorescent proteins (YFP), red fluorescent proteins (RFP), cyan fluorescent proteins (CFP), blue fluorescent proteins, luciferin, UV excitable fluorescent proteins, or any wave-length in between. As used herein, "GFP" shall mean all fluorescent proteins known in the art.

"Unknown or Orphan Receptor" means a GPCR whose ligands are unknown.

"Downstream" means toward a carboxyl-terminus of an amino acid sequence, with respect to the amino-terminus.

"Upstream" means toward an amino-terminus of an amino acid sequence, with respect to the carboxyl-terminus.

Amino acid substitutions may also be introduced to substitute an amino acid with a particularly preferable property. For example, a Cys may be introduced a potential site in order to allow formation of disulfide bridges with another Cys. A H is may be introduced as a particularly "catalytic" residue (i.e., H is can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce some feature of pathology such as for example, elevated blood pressure, respiratory output, etc.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

"Hybridization" means hydrogen bonding, which may be Watson-Crick, Hoogsteen or reversed Hoogsteen hydrogen bonding, between complementary nucleoside or nucleotide bases. For example, adenine (A) and thymine (T) are complementary nucleobases that pair through the formation of hydrogen bonds.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined Tm with washes of higher stringency, if desired.

By "animal" is meant any member of the animal kingdom including vertebrates (e.g., frogs, salamanders, chickens, or horses) and invertebrates (e.g., worms, etc.). "Animal" is also meant to include "mammals." Preferred mammals include livestock animals (e.g., ungulates, such as cattle, buffalo, horses, sheep, pigs and goats), as well as rodents (e.g., mice, hamsters, rats and guinea pigs), canines, felines, primates, lupine, camelid, cervidae, rodent, avian and ichthyes.

"Antagonist(s)" include all agents that interfere with wild-type and/or modified GPCR binding to an agonist, wild-type and/or modified GPCR desensitization, wild-type and/or modified GPCR binding arrestin, wild-type and/or modified GPCR endosomal localization, internalization, and the like, including agents that affect the wild-type and/or modified GPCRs as well as agents that affect other proteins involved in wild-type and/or modified GPCR signaling, desensitization, endosomal localization, resensitization, and the like.

"Modified GPCR" means a GPCR that has one or more modifications in the amino acid sequence of its carboxyl-terminal tail. As such, the carboxyl-terminal tail may be modified in whole or in part. These modifications in the amino acid sequence include mutations of one or more amino acids, insertion of one or more amino acids, deletion of one or more amino acids, and substitutions of one or more amino acids in which one or more amino acids are deleted and one or more amino acids are added in place of the deleted amino acids. Such modified GPCRs are described herein, as well as in U.S. Ser. No. 09/993,844, which is incorporated herein by reference in its entirety.

"GPCR" means G protein-coupled receptor and includes GPCRs naturally occurring in nature, as well as GPCRs which have been modified.

"Putative site of palmitoylation" means an expected site of palmitate addition, preferably a cysteine residue. In the GPCRs used in the present invention, the putative site of palmitoylation is preferably 10 to 25, preferably 15 to 20, amino acid residues downstream of the NPXXY motif.

"Clusters of phosphorylation sites" mean clusters of amino acid residues that may be efficiently phosphorylated and thus readily function as phosphorylation sites. The clusters of amino acids occupy two out of two, two out of three, three out of three positions, three out of four positions, four out of four, four out of five positions, five out of five, and the like consecutive amino acid positions in the carboxyl terminal tail of a GPCR. These clusters of phosphorylation sites are preferably clusters of serine (S) and/or threonine (T) residues. Clusters of phosphorylation sites may be substituted, inserted, or added on to a GPCR sequence so that the resulting modified GPCR binds arrestin with sufficient affinity to recruit arrestin into endosomes.

"NPXXY motif" means a conserved amino acid motif that marks the end of the seventh transmembrane domain. The conserved amino acid motif begins most frequently with asparagine and proline followed by two unspecified amino acids and then a tyrosine. The two unspecified amino acids may vary among GPCRs but the overall NPXXY motif is conserved.

"Abnormal GPCR desensitization" and "abnormal desensitization" mean that the GPCR desensitization pathway is disrupted such that the balance between active receptor and desensitized receptor is altered with respect to wild-type conditions. Either there is more active receptor than normal or there is more desensitized receptor than wild-type conditions. Abnormal GPCR desensitization may be the result of a GPCR that is constitutively active or constitutively desensitized, leading to an increase above normal in the signaling of that receptor or a decrease below normal in the signaling of that receptor.

"Biological sample" is intended to include tissues, cells and biological fluids isolated from a subject, as well as tissues, cells and fluids present within a subject; wherein said sample can be blood, serum, a urine sample, a fecal sample, a tumor sample, a cellular wash, an oral sample, sputum, biological fluid, a tissue extract, freshly harvested cells, or cells which have been incubated in tissue culture.

"Concurrent administration," "administration in combination," "simultaneous administration," or "administered simultaneously" mean that the compounds are administered at the same point in time or sufficiently close in time that the results observed are essentially the same as if the two or more compounds were administered at the same point in time.

"Conserved abnormality" means an abnormality in the GPCR pathway, including but not limited to, abnormalities in GPCRs, GRKs, arresting, AP-2 protein, clathrin, protein phosphatase and the like, that may cause abnormal GPCR signaling. This abnormal GPCR signaling may contribute to a GPCR-related disease.

"Desensitized GPCR" means a GPCR that presently does not have ability to respond to agonist and activate conventional G protein signaling.

"Desensitization pathway" means any cellular component of the desensitization process, as well as any cellular structure implicated in the desensitization process and subsequent processes, including but not limited to, arresting, GRKs, GPCRS, AP-2 protein, clathrin, protein phosphatases, and the like. In the methods of assaying of the present invention, the polypeptides may be detected, for example, in the cytoplasm, at a cell membrane, in clathrin-coated pits, in endocytic vesicles, endosomes, any stages in between, and the like.

"GPCR signaling" means GPCR induced activation of G proteins. This may result in, for example, cAMP production.

"G protein-coupled receptor kinase" (GRK) includes any kinase that has the ability to phosphorylate a GPCR. Certain GRKs which may be used in the present invention are listed in FIG. 2A-2Q. Splice variants, biologically active fragments, modified GRKs, and GRKs from animals and other organisms are included.

"*Homo sapiens* GPCR" means a naturally occurring GPCR in a *Homo sapiens*.

"Inverse agonist" means a compound that, upon binding to the GPCR, inhibits the basal intrinsic activity of the GPCR. An inverse agonist is a type of antagonist.

"Modified GRK" means a GRK modified such that it alters desensitization.

"Naturally occurring GPCR" means a GPCR that is present in nature.

"Odorant ligand" means a ligand compound that, upon binding to a receptor, leads to the perception of an odor including a synthetic compound and/or recombinantly produced compound including agonist and antagonist molecules.

"Odorant receptor" means a receptor protein normally found on the surface of olfactory neurons which, when activated (normally by binding an odorant ligand) leads to the perception of an odor.

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Sensitized GPCR" means a GPCR that presently has ability to respond to agonist and activate conventional G protein signaling.

"Modulation" includes at least an up-regulation or down-regulation of the expression, or an increase or decrease in activity of a protein. Modulation of a protein includes the up-regulation, down-regulation, increase or decrease in activity of a protein or compound that regulates a protein. Modulation also includes the regulation of the gene, the mRNA, or any other step in the synthesis of the protein of interest.

An "overexpressed" protein refers to a protein that is expressed at levels greater than wild-type expression levels.

"Modified GRK" means a GRK that has one or more modifications in the amino acid sequence at the C-terminus of the GRK. The modified GRK constitutively localizes to the plasma membrane. Preferably, the GRK is modified by the addition of a CMX motif.

"CAAX" (SEQ ID NO:95) motif means a four amino acid sequence, wherein C is cysteine; A is an aliphatic amino acid; and X is the C-terminal amino acid of the protein.

A "constitutive" activity means an activity that occurs in the absence of agonist. For example, the modified GRK constitutively localizes to the plasma membrane means that the modified GRK localizes to the plasma membrane in the absence of agonist.

"GRK-C20" refers to a modified GRK which has the ability to have a geranylgeranyl group added to it. GRK2-C20 is a GRK2 modified in this manner. Preferably, the GRK-C20 contains a CAAX motif.

The present inventors developed an agonist-independent method to screen for compounds that alter GPCR desensitization. They developed cell lines in which GPCRs are desensitized in the absence of agonist. These cell lines include GRKs, which may be modified. Using these cell lines, they developed methods to screen for compounds that alter GPCR desensitization in the absence of agonist. These methods eliminate the step of agonist addition from the screening method. The elimination of this step (1) creates more efficient screening methods for compounds that alter desensitization of GPCRs with known agonists, and (2) provides screening methods for compounds that alter desensitization of orphan GPCRs, which have no known agonist. They developed methods to determine if a GPCR is expressed at the plasma membrane, and determine if the GPCR has an affinity for arrestin; preferably these methods utilize an orphan GPCR and host cells containing a GRK, wherein the GPCR is at least partially internalized in an agonist-independent manner upon expression of the GRK, thus eliminating the need for agonist addition. They modified GPCRs to increase their affinities for arrestin. These modified GPCRs are useful in the agonist-independent methods to screen for compounds that alter desensitization.

GPCRs and Desensitization

The exposure of a GPCR to agonist produces rapid attenuation of its signaling ability that involves uncoupling of the receptor from its cognate heterotrimeric G-protein. The cellular mechanism mediating agonist-specific or homologous desensitization is a two-step process in which agonist-occupied receptors are phosphorylated by a G protein-coupled receptor kinases (GRKs) and then bind an arrestin protein.

It is known that after agonists bind GPCRs, G-protein coupled receptor kinases (GRKs) phosphorylate intracellular domains of GPCRs. After phosphorylation, an arrestin protein associates with the GRK-phosphorylated receptor and uncouples the receptor from its cognate G protein. The interaction of the arrestin with the phosphorylated GPCR terminates GPCR signaling and produces a non-signaling, desensitized receptor.

The arrestin bound to the desensitized GPCR targets the GPCR to clathrin-coated pits or other cellular machinery for endocytosis (i.e., internalization) by functioning as an adaptor protein, which links the GPCR to components of the endocytic machinery, such as adaptor protein-2 (AP-2) and clathrin. The internalized GPCRs are dephosphorylated and are recycled back to the cell surface resensitized, or are retained within the cell and degraded. The stability of the interaction of arrestin with the GPCR is one factor that dictates the rate of GPCR dephosphorylation, recycling, and resensitization. The involvement of GPCR phosphorylation and dephosphorylation in the desensitization process has been exemplified in U.S. Ser. No. 09/933,844, filed Nov. 5, 2001, the disclosure of which is hereby incorporated by reference in its entirety.

Using methods described herein, the present inventors identified certain GPCRs which do not have an affinity for arrestin. They modified these GPCRs to comprise one or more sites of phosphorylation, preferably clusters of phosphorylation sites, properly positioned in their carboxyl-terminal tail. This modification allows the modified GPCR to form a stable complex with an arrestin that will internalize as a unit into endosomes. These modified GPCRs may be useful in methods of assaying GPCR activity. These modified GPCRs may be useful to identify agonists of the GPCRs. These modified GPCRs may be useful in the agonist-independent screening methods described herein.

Agonist-independent screening methods using GPCRs altered to contain a DRY motif are described in U.S. Ser. No. 10/054,616, which is incorporated herein by reference in its entirety. The alteration of the GPCR is included in that screening process; each GPCR to be utilized must be altered in that manner.

The present inventors developed agonist-independent screening methods using GRKs, which may be modified. These GRKs phosphorylate GPCRs in the absence of agonist. These phosphorylated GPCRs internalize in the absence of agonist. The present inventors developed agonist-independent methods of screening for antagonists of GPCR internalization utilizing these modified GRKs. These methods do not require the GPCR alterations described in U.S. Ser. No. 10/054,616.

Previously, certain GRKs were shown to constitutively localize in the plasma membrane. Inglese et al constructed GRK2-C20 which was constitutively isoprenylated and localized to the membranes.

The present inventors determined that cellular expression of GRKs that constitutively localize in the plasma membrane results in constitutive desensitization of GPCRs. These GRKs may be over-expressed, their expression may be inducible, the nucleic acids encoding them may be located in a vector or integrated into the genome. The present inventors constructed host cell expressing a GRK that constitutively localizes in the plasma membrane. These host cells may also express arrestin. To these host cells, they introduced a GPCR of interest. Using the GRK-containing cells, they developed methods to determine if a GPCR of interest is expressed at the plasma membrane, analyze the ability of a GPCR to bind arrestin, and detect constitutively desensitized GPCRs. They built upon these desensitization methods and developed agonist-independent methods of identifying compounds that alter GPCR desensitization. These methods are useful for the identification of compounds that alter the internalization of GPCRs, whether the GPCR agonist is known or unknown.

The present inventors also determined that increased expression of wild-type or modified GRKs increased desensitization, irrespective of whether the GRK constitutively localized in the plasma membrane.

The present invention is related to modified GPCRs, polypeptides of modified GPCRs, nucleic acid molecules that encode the modified GPCRs, vectors containing the nucleic acid molecules which encode the modified GPCRs, vectors enabling the nucleic acid construction of the modified GPCRs, and cells containing modified GPCRs. The invention further relates to assay systems using the modified GPCRs, assay systems using the cells containing modified GPCRs, compounds identified using the assay systems, methods of treatment using the compounds identified, methods of disease diagnosis using the assay systems, and kits containing assay reagents of the present invention and cells of the present invention.

Mutations can be made in the GPCR or modified GPCR such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

In a particular embodiment, the modified GPCRs of the present invention include GPCRs that have been modified to have one or more sites of phosphorylation, preferably clusters of phosphorylation sites, properly positioned in its carboxyl-terminal tail. These modified GPCRs recruit arrestin to endosomes within approximately 30 minutes of agonist stimulation. These modified GPCRs recruit arrestin to endosomes in the cells described herein, in which the GPCR is phosphorylated in an agonist-independent manner.

The modified GPCRs of the present invention comprise one or more sites of phosphorylation, preferably one or more clusters of phosphorylation sites, properly positioned in its carboxyl-terminal tail. The present inventors have discovered that GPCRs containing one or more sites of phosphorylation, preferably clusters of phosphorylation sites, properly positioned in its carboxyl-terminal tail have an increased affinity for arrestin and colocalize with arrestin in endosomes upon GPCR phosphorylation, either after stimulation with agonist or in an agonist-independent manner as described herein. The present inventors have also discovered that the one or more sites of phosphorylation, preferably clusters of phosphorylation sites, must be optimally positioned within the GPCR tail for the GPCR to have an increased affinity for arrestin. Therefore, the modified GPCRs may be constructed such that the one or more sites of phosphorylation, preferably clusters of phosphorylation sites, are optimally positioned within the carboxyl-terminal tail. The portions of polypeptides, which are to be fused together to form the modified GPCR, are chosen such that the one or more sites of phosphorylation, preferably clusters of phosphorylation sites, are reliably positioned properly within the carboxyl-terminal tail. In the alternative, the location of discrete point mutations to create the modified GPCR may be chosen so that the one or more sites of phosphorylation, preferably clusters of phosphorylation sites, are properly positioned within the carboxyl-terminal tail.

The present inventors have discovered that the modified GPCRs of the present invention are useful in assays for screening compounds that may alter G protein-coupled receptor (GPCR) activity. Examples of assays in which the present invention may be used include, but are not limited to, those as described in U.S. Pat. Nos. 5,891,646 and 6,110,693, the disclosures of which are hereby incorporated by reference in their entireties. Additional examples of assays in which the present invention may be used include, but are not limited to, assays using Fluorescent Resonance Energy Transfer (FRET) and assays using Bioluminescence Resonance Energy Transfer (BRET) technology as described in Angers, S., Salahpour, A., Joly, E., Hilairet, S., Chelsky, "$β_2$-adrenergic receptor dimerization in living cells using bioluminescence resonance energy transfer (BRET)," Proc. Natl, Acad. Sci. USA 97, 7: 3684-3689.

The present inventors have determined that these modified GPCRs are useful in agonist-independent assays for screening compounds that may alter GPCR internalization. Examples of assays in which the present invention may be used include, but are not limited to, assays described herein.

Methods of Enhancing GPCR Desensitization

Provided in the present invention are methods of enhancing GPCR desensitization. One embodiment is related to the expression of GRKs, which may be modified. The GRKs may be over-expressed or their expression may be inducible. These methods may be used to analyze the desensitization of a GPCR, including a modified GPCR, an orphan GPCR, a taste receptor, a mutant GPCR, the β2AR Y326A GPCR mutant, or another GPCR. Certain GPCRs useful in the present invention are listed in FIG. 1A-1C.

In a preferred embodiment, a cell is provided that contains an expression system and a nucleic acid encoding a GRK. The GRK may be modified such that the expression of the GRK results in constitutive desensitization of the GPCR. The GRK may be over-expressed and its expression may be inducible.

Preferably, host cells are provided which include a GRK, which may be modified, and arrestin. A GPCR is then added to these cells. The agonist-independent desensitization of the GPCR is detected. FIGS. 4, 5, 6, and 7 are examples of this method. Detection methods are described below.

The present invention provides methods of determining if the GPCR of interest is expressed at the plasma membrane. GPCRs expressed at the plasma membrane are useful in the previously mentioned methods of compound identification.

A preferred method of determining if a GPCR of interest is expressed at the plasma membrane includes: (a) providing a cell including a GPCR, an arrestin, and a GRK, wherein the arrestin is detectably labeled; (b) determining the cellular distribution of the arrestin; and (c) correlating the cellular distribution of the arrestin to the ability of the GPCR to be expressed at the plasma membrane.

Preferred embodiments of this aspect of the invention are described in Examples 2, 3, 4, 5, 6, and 7 and illustrated in FIGS. 4, 5, 6, and 7.

Another method of determining if a GPCR of interest is expressed at the plasma membrane includes: (a) providing a cell comprising a GPCR and a GRK, wherein the GRK is detectably labeled; (b) determining the cellular distribution of the GRK; and (c) correlating the cellular distribution of the GRK to the ability of the GPCR to be expressed at the plasma membrane.

The present invention provides methods of analyzing the ability of a GPCR to bind arrestin. GPCRs which bind arrestin are useful in the previously mentioned methods of compound identification.

A preferred method of analyzing the ability of a GPCR to bind arrestin includes: (a) providing a cell including a GPCR, an arrestin, and a GRK, wherein the arrestin is detectably labeled; (b) determining the cellular distribution of the arrestin; and (c) correlating the cellular distribution of the arrestin to the ability of the GPCR to bind arrestin.

Preferred embodiments of this aspect of the invention are described in Examples 2, 3, 4, 5, 6, and 7, and illustrated in FIGS. 4, 5, 6, and 7.

Using this method, certain GPCRs will bind arrestin and desensitize. However, certain GPCRs will not desensitize without modification of the GPCR, as described in U.S. Ser. No. 09/993,844. The present inventors modified several GPCRs, including known and orphan GPCRs, listed in FIG. 3A-3BB. Upon modification, these modified GPCRs constitutively desensitized in the above system.

Modified GPCRs

The present invention is related to modified GPCRs. Modified GPCRs of the present invention may comprise one or more modifications in their carboxyl-terminal tail. These modifications may comprise inserting one or more sites of phosphorylation, preferably clusters of phosphorylation sites, within certain regions of the carboxyl-terminal tail. As such, the carboxyl-terminal tail may be modified in whole or in part. The carboxyl-terminal tail of many GPCRs begins shortly after a conserved NPXXY motif that marks the end of the seventh transmembrane domain (i.e. what follows the NPXXY motif is the carboxyl-terminal tail of the GPCR). The carboxyl-terminal tail of many GPCRs comprises a putative site of palmitoylation approximately 10 to 25 amino acid residues, preferably 15 to 20 amino acid residues, downstream of the NPXXY motif. This site is typically one or more cysteine residues. The carboxyl-terminal tail of a GPCR may be relatively long, relatively short, or virtually non-existent. The present inventors have determined that the carboxyl-terminal tail of a GPCR determines the affinity of arrestin binding.

The present inventors have discovered that specific amino acid motifs in the carboxyl-terminal tail promote formation of a stable GPCR/arrestin complex and thus ultimately may promote recruitment of arrestin to endosomes. These amino acid motifs comprise one or more amino acids, preferably clusters of amino acid residues, that may be efficiently phosphorylated and thus readily function as phosphorylation sites. The clusters of amino acids may occupy two out of two, two out of three, three out of three, three out of four positions, four out of four, four out of five positions, five out of five, and the like consecutive amino acid positions. Accordingly, the clusters of amino acids that promote formation of a stable GPCR/arrestin complex are "clusters of phosphorylation sites." These clusters of phosphorylation sites are preferably clusters of serine and threonine residues.

GPCRs that form stable complexes with arrestin comprise one or more sites of phosphorylation, preferably clusters of phosphorylation sites. In addition to the presence of the one or more sites of phosphorylation, preferably clusters of phosphorylation sites, it has been discovered that the sites must be properly positioned within the carboxyl-terminal tail to promote formation of a stable GPCR/arrestin complex. To promote formation of a stable GPCR/arrestin complex, the one or more sites of phosphorylation, preferably one or more clusters of phosphorylation, may be approximately 15 to 35 (preferably 15 to 25) amino acid residues downstream of a putative site of palmitoylation of the GPCR. In addition, the one or more sites of phosphorylation, preferably one or more clusters of phosphorylation, may be approximately 20 to 55 (preferably 30 to 45) amino acid residues downstream of the NPXXY motif of the GPCR. GPCRs containing one or more sites of phosphorylation, preferably clusters of phosphorylation sites, properly positioned are typically Class B receptors.

By way of example, it has been discovered that the V2R receptor comprises a cluster of phosphorylation sites (SSS) that promotes formation of a stable GPCR/arrestin complex at 19 amino acid residues downstream of the putative site of palmitoylation and 36 amino acid residues downstream of the NPXXY motif. The NTR-2 receptor comprises a cluster of phosphorylation sites (STS) that promotes formation of a stable GPCR/arrestin complex at 26 amino acid residues downstream of the putative site of palmitoylation and 45 amino acid residues downstream of the NPXXY motif. The oxytocin receptor (OTR) receptor comprises two clusters of phosphorylation sites (SSLST (SEQ ID NO: 91) and STLS (SEQ ID NO: 92)) that promote formation of a stable GPCR/arrestin complex, one at 20 amino acid residues downstream of the putative site of palmitoylation and the other at 29 amino acid residues downstream of the putative site of palmitoylation, and one at 38 amino acid residues downstream of the NPXXY motif and the other at 47 amino acid residues downstream of the NPXXY motif, respectively. The substance P receptor (SPR, also known as the neurokinin-1 receptor) comprises a cluster of phosphorylation sites (TTIST) (SEQ ID NO: 93) that promotes formation of a stable GPCR/arrestin complex at 32 amino acid residues downstream of the putative site of palmitoylation and 50 amino acid residues downstream of the NPXXY motif.

The present inventors have determined that GPCRs that lack one or more sites of phosphorylation, preferably clusters of phosphorylation, properly positioned within the carboxyl terminal tail form GPCR/arrestin complexes that are less stable and dissociate at or near the plasma membrane. These GPCRs are typically Class A receptors, olfactory receptors, taste receptors, and the like. However, the present inventors have discovered that stable GPCR/arrestin complexes may be achieved with GPCRs naturally lacking one or more sites of phosphorylation and having a lower affinity for arrestin by modifying the carboxyl-terminal tails of these receptors. Preferably, the carboxyl-terminal tails are modified to include one or more sites of phosphorylation, preferably one or more clusters of phosphorylation sites, properly positioned within the carboxyl terminal tail.

The present invention includes the polypeptide sequences of these modified GPCRs. The modified GPCRs of the present invention include GPCRs that have been modified to have one or more sites of phosphorylation, preferably one or more clusters of phosphorylation, properly positioned in their carboxyl terminal tails. The polypeptide sequences of the modified GPCRs of the present invention also include sequences having one or more additions, deletions, substitutions, or mutations. These mutations are preferably substitution mutations made in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The present invention should be considered to include sequences containing conservative changes which do not significantly alter the activity or binding characteristics of the resulting protein.

The modified GPCRs of the present invention include GPCRs containing a NPXXY motif, a putative site of palmitoylation approximately 10 to 25 amino acid residues (preferably 15 to 20 amino acids) downstream of the NPXXY motif, and a modified carboxyl-terminal tail. The modified carboxyl-terminal tail has one or more sites of phosphorylation, preferably one or more clusters of phosphorylation sites, such that the phosphorylation sites are approximately 15 to 35, preferably 15 to 25, amino acid residues downstream of the putative site of palmitoylation of the modified GPCR. The modified carboxyl-terminal tail may have one or more sites of phosphorylation, preferably one or more clusters of phosphorylation sites, such that the phosphorylation sites are approximately 20 to 55, preferably 30 to 45, amino acid residues downstream of the NPXXY of the modified GPCR.

The present invention further includes isolated nucleic acid molecules that encode modified GPCRs. It should be appreciated that also within the scope of the present invention are DNA sequences encoding modified GPCRs which code for a modified GPCR having the same amino acid sequence as the modified GPCRs, but which are degenerate. By "degenerate to" it is meant that a different three-letter codon is used to specify a particular amino acid.

As one of skill in the art would readily understand, the carboxyl-tail of many GPCRs may be identified by the conserved NPXXY motif that marks the end of the seventh transmembrane domain.

To create a modified GPCR containing a modified carboxyl-terminus region according to the present invention, a GPCR lacking phosphorylation sites or clusters of phosphorylation sites or with a lower or unknown affinity for arrestin may have one or more additions, substitutions, deletions, or mutations of amino acid residues in its carboxyl-terminal tail. These additions, substitutions, deletions, or mutations are performed such that the carboxyl-terminal tail is modified to comprise one or more sites of phosphorylation, preferably clusters of phosphorylation sites. By way of example, discrete point mutations of the amino acid residues may be made to provide a modified GPCR. By way of example three consecutive amino acids may be mutated to serine residues to provide a modified GPCR. These mutations are made such that the one or more sites of phosphorylation, preferably clusters of phosphorylation sites, are properly positioned within the carboxyl terminal tail.

In addition, to create a modified GPCR containing a modified carboxyl-terminal tail region, mutations may be made in a nucleic acid sequence of a GPCR lacking sites of phosphorylation or clusters of phosphorylation sites or with a lower or unknown affinity for arrestin such that a particular codon is changed to a codon which codes for a different amino acid, preferably a serine or threonine. Such a mutation is generally made by making the fewest nucleotide changes possible. A substitution mutation of this sort can be made to change an amino acid in the resulting protein to create one or more sites of phosphorylation, preferably clusters of phosphorylation sites. Also by way of example, discrete point mutations of the nucleic acid sequence may be made. The phosphorylation sites are positioned such that they are located approximately 15 to 35 amino acid residues downstream of the putative site of palmitoylation of the modified GPCR.

Furthermore, to provide modified GPCRs of the present invention, a GPCR lacking properly positioned phosphorylation sites or with a lower or unknown affinity for arrestin may also have its carboxyl-terminal tail, in whole or in part, exchanged with that of a GPCR having properly positioned clusters of phosphorylation sites. The site of exchange may be after or including the conserved NPXXY motif. As an alternative, a putative site of palmitoylation of a GPCR may be identified at approximately 10 to 25 (preferably 15 to 20) amino acid residues downstream of the conserved NPXXY motif, and the site of exchange may be after or including the palmitoylated cysteine(s). Preferably, the carboxyl-terminal tail of a GPCR lacking properly positioned clusters of phosphorylation sites or with a lower or unknown affinity for arrestin is exchanged at an amino acid residue in close proximity to a putative site a palmitoylation. More preferably, the carboxyl-terminal tail of a GPCR lacking properly positioned clusters of phosphorylation sites or with a lower or unknown affinity for arrestin is exchanged at a putative site of palmitoylation approximately 10 to 25 (preferably 15 to 20) amino acid residues downstream of the NPXXY motif, such that the palmitoylated cysteine residue is maintained. Exchanging in the preferred manner allows the clusters of phosphorylation sites to be reliably positioned properly within the carboxyl-terminal tail of the modified GPCR. The tails may be exchanged and the modified GPCRs may be constructed accordingly by manipulation of the nucleic acid sequence or the corresponding amino acid sequence.

In a further alternative, the carboxyl-tail of a GPCR, for example a GPCR not containing the NPXXY motif, may be predicted from a hydrophobicity plot and the site of exchange may be selected accordingly. Based on a hydrophobicity plot, one of skill in the art may predict a site where it is expected that the GPCR may anchor in the membrane and then predict where to introduce a putative site of palmitoylation accordingly. Using this technique GPCRs having neither a NPXXY motif nor a putative site of palmitoylation may be modified to create a point of reference (e.g. a putative site of palmitoylation). The introduced putative site of palmitoylation may then be used to position a tail exchange.

The carboxyl-terminal tail used for the exchange may be from a second GPCR having one or more properly positioned clusters of phosphorylation sites and having a putative site of palmitoylation approximately 10 to 25 (preferably 15 to 20) amino acid residues downstream of a NPXXY motif. The tail as identified may be exchanged, after or including the conserved NPXXY motif. As an alternative, a putative site of palmitoylation of a GPCR may be identified at approximately 10 to 25 (preferably 15 to 20) amino acid residues downstream of the conserved NPXXY motif, and the tail may be exchanged after or including the palmitoylated cysteine(s). Preferably, the carboxyl-terminal tail of a GPCR having clusters of phosphorylation sites is exchanged at an amino acid residue in close proximity to a putative site of palmitoylation. More preferably, the carboxyl-terminal tail of a GPCR having clusters of phosphorylation sites is exchanged at a putative site of palmitoylation approximately 10 to 25 (preferably 15 to 20) amino acid residues downstream of the NPXXY motif, such that the portion of the carboxyl-terminal tail containing the clusters of phosphorylation sites begins at the amino acid residue immediately downstream of the palmitoylated cysteine residue. Exchanging in the preferred manner allows the clusters of phosphorylation sites to be reliably positioned properly within the carboxyl-terminal tail of the modified GPCR. The carboxyl-terminal tail having clusters of phosphorylation sites used for the exchange may have a detectable molecule conjugated to the carboxyl-terminus. The tails may be exchanged and the modified GPCRs may be constructed accordingly by manipulation of the nucleic acid sequence or the corresponding amino acid sequence.

In addition, the carboxyl-terminal tail portion used for the exchange may originate from a polypeptide synthesized to have an amino acid sequence corresponding to an amino acid sequence from a GPCR having one or more sites of phosphorylation, preferably one or more clusters of phosphorylation sites. The synthesized polypeptide may have a putative site of palmitoylation approximately 10 to 25 (preferably 15 to 20) amino acid residues downstream of a NPXXY motif. The synthesized polypeptide may have one or more additions, substitutions, mutations, or deletions of amino acid residues that does not affect or alter the overall structure and function of the polypeptide.

Furthermore, the carboxyl-terminal tail portion used for the exchange may originate from a naturally occurring polypeptide recognized to have an amino acid sequence corresponding to an amino acid sequence from a GPCR having one or more clusters of phosphorylation sites. The polypeptide may have a putative site of palmitoylation approximately 10 to 25 (preferably 15 to 20) amino acid residues downstream of a NPXXY motif. The polypeptide may have one or more additions, substitutions, mutations, or deletions of amino acid residues that does not affect or alter the overall structure and function of the polypeptide.

A modified GPCR containing a modified carboxyl-terminus region may be created by fusing a first carboxyl-terminal tail portion of a GPCR lacking properly positioned clusters of phosphorylation sites or with a lower or unknown affinity for arrestin with a second carboxyl-terminal tail portion of a GPCR or polypeptide having one or more clusters of phosphorylation sites. The second GPCR or polypeptide used for the exchange may have a putative site of palmitoylation approximately 10 to 25 (preferably 15 to 20) amino acid residues downstream of a NPXXY motif. Accordingly, the modified carboxyl-terminus region of the modified GPCR comprises a portion of a carboxyl-terminal tail from a GPCR lacking properly positioned clusters of phosphorylation sites or with a lower or unknown affinity for arrestin fused to a portion of a carboxyl-terminal tail of a GPCR or polypeptide having clusters of phosphorylation sites. The tail of a GPCR lacking properly positioned clusters of phosphorylation sites may be exchanged after or including the conserved NPXXY motif, and fused to a carboxyl-terminal tail containing clusters of phosphorylation sites, after or including the conserved NPXXY motif. As an alternative, the tail of a GPCR lacking properly positioned clusters of phosphorylation sites may be exchanged after or including the palmitoylated cysteine(s), and fused to a tail containing clusters of phosphorylation sites, after or including the palmitoylated cysteine(s). The tails may be exchanged and the modified GPCRs may be constructed accordingly by manipulation of the nucleic acid sequence or the corresponding amino acid sequence.

In a further alternative, the carboxyl-tail of a GPCR, for example a GPCR not containing the NPXXY motif, may be predicted from a hydrophobicity plot and exchanged accordingly. The site of exchange may be selected according to the hydrophobicity plot. Based on a hydrophobicity plot, one of skill in the art may predict a site where it is expected that the GPCR may anchor in the membrane and then predict where to introduce a putative site of palmitoylation accordingly. Using this technique GPCRs having neither a NPXXY motif nor a putative site of palmitoylation may be modified to create a point of reference (e.g. a putative site of palmitoylation). The introduced putative site of palmitoylation may be then used to position a tail exchange. After introduction of a putative site of palmitoylation, the resulting tail may be fused with a second carboxyl-terminal tail portion of a GPCR or polypeptide having one or more clusters of phosphorylation sites and having a putative site of palmitoylation approximately 10 to 25 (preferably 15 to 20) amino acid residues downstream of a NPXXY motif.

Preferably, the modified carboxyl-terminus region of the modified GPCR is fused at amino acid residues in close proximity to a putative site of palmitoylation. More preferably, the modified carboxyl-terminus region of the modified GPCR is fused such that the portion from the first GPCR with a lower affinity for arrestin comprises amino acid residues from the NPXXY motif through a putative site of palmitoylation approximately 10 to 25 (preferably 15 to 20) amino acid residues downstream of the NPXXY motif and the portion from the second GPCR having clusters of phosphorylation sites and a putative site of palmitoylation approximately 10 to 25 (preferably 15 to 20) amino acid residues downstream of a NPXXY motif comprises amino acid residues beginning with an amino acid residue immediately downstream of the putative site of palmitoylation of the second GPCR extending to the end of the carboxyl-terminus. This fusion is preferred because the clusters of phosphorylation sites are reliably positioned properly within the carboxyl-terminal tail and the modified GPCR maintains its structure and ability to function.

By way of example, a Class A receptor or an orphan receptor may have a portion of its carboxyl-terminal tail exchanged with a portion of a carboxyl-terminal tail from a known Class B receptor. Further, receptors having virtually non-existent carboxyl-terminal tails, for example, olfactory receptors and taste receptors, may have a portion of their carboxyl-terminal tails exchanged with a portion of a carboxyl-terminal tail from a known Class B receptor. The Class B receptor tail used for these exchanges may have a detectable molecule fused to the carboxyl-terminus.

Modified GPCRs may be generated by molecular biological techniques standard in the genetic engineering art, including but not limited to, polymerase chain reaction (PCR), restriction enzymes, expression vectors, plasmids, and the like. By way of example, vectors, such as a pEArrB (enhanced arrestin binding), may be designed to enhance the affinity of a GPCR lacking clusters of phosphorylation sites for arrestin. To form a vector, such as a pEArrB vector, PCR amplified DNA fragments of a GPCR carboxyl-terminus, which forms stable complexes with arrestin, may be digested by appropriate restriction enzymes and cloned into a plasmid. A schematic of one such plasmid is illustrated in FIG. 4A. The DNA of a GPCR, which is to be modified, may also be PCR amplified, digested by restriction enzymes at an appropriate location, and subcloned into the vector, such as pEArrB, as illustrated in FIG. 4B. When expressed, the modified GPCR will contain a polypeptide fused to the carboxyl-terminus. The polypeptide will comprise clusters of phosphorylation sites. Preferably, the polypeptide originates from the GPCR carboxyl-terminus of a receptor that forms stable complexes with arrestin.

Such modified GPCRs may also occur naturally as the result of aberrant gene splicing or single nucleotide polymorphisms. Such naturally occurring modified GPCRs would be predicted to have modified endocytic targeting. These naturally occurring modified GPCRs may be implicated in a number of GPCR-related disease states.

As shown in FIG. 3, the present inventors modified several GPCRs. The β2-adrenergic receptor, dopamine D1A receptor, mu opiod receptor, orphan GPR3, orphan GPR6, orphan GPR12, orphan GPR7, orphan GPR8, orphan GPR55, orphan SREB2, and orphan SREB3 were modified as described herein. These modified GPCRs contain a properly positioned V2R cluster of phosphorylation sites (SSS) within the modified GPCR's tail.

As may be shown by standard receptor binding assays, the modified receptors are essentially indistinguishable from their wild-type counterparts except for an increased affinity for arrestin and thus an increased stability of their complex with arrestin and in their ability to traffic with arrestin and in their ability to recycle and resensitize. For example, the modified receptors are appropriately expressed at the membrane and possess similar affinity for agonists or ligands. However, the modified GPCRs have an increased affinity for arrestin and thus form a more stable complex with arrestin than their wild-type counterparts and may remain bound to arrestin when trafficking to endosomes.

These modified GPCRs are useful in assays to screen for an agonist of the GPCR, as well as in agonist-independent assays to identify compounds that alter GPCR desensitization.

Methods of Assaying GPCR Activity Using the Modified GPCRs

The modified GPCRs of the present invention are useful in methods of assaying GPCR activity. The modified GPCRs of the present invention may be used in assays to study GPCRs that have weaker than desired interactions or associations with arrestins and GPCRs that have unknown interactions or associations with arresting. Methods of the present invention that use the modified GPCRs provide a sensitive assay and may provide for enhanced detection, for example, of arrestin/GPCRs in endosomes. The assays using the modified GPCRs of the present invention may be useful for screening compounds and sample solutions for ligands, agonists, antagonists, inverse agonists, desensitization active compounds, and the like. Once identified, these compounds may be useful as drugs capable of modulating GPCR activity and useful in the treatment of one or more of the disease states in which GPCRs have been implicated.

In a preferred assay according to the present invention, cells are provided that express modified GPCRs of the present invention and these cells may further contain a conjugate of an arrestin and a detectable molecule.

Arrestin coupled to a detectable molecule may be detected and monitored as it functions in the GPCR pathway. The location of the arrestin may be detected, for example, evenly distributed in the cell cytoplasm, concentrated at a cell membrane, concentrated in clathrin-coated pits, localized on endosomes, and the like. In response to agonist stimulation, the proximity of arrestin to a GPCR may be monitored, as well as the proximity to any other cell structure. For example, in response to agonist stimulation arrestin may be detected in proximity to GPCRs at a cell membrane, concentrated with GPCRs in clathrin-coated pits, colocalized with a GPCR on endosomes, and the like.

The modified GPCRs of the present invention have an increased affinity for arrestin and provide a stable complex of the GPCR with arrestin, and thereby promote colocalization of the GPCR with arrestin into endosomes. In the methods of assaying of the present invention, arrestin may be detected, for example, in the cytoplasm, concentrated in proximity to GPCRs at a cell membrane, concentrated in proximity to GPCRs in clathrin-coated pits, colocalized with a GPCR on endosomes, and the like. Preferably the arrestin may be detected colocalized with a GPCR on endosomes.

The association of arrestin with a GPCR at a cell membrane may be rapidly detected after agonist addition, for example, approximately 1 second to 2 minutes. The colocalization of arrestin with GPCR on endosomes may be detected within several minutes of agonist addition, for example, approximately 3 to 15 minutes, and may persist for extended periods of time, for example, after 1 hour. The association of arrestin with GPCR on endosomes may give a strong, readily recognizable signal. Under magnification of 40× objective lens, the signal may be doughnut-like in appearance. The signal resulting from the compartmentalization of arrestin and GPCR colocalized in endosomes vesicles is typically easy to detect and may persist for extended periods of time.

A preferred method of assessing GPCR pathway activity of the present invention comprises (a) providing a cell that expresses at least one modified GPCR of the present invention and that further comprises a conjugate of an arrestin and a detectable molecule; (b) inducing translocation of the arrestin; and (c) detecting interaction of the arrestin with the modified GPCR along the translocation pathway.

Interaction of the arrestin with the modified GPCR may be detected, for example, in endosomes, in clathrin-coated pits, concentrated in proximity to a cell membrane, and the like. Preferably, interaction of the arrestin with the modified GPCR is detected in endosomes. Interaction of arrestin with a GPCR in endosomes may be detected within several minutes of agonist addition, for example, approximately 3 to 15 minutes, and may persist for extended periods of time, for example, after 1 hour. The association of arrestin with a GPCR in endosomes may give a strong, readily recognizable signal that persists for extended periods of time.

In a method of screening compounds for GPCR activity of the present invention a cell that expresses at least one modified GPCR is provided. The cell further contains arrestin conjugated to a detectable molecule. The cell is exposed to the compounds to be tested. The location of the arrestin within the cell is detected. The location of the arrestin within the cell in the presence of the compound is compared to the location of the arrestin within the cell in the absence of the compound, and a difference is correlated between (1) the location of the arrestin within the cell in the presence of the compound and (2) the location of the arrestin within the cell in the absence of the compound.

By way of example, compounds and sample solutions may be screened for GPCR agonist activity using the modified GPCRs of the present invention. In this method, cells that express at least one modified GPCR of the present invention and that further comprise a conjugate of an arrestin and a detectable molecule are provided. The cells are exposed to compounds or sample solutions to be tested. It is detected whether interaction of the arrestin with the modified GPCR is increased after exposure to the test compound or solution, an increase in interaction being an indication that the compound or solution has GPCR agonist activity. Interaction of the arrestin with the GPCR may be detected in endosomes, in clathrin-coated pits, in proximity to a cell membrane, and the like. The modified GPCR may also be conjugated to a detectable molecule, preferably at the carboxyl-terminus. As explained above modifications to GPCRs as in the present invention should not affect the GPCRs' natural affinity for agonists or ligands.

Also by way of example, compounds and sample solutions may be screened for GPCR antagonist or inverse agonist activity using the modified GPCRs of the present invention. Cells that express at least one modified GPCR of the present invention and that further comprise a conjugate of an arrestin and a detectable molecule are provided. The cells are exposed to compounds or sample solutions to be tested and to a known agonist for the GPCR. It is detected whether interaction of the arrestin with the modified GPCR is decreased after exposure to the test compound or solution, a decrease in interaction being an indication that the compound or solution has GPCR antagonist or inverse agonist activity. Interaction of the arrestin with the GPCR may be detected in endosomes, in clathrin-coated pits, in proximity to a cell membrane, and the like. The modified GPCR may also be conjugated to a detectable molecule, preferably at the carboxyl-terminus. As explained above modifications to GPCRs as in the present invention should not affect the GPCRs' natural affinity for antagonists or inverse agonists.

Further by way of example, compounds and sample solutions may be screened for GPCR desensitization activity using the modified GPCRs of the present invention. First cells that express at least one first modified GPCR of the present invention and that further comprise a conjugate of an arrestin and a detectable molecule are provided. The first cells are exposed to compounds or sample solutions to be tested and to a known agonist for the first GPCR. It is detected whether interaction of the arrestin with the first modified GPCR is decreased or not increased after exposure to the test compound or solution, a decrease or lack of increase in interaction being an indication that the compound or solution has GPCR desensitization activity. Interaction of the arrestin with the GPCR may be detected in endosomes, in clathrin-coated pits, in proximity to a cell membrane, and the like. Then second cells that express at least one second modified GPCR of the present invention and that further comprise a conjugate of an arrestin and a detectable molecule are provided. The second modified GPCR is not related to the first modified GPCR. The second cells are exposed to the compounds or sample solutions to be tested and to a known agonist for the second GPCR. It is detected whether interaction of the arrestin with the second modified GPCR is decreased or not increased after exposure to the test compound or solution, a decrease or lack of increase in interaction being an indication that the compound or solution has GPCR desensitization activity independent of the GPCR expressed. Interaction of the arrestin with the GPCR may be detected in endosomes, in clathrin-coated pits, in proximity to a cell membrane, and the like.

The methods of assessing GPCR pathway activity of the present invention also include cell-free assays. In cell-free assays of the present invention, a substrate having deposited thereon a modified GPCR of the present invention is provided. A fluid containing a conjugate of an arrestin and a detectable molecule is also provided. Translocation of the arrestin is induced and interaction of the arrestin with the GPCR is detected. The GPCR and arrestin may be obtained from whole cells and used in the cell-free assay after purification. The modified GPCR has arrestin binding sites and agonist binding sites and may be supported in a multilayer or bilayer lipid vesicle. The vesicle supporting the modified GPCR may be deposited on the substrate, and the modified GPCR may be supported in the lipid vesicle and deposited on the substrate such that the arrestin binding sites are exposed to arrestin and the receptor binding sites are accessible to agonists. The substrate may be any artificial substrate on which the GPCR may be deposited, including but not limited to, glass, plastic, diamond, ceramic, semiconductor, silica, fiber optic, diamond, biocompatible monomer, biocompatible polymer, polymer beads (including organic and inorganic polymers), and the like.

The present invention relates to the compounds identified as ligands, agonists, antagonists, inverse agonists, or DACs by the methods of assaying of the present invention. These compounds may be used to treat any one of the disease states in which GPCRs have been implicated. The compounds identified may be administered to a human or a non-human in therapeutically effective doses to treat or ameliorate a condition, disorder, or disease in which GPCRs have been implicated. A therapeutically effective dose refers to that amount of the compound sufficient to result in amelioration of symptoms of such a condition, disorder or disease.

Methods to Identify Compounds that Modulate GPCR Desensitization

The present invention relates to methods of screening for compounds that modulate GPCR desensitization. The methods utilize modified GRKs which constitutively phosphorylate GPCRs, resulting in constitutive desensitization. These may be used to identify compounds that alter the desensitization of GPCRs, even if the GPCR agonist is unknown. Once identified, these compounds may be useful as drugs capable of modulating GPCR activity and useful in the treatment of one or more of the disease states in which GPCRs have been implicated.

In a preferred method according to the present invention, cells are provided that contain an expression system and a nucleic acid encoding a modified GRK, resulting in constitutive desensitization of GPCRs expressed in the cell. These cells may further contain an arrestin conjugated to a GFP.

A preferred method of identifying a compound which inhibits GPCR internalization includes: (a) providing a cell including a GPCR, an arrestin, and a modified GRK; (b) exposing the cell to the compound(s); (c) determining the cellular distribution of the GPCR or arrestin; and (d) correlating a difference between (1) the location of the labeled molecule in the cell in the presence of the compound(s) and (2) the location of the labeled molecule in the cell in the absence of the compound(s) to modulation of GPCR internalization. Non-limiting embodiments of this method are described in FIGS. 4, 5, 6, and 7 and Examples 2, 3, 4, 5, 6, and 7.

The GRK of step (a), as described above, may be GRK 1, 2, 3, 4, 5, 6, or any other GRK, including splice variants, biologically active fragments, or modified GRKs. The GRK may be overexpressed and/or its expression may be inducible. The GRK may include a CAAX motif.

In the above method, agonist may or may not be provided.

Methods of detecting the labeled molecules and determining the cellular distribution of the GPCR or arrestin are described below.

GPCRs useful in the present invention include, but are not limited to GPCRs which have known agonists, GPCRs which do not have known agonists, GPCRs listed in FIG. 1A-1C, GPCRs illustrated in FIGS. 3, 4, 5, 6, and 7, AT1AR, Class A GPCRs, Class B GPCRs, taste receptors, odorant receptors, orphan receptors, modified GPCRs, GPCRs as described in U.S. patent application Ser. Nos. 10/054,616, 09/993,844, 10/095,620, 10/101,235, 09/631,468,10/141, 725, 10/161,916, 09/469,554, 09/772,644, 60/393,789, and 60/379,986, which are herein incorporated by reference, or biologically active fragments of the above GPCRs.

Vectors and Nucleic Acids, Host Cells for Protein Expression

The present invention relates to modified GRKs, including GRKs which are over-expressed, or their expression is inducible.

Nucleic acids encoding modified GRKs are provided. The present invention relates to the expression, over-expression, and the inducible expression of these proteins. The expression may be carried out by a suitable expression system contained in a vector, as described below.

One aspect of the present invention relates to the combination of (1) nucleic acids encoding a modified GRK with (2) a system for expression of modified GRKs resulting in constitutive desensitization of GPCRs. This system for expression of modified GRKs may include a promoter or origin of replication.

Another aspect of the present invention relates to modified GPCRs, nucleic acids encoding modified GPCRs, and host cell for modified GPCR expression.

Nucleic acids encoding modified GPCRs are provided. The present invention relates to the expression, over-expression, and the inducible expression of these proteins. The expression may be carried out by a suitable expression system contained in a vector, as described below.

A feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host. The transforming DNA may or may not be integrated (covalently linked) into chromosomal DNA making up the genome of the cell.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMB9 and their derivatives, plasmids such as RP4; phage DNAS, e.g., the numerous derivatives of phage A, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences— sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces,* fungi such as yeasts, plant cells, nematode cells, and animal cells, such as HEK-293, U20S, CHO, RI. I, B-W and L-M cells, African Green Monkey kidney cells (e.g., COS 1, COS 7, BSC1, BSC40, and BMT10), insect cells (e.g., Sf9), and human cells and plant cells in tissue culture. In one aspect of the present invention, the host cells include a GRK-C20 and an arrestin. In a further aspect of the present invention, the host cells include a GRK-C20, an arrestin, and a GPCR.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that modified GRK analogs may be prepared from nucleotide sequences of the protein complex/ subunit derived within the scope of the present invention. Analogs, such as fragments, may be produced, for example, by pepsin digestion of GRK material. Other analogs, such as muteins, can be produced by standard site-directed mutagenesis of GRK coding sequences. Analogs exhibiting "GRK activity" such as small molecules, whether functioning as promoters or inhibitors, may be identified by known in vivo and/or in vitro assays.

As mentioned above, a DNA sequence encoding a modified GRK6 can be prepared synthetically rather than cloned. The DNA sequence can be designed with the appropriate codons for the GRK amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311 (1984).

Synthetic DNA sequences allow convenient construction of genes which will express GRK analogs or "muteins". Alternatively, DNA encoding muteins can be made by site-directed mutagenesis of native or modified GRK genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, Science, 244:182-188 (April 1989). This method may be used to create analogs with unnatural amino acids.

Additional motifs, such as epitope tags or sequences to aid in purification, may be incorporated into the nucleic acids encoding the modified GRKs or modified GPCRs. Preferably, the nucleic acids encoding the motifs may be at the 5' or 3' end of the nucleic acid, resulting in the presence of the motif at the N or C terminus of the protein.

The Conjugates

The cells used in the methods of assaying of the present invention may comprise a conjugate of an arrestin protein and a detectable molecule. In the cells and methods of the present invention, the cells may also comprise a conjugate of a modified GPCR of the present invention and a detectable molecule.

All forms of arrestin, naturally occurring and engineered variants, including but not limited to, visual arrestin, cone arrestin, βarrestin 1 and βarrestin 2, may be used in the present invention. The modified GPCRs of the present invention may interact to a detectable level with all forms of arrestin.

Detectable molecules that may be used to conjugate with the arrestin include, but are not limited to, molecules that are detectable by spectroscopic, photochemical, biochemical, immunochemical, electrical, radioactive, and optical means, including but not limited to bioluminescence, phosphorescence, and fluorescence. Detectable molecules include, but are not limited to, GFP, luciferase, β-galactosidase, rhodamine-conjugated antibody, and the like. Detectable molecules include radioisotopes, epitope tags, affinity labels, enzymes, fluorescent groups, chemiluminescent groups, and the like. Detectable molecules include molecules which are directly or indirectly detected as a function of their interaction with other molecule(s). These detectable molecules should be a biologically compatible molecule and should not compromise the ability of the arrestin to interact with the GPCR system and the interaction of the arrestin with the GPCR system must not compromise the ability of the detectable molecule to be detected. Preferred detectable molecules are optically detectable molecules, including optically detectable proteins, such that they may be excited chemically, mechanically, electrically, or radioactively to emit fluorescence, phosphorescence, or bioluminescence. More preferred detectable molecules are inherently fluorescent molecules, such as fluorescent proteins, including, for example, Green Fluorescent Protein (GFP). The detectable molecule may be conjugated to the arrestin protein by methods as described in Barak et al. (U.S. Pat. Nos. 5,891,646 and 6,110,693). The detectable molecule may be conjugated to the arrestin at the front-end, at the back-end, or in the middle.

The GPCR or biologically active fragments thereof may also be conjugated with a detectable molecule. Preferably, the carboxyl-terminus of the GPCR is conjugated with a detectable molecule. A carboxyl-terminal tail conjugated or attached to a detectable molecule can be used in a carboxyl-terminal tail exchange to provide the detectably labeled GPCR.

If the GPCR is conjugated with a detectable molecule, proximity of the GPCR with the arrestin may be readily detected. In addition, if the GPCR is conjugated with a detectable molecule, compartmentalization of the GPCR with the arrestin may be readily confirmed. The detectable molecule used to conjugate with the GPCRs may include those as described above, including, for example, optically detectable molecules, such that they may be excited chemically, mechanically, electrically, or radioactively to emit fluorescence, phosphorescence, or bioluminescence. Preferred optically detectable molecules may be detected by immunofluorescence, luminescence, fluorescence, and phosphorescence.

For example, the GPCRs may be antibody labeled with an antibody conjugated to an immunofluorescence molecule or the GPCRs may be conjugated with a luminescent donor. In particular, the GPCRs may be conjugated with, for example, luciferase, for example, *Renilla luciferase*, or a rhodamine-conjugated antibody, for example, rhodamine-conjugated anti-HA mouse monoclonal antibody. Preferably, the carboxyl-terminal tail of the GPCR may be conjugated with a luminescent donor, for example, luciferase. The GPCR, preferably the carboxyl-terminal tail, also may be conjugated with GFP as described in L. S. Barak et al. "Internal Trafficking and Surface Mobility of a Functionally Intact $\beta_2$-Adrenergic Receptor-Green Fluorescent Protein Conjugate", *Mol. Pharm.* (1997) 51, 177-184.

Cell Types and Substrates

The cells of the present invention may express at least one modified GPCR of the present invention. The cells may further comprise a conjugate of an arrestin protein and a detectable molecule. Useful cells include eukaryotic and prokaryotic cells, including, but not limited to, bacterial cells, yeast cells, fungal cells, insect cells, nematode cells, plant cells, and animal cells. Suitable animal cells include, but are not limited to, HEK-293 cells, U2OS cells, HeLa cells, COS cells, and various primary mammalian cells. An animal model expressing a conjugate of an arrestin and a detectable molecule throughout its tissues or within a particular organ or tissue type, may also be used.

The cells of the present invention may express one modified protein that results in agonist-independent localization of GPCRs to endocytic vesicles or endosomes.

A substrate may have deposited thereon a plurality of cells of the present invention. The substrate may be any suitable biologically substrate, including but not limited to, glass, plastic, ceramic, semiconductor, silica, fiber optic, diamond, biocompatible monomer, or biocompatible polymer materials.

Methods of Detection

Methods of detecting the intracellular location of the detectably labeled arrestin, the intracellular location of a detectably labeled GPCR, or interaction of the detectably labeled arrestin, or other member of GPCR/arrestin complex with a GPCR or any other cell structure, including for example, the concentration of arrestin or GPCR at a cell membrane, colocalization of arrestin with GPCR in endosomes, and concentration of arrestin or GPCR in clathrin-coated pits, and the like, will vary dependent upon the detectable molecule(s) used.

One skilled in the art readily will be able to devise detection methods suitable for the detectable molecule(s) used. For optically detectable molecules, any optical method may be used where a change in the fluorescence, bioluminescence, or phosphorescence may be measured due to a redistribution or reorientation of emitted light. Such methods include, for example, polarization microscopy, BRET, FRET, evanescent wave excitation microscopy, and standard or confocal microscopy.

In a preferred embodiment arrestin may be conjugated to GFP and the arrestin-GFP conjugate may be detected by confocal microscopy. In another preferred embodiment, arrestin may conjugated to a GFP and the GPCR may be conjugated to an immunofluorescent molecule, and the conjugates may be detected by confocal microscopy. In an additional preferred embodiment, arrestin may conjugated to a GFP and the carboxy-terminus of the GPCR may be conjugated to a luciferase and the conjugates may be detected by bioluminescence resonance emission technology. In a further preferred embodiment arrestin may be conjugated to a luciferase and GPCR may be conjugated to a GFP, and the conjugates may be detected by bioluminescence resonance emission technology. The methods of the present invention are directed to detecting GPCR activity. The methods of the present invention allow enhanced monitoring of the GPCR pathway in real time.

In a preferred embodiment, the localization pattern of the detectable molecule is determined. In a further preferred embodiment, alterations of the localization pattern of the detectable molecule may be determined. The localization pattern may indicate cellular distribution of the detectable molecule. Certain methods of detection are described in U.S. Ser. No. 10/095,620, filed Mar. 12, 2002, which claims priority to U.S. Provisional Patent Application No. 60/275,339, filed Mar. 13, 2001, the contents of which are incorporated by reference in their entirety.

Molecules may also be detected by their interaction with another detectably labeled molecule, such as an antibody.

Disease Treatment

Another aspect of the invention relates to methods of treating a human or non-human subject suffering from a GPCR-related disease, such as cardiovascular disease, heart failure, asthma, nephrogenic diabetes insipidus, or hypertension. For example, compounds which alter AT1AR internalization may be useful to treat diseases and conditions related to AT1AR. Such diseases and conditions related to AT1AR include, but are not limited to: renal disease, diabetes and nephropathy, diabetes mellitus, type 2 diabetes, nephropathy, hypertension, congesive heart failure, endothelial dysfunction, vascular inflammation, and various heart diseases. Such treatment can be performed either by administering to a subject in need of such treatment, an amount of the compounds identified by the present method sufficient to treat the GPCR-related disease, or at least to lessen the symptoms thereof.

Treatment may also be effected by administering to the subject the naked modified nucleic acid sequences of the invention, such as by direct injection, microprojectile bombardment, delivery via liposomes or other vesicles, or by means of a vector which can be administered by one of the foregoing methods. Gene delivery in this manner may be considered gene therapy.

Pharmaceutical Compositions

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

Losartan is a known angiotensin receptor antagonist, of the following formula:

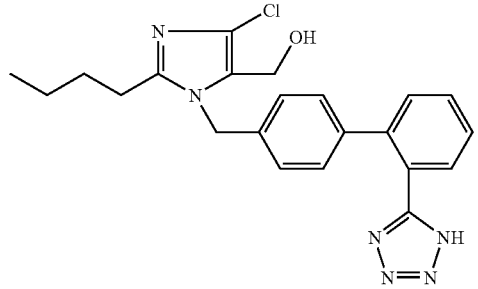

Figure 8:
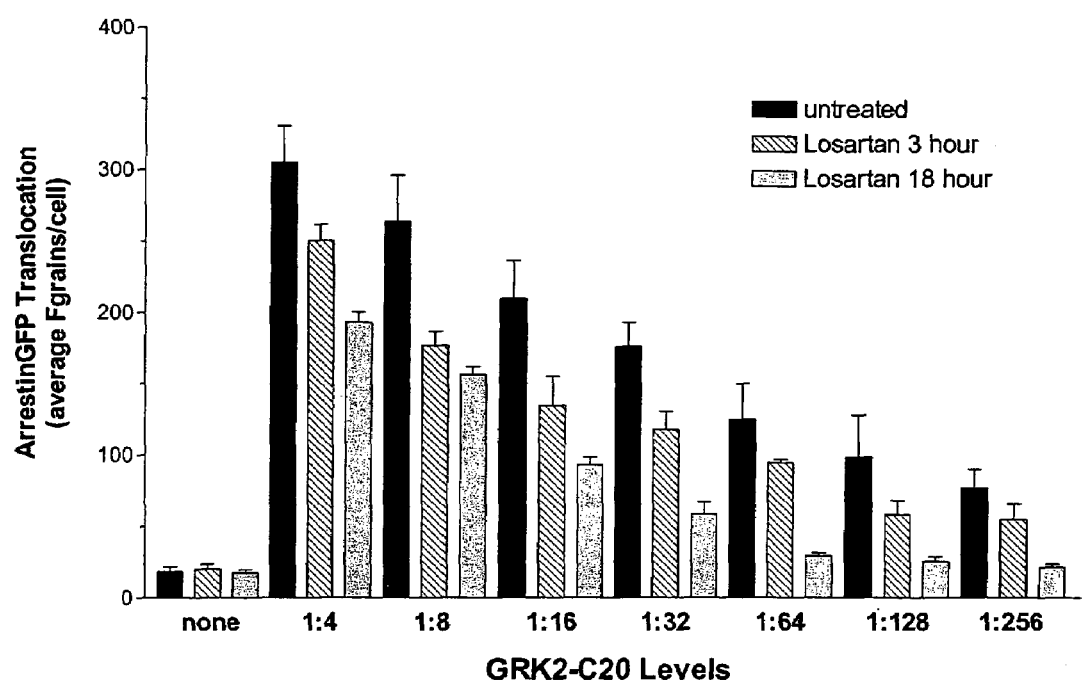
FIG. 8 demonstrates that losartan, a nonpeptide antagonist/inverse agonist of the AT1AR, inhibits the ligand-independent translocation of arrestinGFP to the AT1AR induced by expression of GRK2-C20. Data plotted are the mean ±SD for a representative experiment performed in triplicate.
Figure 9:
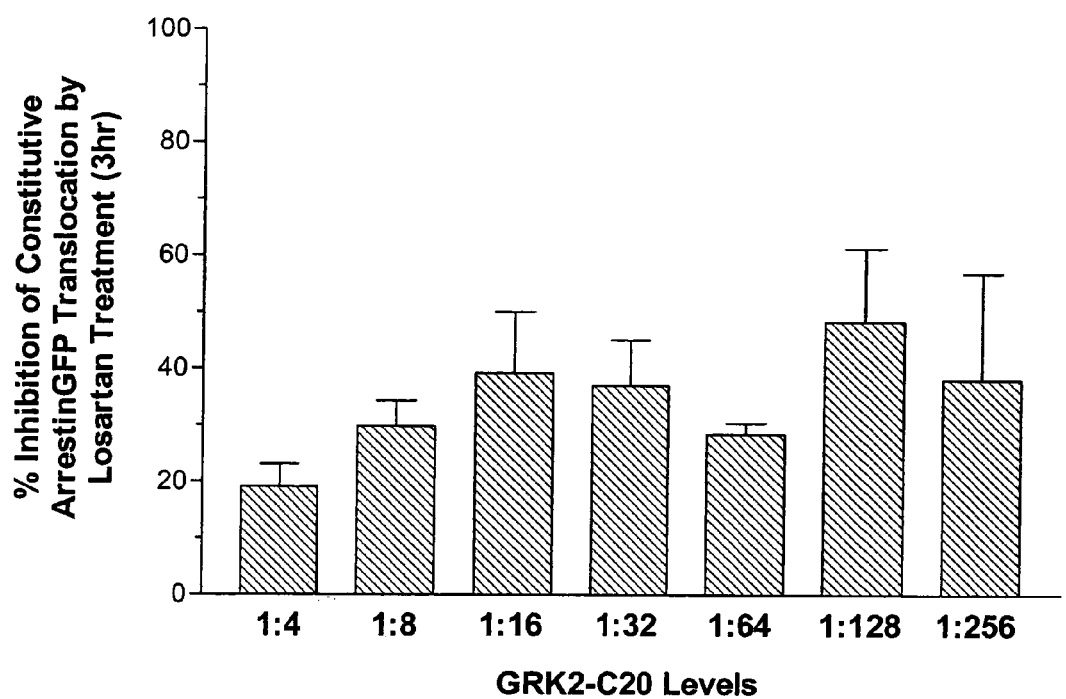
FIG. 9 illustrates the percent inhibition of constitutive, GRK2-C20 induced, arrestinGFP translocation to the AT1AR by losartan treatment for 3 hours.

The present invention describes a new use of losartan: losartan is useful in methods of altering arrestin translocation to the AT1AR receptor (FIGS. 8-9). This method my be used to treat a patient by administering an effective amount of losartan to a patient in need thereof.

A GPCR agonist, antagonist, or DAC obtained by the methods disclosed herein can be formulated into the therapeutic composition as neutralized pharmaceutically acceptable salt forms. Pharmaceutically acceptable salts include the acid addition salts (formed with the free amino groups of the polypeptide or antibody) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent (i.e., carrier, or vehicle).

The data obtained from the cell culture assays and animal studies can be used in formulating a range of dosage for use in humans. The dosage of such compositions lies preferably within a range of circulating concentrations that include the ED50 with little or no toxicity. The dosage may vary within this range depending upon the dosage form employed and the route of administration utilized. For any composition used in the method of the invention, the therapeutically effective dose can be estimated initially from cell culture assays. A dose may be formulated in animal models to achieve a circulating plasma concentration range which includes the IC50 (i.e., the concentration of the test composition which achieves a half-maximal inhibition of symptoms) as determined in cell culture. Such information can be used to more accurately determine useful doses in humans. Levels in plasma may be measured, for example, by high performance liquid chromatography.

The compositions are administered in a manner compatible with the dosage formulation, and in a therapeutically effective amount. The quantity to be administered depends on the subject to be treated, capacity of the subject's immune system to utilize the active ingredient, and degree of modulation of GPCR activity desired. Precise amounts of active ingredient required to be administered depend on the judgment of the practitioner and are peculiar to each individual. However, suitable dosages may range from about 0.001 to 30, preferably about 0.01 to about 25, and more preferably about 0.1 to 20 milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The skilled artisan will appreciate that certain factors may influence the dosage required to effectively treat a subject, including but not limited to, the severity of the disease or condition, disorder, or disease, previous treatments, the general health and/or age of the subject, and other diseases present. Moreover, treatment of a subject with a therapeutically effective amount of the composition(s) can include a single treatment or, preferably, can include a series of treatments. In a preferred example, a subject is treated with the composition in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of the composition used for treatment may increase or decrease over the course of a particular treatment. Changes in dosage may result and become apparent from the results of diagnostic assays as described herein.

The therapeutic compositions may further include an effective amount of the GPCR agonist, antagonist, or DAC and one or more of the following active ingredients: an antibiotic, a steroid, and the like.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention can be prepared as SATE ((S-acetyl-2-thioethyl) phosphate) derivatives according to the methods disclosed for example in WO 93/24510 and in WO 94/26764.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. The compounds for modulating any of the disclosed genes, gene transcripts or proteins encoded thereby include antisense compounds as well as other modulatory compounds.

Pharmaceutically acceptable base addition salts for use with antisense as well as other modulatory compounds are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, e.g., Berge et al., "Pharmaceutical Salts," J. Pharma. Sci., 1977, 66: 1-19). The base addition salts of acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a pharmaceutical addition salt includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are known in the art and include basic salts of a variety of inorganic and organic acids, such as, for example, with inorganic acids (e.g., hydrochloric acid, hydrobromic acid, sulfuric acid or phosphoric acid); with organic carboxylic, sulfonic, sulfo- or phospho-acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid.

Pharmaceutically acceptable salts of compounds may also be prepared with a pharmaceutically acceptable cation. Suitable pharmaceutically acceptable cations are well known in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds and other modulatory compounds described herein can be utilized in pharmaceutical compositions by adding an effective amount of an antisense compound or other modulatory compound to a suitable pharmaceutically acceptable diluent or carrier. Use of the compounds and methods of the invention may also be useful prophylactically.

The antisense compounds of the invention are useful for research and diagnostics, because these compounds hybridize to nucleic acids encoding a gene identified using the systematic discovery technique or a mRNA transcript thereof. Such hybridization allows the use of sandwich and other assays to easily be constructed to exploit this fact. Hybridization of the antisense oligonucleotides of the invention with a nucleic acid encoding a gene or gene transcript identified by a systematic discovery method can be detected by means known in the art. Such means may include, for example, conjugation of an enzyme to the oligonucleotide, radiolabelling of the oligonucleotide or any other suitable detection means. Kits using such detection means for detecting the level of a transcript of a gene in a sample may also be prepared.

The present invention also includes pharmaceutical antisense compositions and formulations which include the antisense compounds and other modulatory compounds and compositions of the invention. The pharmaceutical compositions of the present invention may be administered in a number of ways depending upon whether local or systemic treatment is desired and upon the area to be treated.

In certain embodiments, it may be desirable to administer the pharmaceutical compositions of the invention locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

For topical application, the compositions may be combined with a carrier so that an effective dosage is delivered, based on the desired activity.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer, salts, flavoring, coloring and sweetening agents as appropriate.

Preparations for oral administration may be suitably formulated to give controlled release of the active composition.

The compositions may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For administration by inhalation, the compositions for use according to the present invention are conveniently delivered in the form of an aerosol spray, presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the composition and a suitable powder base such as lactose or starch.

The compositions may also be formulated as a depot preparation. Such long acting formulations may be administered by implantation (for example subcutaneously or intramuscularly) or by intramuscular injection. Thus, for example, the compositions may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

Pharmaceutical compositions (e.g., gene, gene transcript or protein product modulatory agents as described herein) of the present invention include, but are not limited to, solutions, emulsions, and liposome-containing formulations. These compositions may be generated from a variety of components that include, but are not limited to, preformed liquids, self-emulsifying solids and self-emulsifying semi-solids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature, these formulations vary in the components and the consistency of the final product. The preparation of such compositions and formulations is generally known to those skilled in the pharmaceutical and formulation arts and may be applied to the formulation of the compositions of the present invention.

The compositions of the present invention may be prepared and formulated as emulsions. Emulsions are typically heterogenous systems of one liquid dispersed in another in the form of droplets usually exceeding 0.1 m in diameter. See, e.g., Idson, in Pharmaceutical Dosage Forms v. 1, p. 199 (Lieberman, Rieger and Banker (Eds.), 1988, Marcel Dekker, Inc., New York); Rosoff, in Pharmaceutical Dosage Forms, v. 1, p. 245; Block in Pharmaceutical Dosage Forms, v. 2, p. 335; Higuchi et al., in Remington's Pharmaceutical Sciences 301 (Mack Publishing Co., Easton, Pa., 1985). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase.

Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms v. 1, p. 199 (Lieberman, Rieger and Banker (Eds.), 1988, Marcel Dekker, Inc., New York).

Synthetic surfactants, also known as surface active agents, have found wide applicability in the formulation of emulsions and have been reviewed in the literature (Rieger, in Pharmaceutical Dosage Forms, v. 1, p. 285; Idson, in Pharmaceutical Dosage Forms, v. 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: non-ionic, anionic, cationic and amphoteric (Rieger, in Pharmaceutical Dosage Forms).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers, especially in combination with surfactants and in viscous preparations. These include polar inorganic solids, such as heavy metal hydroxides, non-swelling clays (e.g., bentonite, aftapulgite, hectorite, kaolin, montmorillonite, colloidal aluminum silicate and colloidal magnesium aluminum silicate), pigments and nonpolar solids (e.g., carbon or glyceryl tristearate).

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, v. 1 p. 385 (Lieberman, Rieger and Banker (Eds.), 1988, Marcel Dekker, Inc., New York)).

Hydrophilic colloids or hydrocolloids include naturally occurring gums and synthetic polymers, such as polysaccharides (e.g., acacia, agar, alginic acid, carrageenan, guar gum, karaya gum, and tragacanth), cellulose derivatives (e.g., carboxymethylcellulose and carboxypropylcellulose), and synthetic polymers (e.g., carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers (e.g., tocopherols, alkyl gallates, butylated hydroxyanisole, butylated hydroxytoluene) or reducing agents (e.g., ascorbic acid and sodium metabisulfite), and antioxidant synergists (e.g., citric acid, tartaric acid, and lecithin).

The application of emulsion formulations via dermatological, oral and parenteral routes and methods for their manufacture have been reviewed in the literature (Idson, in Pharmaceutical Dosage Forms, v. 1, p. 199). Emulsion formulations for oral delivery have been very widely used because of reasons of ease of formulation, efficacy from an absorption and bioavailability standpoint. (Rosoff, in Pharmaceutical Dosage Forms, v. 1, p. 245 (Lieberman, Rieger and Banker (Eds.), 1988, Marcel Dekker, Inc., New York); Idson, in Pharmaceutical Dosage Forms). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in Pharmaceutical Dosage Forms, v. 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in Controlled Release of Drugs: Polymers and Aggregate Systems, 185-215 (Rosoff, M., Ed., 1989, VCH Publishers, New York). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, 271 (Mack Publishing Co., Easton, Pa., 1985).

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with co-surfactants. The co-surfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Microemulsions may, however, be prepared without the use of co-surfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono-, di-, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharm. Res., 1994, 11:1385-90; Ritschel, Meth. Find. Exp. Clin. Pharmacol., 1993, 13: 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., 1994; Ho et al., J. Pharm. Sci., 1996, 85: 138-143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids and other active agents from the gastrointestinal tract, as well as improve the local cellular uptake of oligonucleotides and nucleic acids and other active agents within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Crit. Rev. Therap. Drug Carrier Systems, 1991, p. 92). Each of these classes has been discussed above.

There are many organized surfactant structures besides microemulsions that have been studied and used for the formulation of drugs. These include monolayers, micelles, bilayers and vesicles. Vesicles, such as liposomes, are useful because of their specificity and the duration of action. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo. Selection of the appropriate liposome depending on the agent to be encapsulated would be evident given what is known in the art.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include: (a) liposomes obtained from natural phospholipids are biocompatible and biodegradable; (b) liposomes can incorporate a wide range of water and lipid soluble drugs; (c) liposomes can protect encapsulated drugs in their internal compartments from metabolism and degradation (Rosoff, in Pharmaceutical Dosage Forms). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Another embodiment also contemplates the use of liposomes for topical administration. Such advantages include reduced side-effects related to high systemic absorption of the administered drug, increased accumulation of the administered drug at the desired target, and the ability to administer a wide variety of drugs, both hydrophilic and hydrophobic, into the skin. Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Comm., 1987, 147:980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., J. Controlled Release, 1992, 19: 269-74).

Another contemplated liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

"Sterically stabilized" liposomes, which refers to liposomes comprising one or more specialized lipids that, when incorporated into liposomes, result in enhanced circulation lifetimes relative to liposomes lacking such specialized lipids are also contemplated. Examples of sterically stabilized liposomes are those in which part of the vesicle-forming lipid portion of the liposome (A) comprises one or more glycolipids, such as monosialoganglioside GM1, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Lett., 1987, 223: 42; Wu et al., Can. Res., 1993, 53: 3765).

Many liposomes comprising lipids derivatized with one or more hydrophilic polymers, and methods of preparation thereof, are known in the art. See, e.g., Sunamoto et al. (Bull. Chem. Soc. Jpn., 1980, 53: 2778) described liposomes comprising a nonionic detergent, 2C12 15G, that contains a PEG moiety. Illum et al. (FEBS Lett., 1984, 167: 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268: 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029: 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by, e.g., Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.). Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

Methods of encapsulating nucleic acids in liposomes is also known in the art. See, WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, p. 285 (Marcel Dekker, Inc., New York, N.Y., 1988, p. 285)).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, 285 (Marcel Dekker, Inc., New York, N.Y., 1988).

In one embodiment, the present invention employs various penetration enhancers to effect the efficient delivery of nucleic acids and other agents, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.

Another embodiment of the invention contemplates pharmaceutical compositions comprising surfactants. Surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Crit. Rev. Therap. Drug Carrier Systems, 1991, 92); and perfluorochemical emulsions, such as FC-43 (Takahashi et al., J. Pharm. Pharmacol., 1988, 40: 252).

Another embodiment contemplates the use of various fatty acids and their derivatives to act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, C1-10 alkyl esters thereof (e.g., methyl, isopropyl and t-butyl), and mono- and di-glycerides thereof (i.e., oleate, laurate, caprate, myristate, palmitate, stearate, linoleate, and the like) (Lee et al., 1991; Muranishi, Crit. Rev. Therap. Drug Carrier Systems, 1990, 7: 1-33; El Hariri et al., J. Pharm. Pharmacol., 1992, 44: 651-4).

The compositions comprising the active agents of the invention may further comprise bile salts. The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, N.Y., 1996, pp. 934-935). Various natural bile salts, and their synthetic derivatives, act as penetration enhancers. Thus, the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., 1991; Swinyard, Chapter 39 In: Remington's Pharmaceutical Sciences, 18th Ed., Gennaro, ed., Mack Publishing Co., Easton, Pa., 1990, pages 782-783; Muranishi, 1990; Yamamoto et al., J. Pharm. Exp. Ther., 1992, 263: 25; Yamashita et al., J. Pharm. Sci., 1990, 79: 579-83).

The invention further contemplates compositions comprising chelating agents. Chelating agents can be defined as compounds that remove metallic ions from solution by forming complexes therewith, with the result that absorption of oligonucleotides through the mucosa is enhanced. With regards to their use as penetration enhancers for use when the active agent is an antisense agent, chelating agents have the added advantage of also serving as DNase inhibitors, as most characterized DNA nucleases require a divalent metal ion for catalysis and are thus inhibited by chelating agents (Jarrett, J. Chromatogr., 1993, 618: 315-39). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., 1991; Muranishi, 1990; Buur et al., J. Control Rel., 1990, 14: 43-51).

The invention also contemplates pharmaceutical compositions comprising active agents and non-chelating non-surfactants. Non-chelating non-surfactant penetration enhancing compounds can be defined as compounds that demonstrate insignificant activity as chelating agents or as surfactants, but that nonetheless enhance absorption of oligonucleotides through the alimentary mucosa (Muranishi, 1990). This class of penetration enhancers include, for example, unsaturated cyclic ureas, 1-alkyl- and 1-alkenylazacyclo-alkanone derivatives (Lee et al., 1991); and non-steroidal anti-inflammatory agents such as diclofenac sodium, indomethacin and phenylbutazone (Yamashita et al., J. Pharm. Pharmacol., 1987, 39: 621-6).

For pharmaceutical compositions comprising oligonucleotides, agents that enhance uptake of oligonucleotides at the cellular level may also be added to the pharmaceutical and other compositions of the present invention. For example, cationic lipids, such as lipofectin (Junichi et al., U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes (e.g., limonene and menthone).

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'-isothiocyano-stilbene-2,2'-disulfonic acid (Miyao et al., Antisense Res. Dev., 1995, 5: 115-121; Takakura et al., Antisense & Nucl. Acid Drug Dev., 1996, 6: 177-183).

The pharmaceutical compositions disclosed herein may also comprise an excipients. In contrast to carrier compounds described above, these excipients include a pharmaceutically acceptable solvent, suspending agent or any other pharmacologically inert vehicle for delivering one or more nucleic acids or other active agents to an animal. The excipient may be liquid or solid and is selected, with the planned manner of administration in mind, so as to provide for the desired bulk, consistency, etc., when combined with a nucleic acid or other active agent and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids and other contemplated active agents may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids or other contemplated active agents can be used.

The compositions of the present invention may additionally contain other adjunct components conventionally found in pharmaceutical compositions, at their art-established usage levels. Thus, for example, the compositions may contain additional, compatible, pharmaceutically-active materials such as, e.g., antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Test Kits

In a further embodiment of this invention, commercial test kits including an assay system for screening potential drugs effective to modulate the activity of the GPCR may be prepared. The test kits may include cells, nucleic acids, or proteins described herein. The test kits may be used to carry out any of the methods described herein. A GPCR of interest may be introduced into host cells of the test kit. The test kit may be useful for determining if the GPCR is expressed at the plasma membrane, if the phosphorylated or unphosphorylated GPCR binds arrestin, or if the phosphorylated or unphosphorylated GPCR is internalized. The test kit may be useful for the identification of compounds that alter the desensitization of the GPCR of interest.

The GPCR may be introduced into a test system, and the prospective drug may also be introduced into the resulting cell culture, and the culture thereafter examined to observe any changes in the GPCR activity (e.g., signaling, recycling, affinity for arrestin, and the like) in the cells.

The following examples are presented in order to more fully illustrate the preferred embodiments of the invention. They should in no way be construed, however, as limiting the broad scope of the invention.

EXAMPLES

Example 1

Experimental Procedures

The present inventors subcloned the Bovine GRK2-C20 cDNA (Inglese et al., Nature 1992) into the expression vector pcDNA3.1zeo+ (Invitrogen). Expression of this cDNA produces GRK2 with a CAAX motif (where C is cysteine, A is a small aliphatic residue, and X is an uncharged amino acid) added to the carboxyl terminus. The specific CAAX motif added to the end of GRK2, CVLL (SEQ ID NO: 94), directs the geranylgeranylation (C20 isoprenylation) of this protein. The enzyme-directed covalent attachment of the 20 carbon geranylgeranyl lipid group to the carboxyl terminus of GRK2 allows it to be localized at the plasma membrane (Inglese et al., Nature 1992).

Cell Culture

Human embryonic kidney (HEK-293) cells were purchased from the American Type Culture Collection (ATCC) and grown in Eagle's minimum essential medium (EMEM) supplemented with 10% (v/v) heat-inactivated fetal calf serum and gentamicin (100 µg/ml). HEK-293 cells stably expressing arrestin-GFP (HEK293-ArrGFP) were generated by standard procedures using G418 selection (0.4 mg/ml).

HEK-293 cells were transiently transfected with arrestin-GFP, the GPCR of interest, and GRK2-C20. For control experiments performed in parallel, HEK-293 cells were transiently transfected with arrestin-GFP, the GPCR of interest, and no GRK2-C20. HEK293 cells were transiently transfected with arrestin-GFP, the GPCR of interest and GRK2-C20. For control experiments performed in parallel, the HEK293 cells were transiently transfected with arrestin-GFP were transiently transfected with the GPCR of interest and no GRK2-C20. All transfections were performed by the calcium phosphate coprecipitation method as previously described (Oakley et al., 1999). Following the transfection, cells were maintained in the culture medium (EMEM supplemented with 10% FCS and 10 μg/ml gentamycin) for approximately 24 hours. The cells were then plated on 35 mm glass bottom dishes (MatTek) and incubated for an additional 16-24 hours. Transfected GPCRs included both known GPCRs (receptors for which the natural ligand is know) and orphan GPCRs (receptors for which the natural ligand has not yet been identified).

Confocal Microscopy

Transfected HEK-293 cells were plated on 35 mm glass bottom dishes (MatTek) and cultured overnight. The next day, the medium was removed and replaced with serum-free medium supplemented with 10 mM HEPES for an additional 1 hour incubation at 37° C. The distribution of arrestin-GFP was then assessed using a Zeiss laser scanning confocal microscope (LSM 5 Pascal). Images were acquired with a 63× oil objective from live cells using single line excitation (488 nm) and a LP505 emission filter.

Example 2

Agonist-Independent Desensitization of Known GPCRs Upon Expression of a Modified GRK The present inventors determined that overexpression of the GRK2-C20, which is expressed at the plasma membrane (Inglese et al., Nature 1992), in a cell line expressing arrestin-GFP promoted the binding of arrestin-GFP to GPCRs in the absence of added ligand.

The HEK293 cells transiently transfected with arrestin-GFP were transiently transfected with the GPCR of interest and with or without GRK2-C20. Using confocal microscopy, the distribution of the arrestin-GFP was determined. The localization of the arrestin-GFP at clathrin coated pits, endocytic vesicles, endosomes, or other stages in the desensitization pathway indicated arrestin-GFP binding to the GPCR. Thus, GPCR desensitization, visualized by the binding of arrestin-GFP to the GPCRs, was analyzed.

In the absence of added agonist, arrestin-GFP localized in small puncta (presumably clathrin coated pits) at the plasma membrane in cells expressing GRK2-C20 and either the cannabinoid type 2 receptor (CB2R) (FIG. 4). Moreover, in the absence of added agonist, arrestin-GFP localized in endocytic vesicles in cells expressing GRK2-C20 and either the angiotensin II type IA receptor (AT1AR), vasopressin V2 receptor (V2R), (FIG. 4) or neurokinin-1/substance P receptor (NK-1 or SPR). In control cells expressing each of the receptors (CB2R, AT1AR, V2R, or SPR) but lacking GRK2-C20, arrestin-GFP was diffusely expressed in the cytoplasm and did not localize to any significant extent in pits at the plasma membrane or vesicles inside the cell (FIG. 4).

Example 3

Agonist-Independent Desensitization of Orphan GPCRs Upon Expression of a Modified GRK The present inventors determined that overexpression of the GRK2-C20, which is expressed at the plasma membrane (Inglese et al., Nature 1992), in a cell line expressing arrestin-GFP promoted the binding of arrestin-GFP to GPCRs in the absence of added ligand.

As above, the HEK293 cells transiently transfected with arrestin-GFP were transiently transfected with the GPCR of interest and with or without GRK2-C20. Using confocal microscopy, the distribution of the arrestin-GFP was determined. The localization of the arrestin-GFP at clathrin coated pits, endocytic vesicles, endosomes, or other stages in the desensitization pathway indicated arrestin-GFP binding to the GPCR. Thus, GPCR desensitization, visualized by the binding of arrestin-GFP to the GPCRs, was analyzed.

Figure 7:
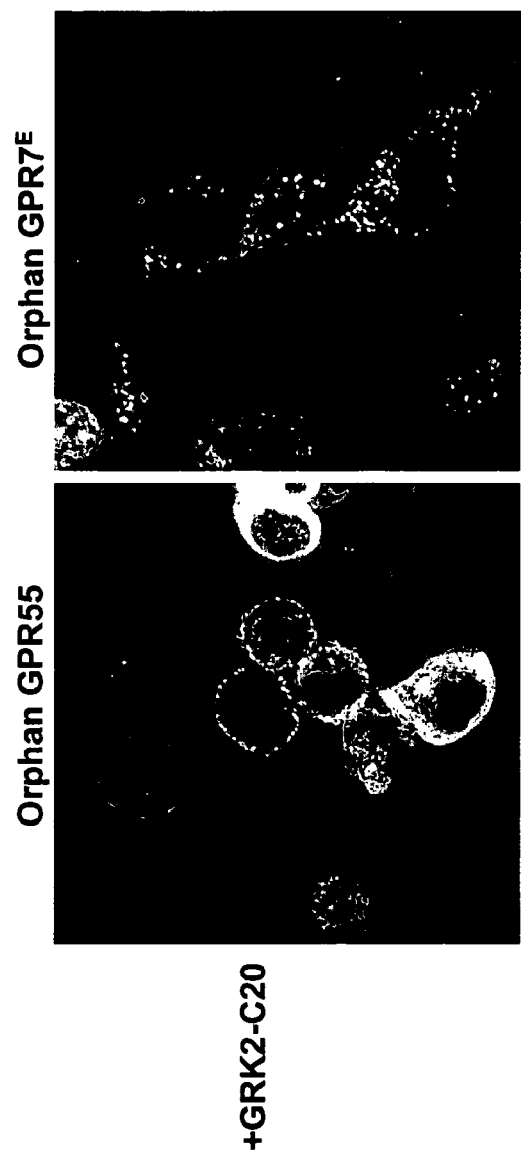
FIG. 7 illustrates the agonist-independent translocation of arrestin-GFP to GPCRs in the presence of GRK2-C20.

In the absence of added agonist, arrestin-GFP localized in small puncta (presumably clathrin coated pits) at the plasma membrane in cells expressing the orphan receptor GPR55 (FIG. 7). In control cells expressing GPR55 but lacking GRK2-C20, arrestin-GFP was diffusely expressed in the cytoplasm and did not localize to any significant extent in pits at the plasma membrane or vesicles inside the cell (FIG. 7). Other orphan GPCRs are described below.

Example 4

Method of Analyzing the Ability of a GPCR to Bind Arrestin

The present inventors developed a method to determine if a GPCR of interest is expressed at the plasma membrane. Preferably, the expression of orphan GPCRs may be analyzed in host cells in which GPCRs desensitize in an agonist-independent manner, as described herein.

As above, the HEK293 cells transiently transfected with arrestin-GFP were transiently transfected with the GPCR of interest and with or without GRK2-C20. Using confocal microscopy, the distribution of the arrestin-GFP was determined. The localization of the arrestin-GFP at clathrin coated pits, endocytic vesicles, endosomes, or other stages in the desensitization pathway indicated arrestin-GFP binding to the GPCR. Thus, GPCR desensitization, visualized by the binding of arrestin-GFP to the GPCRs, was analyzed.

Certain GPCRs, as described above, localized in clathrin coated pits, endocytic vesicles, endosomes, or other stages in the desensitization pathway. This localization indicated that the GPCRs had the ability to bind arrestin, because arrestin binding is requisite for subsequent localization in the desensitization pathway. A GPCR that does not bind arrestin would not enter or localize in the desensitization pathway. GPCRs that do not bind arrestin may be altered such that they do bind arrestin. The present inventors modified certain GPCRs to enhance arrestin affinity, as described below.

Example 5

Method of Increasing the Ability of a GPCR to Bind Arrestin

The present inventors modified GPCRs to enhance their binding to arrestin. These modifications are described in U.S. Ser. No. 09/993,844. GPCRs were modified at their C-terminal tails to be better phosphorylated by GRKs. These modified and phosphorylated GPCRs then had enhanced binding to arrestin. They demonstrated increased internalization. The letter E (for enhanced phosphorylation) is added to the end of the name of the GPCR which has been modified in this manner.

Modified GPCR constructs were generated by polymerase chain reaction following standard protocols and contain the HA epitope. Chimeric receptors were constructed in which the carboxyl-terminal tails of the GPCR and V2R were exchanged (FIG. 3A-3BB), one for the other, after the putative sites of palmitoylation. Sequences of the DNA constructs were confirmed by DNA sequencing.

The nucleic acids of the GPCR of interest were PCR-amplified with primers that introduced a Not I restriction enzyme site (gcggccgc) immediately after the codon for a cysteine residue (a putative site of palmitoylation) 10 to 25 amino acids (preferably 15 to 20) downstream of the NPXXY that is to be fused to the V2R carboxyl terminus. The amplified receptor DNA fragment was then subcloned into the pEArrB-1 vector (described in U.S. patent application Ser. No. 09/993,844) using the Not I restriction enzyme site and an additional restriction enzyme site upstream of the receptor atg start codon. When expressed, the modified GPCR will contain a 31 amino acid peptide fused to the receptor carboxyl terminus. The first two amino acids will be Ala residues contributed by the Not I site, and the last 29 amino acids will be from the V2R carboxyl terminus.

The present inventors modified the carboxyl-terminal tails of the following receptors as described above and in the U.S. patent application Ser. No. 09/993,844: the β2-adrenergic receptor (β2ARE), dopamine D1A receptor (D1ARE), mu opiod receptor (MORE), orphan GPR3 (GPR3E), orphan GPR6 (GPR6E), orphan GPR12 (GPR12E), orphan GPR7 (GPR7E), orphan GPR8 (GPR8E), orphan GPR55 (GPR55E), orphan SREB2 (SREB2E), and orphan SREB3 (SREB3E). The "E" stands for "enhanced arrestin binding". In the absence of added agonist, arrestin-GFP localized in endocytic vesicles for each of the modified GPCRs listed above when co-expressed with GRK2-C20 (FIGS. 4, 5, 6, and 7). For some of these modified receptors (such as orphan GPR6E), a small but significant amount of arrestin-GFP was observed to localize in intracellular vesicles in the control cells lacking the GRK2-C20 (FIG. 5). However, overexpression of GRK2-C20 with these receptors promoted a marked increase in this response (FIG. 5). The amino acid and nucleic acid sequences of these modified GPCRs, the wild-type sequences, and sequences of HA-tagged modified GPCRs are shown in FIG. 3A-3BB and in SEQ ID Nos: 35-90.

Example 6

Method of Determining if a GPCR of interest is Expressed at the Plasma Membrane

The present inventors developed a method to determine if a GPCR of interest is expressed at the plasma membrane.

The HEK293 cells transiently transfected with arrestin-GFP were transiently transfected with the GPCR of interest and with or without GRK2-C20. Using confocal microscopy, the distribution of the arrestin-GFP was determined. The localization of the arrestin-GFP at clathrin coated pits, endocytic vesicles, endosomes, or other stages in the desensitization pathway indicated arrestin-GFP binding to the GPCR. Thus, GPCR desensitization, visualized by the binding of arrestin-GFP to the GPCRs, was analyzed.

Certain GPCRs, as described above, localized in clathrin coated pits, endocytic vesicles, endosomes, or other stages in the desensitization pathway. This localization indicated that the GPCRs were expressed at the plasma membrane, because plasma membrane expression is requisite for subsequent localization in the desensitization pathway. A GPCR that was not expressed at the plasma membrane would not localize in the desensitization pathway. GPCRs that do not express at the plasma membrane may be altered such that they do express at the plasma membrane. For example, the expression of the GPCR may be altered, the amino acid sequence of the GPCR may be altered, or the GPCR may be introduced into another host cell.

Example 7

Monitoring Desensitization of GPCR Mutants

Desensitization may be monitored in cells including GPCR mutants. The desensitization of the GPCR mutant may be dependent on GRK overexpression.

A vector including the human $\beta_2$AR-E-Y326A containing a point mutation, the Tyrosine residue 326 converted to Alanine, will be transfected into cells expressing arrestin-GFP and a GRK, which may be modified. The "E" indicates that the GPCR has been modified, as described above. The Y326A mutation causes the GPCR to be dependent on overexpressed GRK for phosphorylation and subsequent desensitization. The $\beta_2$AR-Y326A will desensitize in the absence of agonist upon expression of GRK-C20. The expression of the GRK may be altered, including methods of altering the amount of GRK nucleic acids in the cell using an inducible promoter, replication controlling machinery such as the origin of replication, or manually altering the amount of vector in the cells.

The cells will be seeded in 96 well or higher density plates and incubated overnight. The next morning the activator of the inducible system or vehicle only will be added to the wells to induce overexpression of the GRK or modified GRK. Agonist will be added to cells expressing the GRK (not the modified GRK).

Compounds of interest will then be added to the wells to see if they alter the internalization of arrestin-GFP. The cells will then be fixed with 2% paraformaldehyde and the amount of arrestin-GFP translocation will be measured using image analysis systems.

Example 8

Nonpeptide Antagonist/Inverse GPCR Agonist Inhibits Constitutive Translocation of ArrestinGFP Induced by Expression of GRK2-C20

U2OS cells stably expressing arrestinGFP and the angiotensin II type 1A receptor (AT1 AR) were transiently transduced with human GRK2-C20 using a baculovirus expression system. A range of GRK2-C20 expression levels was obtained by using varying amounts (serial dilution) of the GRK2-C20 baculovirus. As shown by the black bars in FIG. 8, addition of GRK2-C20 promotes ligand-independent translocation of arrestinGFP to the AT1AR. A maximum arrestinGFP translocation response of 305±25 Fgrains and a minimum of 77±13 Fgrains was achieved with the 1:4 and 1:256 dilutions, respectively, of GRK2-C20 baculovirus. In the absence of added GRK2-C20 (none), no translocation was observed (18±3 Fgrains).

To test whether the ligand-independent arrestinGFP translocation could be blocked by an antagonist/inverse agonist of the AT1AR, the cells were treated with losartan. Losartan is a nonpeptide molecule that functions as an antagonist/inverse agonist of the AT1AR. Losartan (1 μM final concentration) was added to the cells either immediately after transduction for an 18 hour incubation or 15 hours after transduction for a 3 hour incubation. At the end of the incubation, the cells were analyzed for arrestinGFP translocation using the INCell Analyzer system.

Figure 10:
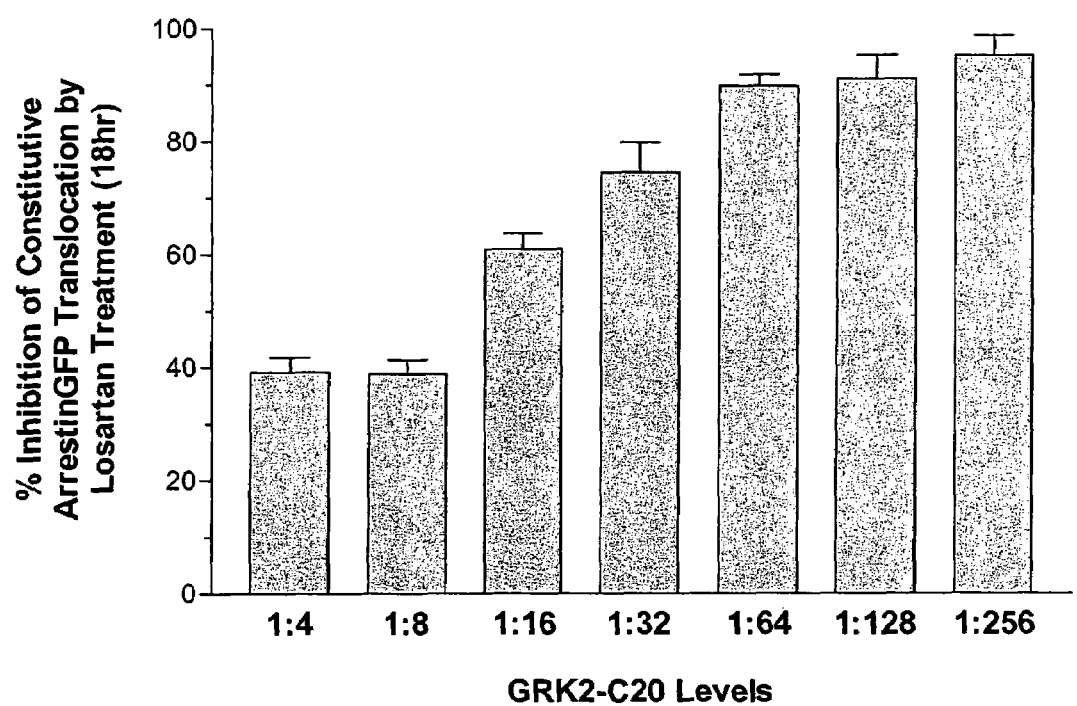
FIG. 10 illustrates the percent inhibition of constitutive, GRK2-C20 induced, arrestinGFP translocation to the AT1AR by losartan treatment for 18 hours.

As shown in FIGS. 8, 9, and 10, losartan treatment blocks the ligand-independent translocation of arrestinGFP to the AT1AR induced by expression of GRK2-C20. The most dramatic effect was observed after an 18 hour incubation with losartan (FIGS. 8 and 10). At the lower levels of GRK2-C20 expression (1:64, 1:128, and 1:256 dilutions), this treatment paradigm results in the inhibition of greater than 90% of the ligand-independent translocation of arrestinGFP to the AT1AR.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

The following is a list of documents related to the above disclosure and particularly to the experimental procedures and discussions. The following documents, as well as any documents referenced in the foregoing text, should be considered as incorporated by reference in their entirety.

Attramadal, H., Arriza, J. L., Aoki, C., Dawson, T. M., Codina, J., Kwatra, M. M., Snyder, S. H., Caron, M. G. & Lefkowitz, R. J. (1992) J. Biol. Chem. 267, 17882-17890

Barak, L. S., Oakley, R. H., Laporte, S. A. and Caron, M. G. (2001) Proc. Natl. Acad. Sci. USA 98, 93-98

Barak, L. S., Warabi, K., Feng, X., Caron, M. G. & Kwatra, M. M. (1999) J. Biol. Chem. 274, 7565-7569

Barak, L. S., Ferguson, S. S., Zhang, J. & Caron, M. G. (1997) J. Biol. Chem. 272, 27497-27500

Barak, L. S., Ferguson, S. S., Zhang, J., Martenson, C., Meyer, T. &

Caron, M. G. (1997) Mol. Pharmacol. 51, 177-184

Barak, L. S., Menard, L., Ferguson, S. S., Colapietro, A. M. & Caron, M. G. (1995) Biochemistry 34, 15407-15414

Ferguson, S. S., Barak, L. S., Zhang, J. & Caron, M. G. (1996) Can. J. Physiol. Pharmacol. 74, 1095-1110

Ferguson, S. S., Menard, L., Barak, L. S., Koch, W. J., Colapietro, A. M. & Caron, M. G. (1995) J. Biol. Chem. 270, 24782-24789

Inglese, J., Koch, W. J., Caron, M. G., Lefkowitz, R. J. (1992) Nature 359:147-150

Kim, K.-M., Valenzano, K. J., Robinson, S. R., Yao, W. D., Barak, L. S., Caron, M. G. (2001) J. Biol. Chem. 276: 37409-37414

Laporte, S. A., Oakley, R. H., Holt, J. A., Barak, L. S. & Caron, M. G. (2000) J. Biol. Chem. 275, 23120-23126

Laporte, S. A., Oakley, R. H., Zhang, J., Holt, J. A., Ferguson, S. S., Caron, M. G. & Barak, L. S. (1999) Proc. Natl. Acad. Sci. USA 96, 3712-3717

Menard, L., Ferguson, S. S., Zhang, J., Lin, F. T., Lefkowitz, R. J., Caron, M. G. & Barak, L. S. (1997) Mol. Pharmacol. 51, 800-808

Mhaouty-Kodja, S., Barak, L. S., Scheer, A., Abuin, L., Diviani, D., Caron, M. G. & Cotecchia, S. (1999) Mol. Pharmacol. 55, 339-347

Oakley, R. H., Laporte, S. A., Holt, J. A., Barak, L. S., Caron, M. G. (2001). J. Biol. Chem. 276: 19452-19460

Oakley, R. H., Laporte, S. A., Holt, J. A., Caron, M. G. & Barak, L. S. (2000) J. Biol. Chem. 275, 17201-17210

Oakley, R. H., Laporte, S. A., Holt, J. A., Barak, L. S. & Caron, M. G. (1999) J. Biol. Chem. 274, 32248-32257

Zhang, J., Barak, L. S., Anborgh, P. H., Laporte, S. A., Caron, M. G. & Ferguson, S. S. (1999) J. Biol. Chem. 274, 10999-11006

Zhang, J., Barak, L. S., Winkler, K. E., Caron, M. G. & Ferguson, S. S. (1997) J. Biol. Chem. 272, 27005-27014

---

The invention claimed is:

1. A method of identifying a compound which alters G protein-coupled receptor (GPCR) internalization, comprising:
   a) providing a cell comprising a CPCR, an arrestin, and a modified G protein-coupled receptor kinase (GRK) comprising one or more modifications in the amino acid sequence of the four C-terminal amino acids of the GRK as compared to a wild type GRK, wherein said GPCR is at least partially internalized in an agonist-independent manner upon expression of said modified GRK;
   b) exposing said cell to the compound(s);
   c) determining the cellular distribution of the GPCR, arrestin, or modified GRK, wherein said modified GRK alters GPCR desensitization in the absence of an agonist as compared to a wild type GRK; and
   d) monitoring a difference between (1) the distribution of the GPCR, arrestin, or modified GRK in the cell in the presence of the compound(s) and (2) the distribution of the GPCR, arrestin, or modified GRK in the cell in the absence of the compound(s).

2. The method of claim 1, wherein the expression of the modified GRK of step (a) is inducible.

3. The method of claim 1, wherein the modified GRK comprises a CAAX (SEQ ID NO:95) motif, wherein C is cysteine, A is an aliphatic amino acid, and X is the wild type C-terminal amino acid of GRK.

4. The method of claim 1, wherein the GPCR comprises one or more modifications in the amino acid sequence of its carboxy-terminal tail, to have enhanced phosphorylation by the modified GRK as compared to a wild type GPCR.

5. The method of claim 1, wherein the CPCR is ($\beta_2$AR (Y326A).

6. The method of claim 1, wherein the GPCR is a GPCR listed in FIG. 1, an orphan GPCR, a taste receptor, a Class A GPCR, a Class B GPCR, a mutant GPCR, or a biologically active fragment thereof.

7. The method of claim 1, wherein the modified or wild type GRK is GRK1, GRK2, GRK3, GRK4, GRK5, GRK6, or a biologically active fragment thereof.

8. The method of claim 1, wherein the GPCR, GRK, or arrestin is detectably labeled.

9. The method of claim 1, wherein a molecule involved in GPCR desensitization is detectably labeled, or a molecule that interacts with a molecule involved in GPCR desensitization is detectably labeled.

10. The method of claim 1, wherein the arrestin is visual arrestin, cone arrestin, $\beta$-arrestin 1, $\beta$-arrestin 2, or a biologically active fragment thereof.

11. The method of claim 1, wherein an agonist of said GPCR is not provided.

12. The method of claim 1, wherein a difference between (1) and (2) of step (d) indicates modulation of GPCR internalization.

13. The method of claim 1, wherein the GPCR is AT1AR.

14. The method of claim 3, wherein said CAAX motif is CVLL (SEQ ID NO:94).

* * * * *